US012617797B2

(12) United States Patent
Fernandez-Donis et al.

(10) Patent No.: US 12,617,797 B2
(45) Date of Patent: May 5, 2026

(54) SUBSTITUTED PYRAZOLO [1,5-A]PYRIMIDINES HAVING MULTIMODAL ACTIVITY AGAINST PAIN

(71) Applicant: ESTEVE PHARMACEUTICALS, S.A., Barcelona (ES)

(72) Inventors: Ariadna Fernandez-Donis, Barcelona (ES); José-Luís Díaz-Fernández, Manresa (ES); Carmen Almansa-Rosales, Barcelona (ES); Mónica Garcia-Lopez, Barcelona (ES); Joan-Carles Fernandez-Collado, Barcelona (ES); Jordi Gonzalez-Garcia, Olesa de Montserrat (ES); Maria Garrido-Martinez, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 660 days.

(21) Appl. No.: 17/999,421

(22) PCT Filed: May 20, 2021

(86) PCT No.: PCT/EP2021/063411
§ 371 (c)(1),
(2) Date: Nov. 21, 2022

(87) PCT Pub. No.: WO2021/239558
PCT Pub. Date: Dec. 2, 2021

(65) Prior Publication Data

US 2024/0059690 A1 Feb. 22, 2024

(30) Foreign Application Priority Data

May 27, 2020 (EP) .................................... 20382447

(51) Int. Cl.
*A61K 31/519* (2006.01)
*A61P 29/02* (2006.01)
*C07D 487/04* (2006.01)

(52) U.S. Cl.
CPC ............ *C07D 487/04* (2013.01); *A61P 29/02* (2018.01)

(58) Field of Classification Search
CPC ............................ A61K 31/519; C07D 487/04
USPC ....................................... 514/259.3; 544/281
See application file for complete search history.

(56) References Cited

U.S. PATENT DOCUMENTS

| | | | |
|---|---|---|---|
| 9,796,724 | B2 | 10/2017 | Allen et al. |
| 2010/0016330 | A1 | 1/2010 | Heer |
| 2017/0096399 | A1 | 4/2017 | Siegrist et al. |
| 2019/0345146 | A1 | 11/2019 | Almansa-Rosales |
| 2019/0365763 | A1 | 12/2019 | Allen et al. |
| 2020/0129515 | A1 | 4/2020 | Borza et al. |
| 2023/0141433 | A1 | 5/2023 | Shaikh et al. |

FOREIGN PATENT DOCUMENTS

| | | | |
|---|---|---|---|
| CA | 2776842 | 4/2011 | |
| CA | 3180058 A1 * | 12/2021 | ........... C07D 487/04 |
| CL | 201200059 | 7/2012 | |
| CL | 201200885 | 11/2012 | |
| CL | 201203227 | 2/2013 | |
| CL | 201603892 | 5/2017 | |
| CL | 201902601 | 1/2020 | |
| CL | 202202834 | 3/2023 | |
| JP | 2007332061 | 12/2007 | |
| WO | WO2004006836 | 1/2004 | |
| WO | WO2018/154133 | 8/2018 | |
| WO | WO2018219921 | 12/2018 | |
| WO | WO2019077106 | 4/2019 | |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Chien CC, Pasternak GW, Neurosci. Lett. 1995, 198, 137-9.
Davies et al., Trends Pharmacol. Sci. 2007, 28, 220-8.
Dolphin AC, Biochim. Biophys. Acta 2013, 1828, 1541-9.
Dolphin AC, Nav Rev Neurosci, 2012, 13, 542-55.
Gilron et al., Lancet Neurol, 2013, 12, 1084-95.
Goldberg DS, McGee SJ, BMC Public Health, 2611, 13, 770.
Hopkins et al , Nat. Chem. Biol. 2008, 4, 682-90.
Lehar et al., Nat Biotechnol. 2009, 27, 659-666.
Mao J, Gold MS, Backonja M. J. Pain, 2011, 12, 157-166.
Neumaier et al., Prog. Neurobiol. 2015, 129, 1-36.
Perret and Luo, Neurotherapeutics 2009, 6, 679-92.
Romero et al. Br J Pharmacol. 2012, 166, 2289-306.
Schroder et al., J. Pharmacol. Exp Ther. 2011, 397, 312-20. Erratum in: J. Pharmacol. Exp. Ther. 2012, 342, 232.
Turk OC, Wilson HD, Cahana A. Lancet; 2011, 377, 2226-2235.

(Continued)

*Primary Examiner* — Douglas M Willis
(74) *Attorney, Agent, or Firm* — HUESCHEN AND SAGE

(57) ABSTRACT

The present invention relates to pyrazolopyrimidine derivatives of Formula (I) having dual pharmacological activity towards both the $\alpha_2\delta$ subunit of the voltage-gated calcium channel and the sigma-1 ($\sigma$1) receptor, to processes of preparation of such compounds, to pharmaceutical compositions comprising them, and to their use in therapy, in particular for the treatment of pain.

(I)

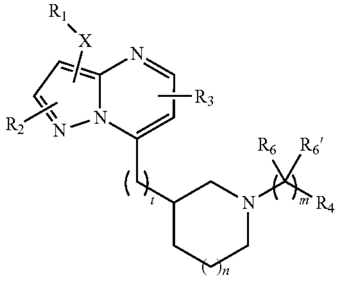

13 Claims, No Drawings

(56) References Cited

OTHER PUBLICATIONS

Vink and Alewood, Br. J. Pharmacol, 2012, 167, 970-89.
Zamanillo D, Romero L, Merlos M, Vela JM. Eur. J. Pharmacol. , 2013, 716, 78-93.
Zamponi et al., Pharmacol. Rev. 2015, 67, 821-70.
Zhang et al., Cell Death Dis. 2014, 5:e1138.
International Search Report for PCT/EP2021/063411 dated Jun. 23, 2021.
English Abstract for JP 2007332061, Dec. 27, 2007.
STN Chemical Database Registry No. RN 2059011-12-8, Entered STN: Jan. 25, 2017.
STN Chemical Database Registry No. RN 2060477-31-6, Entered STN: Jan. 27, 2017.
STN Chemical Database Registry No. RN 2061588-05-2, Entered STN: Jan. 30, 2017.
STN Chemical Database Registry No. RN 2061806-28-6, Entered STN: Jan. 30, 2017.
STN Chemical Database Registry No. RN 2062236-17-1. Entered STN: Jan. 31, 2017.
STN Chemical Database Registry No. RN 2062236-18-2, Entered STN: Jan. 31, 2017.
STN Chemical Database Registry No. RN 2062236-38-6. Entered STN: Jan. 31, 2017.
STN Chemical Database Registry No. RN 2062236-78-4, Entered STN: Jan. 31, 2017.
STN Chemical Database Registry No. RN 2127202-39-3, Entered STN: Sep. 14, 2017.
STN Chemical Database Registry No. RN 2216485-23-1, Entered STN: Apr. 20, 2018.

* cited by examiner

SUBSTITUTED PYRAZOLO [1,5-A]PYRIMIDINES HAVING MULTIMODAL ACTIVITY AGAINST PAIN

FIELD OF THE INVENTION

The present invention relates to compounds having dual pharmacological activity towards both the $\alpha_2\delta$ subunit of the voltage-gated calcium channel, and the sigma-1 ($\sigma$1) receptor. More particularly, the present invention relates to pyrazolo[1,5-a]pyrimidine-derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved (Turk D C, Wilson H D, Cahana A. *Lancet;* 2011, 377, 2226-2235). Pain affects a big portion of the population with an estimated prevalence of 20% and its incidence, particularly in the case of chronic pain, is increasing due to the population ageing. Additionally, pain is clearly related to comorbidities, such as depression, anxiety and insomnia, which leads to important productivity losses and socio-economical burden (Goldberg D S, McGee S J, *BMC Public Health,* 2011, 11, 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al., *Pharmacol. Rev.* 2015, 67, 821-70). The VGCC are assembled through interactions of different subunits, namely $\alpha_1$ ($Ca_v\alpha_1$), $\beta$ ($Ca_v\beta$) $\alpha_2\delta$ ($Ca_v\alpha_2\delta$) and $\gamma$ ($Ca_v\gamma$). The $\alpha_1$ subunits are the key porous forming units of the channel complex, being responsible for the $Ca^{2+}$ conduction and generation of $Ca^{2+}$ influx. The $\alpha_2\delta$, $\beta$, and $\gamma$ subunits are auxiliary, although very important for the regulation of the channel, since they increase the expression of the $\alpha_1$ subunits in the plasma membrane as well as modulate their function, resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N—($Ca_v2.2$), P/Q-($Ca_v2.1$), and R—($Ca_v2.3$) types, depending on the channel forming $Ca_v\alpha$ subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo, *Neurotherapeutics* 2009, 6, 679-92; Zamponi et al., 2015 supra; Neumaier et al., *Prog. Neurobiol.* 2015, 129, 1-36). A large body of data has clearly indicated that VGCC are implicated in mediating various disease states including pain processing. Drugs interacting with the different calcium channel subtypes and subunits have been developed. Current therapeutic agents include drugs targeting L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of N-type ($Ca_v2.2$) calcium channels, has been approved as a treatment of intractable pain (Perret and Luo, 2009, supra; Vink and Alewood, *Br. J. Pharmacol.* 2012, 167, 970-89).

The $Ca_v1$ and $Ca_v2$ subfamilies contain an auxiliary $\alpha_2\delta$ subunit, which is the therapeutic target of the gabapentinoid drugs of value in certain epilepsies and chronic neuropathic pain. To date, there are four known $\alpha_2\delta$ subunits, each encoded by a unique gene and all possessing splice variants. Each $\alpha_2\delta$ protein is encoded by a single messenger RNA and is posttranslationally cleaved and then linked by disulfide bonds. Four genes encoding $\alpha_2\delta$ subunits have now been cloned. $\alpha_2\delta$-1 was initially cloned from skeletal muscle and shows a fairly ubiquitous distribution. The $\alpha_2\delta$-2 and $\alpha_2\delta$-3 subunits were subsequently cloned from brain. The most recently identified subunit, $\alpha_2\delta$-4, is largely nonneuronal. The human $\alpha_2\delta$-4 protein sequence shares 30, 32 and 61% identity with the human $\alpha_2\delta$-1, $\alpha_2\delta$-2 and $\alpha_2\delta$-3 subunits, respectively. The gene structure of all $\alpha_2\delta$ subunits is similar. All $\alpha_2\delta$ subunits show several splice variants (Davies et al., *Trends Pharmacol. Sci.* 2007, 28, 220-8; Dolphin A C, *Nat Rev Neurosci.* 2012, 13, 542-55, *Biochim. Biophys. Acta* 2013, 1828, 1541-9).

The $Ca_v\alpha_2\delta$-1 subunit may play an important role in neuropathic pain development (Perret and Luo, 2009, supra; Vink and Alewood, 2012, supra). Biochemical data have indicated a significant $Ca_v\alpha_2\delta$-1, but not $Ca_v\alpha_2\delta$-2, subunit upregulation in the spinal dorsal horn, and DRG (dorsal root ganglia) after nerve injury that correlates with neuropathic pain development. In addition, blocking axonal transport of injury-induced DRG $Ca_v\alpha_2\delta$-1 subunit to the central presynaptic terminals diminishes tactile allodynia in nerve injured animals, suggesting that elevated DRG $Ca_v\alpha_2\delta$-1 subunit contributes to neuropathic allodynia.

The $Ca_v\alpha_2\delta$-1 subunit (and the $Ca_v\alpha_2\delta$-2, but not $Ca_v\alpha_2\delta$-3 and $Ca_v\alpha_2\delta$-4, subunits) is the binding site for gabapentin which has anti-allodynic/hyperalgesic properties in patients and animal models. Because injury-induced $Ca_v\alpha_2\delta$-1 expression correlates with neuropathic pain development and maintenance, and various calcium channels are known to contribute to spinal synaptic neurotransmission and DRG neuron excitability, injury-induced $Ca_v\alpha_2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_v\alpha_2\delta$-1 subunit can block nerve injury-induced $Ca_v\alpha_2\delta$-1 upregulation and prevent the onset of allodynia and reserve established allodynia.

As mentioned above, the $\alpha_2\delta$ subunits of VGCC form the binding site for gabapentin and pregabalin, which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha_2\delta$ subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009, supra; Vink and Alewood, 2012, supra, Zamponi et al., 2015, supra).

The sigma-1 (σ1) receptor was discovered 40 years ago and initially assigned to a new subtype of the opioid family. This receptor is expressed both in the endoplasmic reticulum and in the plasma membrane and plays an important role in the regulation of intracellular calcium concentration. A signaling pathway associated with the activation of the σ1 receptor has not been described, although it is believed that it has an amplification function of activation of intracellular cascades. In this sense, the σ1 receptor regulates and modulates the activity of numerous voltage-dependent ion channels, including Ca2+−, K+−, Na+, Cl−, SK, and NMDA channels and the IP3 receptor.

It is also known that the σ1 receptor is linked to analgesia, since σ1 receptor agonists counteract opioid receptor mediated analgesia, while σ1 receptor antagonists, such as haloperidol, potentiated it (Chien C C, Pasternak G W. *Neurosci. Lett.* 1995, 190, 137-9).

Many additional preclinical evidences have indicated a clear role of the σ1 receptor in the treatment of pain (Zamanillo D, Romero L, Merlos M, Vela J M. *Eur. J. Pharmacol.,* 2013, 716, 78-93). The development of the σ1 receptor knockout mice, which show no obvious phenotype and perceive normally sensory stimuli, was a key milestone in this endeavour. In physiological conditions the responses of the σ1 receptor knockout mice to mechanical and thermal stimuli were found to be undistinguishable from WT ones but they were shown to possess a much higher resistance to develop pain behaviours than WT mice when hypersensitivity entered into play. Hence, in the σ1 receptor knockout mice, capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of σ1 receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that σ1 receptor antagonism relieves neuropathic pain and also address some of the comorbidities (i.e., anhedonia, a core symptom in depression) related to pain states (Romero et al. *Br J Pharmacol.* 2012, 166, 2289-306).

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al., *Nat. Biotechnol.* 2009, 27, 659-666).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al., *Lancet Neurol.* 2013, 12, 1084-95). In fact, positive synergistic interaction for several compounds, including analgesics, has been described (Schroder et al., *J. Pharmacol. Exp Ther.* 2011, 337, 312-20. Erratum in: *J. Pharmacol. Exp. Ther.* 2012, 342, 232; Zhang et al., *Cell Death Dis.* 2014, 5:e1138; Gilron et al., 2013, supra).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins et al, *Nat. Chem. Biol.* 2008, 4, 682-90).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008, supra).

As described above, the σ1 receptor, as well as the α2δ1 subunit, modulate intracellular calcium concentration and the activity of voltage-dependent calcium channels. There is also robust clinical and pre-clinical evidence linking both targets with the treatment of chronic neuropathic pain. Thus, the present application, also relates to the advantages of having dual activity, for the $\alpha_2\delta$-1 subunit of voltage-gated calcium channels and the σ1 receptor, in the same molecule to treat chronic pain.

Pain is multimodal in nature, since in nearly all pain states several mediators, signaling pathways and molecular mechanisms are implicated. Consequently, monomodal therapies can be complemented with a dual mechanism of action to provide complete pain relief. Currently, combining existing therapies is a common clinical practice and many efforts are directed to assess the best combination of available drugs in clinical studies (Mao J, Gold M S, Backonja M. *J. Pain,* 2011, 12, 157-166).

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

The authors of the present invention, have found a series of compounds that show a primary pharmacological activity towards the $\alpha_2\delta$ subunit, in particular the $\alpha_2\delta$-1 subunit, of the voltage-gated calcium channel, or compounds that show dual pharmacological activity towards both the $\alpha_2\delta$ subunit, in particular the $\alpha_2\delta$-1 subunit, of the voltage-gated calcium channel and the $\sigma$1 receptor resulting in an innovative, effective, complementary and alternative solution for the treatment of pain.

In view of the existing results of the currently available therapies and clinical practices, the present invention offers a solution by combining in a single compound binding to two different targets relevant for the treatment of pain. This was mainly achieved by providing the compounds according to the invention that bind to both the $\sigma$1 receptor and the $\alpha_2\delta$ subunit, in particular the $\alpha_2\delta$-1 subunit, of the voltage-gated calcium channel.

Document WO 2018154133 discloses [1,2,4]Triazolo[1,5-a]pyrimidinyl derivatives substituted with piperidine, morpholine or piperazine as O-GlcNAc hydrolase inhibitors useful for the treatment Alzheimer but is silent on dual activity for the treatment of pain.

SUMMARY OF THE INVENTION

In this invention a family of structurally distinct pyrazolo[1,5-a]pyrimidine derivatives, encompassed by formula (I), which have a pharmacological activity towards both the $\alpha_2\delta$ subunit, in particular the $\alpha_2\delta$-1 subunit, of the voltage-gated calcium channel and the $\sigma$1 receptor, were identified thus solving the above problem of identifying alternative or improved pain treatments by offering such compounds.

The main object of the invention is directed to a compound having a dual activity binding to the $\alpha_2\delta$ subunit, in particular the $\alpha_2\delta$-1 subunit, of the voltage-gated calcium channel and the $\sigma$1 receptor for use in the treatment of pain.

The invention is directed in a main aspect to a compound of general Formula (I), (I)

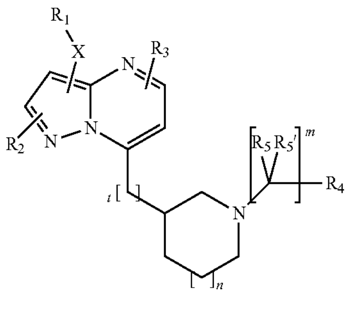

wherein $R_1$, $R_2$, $R_3$, $R_4$, $R_5$, $R_5$', X, m, n and t are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct pyrazolo[1,5-a]pyrimidine derivatives, which have dual pharmacological activity towards both the $\alpha_2\delta$ subunit, in particular the $\alpha_2\delta$-1 subunit, of the voltage-gated calcium channel and the $\sigma_1$ receptor.

The invention is directed to compounds having a dual activity binding to the $\alpha_2\delta$ subunit, in particular the $\alpha_2\delta$-1 subunit, of the voltage-gated calcium channel and the $\sigma_1$ receptor for use in the treatment of pain and related disorders.

As this invention is aimed at providing a compound or a chemically related series of compounds which act as dual ligands of the $\alpha_2\delta$ subunit, in particular the $\alpha_2\delta$-1 subunit, of the voltage-gated calcium channel and the $\sigma_1$ receptor it is a preferred embodiment if the compound has a binding expressed as $K_i$ responding to the following scales:

$K_i(\sigma_1)$ is preferably <1000 nM, more preferably <500 nM, even more preferably <100 nM.

$K_i(\alpha_2\delta-1)$ is preferably <10000 nM, more preferably <5000 nM, even more preferably <500 nM or even more preferably <100 nM.

Preferably, when $K_i$ $(\sigma_1)$>1000 nM, the following scale has been adopted for representing the binding to the $\sigma$1-receptor:

$K_i$ $(\sigma_1)$>1000 nM or inhibition ranges between 1% and 50%.

Preferably, when $K_i(\alpha_2\delta$-1)>5000 nM, the following scale has been adopted for representing the binding to the $\alpha_2\delta$-1 subunit of voltage-gated calcium channels:

+$K_i(\alpha_2\delta$-1)>5000 nM or inhibition ranges between 1% and 50%

The applicant has surprisingly found that the problem of providing a new effective and alternative solution for treating pain and pain related disorders can be solved by using an analgesic approach combining two activities in a single drug (i.e., dual ligands which are bifunctional and bind to $\sigma$1 receptor and to $\alpha_2\delta$ subunit, in particular the $\alpha_2\delta$-1 subunit, of the voltage-gated calcium channel).

As described above, the $\sigma$1 receptor as well as the $\alpha_2\delta$1 subunit, modulate intracellular calcium concentration and the activity of voltage-dependent calcium channels. There is also a robust clinical and pre-clinical evidence linking both targets with the treatment of chronic neuropathic pain. Thus, the present invention, also relates to the advantages of having dual activity, for the $\alpha_2\delta$-1 subunit of voltage-gated calcium channels and the $\sigma$1 receptor, in the same molecule to treat pain, i.e. binding to two different targets relevant for the treatment of pain.

A dual compound that possess binding to both the $\sigma_1$ receptor and to the $\alpha_2\delta$ subunit of the voltage-gated calcium channel shows a highly valuable therapeutic potential by achieving an outstanding analgesia.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies.

It has to be noted, though, that functionalities "antagonism" and "agonism" are also subdivided in their effect into subfunctionalities like partial agonism or inverse agonism. Accordingly, the functionalities of the compounds should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

In its broader aspect, the present invention is directed to compounds of general Formula (I):

(I)

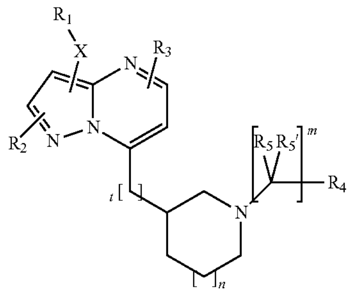

wherein m is 1, 2, 3 or 4;

n is 1 or 2;

t is 0 or 1;

X is selected from the group consisting of a bond, $-[CH_2]_p-$, $-[CH_2]_pNR_x[CH_2]_q-$, $-[CH_2]_pO[CH_2]_q-$, $-[CH_2]_pNR_xC(O)[CH_2]_q-$ and $-[CH_2]_pNR_xCH(CH_3)-$;

wherein p is 0, 1, 2, 3 or 4;

q is 0, 1, 2, 3 or 4;

$R_x$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, $-OR_6$, $-NR_6R_6'$, $-CN$, cycloalkyl, aryl and heterocyclyl;

$R_6$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

$R_6'$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

alternatively $R_6$ and $R_6'$, taken together with the nitrogen atom to which they are attached, form a substituted or unsubstituted heterocyclyl;

$R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and $-OR_7$;

$R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

$R_3$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy and $-OR_8$;

$R_8$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_5$ and $R_5'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl and haloalkoxy;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

Note that "or a corresponding salt thereof" does also mean "or a corresponding pharmaceutically acceptable salt thereof". This does apply to all below described embodiments and uses of "salt" being thus equivalent to "pharmaceutically acceptable salt".

In a particular embodiment, the following compound is excluded:

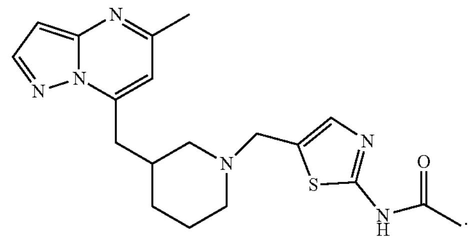 [SMILES: CC(=O)Nc1ncc(CN2CCCC(Cc3cc(C)nc4ccnn34)C2)s1]

In a particular embodiment, the heterocyclcyl in $R_4$ is not thiazole.

In a particular embodiment, the heterocyclcyl in $R_4$ is a heterocyclyl containing no sulfur atom.

In a particular embodiment, the heterocyclcyl in $R_4$ is a monocyclic heterocyclyl containing no sulfur atom.

In a particular embodiment, the heterocyclyl in $R_4$ is a monocyclic heterocyclyl selected from the group consisting of oxazepan, pyrrolidine, imidazole, oxadiazole, tetrazole, azetidine, pyridine, pyrimidine, piperidine, piperazine, isothiazole, tetrahydropyran, tetrahydrofuran, morpholine, thiomorpholine, furan, triazole, isoxazole, pyrazole, thiophene, pyrrole, pyrazine, oxopyrrolidine and pyrimidine.

In a particular embodiment, $R_1$ is selected from the group consisting of substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, $—OR_6$, $—NR_6R_6'$, —CN, cycloalkyl, aryl and heterocyclyl;

In a particular embodiment, $R_2$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and $—OR_7$;

In a further embodiment the compound according to the invention is a compound of general Formula (I)

(I)

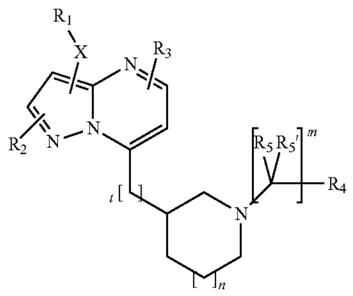

wherein m is 1, 2, 3 or 4;

n is 1 or 2;

t is 0 or 1;

X is selected from the group consisting of a bond, $—[CH_2]_p—$, $—[CH_2]_pNR_x[CH_2]_q—$, $—[CH_2]_pO[CH_2]_q—$, $—[CH_2]_pNR_xC(O)[CH_2]_q—$ and $—[CH_2]_pNR_xCH(CH_3)—$;

wherein p is 0, 1, 2, 3 or 4;

q is 0, 1, 2, 3 or 4;

$R_x$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

wherein the alkyl, alkenyl or alkynyl in $R_x$, if substituted, is substituted with one or more substituent/s selected from halogen, —CN, haloalkyl and haloalkoxy;

$R_1$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, $—OR_6$, $—NR_6R_6'$, —CN, cycloalkyl, aryl and heterocyclyl;

$R_6$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

$R_6'$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

alternatively $R_6$ and $R_6'$, taken together with the nitrogen atom to which they are attached, form a substituted or unsubstituted heterocyclyl;

wherein the alkyl, alkenyl or alkynyl in $R_1$, if substituted, is substituted with one or more substituent/s selected from $—OR_{11}$, halogen, —CN, haloalkyl, haloalkoxy and $—NR_{11}R_{11}'$;

wherein said cycloalkyl, aryl or heterocyclyl in $R_1$, if substituted, is substituted with one or more substituent/s selected from halogen, $—R_{11}$, $—[CH_2]_rOR_{11}$, =O, $—NO_2$, $—[CH_2]_rNR_{11}R_{11}'$, $—NR_{11}C(O)R_{11}'$, $—NR_{11}S(O)_2R_{11}'$, $—S(O)_2NR_{11}R_{11}'$, $—NR_{11}C(O)NR_{11}'R_{11}''$, $—SR_{11}$, $—S(O)R_{11}$, $—S(O)_2R_{11}$, —CN, haloalkyl, haloalkoxy, $—C(O)R_{11}$, $—C(O)OR_{11}$, $—C(O)NR_{11}R_{11}'$, $—OCH_2CH_2OR_{11}$, $—NR_{11}S(O)_2NR_{11}'R_{11}''$ and $—C(CH_3)_2OR_{11}$;

wherein $R_{11}$, $R_{11}'$ and $R_{11}''$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

$R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and $—OR_7$;

$R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

wherein the alkyl, alkenyl or alkynyl in $R_2$, if substituted, is substituted with one or more substituent/s selected from $—OR_{21}$, halogen, —CN, haloalkyl, haloalkoxy and $—NR_{21}R_{21}'$;

wherein said cycloalkyl in $R_2$, also in alkylcycloalkyl, if substituted, is substituted with one or more substituent/s selected from halogen, $—R_{21}$, $—[CH_2]_rOR_{21}$, =O, $—NO_2$, $—[CH_2]_rNR_{21}R_{21}'$, $—NR_{21}C(O)R_{21}'$, $—NR_{21}S(O)_2R_{21}'$, $—S(O)_2NR_{21}R_{21}'$, $—NR_{21}C(O)NR_{21}'R_{21}''$, $—SR_{21}$, $—S(O)R_{21}$, $—S(O)_2R_{21}$, —CN, haloalkyl, haloalkoxy, $—C(O)R_{21}$, $—C(O)OR_{21}$, $—C(O)NR_{21}R_{21}'$, $—OCH_2CH_2OR_{21}$, $—NR_{21}S(O)_2NR_{21}'R_{21}''$ and $—C(CH_3)_2OR_{21}$;

wherein $R_{21}$ and $R_{21}'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_3$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy and $—OR_8$;

$R_8$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

wherein the alkyl, alkenyl or alkynyl in $R_3$, if substituted, is substituted with one or more substituent/s selected from —$OR_{31}$, halogen, —CN, haloalkyl, haloalkoxy and —$NR_{31}R_{31}'$;

wherein $R_{31}$ and $R_{31}'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

wherein the alkyl, alkenyl or alkynyl in $R_4$, if substituted, is substituted with one or more substituent/s selected from —$OR_{41}$, halogen, —CN, haloalkyl, haloalkoxy, —$NR_{41}R_{41}'$;

wherein said cycloalkyl, aryl or heterocyclyl in $R_4$, if substituted, is substituted with one or more substituent/s selected from halogen, —$R_{41}$, —$[CH_2]_rOR_{41}$, =O, —$NO_2$, —$[CH_2]_rNR_{41}R_{41}'$, —$NR_{41}C(O)R_{41}'$, —$NR_{41}S(O)_2R_{41}'$, —$S(O)_2NR_{41}R_{41}'$, —$NR_{41}C(O)NR_{41}'R_{41}''$, —$SR_{41}$, —$S(O)R_{41}$, —$S(O)_2R_{41}$, —CN, haloalkyl, haloalkoxy, —$C(O)R_{41}$, —$C(O)OR_{41}$, —$C(O)NR_{41}R_{41}'$, —$OCH_2CH_2OR_{41}$, —$NR_{41}S(O)_2NR_{41}'R_{41}''$ and —$C(CH_3)_2OR_{41}$;

wherein $R_{41}$, $R_{41}'$ and $R_{41}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_5$ and $R_5'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl and haloalkoxy;

wherein the alkyl, alkenyl or alkynyl in $R_5$ and $R_5'$, if substituted, is substituted with one or more substituent/s selected from —$OR_{51}$, halogen, —CN, haloalkyl, haloalkoxy, —$NR_{51}R_{51}'$;

wherein $R_{51}$ and $R_{51}'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

the alkyl, alkenyl or alkynyl, if substituted, and not defined otherwise, is substituted with one or more substituent/s selected from —$OR_{13}$, halogen, —CN, haloalkyl, haloalkoxy and —$NR_{13}R_{13}'$;

wherein $R_{13}$ and $R_{13}'$ are independently selected from hydrogen, unsubstituted $C_{1-6}$ alkyl, unsubstituted $C_{2-6}$ alkenyl and unsubstituted $C_{2-6}$ alkynyl;

the aryl, heterocyclyl or cycloalkyl, also in alkylcycloalkyl, alkylaryl and alkylheterocyclyl, if substituted, and not defined otherwise, is substituted with one or more substituent/s selected from halogen, —$R_{14}$, —$[CH_2]_rOR_{14}$, =O, —$NO_2$, —$[CH_2]_rNR_{14}R_{14}'$, —$NR_{14}C(O)R_{14}'$, —$NR_{14}S(O)_2R_{14}'$, —$S(O)_2NR_{14}R_{14}'$, —$NR_{14}C(O)NR_{14}'R_{14}''$, —$SR_{14}$, —$S(O)R_{14}$, $S(O)_2R_{14}$, —CN, haloalkyl, haloalkoxy, —$C(O)R_{14}$, —$C(O)OR_{14}$, —$C(O)NR_{14}R_{14}'$, —$OCH_2CH_2OR_{14}$, —$NR_{14}S(O)_2NR_{14}'R_{14}''$ and —$C(CH_3)_2OR_{14}$;

wherein $R_{14}$, $R_{14}'$ and $R_{14}''$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

wherein r is 0, 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula (I)

(I')

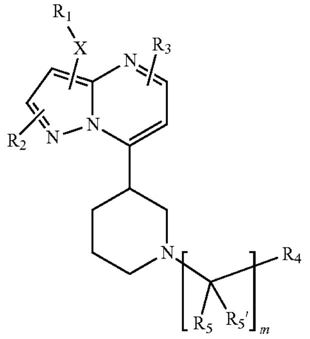

wherein $R_1$, $R_2$, $R_3$, $R_4$, $R_5$, $R_5'$, X and m, are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula ($I^{2}$')

($I^{2}$')

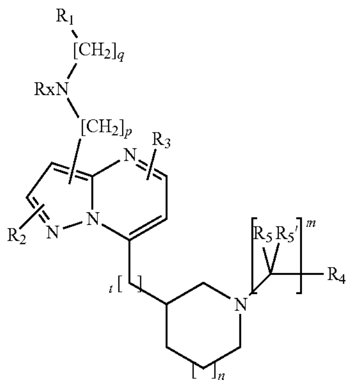

wherein $R_1$, $R_2$, $R_3$, $R_4$, $R_5$, $R_5'$, $R_x$, m, n, t, p and q are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula ($I^{2'}$)

($I^{2a'}$)

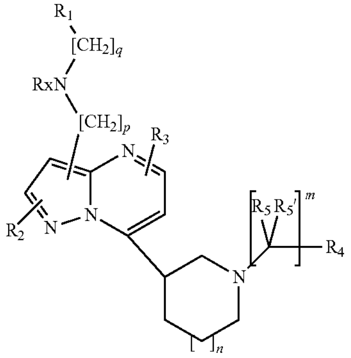

wherein $R_1$, $R_2$, $R_3$, $R_4$, $R_5$, $R_5'$, $R_x$, m, n, p and q are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula ($I^{3'}$)

($I^{3'}$)

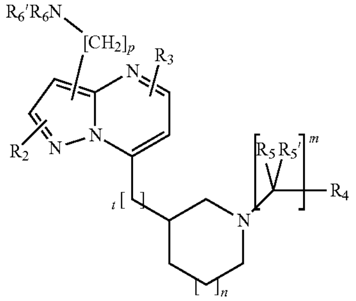

wherein $R_1$, $R_2$, $R_3$, $R_4$, $R_5$, $R_5'$, $R_6$, $R_{6'}$, m, n, t and p are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula ($I^{3'}$)

($I^{3a'}$)

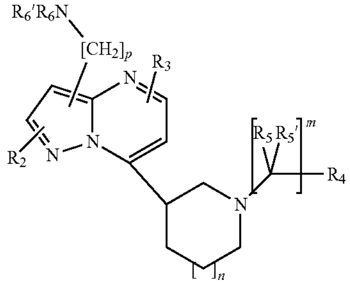

wherein $R_1$, $R_2$, $R_3$, $R_4$, $R_5$, $R_5'$, $R_6$, $R_{6'}$, m, n, and p are as defined below in the detailed description;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

For clarity purposes, all groups and definitions described in the present description and referring to compounds of general Formula (I), also apply to compounds of general Markush Formulae (I'), ($I^{2'}$), ($I^{2a'}$), ($I^{3'}$) or ($I^{3a'}$) (where applicable), and to all intermediate of synthesis, when those groups are present in the mentioned general Markush formulae, since compounds of general Markush Formulae (I'), ($I^{2'}$), ($I^{2a'}$), ($I^{3'}$) or ($I^{3a'}$) are included within the scope of the larger definition of general Markush Formula (I).

For clarity purposes, the expression e.g. "the cycle in $R_8$-$R_8$'", means the cycle resulting when $R_8$ and $R_8$' form a cycle together with the atom(s) to which they are attached. This cycle can then be substituted or not. This definition is also generally applicable and can be also applied as a definition of any other cycle (preferably cycloalkyls, heterocyclyls or aryls) formed from two different functional groups like e.g. "the cycle in $R_i$—$R_{i'}$" means the cycle resulting when $R_i$ and $R_i$' form a cycle together with the atom(s) to which they are attached. This cycle can then be substituted or not.

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_1$-s-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$ alkyl like methyl, ethyl, propyl, butyl, pentyl, hexyl, heptyl, or octyl; preferably is $C_{1-6}$ alkyl like methyl, ethyl, propyl, butyl, pentyl, or hexyl; more preferably is $C_{1-4}$ alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylene.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —$NR_kR_{k'}$, —$SR_k$, —$S(O)R_k$, —$S(O)_2R_k$, —$OR_k$, —$C(O)R_k$, —$C(O)OR_k$, —CN, —$C(O)NR_kR_{k'}$, haloalkyl, haloalkoxy, being $R_k$ represented by $R_{11}$, $R_{13}$, $R_{21}$, $R_{31}$, $R_{41}$ or $R_{51}$ (being $R_{k'}$ represented by $R_{11}'$, $R_{13}'$, $R_{21}'$, $R_{31}'$, $R_{41}'$ or $R_{51}'$), wherein $R_1$ to $R_{51}'$ are as defined in the description, and wherein when different radicals $R_1$ to $R_{51}'$ or when m, n, t or rare present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted with one or more of halogen (F, Cl, Br, I), —$NR_kR_{k'}$, —$OR_k$, —CN, —$SR_k$, haloalkyl, haloalkoxy, being $R_k$ represented by $R_{11}$, $R_{13}$, $R_{21}$, $R_{31}$, $R_{41}$ or $R_{51}$ (being $R_{k'}$ represented by $R_{11}'$, $R_{13}'$, $R_{21}'$, $R_{31}'$, $R_{41}'$ or $R_{51}'$), wherein wherein $R_1$ to $R_{51}'$ are as defined in the description, and wherein when different radicals $R_1$ to $R_{51}'$ or when m, n, t or rare present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkoxy is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, C3-s-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-3}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl. Preferably in the context of this invention cycloalkyl is $C_{3-8}$ cycloalkyl like cyclopropyl, cyclobutyl, cyclopentyl, cyclohexyl, cycloheptyl, or cyclooctyl; or is $C_{3-7}$ cycloalkyl like cyclopropyl, cyclobutyl, cyclopentyl, cyclohexyl, or cycloheptyl; or is $C_{3-6}$ cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphthyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms selected from the group consisting of nitrogen, oxygen and/or sulfur in the ring. A heterocyclic group can also be substituted once or several times.

Subgroups inside the heterocyclyls as understood herein include heteroaryls and non-aromatic heterocyclyls.

- the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms selected from the group consisting of nitrogen, oxygen and/or sulfur in the ring; preferably is a 5 to 18 membered mono or polycyclic aromatic heterocyclic ring system of one or two rings of which at least one aromatic ring contains one or more heteroatoms selected from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;
- the non-aromatic heterocyclyl is a 5 to 18 membered mono or polycyclic heterocyclic ring system of one or more rings of which at least one ring—with this (or these) ring(s) then not being aromatic—contains one or more heteroatoms selected from the group consisting of nitrogen, oxygen and/or sulfur in the ring; preferably is a 5 to 18 membered mono or polycyclic heterocyclic ring system of one or two rings of which one or both rings—with this one or two rings then not being aromatic—contain/s one or more heteroatoms selected from the group consisting of nitrogen, oxygen and/or sulfur in the ring, more preferably is selected from oxazepane, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms selected from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms selected from the group consisting of nitrogen, oxygen and/or sulfur in the ring.

Preferred examples of heterocyclyls include oxazepane, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, tetrahydroisoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyran, pyrazole, imidazole, piperidine, thiophene, indole, benzimidazole, pyrrolo[2,3b]pyridine, benzoxazole, oxopyrrolidine, pyrimidine, oxazepane, azetidine and pyrrolidine.

In the context of this invention oxopyrrolidine is understood as meaning pyrrolidin-2-one.

An N-containing heterocyclyl is a heterocyclic ring system of one or more saturated or unsaturated rings of which at least one ring contains a nitrogen and optionally one or more further heteroatoms selected from the group consisting of nitrogen, oxygen and/or sulfur in the ring; preferably is a heterocyclic ring system of one or two saturated or unsaturated rings of which at least one ring contains a nitrogen and optionally one or more further heteroatoms selected from the group consisting of nitrogen, oxygen and/or sulfur in the ring, more preferably is selected from oxazepane, pyrrolidine, imidazole, oxadiazole, tetrazole, azetidine, pyridine, pyrimidine, piperidine, piperazine, benzimidazole, indazole, benzothiazole, benzodiazole, morpholine, indoline, triazole, isoxazole, pyrazole, pyrrole, pyrazine, pyrrolo[2,3b]pyridine, quinoline, quinolone, isoquinoline, tetrahydrothienopyridine, phthalazine, benzo-1,2,5-thiadiazole, indole, benzotriazole, benzoxazole oxopyrrolidine, carbazole or thiazole.

In the context of this invention, a cyclic amide is defined as a subgroup of a heterocyclyl (as defined above) formed through the cyclization of a carbon sequence, containing at least the sequence

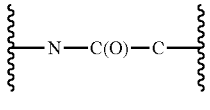

forming part of the cycle. Said cyclic amide may optionally be fused to a ring system. Preferably the cyclic amide is an "indoline-2-one". A cyclic amide may be substituted or unsubstituted as defined for heterocyclyl above.

In the context of this invention, a cyclic urea is defined as a subgroup of a heterocyclyl (as defined above) formed through the cyclization of a carbon sequence containing at least the sequence

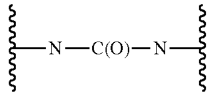

forming part of the cycle. Said cyclic urea may optionally be fused to a ring system. Preferably the cyclic urea is "1H-benzo[d]imidazol-2 (3H)-one". A cyclic urea may be substituted or unsubstituted as defined for heterocyclyl above.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 ($—CH_2—$) groups. Most preferably alkylaryl is benzyl (i.e. $—CH_2$-phenyl). More preferably, the "alkyl" in alkylaryl is an unsubstituted alkyl.

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning a heterocyclyl group (see above) being connected to another atom through 1 to 4 ($—CH_2—$) groups. Most preferably alkylheterocyclyl is $—CH_2$-pyridine. More preferably, the "alkyl" in alkylheterocyclyl is an unsubstituted alkyl.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning a cycloalkyl group (see above) being connected to another atom through 1 to 4 ($—CH_2—$) groups. Most preferably alkylcycloalkyl is $—CH_2$-cyclopropyl. More preferably, the "alkyl" in alkylcycloalkyl is an unsubstituted alkyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

An heterocyclyl is a ring system of one or more saturated and/or unsaturated rings of which at least one ring contains one or more heteroatoms selected from the group consisting of nitrogen, oxygen and/or sulfur in the ring; preferably is a ring system of one saturated and/or unsaturated ring containing one or more heteroatoms selected from the group consisting of nitrogen, oxygen and/or sulfur in the ring, or a ring system of two saturated and/or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, furan, benzofuran, benzimidazole, indazole, benzothiazole, benzodiazole, thiazole, isothiazole, tetrahydropyran, tetrahydrofuran, morpholine, thiomorpholine, indoline, triazole, isoxazole, pyrazole, thiophene, benzothiophene, pyrrole, pyrazine, pyrrolo[2,3b]pyridine, quinoline, quinolone, isoquinoline, tetrahydroisoquinoline, tetrahydrothienopyridine, phthalazine, benzo-1,2,5-thiadiazole, indole, benzotriazole, benzoxazole oxopyrrolidine, benzodioxolane, benzodioxane, carbazole, octahydro-ethanopyrrolo-pyridine, oxaspirodecane, oxadiazaspiroundecane, indoline-2-one and quinazoline.

In general, such a heterocyclyl may contain between 3 and 32 atoms in the rings (preferably 4 to 20 atoms in the rings, or most preferably 5 to 18 atoms in the rings). Thus, a heterocyclyl may contain between 3 and 12 atoms in the ring (preferably 4 to 10 atoms in the ring, or 5 to 8 atoms in the ring, or 5 to 6 atoms in the ring) in case of a heterocyclyl of one ring. Such a heterocyclyl may also contain between 5 and 22 atoms in both rings together (preferably 6 to 16 atoms in both rings together, or 7 to 12 atoms in both rings together or 8 to 10 atoms in both rings together) in case of a heterocyclyl of two rings. Such a heterocyclyl may also contain between 7 and 32 atoms in the 3 rings together (preferably 10 to 22 atoms in the three rings together, or 12 to 20 atoms in the three rings together or 10 to 18 atoms in the three rings together) in case of a heterocyclyl of three rings. Each ring of the ring system, independently of each other, can be saturated or unsaturated.

For clarity purposes, the general Markush Formula (I) is equivalent to (IZ), (IZ)

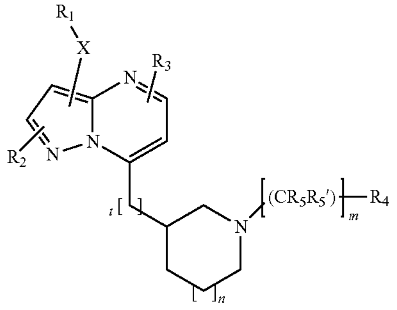

wherein only —$C(R_5R_{5'})$— is included into the brackets, and m means the number of times that —$C(R_5R_{5'})$— is repeated. The same would apply, when applicable, to general Markush Formulae (I), (I'), ($I^{2'}$), ($I^{2a'}$), ($I^{3'}$) or ($I^{3a'}$) and to all intermediates of synthesis.

In addition, and for clarity purposes, it should further be understood that naturally if t is 0, the pyrazolopyrimidine core and the piperidine ring are still present, when applicable, in general Markush Formulae (I), (I'), ($I^{2'}$), ($I^{2a'}$), ($I^{3'}$) or ($I^{3a'}$) and to all intermediates of synthesis.

For clarity purposes, reference is also made to the following statements below in the definitions of substitutions on alkyl etc. or aryl etc. that "when different radicals $R_1$ to $R_{51}$' or when m, n, t or r are present simultaneously in Formula I they may be identical or different". This statement is reflected in the below general Formula ($I^d$) being derived from and falling into general Formula (I), ($I^d$)

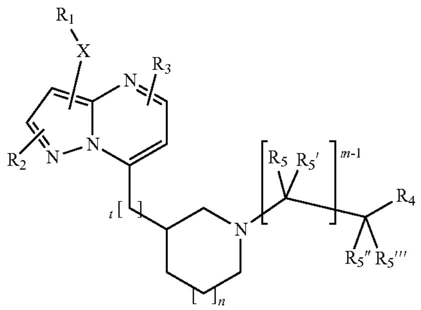

wherein $R_1$, $R_2$, $R_3$, $R_4$, $R_5$, $R_5$', X, m, n and t are as defined in the description. In addition, $R_5$'' and $R_5$''' are added. As said above, this statement is thus reflected in that $R_5$'' and $R_5$''' are or could be different from $R_5$ and $R_5$' or not.

The same would be applicable mutatis mutandis for general Formulas like general Formula (I) as well as the other general Formulas (I'), ($I^{2'}$), ($I^{2a'}$), ($I^{3'}$) or ($I^{3a'}$) and to all intermediates of synthesis.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_k$, —$OR_k$, —$[CH_2]_rOR_k$, —CN, —$NO_2$, —$NR_kR_{k'}$, —$[CH_2]_rNR_kR_{k'}$, —$C(O)OR_k$, —$C(O)R_k$, —$NR_kC(O)R_{k'}$, —$C(O)NR_kR_{k'}$, —$NR_kS(O)_2R_{k'}$, =O, —$OCH_2CH_2OH$, —$NR_kC(O)NR_kR_k$—, —$S(O)_2NR_kR_{k'}$, —$NR_kS(O)_2NR_kR_{k''}$, haloalkyl, haloalkoxy, —$SR_k$, —$S(O)R_k$, —$S(O)_2R_k$ or —$C(CH_3)OR_k$, or substituted or unsubstituted alkylcycloalkyl, substituted or unsubstituted alkylaryl, substituted or unsubstituted alkylheterocyclyl, with $R_k$, $R_{k'}$ and $R_{k''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_k$ one of $R_{11}$, $R_{14}$, $R_{21}$ or $R_{41}$, (being $R_k$' one of $R_{11}$', $R_{14}$', $R_{21}$' or $R_{41}$', being $R_k$" one of $R_{11}$", $R_{14}$", $R_{21}$" or $R_{41}$"), wherein $R_1$ to $R_{51}$' are as defined in the description, and wherein when different radicals $R_1$ to $R_{51}$' or when m, n, t or rare present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alkylaryl, alkylcycloalkyl or alkylheterocyclyl) with one or more of halogen (F, Cl, Br, I), —$R_k$, —$OR_k$, —$[CH_2]_rOR_{k'}$, —CN, —$NO_2$, —$NR_kR_{k'''}$, —$[CH_2]_rNR_kR_k$', —$C(O)R_k$, $NR_kC(O)R_{k'}$, —$NR_kS(O)_2R_{k'}$, =O, —$S(O)_2NR_kR_{k'}$, —$NR_kC(O)NR_kR_{k''}$, haloalkyl, haloalkoxy, —$SR_k$, —$S(O)R_k$ or —$S(O)_2R_k$, or substituted or unsubstituted alkylcycloalkyl, substituted or unsubstituted alkylaryl, substituted or unsubstituted alkylheterocyclyl, being $R_k$ one of $R_{11}$, $R_{14}$, $R_{21}$ or $R_{41}$, (being $R_{k'}$ one of $R_{11}$', $R_{14}$', $R_{21}$' or $R_{41}$', being $R_{k''}$ one of $R_{11}$", $R_{14}$", $R_{21}$" or $R_{41}$"), wherein $R_1$ to $R_{51}$' are as defined in the description, and wherein when different radicals $R_1$ to $R_{51}$' or when m, n, t or rare present simultaneously in Formula I they may be identical or different.

In connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl, non-aromatic heterocyclyl or non aromatic alkyl-heterocyclyl with

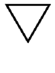

(leading to a spiro structure) and/or with =O.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl, non-aromatic heterocyclyl or non aromatic alkyl-heterocyclyl is spiro substituted or substituted with =O.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl, non-aromatic heterocyclyl or non aromatic alkyl-heterocyclyl with =O.

A ring system is an organic system consisting of at least one ring of connected atoms but including also systems in which two or more rings of connected atoms are joined with "joined" meaning that the respective rings are sharing one (like a spiro structure), two or more atoms being a member or members of both joined rings.

The term "polycyclic ring system" means that the ring system is made of two or more rings joined by sharing at least one atom.

Any compound that is a N-oxide of a compound according to the invention like a compound according to general formula I defined above is understood to be also covered by the scope of the invention.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated-especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula (I) defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well-known methods of producing a prodrug of a given acting compound are known to those skilled in the art and can be found e.g. in Krogsgaard-Larsen et al. "Textbook of Drug design and Discovery" Taylor & Francis (April 2002).

Any compound that is an N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention. This would especially also apply to the provisos described above so that any mentioning of hydrogen or any "H" in a formula would also cover deuterium or tritium.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein m is 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein p is 0, 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_x$ is selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein r is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein t is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein t is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, —$OR_6$, —$NR_6R_6'$, —CN, cycloalkyl, aryl and heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of substituted or unsubstituted $C_{1-6}$ alkyl, halogen, haloalkyl, haloalkoxy, —$OR_6$, —$NR_6R_6$', —CN, cycloalkyl, aryl and heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of substituted or unsubstituted $C_{1-6}$ alkyl, halogen, haloalkyl, —$OR_6$, —$NR_6R_6$', —CN, cycloalkyl, aryl and heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of hydrogen, substituted or unsubstituted $C_{1-6}$ alkyl, halogen, haloalkyl, haloalkoxy, —$OR_6$, —$NR_6R_6$', —CN, cycloalkyl, aryl and heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of hydrogen, substituted or unsubstituted $C_{1-6}$ alkyl, halogen, haloalkyl, —$OR_6$, —$NR_6R_6$', —CN, cycloalkyl, aryl and heterocyclyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of substituted or unsubstituted $C_{1-6}$ alkyl, substituted or unsubstituted $C_{2-6}$ alkenyl, substituted or unsubstituted $C_{2-6}$ alkynyl and haloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of halogen, haloalkoxy, —$OR_6$ and —CN;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from the group consisting of cycloalkyl, aryl and heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is —$NR_6R_6$';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from the group consisting of substituted or unsubstituted $C_{1-6}$ alkyl, substituted or unsubstituted cycloalkyl, substituted or unsubstituted alkylcycloalkyl, halogen, haloalkyl, haloalkoxy and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from the group consisting of substituted or unsubstituted $C_{1-6}$ alkyl, substituted or unsubstituted cycloalkyl, halogen and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from the group consisting of hydrogen, substituted or unsubstituted $C_{1-6}$ alkyl, substituted or unsubstituted cycloalkyl, substituted or unsubstituted alkylcycloalkyl, halogen, haloalkyl, haloalkoxy and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from the group consisting of substituted or unsubstituted $C_{1-6}$ alkyl, substituted or unsubstituted cycloalkyl, substituted or unsubstituted alkylcycloalkyl, halogen, haloalkyl, haloalkoxy and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof. In a further embodiment the compound according to the invention of general Formula (I) is a compound wherein $R_2$ is selected from the group consisting of hydrogen, substituted or unsubstituted $C_{1-6}$ alkyl, substituted or unsubstituted cycloalkyl, halogen and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_3$ is selected from the group consisting of hydrogen, substituted or unsubstituted $C_{1-6}$ alkyl, halogen, haloalkyl, haloalkoxy and —$OR_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_3$ is selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from the group consisting of substituted or unsubstituted $C_{1-6}$ alkyl, substituted or unsubstituted cycloalkyl, substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from the group consisting of substituted or unsubstituted $C_{1-6}$ alkyl, substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from the group consisting of substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from the group consisting of substituted or unsubstituted cycloalkyl, substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ is selected from the group consisting of substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_5$ and $R_5'$ are independently selected from the group consisting of hydrogen, substituted or unsubstituted $C_{1-6}$ alkyl, haloalkyl and haloalkoxy;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_5$ and $R_5'$ are independently selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_6$ is selected from the group consisting of hydrogen, substituted or unsubstituted $C_{1-6}$ alkyl, haloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_6$ is selected from the group consisting of hydrogen, substituted or unsubstituted $C_{1-6}$ alkyl, haloalkyl, substituted or unsubstituted heterocyclyl, substituted or unsubstituted alkylcycloalkyl, substituted or unsubstituted alkylaryl and substituted or unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_6$ and $R_6'$, taken together with the nitrogen atom to which they are attached, form a substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_6'$ is selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_7$ is selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_8$ is selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{11}$, $R_{11}'$ and $R_{11}''$ are independently selected from hydrogen, substituted or unsubstituted $C_{1-6}$ alkyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$, $R_{11}'$ and $R_{11}''$ are independently selected from hydrogen, substituted or unsubstituted $C_{1-6}$ alkyl, substituted or unsubstituted aryl, substituted or unsubstituted heterocyclyl and substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{11}$, $R_{11}'$ and $R_{11}''$ are independently selected from hydrogen, substituted or unsubstituted $C_{1-6}$ alkyl, substituted or unsubstituted heterocyclyl and substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{13}$ and $R_{13}'$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{14}$, $R_{14}'$ and $R_{14}''$ are independently selected from hydrogen, unsubstituted $C_{1-6}$ alkyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{14}$, $R_{14}'$ and $R_{14}''$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{21}$ and $R_{21}'$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{31}$ and $R_{31}'$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{41}$, $R_{41}'$ and $R_{41}''$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{51}$ and $R_{51}'$ are independently selected from hydrogen, substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{51}$ and $R_{51}'$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl in $R_1$, if substituted, is substituted with one or more substituent/s selected from $—OR_{11}$, halogen, —CN, haloalkyl, haloalkoxy and $—NR_{11}R_{11}'$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the cycloalkyl, aryl or heterocyclyl in $R_1$, if substituted, is substituted with one or more substituent/s selected from halogen, $—R_{11}$, $—[CH_2]_rOR_{11}$, =O, $—NO_2$, $—[CH_2]_rNR_{11}R_{11}'$, $—NR_{11}C(O)R_{11}'$, $—NR_{11}S(O)_2R_{11}'$, $—S(O)_2NR_{11}R_{11}'$, $—NR_{11}C(O)NR_{11}'R_{11}''$, $—SR_{11}$, $—S(O)R_{11}$, $—S(O)_2R_{11}$, —CN, haloalkyl, haloalkoxy, $—C(O)R_{11}$, $—C(O)OR_{11}$, $—C(O)NR_{11}R_{11}'$, $—OCH_2CH_2OR_{11}$, $—NR_{11}S(O)_2NR_{11}'R_{11}''$ and $—C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the cycloalkyl, aryl or heterocyclyl in $R_1$, if substituted, is substituted with one or more substituent/s selected from halogen, $—R_{11}$, $—[CH_2]_rOR_{11}$, =O, $—[CH_2]_rNR_{11}R_{11}'$, $—S(O)_2R_{11}$, —CN, haloalkyl, $—C(O)R_{11}$ and $—C(O)NR_{11}R_{11}'$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl in $R_2$, if substituted, is substituted with one or more substituent/s selected from $—OR_{21}$, halogen, —CN, haloalkyl, haloalkoxy and $—NR_{21}R_{21}'$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the cycloalkyl in $R_2$, also in alkylcycloalkyl, if substituted, is substituted with one or more substituent/s selected from halogen, $—R_{21}$, $—[CH_2]_rOR_{21}$, =O, $—NO_2$, $—[CH_2]_rNR_{21}R_{21}'$, $—NR_{21}C(O)R_{21}'$, $—NR_{21}S(O)_2R_{21}'$, $—S(O)_2NR_{21}R_{21}'$, $—NR_{21}C(O)NR_{21}'R_{21}''$, $—SR_{21}$, $—S(O)R_{21}$, $—S(O)_2R_{21}$, —CN, haloalkyl, haloalkoxy, $—C(O)R_{21}$, $—C(O)OR_{21}$, $—C(O)NR_{21}R_{21}'$, $—OCH_2CH_2OR_{21}$, $—NR_{21}S(O)_2NR_{21}'R_{21}''$ and $—C(CH_3)_2OR_{21}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl in $R_3$, if substituted, is substituted with one or more substituent/s selected from —$OR_{31}$, halogen, —CN, haloalkyl, haloalkoxy and —$NR_{31}R_{31}$';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl in $R_4$, if substituted, is substituted with one or more substituent/s selected from —$OR_{41}$, halogen, —CN, haloalkyl, haloalkoxy, —$NR_{41}R_{41}$';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the cycloalkyl, aryl or heterocyclyl in $R_4$, if substituted, is substituted with one or more substituent/s selected from halogen, —$R_{41}$, —$[CH_2]_rOR_{41}$, =O, —$NO_2$, —$[CH_2]_rNR_{41}R_{41}$', —$NR_{41}C(O)R_{41}$', —$NR_{41}S(O)_2R_{41}$', —$S(O)_2NR_{41}R_{41}$', —$NR_{41}C(O)NR_{41}$'$R_{41}$", —$SR_{41}$, —$S(O)R_{41}$, —$S(O)_2R_{41}$, —CN, haloalkyl, haloalkoxy, —$C(O)R_{41}$, —$C(O)OR_{41}$, —$C(O)NR_{41}R_{41}$', —$OCH_2CH_2OR_{41}$, —$NR_{41}S(O)_2NR_{41}$'$R_{41}$" and —$C(CH_3)_2OR_{41}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the cycloalkyl, aryl or heterocyclyl in $R_4$, if substituted, is substituted with one or more substituent/s selected from halogen, —$R_{41}$, —$[CH_2]_rOR_{41}$, —CN and haloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl in $R_5$ and $R_5$', if substituted, is substituted with one or more substituent/s selected from —$OR_{51}$, halogen, —CN, haloalkyl, haloalkoxy, —$NR_{51}R_{51}$';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl in $R_5$ and $R_5$', if substituted, is substituted with one or more —$OR_{51}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the alkyl, alkenyl or alkynyl, if substituted, and not defined otherwise, is substituted with one or more substituent/s selected from —$OR_{13}$, halogen, —CN, haloalkyl, haloalkoxy and —$NR_{13}R_{13}$';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the aryl, heterocyclyl or cycloalkyl, also in alkylcycloalkyl, alkylaryl and alkylheterocyclyl, if substituted, and not defined otherwise, is substituted with one or more substituent/s selected from halogen, —$R_{14}$, —$[CH_2]_rOR_{14}$, =O, —$NO_2$, —$[CH_2]_rNR_{14}R_{14}$', —$NR_{14}C(O)R_{14}$', —$NR_{14}S(O)_2R_{14}$', —$S(O)_2NR_{14}R_{14}$', —$NR_{14}C(O)NR_{14}$'$R_{14}$", —$SR_{14}$, —$S(O)R_{14}$, $S(O)_2R_{14}$, —CN, haloalkyl, haloalkoxy, —$C(O)R_{14}$, —$C(O)OR_{14}$, —$C(O)NR_{14}R_{14}$', —$OCH_2CH_2OR_{14}$, —$NR_{14}S(O)_2NR_{14}$'$R_{14}$" and —$C(CH_3)_2OR_{14}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein the aryl, heterocyclyl or cycloalkyl, also in alkylcycloalkyl, alkylaryl and alkylheterocyclyl, if substituted, and not defined otherwise, is substituted with one or more substituent/s selected from —$R_{14}$ and —$[CH_2]_rNR_{14}R_{14}$';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2, 3 or 4;

and/or n is 1 or 2;

and/or t is 0 or 1;

and/or r is 0, 1, 2 or 3;

and/or

X is selected from the group consisting of a bond, —$[CH_2]_p$—, —$[CH_2]_pNR_x[CH_2]_q$—, —$[CH_2]_pO[CH_2]_q$—, —$[CH_2]_pNR_xC(O)[CH_2]_q$— and —$[CH_2]_pNR_xCH(CH_3)$—;

and/or p is 0, 1, 2, 3 or 4;

and/or q is 0, 1, 2, 3 or 4;

and/or $R_x$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_1$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, —$OR_6$, —$NR_6R_6'$, —CN, cycloalkyl, aryl and heterocyclyl;

and/or $R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and —$OR_7$;

and/or $R_3$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy and —$OR_8$;

and/or $R_4$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

and/or $R_5$ and $R_5'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl and haloalkoxy;

and/or $R_6$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

and/or $R_6'$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_6$ and $R_6'$, taken together with the nitrogen atom to which they are attached, form a substituted or unsubstituted heterocyclyl;

and/or $R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_8$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{11}$, $R_{11}'$ and $R_{11}''$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl;

and/or $R_{13}$ and $R_{13}'$ are independently selected from hydrogen, unsubstituted $C_{1-6}$ alkyl, unsubstituted $C_{2-6}$ alkenyl and unsubstituted $C_{2-6}$ alkynyl;

and/or $R_{14}$, $R_{14}'$ and $R_{14}''$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and/or $R_{21}$ and $R_{21}'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{31}$ and $R_{31}'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{41}$, $R_{41}'$ and $R_{41}''$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and/or $R_{51}$ and $R_{51}'$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2, or 3;

and/or n is 1;

and/or t is 0 or 1;

and/or r is 0 or 1;

and/or

X is selected from the group consisting of a bond, —$[CH_2]_p$—, —$[CH_2]_pNR_x[CH_2]_q$—, —$[CH_2]_pO[CH_2]_q$—, —$[CH_2]_pNR_xC(O)[CH_2]_q$— and —$[CH_2]_pNR_xCH(CH_3)$—;

and/or p is 0, 1, 2 or 3;

and/or q is 0, 1, 2, 3 or 4;

and/or $R_x$ is selected from the group consisting of hydrogen and substituted or unsubstituted $C_{1-6}$ alkyl;

and/or $R_1$ is selected from the group consisting of hydrogen, substituted or unsubstituted $C_{1-6}$ alkyl, halogen, haloalkyl, —$OR_6$, —$NR_6R_6'$, —CN, cycloalkyl, aryl and heterocyclyl;

and/or $R_2$ is selected from the group consisting of hydrogen, substituted or unsubstituted $C_{1-6}$ alkyl, substituted or unsubstituted cycloalkyl, halogen and —$OR_7$;

and/or $R_3$ is selected from the group consisting of hydrogen and substituted or unsubstituted $C_{1-6}$ alkyl;

and/or $R_4$ is selected from the group consisting of substituted or unsubstituted $C_{1-6}$ alkyl, substituted or unsubstituted aryl and substituted or unsubstituted heterocyclyl;

and/or $R_5$ and $R_5'$ are independently selected from the group consisting of hydrogen and substituted or unsubstituted $C_{1-6}$ alkyl;

and/or $R_6$ is selected from the group consisting of hydrogen, substituted or unsubstituted $C_{1-6}$ alkyl, haloalkyl, substituted or unsubstituted heterocyclyl, substituted or unsubstituted alkylcycloalkyl, substituted or unsubstituted alkylaryl and substituted or unsubstituted alkylheterocyclyl;

and/or $R_6'$ is selected from the group consisting of hydrogen and substituted or unsubstituted $C_{1-6}$ alkyl;

and/or $R_6$ and $R_6'$, taken together with the nitrogen atom to which they are attached, form a substituted or unsubstituted heterocyclyl;

and/or $R_7$ is selected from the group consisting of hydrogen and substituted or unsubstituted $C_{1-6}$ alkyl;

and/or $R_{11}$, $R_{11}'$ and $R_{11}''$ are independently selected from hydrogen, substituted or unsubstituted $C_{1-6}$ alkyl, substituted or unsubstituted aryl, substituted or unsubstituted heterocyclyl and substituted or unsubstituted alkylcycloalkyl;

and/or $R_{13}$ and $R_{13}'$ are independently selected from hydrogen and unsubstituted $C_{1-6}$ alkyl;

and/or $R_{14}$, $R_{14}'$ and $R_{14}''$ are independently selected from hydrogen and unsubstituted $C_{1-6}$ alkyl;

and/or $R_{41}$, $R_{41}'$ and $R_{41}''$ are independently selected from hydrogen and substituted or unsubstituted $C_{1-6}$ alkyl;

and/or $R_{51}$ and $R_{51}'$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention, The alkyl in haloalkyl or haloalkoxy is $C_{1-6}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl, ethyl, isopropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, furan, benzofuran, benzimidazole, indazole, benzothiazole, benzodiazole, thiazole, isothiazole, tetrahydropyran, tetrahydrofuran, morpholine, thiomorpholine, indoline, triazole, isoxazole, pyrazole, thiophene, benzothiophene, pyrrole, pyrazine, pyrrolo[2,3b]pyridine, quinoline, quinolone, isoquinoline, tetrahydroisoquinoline, tetrahydrothienopyridine, phthalazine, benzo-1,2,5-thiadiazole, indole, benzotriazole, benzoxazole oxopyrrolidine, benzodioxolane, benzodioxane, carbazole, octahydro-ethanopyrrolo-pyridine, oxaspirodecane, oxadiazaspiroundecane, indoline-2-one and quinazoline; preferably the heterocyclyl is pyridine, piperidine, pyrrolidine, piperazine, pyrazole, pyrimidine, isoxazole, isothiazole, imidazole, morpholine, thiomorpholine, tetrahydropyran, tetrahydrofuran and thiophene;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention, The alkyl in alkylcycloalkyl, haloalkyl or haloalkoxy is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, The alkyl in haloalkyl or haloalkoxy is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl; and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl, ethyl, isopropyl or isobutyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-6}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, furan, benzofuran, benzimidazole, indazole, benzothiazole, benzodiazole, thiazole, isothiazole, tetrahydropyran, tetrahydrofuran, morpholine, thiomorpholine, indoline, triazole, isoxazole, pyrazole, thiophene, benzothiophene, pyrrole, pyrazine, pyrrolo[2,3b]pyridine, quinoline, quinolone, isoquinoline, tetrahydroisoquinoline, tetrahydrothienopyridine, phthalazine, benzo-1,2,5-thiadiazole, indole, benzotriazole, benzoxazole oxopyrrolidine, benzodioxolane, benzodioxane, carbazole, octahydro-ethanopyrrolo-pyridine, oxaspirodecane, oxadiazaspiroundecane, indoline-2-one and quinazoline; preferably the heterocyclyl is tetrahydropyran or pyridine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_5'$ as defined in any of the embodiments of the present invention, the alkyl in haloalkyl or haloalkoxy is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_6$' as defined in any of the embodiments of the present invention, the alkyl in alkylaryl, alkylheterocyclyl, alkylcycloalkyl, haloalkyl or haloalkoxy is $C_{1-6}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl, ethyl or isopropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, furan, benzofuran, benzimidazole, indazole, benzothiazole, benzodiazole, thiazole, isothiazole, tetrahydropyran, tetrahydrofuran, morpholine, thiomorpholine, indoline, triazole, isoxazole, pyrazole, thiophene, benzothiophene, pyrrole, pyrazine, pyrrolo [2,3b]pyridine, quinoline, quinolone, isoquinoline, tetrahydroisoquinoline, tetrahydrothienopyridine, phthalazine, benzo-1,2,5-thiadiazole, indole, benzotriazole, benzoxazole oxopyrrolidine, benzodioxolane, benzodioxane, carbazole, octahydro-ethanopyrrolo-pyridine, oxaspirodecane, oxadiazaspiroundecane, indoline-2-one and quinazoline; preferably the heterocyclyl is piperidine, tetrahydropyran, morpholine, thiomorpholine, pyrrolidine or piperazine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11}$' and $R_{11}$" as defined in any of the embodiments of the present invention, the alkyl in alkylaryl, alkylheterocyclyl, alkylcycloalkyl, haloalkyl or haloalkoxy is $C_{1-6}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl; more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, furan, benzofuran, benzimidazole, indazole, benzothiazole, benzodiazole, thiazole, isothiazole, tetrahydropyran, tetrahydrofuran, morpholine, thiomorpholine, indoline, triazole, isoxazole, pyrazole, thiophene, benzothiophene, pyrrole, pyrazine, pyrrolo[2,3b]pyridine, quinoline, quinolone, isoquinoline, tetrahydroisoquinoline, tetrahydrothienopyridine, phthalazine, benzo-1,2,5-thiadiazole, indole, benzotriazole, benzoxazole oxopyrrolidine, benzodioxolane, benzodioxane, carbazole, octahydro-ethanopyrrolo-pyridine, oxaspirodecane, oxadiazaspiroundecane, indoline-2-one and quinazoline; preferably the heterocyclyl is triazole, oxadiazole or pyridine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13}'$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14}'$ and $R_{14}''$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, furan, benzofuran, benzimidazole, indazole, benzothiazole, benzodiazole, thiazole, isothiazole, tetrahydropyran, tetrahydrofuran, morpholine, thiomorpholine, indoline, triazole, isoxazole, pyrazole, thiophene, benzothiophene, pyrrole, pyrazine, pyrrolo[2,3b]pyridine, quinoline, quinolone, isoquinoline, tetrahydroisoquinoline, tetrahydrothienopyridine, phthalazine, benzo-1,2,5-thiadiazole, indole, benzotriazole, benzoxazole oxopyrrolidine, benzodioxolane, benzodioxane, carbazole, octahydro-ethanopyrrolo-pyridine, oxaspirodecane, oxadiazaspiroundecane, indoline-2-one and quinazoline, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{21}$, $R_{21}'$ and $R_{21}''$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{31}$, $R_{31}'$ and $R_{31}''$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{41}$, $R_{41}'$ and $R_{41}''$ as defined in any of the embodiments of the present invention, the $C_{1-6}$ alkyl is preferably selected from methyl, ethyl, propyl, butyl, pentyl, hexyl, isopropyl, or 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{51}$ and $R_{51}'$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2, 3 or 4; preferably m is 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein n is 1 or 2; preferably n is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein t is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein r is 0, 1, 2 or 3; preferably r is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from the group consisting of a bond, $—[CH_2]_p—$, $—[CH_2]_pNR_x[CH_2]_q—$, $—[CH_2]_pO[CH_2]_q—$, $—[CH_2]_pNR_xC(O)[CH_2]_q—$ and $—[CH_2]_pNR_xCH(CH_3)—$; preferably X is selected from the group consisting of a bond, $—CH_2—$, $—CH_2CH_2—$, $—CH_2CH_2CH_2—$, $—CH_2O—$, $—CH_2OCH_2—$, $—NHC(O)CH_2—$, $—NHCH_2CH_2—$, $—CH_2NHCH_2—$, $—CH_2NH(CH_2)_2—$, $—CH_2NH(CH_2)_3—$, $—CH_2NH(CH_2)_4—$, $—CH_2N$(methyl)$CH_2—$, $—CH_2N(iPr)CH_2—$, $—CH_2N(CH_2CF_3)CH_2—$, $—CH_2NHCH$(methyl)-, $—CH_2N$(methyl)$CH_2CH_2—$, —N(methyl)-, —N(methyl)$CH_2—$, —N(methyl)$CH_2CH_2—$ and $—CH_2N$(isopropyl)$CH_2—$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 0, 1, 2, 3 or 4; preferably p is 0, 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein q is 0, 1, 2, 3 or 4;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_x$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_x$ is selected from the group consisting of hydrogen and substituted or unsubstituted $C_{1-6}$ alkyl; more preferably $R_x$ is hydrogen or a substituted or unsubstituted group selected from methyl, ethyl, isopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_1$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, —$OR_6$, —$NR_6R_6'$, —CN, cycloalkyl, aryl and heterocyclyl; preferably, $R_1$ is selected from the group consisting of hydrogen, substituted or unsubstituted $C_{1-6}$ alkyl, halogen, haloalkyl, —$OR_6$, —$NR_6R_6'$, —CN, cycloalkyl, aryl and heterocyclyl; more preferably $R_1$ is hydrogen, bromine, chlorine, —CN or a substituted or unsubstituted group selected from methyl, ethyl, isopropyl, —$CF_3$, —OH, methoxy, —O— isopropyl, —$NH_2$, —$NHCH_3$, —$N(CH_3)_2$, —$N(CH_3)(CH_2$-cyclopropyl), —$N(CH_3)$(benzyl), —$N(CH_3)$(piperidine), —$N(CH_2CF_3)(CH_2$-tetrahydropyran), cyclopropyl, phenyl, pyridine, piperidine, pyrrolidine, piperazine, pyrimidine, pyrazole, isoxazole, isothiazole, imidazole, morpholine, thiomorpholine, tetrahydropyran, tetrahydrofuran and thiophene;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and —$OR_7$; preferably $R_2$ is selected from the group consisting of hydrogen, substituted or unsubstituted $C_{1-6}$ alkyl, substituted or unsubstituted cycloalkyl, substituted or unsubstituted alkylcycloalkyl, halogen, haloalkyl, haloalkoxy and —$OR_7$; more preferably $R_2$ is selected from the group consisting of hydrogen, substituted or unsubstituted $C_{1-6}$ alkyl, substituted or unsubstituted cycloalkyl, halogen and —$OR_7$; even more preferably $R_2$ is hydrogen, bromine, chlorine or a substituted or unsubstituted group selected from methyl, ethyl, cyclopropyl, —OH and methoxy;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_3$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy and —$OR_8$; preferably $R_3$ is selected from the group consisting of hydrogen, substituted or unsubstituted $C_{1-6}$ alkyl, halogen, haloalkyl, haloalkoxy and —$OR_8$; more preferably $R_3$ is selected from the group consisting of hydrogen and substituted or unsubstituted $C_{1-6}$ alkyl; even more preferably $R_3$ is hydrogen or substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_4$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl; preferably $R_4$ is selected from the group consisting of substituted or unsubstituted $C_{1-6}$ alkyl, substituted or unsubstituted cycloalkyl, substituted or unsubstituted aryl and substituted or unsubstituted heterocyclyl; more preferably $R_4$ is selected from the group consisting of substituted or unsubstituted $C_{1-6}$ alkyl, substituted or unsubstituted aryl and substituted or unsubstituted heterocyclyl; even more preferably $R_4$ is a substituted or unsubstituted group selected from methyl, ethyl, isopropyl, isobutyl, phenyl, pyridine and tetrahydropyran;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_5$ and $R_5$' are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl and haloalkoxy; preferably $R_5$ and $R_5$' are independently selected from the group consisting of hydrogen, substituted or unsubstituted $C_{1-6}$ alkyl, haloalkyl and haloalkoxy; more preferably $R_5$ and $R_5$' are independently selected from the group consisting of hydrogen and substituted or unsubstituted $C_{1-6}$ alkyl; even more preferably $R_5$ and $R_5$' are independently selected from hydrogen or a substituted or unsubstituted group selected from methyl and methyl-OH;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_6$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; preferably $R_6$ is selected from the group consisting of hydrogen, substituted or unsubstituted $C_{1-6}$ alkylhaloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; more preferably $R_6$ is selected from the group consisting of hydrogen, substituted or unsubstituted $C_{1-6}$ alkylhaloalkyl, substituted or unsubstituted heterocyclyl, substituted or unsubstituted alkylcycloalkyl, substituted or unsubstituted alkylaryl and substituted or unsubstituted alkylheterocyclyl; even more preferably $R_6$ is hydrogen or a substituted or unsubstituted group selected from methyl, isopropyl, benzyl, piperidine, —$CH_2$-cyclopropyl and —$CH_2$-tetrahydropyran;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_6$' is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_6$' is selected from the group consisting of hydrogen and substituted or unsubstituted $C_{1-6}$ alkyl; more preferably $R_6$' is hydrogen or a substituted or unsubstituted group selected from methyl and —$CH_2CF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_7$ is selected from the group consisting of hydrogen and substituted or unsubstituted $C_{1-6}$ alkyl; more preferably $R_7$ is hydrogen or substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_8$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_8$ is selected from the group consisting of hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{11}$, $R_{11}$' and $R_{11}$" are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; preferably $R_{11}$, $R_{11}$' and $R_{11}$" are independently selected from hydrogen, substituted or unsubstituted $C_{1-6}$ alkyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; more preferably $R_{11}$, $R_{11}$' and $R_{11}$" are independently selected from hydrogen, substituted or unsubstituted $C_{1-6}$ alkyl, substituted or unsubstituted aryl, substituted or unsubstituted heterocyclyl and substituted or unsubstituted alkylcycloalkyl; even more preferably $R_{11}$, $R_{11}$' and $R_{11}$" are hydrogen or a substituted or unsubstituted group selected from methyl, ethyl, —$CH_2$-cyclopropyl, phenyl, pyridine, triazole and oxadiazole;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{13}$ and $R_{13}$' are independently selected from hydrogen, unsubstituted $C_{1-6}$ alkyl, unsubstituted $C_{2-6}$ alkenyl and unsubstituted $C_{2-6}$ alkynyl; preferably $R_{13}$ and $R_{13}$' are independently selected from hydrogen and unsubstituted $C_{1-6}$ alkyl; more preferably $R_{13}$ and $R_{13}$' are independently selected from the group consisting of hydrogen and unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{14}$, $R_{14}$' and $R_{14}$" are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl; preferably $R_{14}$, $R_{14}$' and $R_{14}$" are independently selected from hydrogen, unsubstituted $C_{1-6}$ alkyl, unsubstituted aryl, unsubstituted cycloalkyl and unsubstituted heterocyclyl; more preferably $R_{14}$, $R_{14}$' and $R_{14}$" are independently selected from hydrogen and unsubstituted $C_{1-6}$ alkyl; even more preferably $R_{14}$, $R_{14}$' and $R_{14}$" are independently selected from hydrogen and unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{21}$ and $R_{21}$' are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{21}$ and $R_{21}$' are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{31}$ and $R_{31}$' are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{31}$ and $R_{31}$' are independently selected from hydrogen, substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{41}$, $R_{41}$' and $R_{41}$" are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{41}$, $R_{41}$' and $R_{41}$" are independently selected from hydrogen and substituted or unsubstituted $C_{1-6}$ alkyl; more preferably $R_{41}$, $R_{41}$' and $R_{41}$" are independently selected from the group consisting of hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{51}$ and $R_{51}$' are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{51}$ and $R_{51}$' are independently selected from hydrogen and substituted or unsubstituted $C_{1-6}$ alkyl; more preferably $R_{51}$ and $R_{51}$' are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein the cycloalkyl, aryl or heterocyclyl in $R_1$, if substituted, is substituted with one or more substituent/s selected from halogen, —$R_{11}$, —$[CH_2]_r OR_{11}$, =O, —$NO_2$, —$[CH_2]_r NR_{11}R_{11}$', —$NR_{11}C(O)R_{11}$', —$NR_{11}S(O)_2R_{11}$', —$S(O)_2NR_{11}R_{11}$', —$NR_{11}C(O)NR_{11}$'$R_{11}$", —$SR_{11}$, —$S(O)R_{11}$, —$S(O)_2R_{11}$, —CN, haloalkyl, haloalkoxy, —$C(O)R_{11}$, —$C(O)OR_{11}$, —$C(O)NR_{11}R_{11}$', —$OCH_2CH_2OR_{11}$, —$NR_{11}S(O)_2NR_1$'$R_{11}$" and —$C(CH_3)_2OR_{11}$; preferably the cycloalkyl, aryl or heterocyclyl in $R_1$, if substituted, is substituted with one or more substituent/s selected from halogen, —$R_{11}$, —$[CH_2]_r OR_{11}$, =O, —$[CH_2]_r NR_{11}R_{11}$', —$S(O)_2R_{11}$, —CN, haloalkyl, —$C(O)R_{11}$ and —$C(O)NR_{11}R_{11}$'; more preferably the cycloalkyl, aryl or heterocyclyl in $R_1$, if substituted, is substituted with one or more substituent/s selected from fluorine, chlorine, methyl, ethyl, —$CF_3$, —CN, —$CH_2OH$, —$CH_2OCH_3$, —OH—$OCH_3$, —$OCH_2CH_3$, —$OCH_2$-cyclopropyl, =O, $—CH_2NHCH_3$, $—NH_2$, $—NHCH_3$, $—N(CH_3)_2$, $—C(O)CH_3$, $—C(O)NH_2$, $—C(O)N(CH_3)_2$, $—S(O)_2CH_3$, triazole, oxadiazole, phenyl and pyridine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein the cycloalkyl, aryl or heterocyclyl in $R_4$, if substituted, is substituted with one or more substituent/s selected from halogen, $—R_{41}$, $—[CH_2]_rOR_{41}$, =O, $—NO_2$, $—[CH_2]_rNR_{41}R_{41}'$, $—NR_{41}C(O)R_{41}'$, $—NR_{41}S(O)_2R_{41}'$, $—S(O)_2NR_{41}R_{41}'$, $—NR_{41}C(O)NR_{41}'R_{41}''$, $—SR_{41}$, $—S(O)R_{41}$, $—S(O)_2R_{41}$, —CN, haloalkyl, haloalkoxy, $—C(O)R_{41}$, $—C(O)OR_{41}$, $—C(O)NR_{41}R_{41}'$, $—OCH_2CH_2OR_{41}$, $—NR_{41}S(O)_2NR_{41}'R_{41}''$ and $—C(CH_3)_2OR_{41}$; preferably the cycloalkyl, aryl or heterocyclyl in $R_4$, if substituted, is substituted with one or more substituent/s selected from halogen, $—R_{41}$, $—[CH_2]_rOR_{41}$, —CN and haloalkyl; more preferably the cycloalkyl, aryl or heterocyclyl in $R_4$, if substituted, is substituted with one or more substituent/s selected from fluorine, chlorine, $—CH_3$, $—CF_3$, —CN, —OH and $—OCH_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein the alkyl, alkenyl or alkynyl in $R_5$ and $R_5'$, if substituted, is substituted with one or more substituent/s selected from $—OR_{51}$, halogen, —CN, haloalkyl, haloalkoxy, $—NR_{51}R_{51}'$; preferably the alkyl, alkenyl or alkynyl in $R_5$ and $R_5'$, if substituted, is substituted with one or more $—OR_{51}$; more preferably the alkyl, alkenyl or alkynyl in $R_5$ and $R_5'$, if substituted, is substituted with one or more —OH;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein the alkyl, alkenyl or alkynyl, if substituted, and not defined otherwise, is substituted with one or more substituent/s selected from $—OR_{13}$, halogen, —CN, haloalkyl, haloalkoxy and $—NR_{13}R_{13}'$; preferably the alkyl, alkenyl or alkynyl, if substituted, and not defined otherwise, is substituted with one or more substituent/s selected from $—OR_{13}$ and $—NR_{13}R_{13}'$; more preferably the alkyl, alkenyl or alkynyl, if substituted, and not defined otherwise, is substituted with one or more substituent/s selected from —OH, $—OCH_3$ and $—NHCH_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein the aryl, heterocyclyl or cycloalkyl, also in alkylcycloalkyl, alkylaryl and alkylheterocyclyl, if substituted, and not defined otherwise, is substituted with one or more substituent/s selected from halogen, $—R_{14}$, $—[CH_2]_rOR_{14}$, =O, $—NO_2$, $—[CH_2]_rNR_{14}R_{14}'$, $—NR_{14}C(O)R_{14}'$, $—NR_{14}S(O)_2R_{14}'$, $—S(O)_2NR_{14}R_{14}'$, $—NR_{14}C(O)NR_{14}'R_{14}''$, $—SR_{14}$, $—S(O)R_{14}$, $S(O)_2R_{14}$, —CN, haloalkyl, haloalkoxy, $—C(O)R_{14}$, $—C(O)OR_{14}$, $—C(O)NR_{14}R_{14}'$, $—OCH_2CH_2OR_{14}$, $—NR_{14}S(O)_2NR_{14}'R_{14}''$ and $—C(CH_3)_2OR_{14}$; preferably the aryl, heterocyclyl or cycloalkyl, also in alkylcycloalkyl, alkylaryl and alkylheterocyclyl, if substituted, and not defined otherwise, is substituted with one or more substituent/s selected from $—R_{14}$ and $—[CH_2]_rNR_{14}R_{14}'$; more preferably the aryl, heterocyclyl or cycloalkyl, also in alkylcycloalkyl, alkylaryl and alkylheterocyclyl, if substituted, and not defined otherwise, is substituted with one or more substituent/s selected from methyl and $—CH_2NHCH_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2, 3 or 4; preferably m is 1, 2 or 3;

and/or n is 1 or 2; preferably n is 1;

and/or t is 0 or 1;

and/or p is 0, 1, 2, 3 or 4; preferably p is 0, 1, 2 or 3;

and/or q is 0, 1, 2, 3 or 4;

and/or r is 0, 1, 2 or 3; preferably r is 0 or 1;

and/or

X is selected from the group consisting of a bond, $—[CH_2]_p—$, $—[CH_2]_pNR_x[CH_2]_q—$, $—[CH_2]_pO[CH_2]_q—$, $—[CH_2]_pNR_xC(O)[CH_2]_q—$ and $—[CH_2]_pNR_xCH(CH_3)—$; preferably X is selected from the group consisting of a bond, $—CH_2—$, $—CH_2CH_2—$, $—CH_2CH_2CH_2—$, $—CH_2O—$, $—CH_2OCH_2—$, $—NHC(O)CH_2—$, $—NHCH_2CH_2—$, $—CH_2NHCH_2—$, $—CH_2NH(CH_2)_2—$, $—CH_2NH(CH_2)_3—$, $—CH_2NH(CH_2)_4—$, $—CH_2N(methyl)CH_2—$, $—CH_2N(iPr)CH_2—$, $—CH_2N(CH_2CF_3)CH_2—$, $—CH_2NHCH(methyl)$-, $—CH_2N(methyl)CH_2CH_2—$, —N(methyl)-, $—N(methyl)CH_2—$, $—N(methyl)CH_2CH_2—$ and $—CH_2N(isopropyl)CH_2—$;

and/or $R_x$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_x$ is selected from the group consisting of hydrogen and substituted or unsubstituted $C_{1-6}$ alkyl; more preferably $R_x$ is hydrogen or a substituted or unsubstituted group selected from methyl, ethyl, isopropyl;

and/or $R_1$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy, —$OR_6$, —$NR_6R_6'$, —CN, cycloalkyl, aryl and heterocyclyl; preferably, $R_1$ is selected from the group consisting of hydrogen, substituted or unsubstituted $C_{1-6}$ alkyl, halogen, haloalkyl, —$OR_6$, —$NR_6R_6'$, —CN, cycloalkyl, aryl and heterocyclyl; more preferably $R_1$ is hydrogen, bromine, chlorine, —CN or a substituted or unsubstituted group selected from methyl, ethyl, isopropyl, —$CF_3$, —OH, methoxy, —O— isopropyl, —$NH_2$, —$NHCH_3$, —$N(CH_3)_2$, —$N(CH_3)(CH_2$-cyclopropyl), —$N(CH_3)$(benzyl), —$N(CH_3)$(piperidine), —$N(CH_2CF_3)(CH_2$-tetrahydropyran), cyclopropyl, phenyl, pyridine, piperidine, pyrrolidine, piperazine, pyrimidine, pyrazole, isoxazole, isothiazole, imidazole, morpholine, thiomorpholine, tetrahydropyran, tetrahydrofuran and thiophene;

and/or $R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted alkylcycloalkyl, halogen, haloalkyl, haloalkoxy and —$OR_7$; preferably $R_2$ is selected from the group consisting of hydrogen, substituted or unsubstituted $C_{1-6}$ alkyl, substituted or unsubstituted cycloalkyl, substituted or unsubstituted alkylcycloalkyl, halogen, haloalkyl, haloalkoxy and —$OR_7$; more preferably $R_2$ is selected from the group consisting of hydrogen, substituted or unsubstituted $C_{1-6}$ alkyl, substituted or unsubstituted cycloalkyl, halogen and —$OR_7$; even more preferably $R_2$ is hydrogen, bromine, chlorine or a substituted or unsubstituted group selected from methyl, ethyl, cyclopropyl, —OH and methoxy;

and/or $R_3$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, halogen, haloalkyl, haloalkoxy and —$OR_8$; preferably $R_3$ is selected from the group consisting of hydrogen, substituted or unsubstituted $C_{1-6}$ alkyl, halogen, haloalkyl, haloalkoxy and —$OR_8$; more preferably $R_3$ is selected from the group consisting of hydrogen and substituted or unsubstituted $C_{1-6}$ alkyl; even more preferably $R_3$ is hydrogen or substituted or unsubstituted methyl;

and/or $R_4$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl; preferably $R_4$ is selected from the group consisting of substituted or unsubstituted $C_{1-6}$ alkyl, substituted or unsubstituted cycloalkyl, substituted or unsubstituted aryl and substituted or unsubstituted heterocyclyl; more preferably $R_4$ is selected from the group consisting of substituted or unsubstituted $C_{1-6}$ alkyl, substituted or unsubstituted aryl and substituted or unsubstituted heterocyclyl; even more preferably $R_4$ is a substituted or unsubstituted group selected from methyl, ethyl, isopropyl, isobutyl, phenyl, pyridine, tetrahydropyran;

and/or $R_5$ and $R_5'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl and haloalkoxy; preferably $R_5$ and $R_5'$ are independently selected from the group consisting of hydrogen, substituted or unsubstituted $C_{1-6}$ alkyl, haloalkyl and haloalkoxy; more preferably $R_5$ and $R_5'$ are independently selected from the group consisting of hydrogen and substituted or unsubstituted $C_{1-6}$ alkyl; even more preferably $R_5$ and $R_5'$ are independently selected from hydrogen or a substituted or unsubstituted group selected from methyl and methyl-OH;

and/or $R_6$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, haloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; preferably $R_6$ is selected from the group consisting of hydrogen, substituted or unsubstituted $C_{1-6}$ alkylhaloalkyl, haloalkoxy; substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; more preferably $R_6$ is selected from the group consisting of hydrogen, substituted or unsubstituted $C_{1-6}$ alkylhaloalkyl, substituted or unsubstituted heterocyclyl, substituted or unsubstituted alkylcycloalkyl, substituted or unsubstituted alkylaryl and substituted or unsubstituted alkylheterocyclyl; even more preferably $R_6$ is hydrogen or a substituted or unsubstituted group selected from methyl, isopropyl, benzyl, piperidine, —$CH_2$-cyclopropyl, —$CH_2$-tetrahydropyran;

and/or $R_6'$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_6'$ is selected from the group consisting of hydrogen and substituted or unsubstituted $C_{1-6}$ alkyl; more preferably $R_6'$ is hydrogen or a substituted or unsubstituted group selected from methyl and —$CH_2CF_3$;

and/or $R_6$ and $R_6'$, taken together with the nitrogen atom to which they are attached, form a substituted or unsubstituted heterocyclyl selected from the group consisting of morpholine, thiomorpholine, pyrrolidine and piperazine;

and/or $R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl; preferably $R_7$ is selected from the group consisting of hydrogen and substituted or unsubstituted $C_{1-6}$ alkyl; more preferably $R_7$ is hydrogen or substituted or unsubstituted methyl;

and/or $R_{11}$, $R_{11}$' and $R_{11}$" are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; preferably $R_{11}$, $R_{11}$' and $R_{11}$" are independently selected from hydrogen, substituted or unsubstituted $C_{1-6}$ alkyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl and substituted or unsubstituted alkylheterocyclyl; more preferably $R_{11}$, $R_{11}$' and $R_{11}$" are independently selected from hydrogen, substituted or unsubstituted $C_{1-6}$ alkyl, substituted or unsubstituted aryl, substituted or unsubstituted heterocyclyl and substituted or unsubstituted alkylcycloalkyl; even more preferably $R_{11}$, $R_{11}$' and $R_{11}$" are hydrogen or a substituted or unsubstituted group selected from methyl, ethyl, —$CH_2$-cyclopropyl, phenyl, pyridine, triazole and oxadiazole;

and/or $R_{13}$ and $R_{13}$' are independently selected from hydrogen, unsubstituted $C_{1-6}$ alkyl, unsubstituted $C_{2-6}$ alkenyl and unsubstituted $C_{2-6}$ alkynyl; preferably $R_{13}$ and $R_{13}$' are independently selected from hydrogen and unsubstituted $C_{1-6}$ alkyl; more preferably $R_{13}$ and $R_{13}$' are independently selected from hydrogen and unsubstituted methyl;

and/or $R_{14}$, $R_{14}$' and $R_{14}$" are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl; preferably $R_{14}$, $R_{14}$' and $R_{14}$" are independently selected from hydrogen, unsubstituted $C_{1-6}$ alkyl, unsubstituted aryl, unsubstituted cycloalkyl and unsubstituted heterocyclyl; more preferably $R_{14}$, $R_{14}$' and $R_{14}$" are independently selected from hydrogen and unsubstituted $C_{1-6}$ alkyl; even more preferably $R_{14}$, $R_{14}$' and $R_{14}$" are independently selected from hydrogen and unsubstituted methyl;

and/or $R_{41}$, $R_{41}$' and $R_{41}$" are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{41}$, $R_{41}$' and $R_{41}$" are independently selected from hydrogen and substituted or unsubstituted $C_{1-6}$ alkyl; more preferably $R_{41}$, $R_{41}$' and $R_{41}$" are independently selected from hydrogen and substituted or unsubstituted methyl;

and/or $R_{51}$ and $R_{51}$' are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{51}$ and $R_{51}$' are independently selected from hydrogen and substituted or unsubstituted $C_{1-6}$ alkyl; more preferably $R_{51}$ and $R_{51}$' are both hydrogen; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment m is 1, 2 or 3.

In a preferred embodiment n is 1.

In a preferred embodiment t is 0 or 1.

In a preferred embodiment t is 0.

In a preferred embodiment p is 0, 1, 2 or 3.

In a preferred embodiment q is 0, 1, 2, 3 or 4.

In a preferred embodiment r is 0 or 1.

In a preferred embodiment

X is selected from the group consisting of a bond, —$CH_2$—, —$CH_2CH_2$—, —$CH_2CH_2CH_2$—, —$CH_2O$—, —$CH_2OCH_2$—, —NHC(O)$CH_2$—, —$NHCH_2CH_2$—, —$CH_2NHCH_2$—, —$CH_2NH(CH_2)_2$—, —$CH_2NH(CH_2)_3$—, —$CH_2NH(CH_2)_4$—, —$CH_2$N(methyl)$CH_2$—, —$CH_2$N(iPr)$CH_2$—, —$CH_2N(CH_2CF_3)CH_2$—, —$CH_2$NHCH(methyl)-, —$CH_2$N(methyl)$CH_2CH_2$—, —N(methyl)-, —N(methyl)$CH_2$—, —N(methyl)$CH_2CH_2$— and —$CH_2$N(isopropyl)$CH_2$—.

In a preferred embodiment

X is selected from the group consisting of —$CH_2$—, —$CH_2CH_2$— and —$CH_2CH_2CH_2$—.

In a preferred embodiment

X is selected from the group consisting of —$NHCH_2CH_2$—, —$CH_2NHCH_2$—, —$CH_2NH(CH_2)_2$—, —$CH_2NH(CH_2)_3$—, —$CH_2NH(CH_2)_4$—, —$CH_2$N(methyl)$CH_2$—, —$CH_2$N(iPr)$CH_2$—, —$CH_2N(CH_2CF_3)CH_2$—, —$CH_2$NHCH(methyl)-, —$CH_2$N(methyl)$CH_2CH_2$—, —N(methyl)-, —N(methyl)$CH_2$—, —N(methyl)$CH_2CH_2$— and —$CH_2$N(isopropyl)$CH_2$—.

In a preferred embodiment $R_x$ is hydrogen or a substituted or unsubstituted group selected from methyl, ethyl, isopropyl.

In a preferred embodiment $R_1$ is hydrogen, bromine, chlorine, —CN or a substituted or unsubstituted group selected from methyl, ethyl, isopropyl, —$CF_3$, —OH, methoxy, —O-isopropyl, —$NH_2$, —$NHCH_3$, —$N(CH_3)_2$, —$N(CH_3)(CH_2$-cyclopropyl), —$N(CH_3)$(benzyl), —$N(CH_3)$(piperidine), —$N(CH_2CF_3)(CH_2$-tetrahydropyran), cyclopropyl, phenyl, pyridine, piperidine, pyrrolidine, piperazine, pyrimidine, pyrazole, isoxazole, isothiazole, imidazole, morpholine, thiomorpholine, tetrahydropyran, tetrahydrofuran and thiophene.

In a preferred embodiment $R_2$ is hydrogen, bromine, chlorine or a substituted or unsubstituted group selected from methyl, ethyl, cyclopropyl, —OH and methoxy.

In a preferred embodiment $R_3$ is hydrogen or substituted or unsubstituted methyl.

In a preferred embodiment $R_4$ is a substituted or unsubstituted group selected from methyl, ethyl, isopropyl, isobutyl, phenyl, pyridine and tetrahydropyran.

In a preferred embodiment $R_5$ and $R_5$' are independently selected from hydrogen or a substituted or unsubstituted group selected from methyl and methyl-OH.

In a preferred embodiment $R_5$ is selected from hydrogen, methyl and methyl-OH.

In a preferred embodiment $R_5$' is hydrogen.

In a preferred embodiment $R_5$ is selected from hydrogen, methyl and methyl-OH, while $R_5$' is hydrogen.

In a preferred embodiment $R_6$ is hydrogen or a substituted or unsubstituted group selected from methyl, isopropyl, benzyl, piperidine, —$CH_2$-cyclopropyl, —$CH_2$-tetrahydropyran.

In a preferred embodiment $R_6$' is hydrogen or a substituted or unsubstituted group selected from methyl and —$CH_2CF_3$.

In a preferred embodiment $R_6$ is hydrogen or a substituted or unsubstituted group selected from methyl, isopropyl, benzyl, piperidine, —$CH_2$-cyclopropyl, —$CH_2$-tetrahydropyran, while $R_6$' is hydrogen or a substituted or unsubstituted group selected from methyl and —$CH_2CF_3$.

In a preferred embodiment $R_6$ is hydrogen.

In a preferred embodiment $R_6$ is substituted or unsubstituted methyl.

In a preferred embodiment $R_6$ is substituted or unsubstituted isopropyl.

In a preferred embodiment $R_6$ is substituted or unsubstituted methyl, while $R_6$' is hydrogen or substituted or unsubstituted methyl.

In a preferred embodiment $R_6$ is substituted or unsubstituted methyl, while $R_6$' is hydrogen.

In a preferred embodiment $R_6$ and $R_6$' are both substituted or unsubstituted methyl.

In a preferred embodiment $R_6$ and $R_6$' are both hydrogen.

In a preferred embodiment $R_6$ is substituted or unsubstituted piperidine, while $R_6$' is substituted or unsubstituted methyl.

In a preferred embodiment $R_6$ is substituted or unsubstituted benzyl, while $R_6$' is substituted or unsubstituted methyl.

In a preferred embodiment $R_6$ is substituted or unsubstituted —$CH_2$-cyclopropyl, while $R_6$' is substituted or unsubstituted methyl.

In a preferred embodiment $R_6$ is substituted or unsubstituted —$CH_2$-tetrahydropyran, while $R_6$' is substituted or unsubstituted —$CH_2CF_3$.

In a preferred embodiment $R_6$ and $R_6$', taken together with the nitrogen atom to which they are attached, form a substituted or unsubstituted heterocyclyl selected from the group consisting of morpholine, thiomorpholine, pyrrolidine and piperazine.

In a preferred embodiment $R_7$ is hydrogen or substituted or unsubstituted methyl.

In a preferred embodiment $R_{11}$, $R_{11}$' and $R_{11}$" are hydrogen or a substituted or unsubstituted group selected from methyl, ethyl, —$CH_2$-cyclopropyl, phenyl, pyridine, triazole and oxadiazole.

In a preferred embodiment $R_{11}$ is hydrogen or a substituted or unsubstituted group selected from methyl, ethyl, —$CH_2$-cyclopropyl, phenyl, pyridine, triazole and oxadiazole.

In a preferred embodiment $R_{11}$' is hydrogen or substituted or unsubstituted methyl.

In a preferred embodiment $R_{11}$ is hydrogen or a substituted or unsubstituted group selected from methyl, ethyl, —$CH_2$-cyclopropyl, phenyl, pyridine, triazole and oxadiazole, while $R_{11}$' is hydrogen or substituted or unsubstituted methyl.

In a preferred embodiment $R_{11}$ is substituted or unsubstituted methyl, while $R_{11}$' is hydrogen or substituted or unsubstituted methyl.

In a preferred embodiment $R_{11}$ is substituted or unsubstituted methyl, while $R_{11}$' is hydrogen.

In a preferred embodiment $R_{11}$ and $R_{11}$' are both hydrogen.

In a preferred embodiment $R_{11}$ and $R_{11}$' are both substituted or unsubstituted methyl.

In a preferred embodiment $R_{13}$ and $R_{13}$' are independently selected from hydrogen and unsubstituted methyl.

In a preferred embodiment $R_{13}$ is selected from hydrogen and unsubstituted methyl.

In a preferred embodiment $R_{13}$' is hydrogen.

In a preferred embodiment $R_{13}$ is hydrogen or unsubstituted methyl, while $R_{13}$' is hydrogen.

In a preferred embodiment $R_{14}$, $R_{14}$' and $R_{14}$" are independently selected from hydrogen and unsubstituted methyl.

In a preferred embodiment $R_{14}$ is unsubstituted methyl.

In a preferred embodiment $R_{14}$ is unsubstituted methyl, while $R_{14}$' is hydrogen.

In a preferred embodiment $R_{41}$, $R_{41}$' and $R_{41}$" are independently selected from hydrogen and substituted or unsubstituted methyl.

In a preferred embodiment $R_{41}$ is selected from hydrogen and substituted or unsubstituted methyl.

In a preferred embodiment $R_{51}$ is hydrogen.

In a preferred embodiment the cycloalkyl, aryl or heterocyclyl in $R_1$, if substituted, is substituted with one or more substituent/s selected from fluorine, chlorine, methyl, ethyl, —$CF_3$, —CN, —$CH_2OH$, —$CH_2OCH_3$, —OH—$OCH_3$, —$OCH_2CH_3$, —$OCH_2$-cyclopropyl, =O, —$CH_2NHCH_3$, —$NH_2$, —$NHCH_3$, —$N(CH_3)_2$, —$C(O)CH_3$, —$C(O)NH_2$, —$C(O)N(CH_3)_2$, —$S(O)_2CH_3$, triazole, oxadiazole, phenyl and pyridine.

In a preferred embodiment the cycloalkyl, aryl or heterocyclyl in $R_4$, if substituted, is substituted with one or more substituent/s selected from fluorine, chlorine, —$CH_3$, —$CF_3$, —CN, —OH and —$OCH_3$.

In a preferred embodiment the alkyl, alkenyl or alkynyl in $R_5$ and $R_5$', if substituted, is substituted with one or more —OH.

In a preferred embodiment the alkyl, alkenyl or alkynyl, if substituted, and not defined otherwise, is substituted with one or more substituent/s selected from —OH, —$OCH_3$ and —$NHCH_3$.

In a preferred embodiment the aryl, heterocyclyl or cycloalkyl, also in alkylcycloalkyl, alkylaryl and alkylheterocyclyl, if substituted, and not defined otherwise, is substituted with one or more substituent/s selected from methyl and —$CH_2NHCH_3$.

In a preferred embodiment the haloalkyl is —$CF_3$.

In a preferred embodiment the haloalkoxy is —$OCF_3$.

In a preferred embodiment, the compounds are selected which act as dual ligands of the α2δ subunit, particularly the α2δ-1 subunit, of the voltage-gated calcium channel and the $\sigma_1$ receptor:

| EX | CHEMICAL NAME |
|---|---|
| 1 | 7-(1-Benzylpiperidin-3-yl)-2-bromopyrazolo[1,5-a]pyrimidine |
| 2 | 7-(1-Benzylpiperidin-3-yl)pyrazolo[1,5-a]pyrimidine |
| 3 | 7-(1-Benzylpiperidin-3-yl)-2-methylpyrazolo[1,5-a]pyrimidine |
| 4 | 7-(1-Benzylpiperidin-3-yl)-2-ethylpyrazolo[1,5-a]pyrimidine |
| 5 | 7-(1-Benzylpiperidin-3-yl)-3-bromopyrazolo[1,5-a]pyrimidine |
| 6 | 7-(1-Benzylpiperidin-3-yl)-3-bromo-2,6-dimethylpyrazolo[1,5-a]pyrimidine |
| 7 | 7-(1-Benzylpiperidin-3-yl)-3-bromo-6-methylpyrazolo[1,5-a]pyrimidine |
| 8 | N-(7-(1-Benzylpiperidin-3-yl)-2-methylpyrazolo[1,5-a]pyrimidin-3-yl)acetamide |
| 9 | N-(7-(1-Benzylpiperidin-3-yl)-3-methylpyrazolo[1,5-a]pyrimidin-2-yl)acetamide |
| 10 | 7-(1-Benzylpiperidin-3-yl)-3-bromo-2-methylpyrazolo[1,5-a]pyrimidine |
| 11 | 7-(1-Benzylpiperidin-3-yl)-3-bromo-2-ethylpyrazolo[1,5-a]pyrimidine |
| 12 | 7-(1-Benzylpiperidin-3-yl)-2-phenylpyrazolo[1,5-a]pyrimidine |
| 13 | 7-(1-Benzylpiperidin-3-yl)-2-(4-ethoxyphenyl)pyrazolo[1,5-a]pyrimidine |
| 14 | 7-(1-Benzylpiperidin-3-yl)-2-(2-fluorophenyl)pyrazolo[1,5-a]pyrimidine |
| 15 | 7-(1-Benzylpiperidin-3-yl)-2-(4-chlorophenyl)pyrazolo[1,5-a]pyrimidine |
| 16 | 7-(1-Benzylpiperidin-3-yl)-2-(pyridin-4-yl)pyrazolo[1,5-a]pyrimidine |
| 17 | 7-(1-Benzylpiperidin-3-yl)-2-(pyridin-3-yl)pyrazolo[1,5-a]pyrimidine |
| 18 | 7-(1-Benzylpiperidin-3-yl)-2-(3,5-dichloropyridin-4-yl)pyrazolo[1,5-a]pyrimidine |
| 19 | 7-(1-Benzylpiperidin-3-yl)-2-(thiophen-2-yl)pyrazolo[1,5-a]pyrimidine |
| 20 | 4-(7-(1-Benzylpiperidin-3-yl)pyrazolo[1,5-a]pyrimidin-2-yl)isothiazole |
| 21 | 7-(1-Benzylpiperidin-3-yl)-2-(1-methyl-1H-imidazol-5-yl)pyrazolo[1,5-a]pyrimidine |
| 22 | 4-(7-(1-Benzylpiperidin-3-yl)pyrazolo[1,5-a]pyrimidin-2-yl)-N,N-dimethylaniline |
| 23 | 7-(1-Benzylpiperidin-3-yl)-2-(pyrimidin-5-yl)pyrazolo[1,5-a]pyrimidine |
| 24 | 5-(7-(1-Benzylpiperidin-3-yl)pyrazolo[1,5-a]pyrimidin-2-yl)pyridin-2-amine |
| 25 | 7-(1-Benzylpiperidin-3-yl)-2-(1-methyl-1H-pyrazol-4-yl)pyrazolo[1,5-a]pyrimidine |
| 26 | 7-(1-Benzylpiperidin-3-yl)-2-(pyridin-2-yl)pyrazolo[1,5-a]pyrimidine |
| 27 | 7-(1-Benzylpiperidin-3-yl)-2-(2-methoxypyridin-3-yl)pyrazolo[1,5-a]pyrimidine |
| 28 | 7-(1-Benzylpiperidin-3-yl)-2-(6-methoxypyridin-3-yl)pyrazolo[1,5-a]pyrimidine |
| 29 | 7-(1-Benzylpiperidin-3-yl)-2-(2-methoxyphenyl)pyrazolo[1,5-a]pyrimidine |
| 30 | 7-(1-Benzylpiperidin-3-yl)-2-(6-methoxypyridin-2-yl)pyrazolo[1,5-a]pyrimidine |
| 31 | 7-(1-Benzylpiperidin-3-yl)-2-(5-methoxypyridin-3-yl)pyrazolo[1,5-a]pyrimidine |
| 32 | 7-(1-Benzylpiperidin-3-yl)-2-(2-methoxypyridin-4-yl)pyrazolo[1,5-a]pyrimidine |
| 33 | 7-(1-Benzylpiperidin-3-yl)-2-(3-methoxypyridin-4-yl)pyrazolo[1,5-a]pyrimidine |
| 34 | 7-(1-Benzylpiperidin-3-yl)-2-(4-methoxypyridin-3-yl)pyrazolo[1,5-a]pyrimidine |
| 35 | 7-(1-Benzylpiperidin-3-yl)-3-phenylpyrazolo[1,5-a]pyrimidine |
| 36 | 7-(1-Benzylpiperidin-3-yl)-3-(pyridin-4-yl)pyrazolo[1,5-a]pyrimidine |
| 37 | 7-(1-Benzylpiperidin-3-yl)-3-(pyridin-3-yl)pyrazolo[1,5-a]pyrimidine |
| 38 | 7-(1-Benzylpiperidin-3-yl)-3-(2-methoxypyridin-4-yl)pyrazolo[1,5-a]pyrimidine |
| 39 | 7-(1-Benzylpiperidin-3-yl)-3-(4-ethoxyphenyl)pyrazolo[1,5-a]pyrimidine |
| 40 | 7-(1-Benzylpiperidin-3-yl)-3-(2-methoxypyridin-3-yl)pyrazolo[1,5-a]pyrimidine |
| 41 | 7-(1-Benzylpiperidin-3-yl)-6-methyl-3-(pyridin-4-yl)pyrazolo[1,5-a]pyrimidine |
| 42 | 7-(1-Benzylpiperidin-3-yl)-2-methyl-3-(pyridin-4-yl)pyrazolo[1,5-a]pyrimidine |
| 43 | 7-(1-Benzylpiperidin-3-yl)-3-(2-methoxypyridin-3-yl)-2-methylpyrazolo[1,5-a]pyrimidine |
| 44 | 7-(1-Benzylpiperidin-3-yl)-2-methyl-3-phenylpyrazolo[1,5-a]pyrimidine |
| 45 | 7-(1-Benzylpiperidin-3-yl)-3-(4-ethoxyphenyl)-2-methylpyrazolo[1,5-a]pyrimidine |
| 46 | 7-(1-Benzylpiperidin-3-yl)-3-(2-methoxypyridin-4-yl)-2-methylpyrazolo[1,5-a]pyrimidine |
| 47 | 4-(7-(1-Benzylpiperidin-3-yl)-2-methylpyrazolo[1,5-a]pyrimidin-3-yl)-N,N-dimethylaniline |
| 48 | 7-(1-Benzylpiperidin-3-yl)-3-(2-fluorophenyl)-2-methylpyrazolo[1,5-a]pyrimidine |
| 49 | 7-(1-Benzylpiperidin-3-yl)-2-methyl-3-(3-methylpyridin-4-yl)pyrazolo[1,5-a]pyrimidine |
| 50 | 7-(1-Benzylpiperidin-3-yl)-3-(2-fluoropyridin-4-yl)-2-methylpyrazolo[1,5-a]pyrimidine |
| 51 | 7-(1-Benzylpiperidin-3-yl)-2-methyl-3-(2-methylpyridin-4-yl)pyrazolo[1,5-a]pyrimidine |
| 52 | 7-(1-Benzylpiperidin-3-yl)-3-(3-fluoropyridin-4-yl)-2-methylpyrazolo[1,5-a]pyrimidine |
| 53 | 7-(1-Benzylpiperidin-3-yl)-2-methyl-3-(2-(trifluoromethyl)pyridin-4-yl)pyrazolo[1,5-a]pyrimidine |
| 54 | 7-(1-Benzylpiperidin-3-yl)-3-(2-ethylpyridin-4-yl)-2-methylpyrazolo[1,5-a]pyrimidine |
| 55 | 3-(3-(7-(1-Benzylpiperidin-3-yl)-2-methylpyrazolo[1,5-a]pyrimidin-3-yl)phenyl)-5-methyl-1,2,4-oxadiazole |
| 56 | 2-(3-(7-(1-Benzylpiperidin-3-yl)-2-methylpyrazolo[1,5-a]pyrimidin-3-yl)phenyl)-5-methyl-1,3,4-oxadiazole |
| 57 | 7-(1-Benzylpiperidin-3-yl)-3-(3-methoxypyridin-4-yl)-2-methylpyrazolo[1,5-a]pyrimidine |
| 58 | 7-(1-Benzylpiperidin-3-yl)-2,6-dimethyl-3-(pyridin-4-yl)pyrazolo[1,5-a]pyrimidine |
| 59 | 7-(1-Benzylpiperidin-3-yl)-2,5-dimethyl-3-(pyridin-4-yl)pyrazolo[1,5-a]pyrimidine |
| 60 | 7-(1-Benzylpiperidin-3-yl)-2-ethyl-3-(pyridin-4-yl)pyrazolo[1,5-a]pyrimidine |
| 61 | 1-(1-(3-(7-(1-Benzylpiperidin-3-yl)-2-methylpyrazolo[1,5-a]pyrimidin-3-yl)phenyl)-1H-1,2,3-triazol-4-yl)-N-methylmethanamine |
| 62 | 1-(4-(7-(1-Benzylpiperidin-3-yl)-2-methylpyrazolo[1,5-a]pyrimidin-3-yl)pyridin-2-yl)-N-methylmethanamine |
| 63 | 7-(1-(2-Fluorobenzyl)piperidin-3-yl)-2-methylpyrazolo[1,5-a]pyrimidine |
| 64 | 7-(1-Butylpiperidin-3-yl)-2-methylpyrazolo[1,5-a]pyrimidine |

-continued

| EX | CHEMICAL NAME |
|---|---|
| 65 | 7-(1-(2,6-Difluorobenzyl)piperidin-3-yl)-2-methylpyrazolo[1,5-a]pyrimidine |
| 66 | 2-Methyl-7-(1-(pyridin-2-ylmethyl)piperidin-3-yl)pyrazolo[1,5-a]pyrimidine |
| 67 | 2-Methyl-7-(1-phenethylpiperidin-3-yl)pyrazolo[1,5-a]pyrimidine |
| 68 | 3-((3-(2-Methylpyrazolo[1,5-a]pyrimidin-7-yl)piperidin-1-yl)methyl)phenol |
| 69 | 7-(1-Ethylpiperidin-3-yl)-2-methyl-3-(pyridin-4-yl)pyrazolo[1,5-a]pyrimidine |
| 70 | 2-Methyl-7-(1-propylpiperidin-3-yl)-3-(pyridin-4-yl)pyrazolo[1,5-a]pyrimidine |
| 71 | 7-(1-Isobutylpiperidin-3-yl)-2-methyl-3-(pyridin-4-yl)pyrazolo[1,5-a]pyrimidine |
| 72 | 2-Methyl-7-(1-(pyridin-2-ylmethyl)piperidin-3-yl)-3-(pyridin-4-yl)pyrazolo[1,5-a]pyrimidine |
| 73 | 6-Methyl-7-(1-phenethylpiperidin-3-yl)-3-(pyridin-4-yl)pyrazolo[1,5-a]pyrimidine |
| 74 | 6-Methyl-7-(1-(pyridin-2-ylmethyl)piperidin-3-yl)-3-(pyridin-4-yl)pyrazolo[1,5-a]pyrimidine |
| 75 | 2-Methyl-7-(1-(2-methylbenzyl)piperidin-3-yl)-3-(pyridin-4-yl)pyrazolo[1,5-a]pyrimidine |
| 76 | 2-Methyl-7-(1-(4-methylbenzyl)piperidin-3-yl)-3-(pyridin-4-yl)pyrazolo[1,5-a]pyrimidine |
| 77 | 2-Methyl-7-(1-(3-methylbenzyl)piperidin-3-yl)-3-(pyridin-4-yl)pyrazolo[1,5-a]pyrimidine |
| 78 | 7-(1-Benzylpiperidin-3-yl)-2-(pyrrolidin-1-yl)pyrazolo[1,5-a]pyrimidine |
| 79 | 2-((7-(1-Benzylpiperidin-3-yl)pyrazolo[1,5-a]pyrimidin-2-yl)(methyl)amino)ethanol |
| 80 | $N^1$-(7-(1-Benzylpiperidin-3-yl)pyrazolo[1,5-a]pyrimidin-2-yl)-$N^1$-methylethane-1,2-diamine |
| 81 | $N^1$-(7-(1-Benzylpiperidin-3-yl)pyrazolo[1,5-a]pyrimidin-2-yl)-$N^1$ , $N^2$-dimethylethane-1,2-diamine |
| 82 | 7-(1-Benzylpiperidin-3-yl)-N-methyl-N-(piperidin-4-yl)pyrazolo[1,5-a]pyrimidin-2-amine |
| 83 | $N^1$-(7-(1-Benzylpiperidin-3-yl)pyrazolo[1,5-a]pyrimidin-2-yl)-$N^2$-methylethane-1,2-diamine |
| 84 | (R)-1-(7-((R)-1-Benzylpiperidin-3-yl)pyrazolo[1,5-a]pyrimidin-2-yl)-N-methylpyrrolidin-3-amine |
| 85 | (S)-1-(7-((S)-1-Benzylpiperidin-3-yl)pyrazolo[1,5-a]pyrimidin-2-yl)-N-methylpyrrolidin-3-amine |
| 86 | (S)-1-(7-((R)-1-Benzylpiperidin-3-yl)pyrazolo[1,5-a]pyrimidin-2-yl)-N-methylpyrrolidin-3-amine |
| 87 | (R)-1-(7-((S)-1-Benzylpiperidin-3-yl)pyrazolo[1,5-a]pyrimidin-2-yl)-N-methylpyrrolidin-3-amine |
| 88 | 7-(1-Benzylpiperidin-3-yl)-3-(pyrrolidin-1-yl)pyrazolo[1,5-a]pyrimidine |
| 89 | 7-(1-Benzylpiperidin-3-yl)-2-methyl-3-(pyrrolidin-1-yl)pyrazolo[1,5-a]pyrimidine |
| 90 | 7-(1-Benzylpiperidin-3-yl)-2-methylpyrazolo[1,5-a]pyrimidin-3-amine |
| 91 | 7-(1-Benzylpiperidin-3-yl)pyrazolo[1,5-a]pyrimidine-2-carbonitrile |
| 92 | 1-(7-(1-Benzylpiperidin-3-yl)pyrazolo[1,5-a]pyrimidin-2-yl)-N,N-dimethylmethanamine |
| 93 | 1-(7-(1-Benzylpiperidin-3-yl)pyrazolo[1,5-a]pyrimidin-2-yl)-N-methylmethanamine |
| 94 | N-Benzyl-1-(7-(1-benzylpiperidin-3-yl)pyrazolo[1,5-a]pyrimidin-2-yl)methanamine |
| 95 | (7-(1-Benzylpiperidin-3-yl)-2-methylpyrazolo[1,5-a]pyrimidin-3-yl)methanol |
| 96 | 1-(7-(1-Benzylpiperidin-3-yl)-2-methylpyrazolo[1,5-a]pyrimidin-3-yl)-N-methylmethanamine |
| 97 | N-((7-(1-Benzylpiperidin-3-yl)-2-methylpyrazolo[1,5-a]pyrimidin-3-yl)methyl)-2-phenylethanamine |
| 98 | N-Benzyl-1-(7-(1-benzylpiperidin-3-yl)-2-methylpyrazolo[1,5-a]pyrimidin-3-yl)methanamine |
| 99 | (7-(1-Benzylpiperidin-3-yl)-2-methylpyrazolo[1,5-a]pyrimidin-3-yl)methanamine |
| 100 | 7-(1-Benzylpiperidin-3-yl)-2-methyl-3-(piperazin-1-ylmethyl)pyrazolo[1,5-a]pyrimidine |
| 101 | 3-((Benzyloxy)methyl)-7-(1-benzylpiperidin-3-yl)-2-methylpyrazolo[1,5-a]pyrimidine |
| 102 | 7-(1-Benzylpiperidin-3-yl)-2-methyl-3-(phenoxymethyl)pyrazolo[1,5-a]pyrimidine |
| 103 | 3-(7-(1-Benzylpiperidin-3-yl)-2-methylpyrazolo[1,5-a]pyrimidin-3-yl)propan-1-amine |
| 104 | 7-(1-Benzylpiperidin-3-yl)pyrazolo[1,5-a]pyrimidin-2-ol |
| 105 | 7-(1-Benzylpiperidin-3-yl)-3-bromopyrazolo[1,5-a]pyrimidin-2-ol |
| 106 | (S)-2-((R)-3-(2-Methyl-3-(pyridin-4-yl)pyrazolo[1,5-a]pyrimidin-7-yl)piperidin-1-yl)-2-phenylethanol |
| 107 | (S)-2-((S)-3-(2-methyl-3-(pyridin-4-yl)pyrazolo[1,5-a]pyrimidin-7-yl)piperidin-1-yl)-2-phenylethanol |
| 108 | (R)-2-((S)-3-(2-Methyl-3-(pyridin-4-yl)pyrazolo[1,5-a]pyrimidin-7-yl)piperidin-1-yl)-2-phenylethanol |
| 109 | (R)-2-((R)-3-(2-Methyl-3-(pyridin-4-yl)pyrazolo[1,5-a]pyrimidin-7-yl)piperidin-1-yl)-2-phenylethanol |
| 110 | 2-Bromo-7-(1-(4-chlorobenzyl)piperidin-3-yl)pyrazolo[1,5-a]pyrimidine |
| 111 | 2-Bromo-7-(1-(3-chlorobenzyl)piperidin-3-yl)pyrazolo[1,5-a]pyrimidine |
| 112 | 2-Bromo-7-(1-(3,4-dichlorobenzyl)piperidin-3-yl)pyrazolo[1,5-a]pyrimidine |
| 113 | 2-Bromo-7-(1-(3,4-difluorobenzyl)piperidin-3-yl)pyrazolo[1,5-a]pyrimidine |
| 114 | 7-(1-(4-Chlorobenzyl)piperidin-3-yl)-2-(2-methoxypyridin-3-yl)pyrazolo[1,5-a]pyrimidine |
| 115 | 3-(7-(1-(4-Chlorobenzyl)piperidin-3-yl)pyrazolo[1,5-a]pyrimidin-2-yl)pyridin-2-ol |
| 116 | 7-(1-(3-Chlorobenzyl)piperidin-3-yl)-2-(2-methoxypyridin-3-yl)pyrazolo[1,5-a]pyrimidine |
| 117 | 3-(7-(1-(3-Chlorobenzyl)piperidin-3-yl)pyrazolo[1,5-a]pyrimidin-2-yl)pyridin-2-ol |
| 118 | 7-(1-(3,4-Dichlorobenzyl)piperidin-3-yl)-2-(2-methoxypyridin-3-yl)pyrazolo[1,5-a]pyrimidine |
| 119 | 7-(1-(3,4-Difluorobenzyl)piperidin-3-yl)-2-(2-methoxypyridin-3-yl)pyrazolo[1,5-a]pyrimidine |
| 120 | 1-(2-Bromo-7-(1-(4-chlorobenzyl)piperidin-3-yl)pyrazolo[1,5-a]pyrimidin-3-yl)-N-((tetrahydro-2H-pyran-4-yl)methyl)methanamine |
| 121 | 7-(1-(4-Chlorobenzyl)piperidin-3-yl)-2-methyl-3-(pyridin-4-yl)pyrazolo[1,5-a]pyrimidine |
| 122 | 7-(1-(3-Chlorobenzyl)piperidin-3-yl)-2-methyl-3-(pyridin-4-yl)pyrazolo[1,5-a]pyrimidine |
| 123 | 7-(1-(3,4-Dichlorobenzyl)piperidin-3-yl)-2-methyl-3-(pyridin-4-yl)pyrazolo[1,5-a]pyrimidine |
| 124 | 7-(1-(2,4-Dichlorobenzyl)piperidin-3-yl)-2-methyl-3-(pyridin-4-yl)pyrazolo[1,5-a]pyrimidine |
| 125 | 7-(1-(3,4-Difluorobenzyl)piperidin-3-yl)-2-methyl-3-(pyridin-4-yl)pyrazolo[1,5-a]pyrimidine |
| 126 | 2-Methyl-3-(pyridin-4-yl)-7-(1-(4-(trifluoromethyl)benzyl)piperidin-3-yl)pyrazolo[1,5-a]pyrimidine |

-continued

| EX | CHEMICAL NAME |
|---|---|
| 127 | 7-(1-Isopentylpiperidin-3-yl)-2-methyl-3-(pyridin-4-yl)pyrazolo[1,5-a]pyrimidine |
| 128 | 3-(7-(1-(4-Chlorobenzyl)piperidin-3-yl)-2-methylpyrazolo[1,5-a]pyrimidin-3-yl)-N,N-dimethylbenzamide |
| 129 | 4-(7-(1-(4-Chlorobenzyl)piperidin-3-yl)-2-methylpyrazolo[1,5-a]pyrimidin-3-yl)benzamide |
| 130 | 7-(1-(4-Chlorobenzyl)piperidin-3-yl)-2-methyl-3-(pyrimidin-5-yl)pyrazolo[1,5-a]pyrimidine |
| 131 | 5-(7-(1-(4-Chlorobenzyl)piperidin-3-yl)-2-methylpyrazolo[1,5-a]pyrimidin-3-yl)pyrimidin-2-amine |
| 132 | 7-(1-(4-Chlorobenzyl)piperidin-3-yl)-2-methyl-3-(1-methyl-1H-pyrazol-4-yl)pyrazolo[1,5-a]pyrimidine |
| 133 | 4-(7-(1-(4-Chlorobenzyl)piperidin-3-yl)-2-methylpyrazolo[1,5-a]pyrimidin-3-yl)-3,5-dimethylisoxazole |
| 134 | (4-(7-(1-(4-Chlorobenzyl)piperidin-3-yl)-2-methylpyrazolo[1,5-a]pyrimidin-3-yl)pyridin-2-yl)methanol |
| 135 | (5-(7-(1-(4-Chlorobenzyl)piperidin-3-yl)-2-methylpyrazolo[1,5-a]pyrimidin-3-yl)pyridin-2-yl)methanol |
| 136 | 7-(1-(4-Chlorobenzyl)piperidin-3-yl)-3-(2-ethoxypyridin-4-yl)-2-methylpyrazolo[1,5-alpyrimidine |
| 137 | 7-(1-(4-Chlorobenzyl)piperidin-3-yl)-3-(2-(cyclopropylmethoxy)pyridin-4-yl)-2-methylpyrazolo[1,5-a]pyrimidine |
| 138 | 7-(1-(4-Chlorobenzyl)piperidin-3-yl)-2-methyl-3-(1-methyl-1H-imidazol-5-yl)pyrazolo[1,5-a]pyrimidine |
| 139 | 7-(1-(4-Chlorobenzyl)piperidin-3-yl)-2-methyl-3-(pyrimidin-4-yl)pyrazolo[1,5-a]pyrimidine |
| 140 | 4-(7-(1-(4-Chlorobenzyl)piperidin-3-yl)-2-methylpyrazolo[1,5-a]pyrimidin-3-yl)pyrimidin-2-amine |
| 141 | 7-(1-(4-Chlorobenzyl)piperidin-3-yl)-N,N,2-trimethylpyrazolo[1,5-a]pyrimidin-3-amine |
| 142 | 7-(1-Benzylpiperidin-3-yl)-N,N,2-trimethylpyrazolo[1,5-a]pyrimidin-3-amine |
| 143 | N-Benzyl-7-(1-benzylpiperidin-3-yl)-N,2-dimethylpyrazolo[1,5-a]pyrimidin-3-amine |
| 144 | N-Benzyl-1-(7-(1-(4-chlorobenzyl)piperidin-3-yl)-2-methylpyrazolo[1,5-a]pyrimidin-3-yl)methanamine |
| 145 | N-Benzyl-1-(7-(1-(4-chlorobenzyl)piperidin-3-yl)-2-methylpyrazolo[1,5-a]pyrimidin-3-yl)-N-methylmethanamine |
| 146 | 1-(7-(1-(4-Chlorobenzyl)piperidin-3-yl)-2-methylpyrazolo[1,5-a]pyrimidin-3-yl)-N-(4-fluorobenzyl)methanamine |
| 147 | (4-((((7-(1-(4-Chlorobenzyl)piperidin-3-yl)-2-methylpyrazolo[1,5-a]pyrimidin-3-yl)methyl)amino)methyl)phenyl)methanol |
| 148 | 1-(7-(1-(4-Chlorobenzyl)piperidin-3-yl)-2-methylpyrazolo[1,5-a]pyrimidin-3-yl)-N-(pyridin-4-ylmethyl)methanamine |
| 149 | 1-(7-(1-(4-Chlorobenzyl)piperidin-3-yl)-2-methylpyrazolo[1,5-a]pyrimidin-3-yl)-N-(thiophen-2-ylmethyl)methanamine |
| 150 | 1-(7-(1-(4-Chlorobenzyl)piperidin-3-yl)-2-methylpyrazolo[1,5-a]pyrimidin-3-yl)-N-((5-methylthiophen-2-yl)methyl)methanamine |
| 151 | 1-(7-(1-(4-Chlorobenzyl)piperidin-3-yl)-2-methylpyrazolo[1,5-a]pyrimidin-3-yl)-N-((1-methyl-1H-pyrazol-3-yl)methyl)methanamine |
| 152 | 1-(7-(1-(4-Chlorobenzyl)piperidin-3-yl)-2-methylpyrazolo[1,5-a]pyrimidin-3-yl)-N-((5-methyl-1,3,4-oxadiazol-2-yl)methyl)methanamine |
| 153 | N-((7-(1-(4-Chlorobenzyl)piperidin-3-yl)-2-methylpyrazolo[1,5-a]pyrimidin-3-yl)methyl)-2-phenylethan-1-amine |
| 154 | N-((7-(1-(4-Chlorobenzyl)piperidin-3-yl)-2-methylpyrazolo[1,5-a]pyrimidin-3-yl)methyl)-2-(4-methoxyphenyl)ethan-1-amine |
| 155 | N-((7-(1-(4-Chlorobenzyl)piperidin-3-yl)-2-methylpyrazolo[1,5-a]pyrimidin-3-yl)methyl)ethanamine |
| 156 | N-((7-(1-(4-Chlorobenzyl)piperidin-3-yl)-2-methylpyrazolo[1,5-a]pyrimidin-3-yl)methyl)-2,2,2-trifluoroethan-1-amine |
| 157 | 1-(7-(1-(4-Chlorobenzyl)piperidin-3-yl)-2-methylpyrazolo[1,5-a]pyrimidin-3-yl)-N-(cyclopropylmethyl)methanamine |
| 158 | 2-(((7-(1-(4-Chlorobenzyl)piperidin-3-yl)-2-methylpyrazolo[1,5-a]pyrimidin-3-yl)methyl)amino)ethan-1-ol |
| 159 | N-((7-(1-(4-Chlorobenzyl)piperidin-3-yl)-2-methylpyrazolo[1,5-a]pyrimidin-3-yl)methyl)propan-2-amine |
| 160 | N-((7-(1-(4-Chlorobenzyl)piperidin-3-yl)-2-methylpyrazolo[1,5-a]pyrimidin-3-yl)methyl)-2-methylpropan-1-amine |
| 161 | N-((7-(1-(4-Chlorobenzyl)piperidin-3-yl)-2-methylpyrazolo[1,5-a]pyrimidin-3-yl)methyl)-3-methylbutan-1-amine |
| 162 | N-((7-(1-(4-Chlorobenzyl)piperidin-3-yl)-2-methylpyrazolo[1,5-a]pyrimidin-3-yl)methyl)-2-isopropoxyethan-1-amine |
| 163 | N-((7-(1-(4-Chlorobenzyl)piperidin-3-yl)-2-methylpyrazolo[1,5-a]pyrimidin-3-yl)methyl)-4-methoxybutan-1-amine |
| 164 | (2S,6R)-4-((7-(1-(4-Chlorobenzyl)piperidin-3-yl)-2-methylpyrazolo[1,5-a]pyrimidin-3-yl)methyl)-2,6-dimethylmorpholine |
| 165 | 4-((7-(1-(4-Chlorobenzyl)piperidin-3-yl)-2-methylpyrazolo[1,5-a]pyrimidin-3-yl)methyl)morpholine |
| 166 | N-((7-(1-(4-Chlorobenzyl)piperidin-3-yl)-2-methylpyrazolo[1,5-a]pyrimidin-3-yl)methyl)-2-morpholinoethan-1-amine |

-continued

| EX | CHEMICAL NAME |
|---|---|
| 167 | 4-((7-(1-(4-Chlorobenzyl)piperidin-3-yl)-2-methylpyrazolo[1,5-a]pyrimidin-3-yl)methyl)thiomorpholine |
| 168 | 4-((7-(1-(4-Chlorobenzyl)piperidin-3-yl)-2-methylpyrazolo[1,5-a]pyrimidin-3-yl)methyl)thiomorpholine 1,1-dioxide |
| 169 | 7-(1-(4-Chlorobenzyl)piperidin-3-yl)-2-methyl-3-(piperidin-1-ylmethyl)pyrazolo[1,5-a]pyrimidine |
| 170 | 7-(1-(4-Chlorobenzyl)piperidin-3-yl)-3-((4-(methoxymethyl)piperidin-1-yl)methyl)-2-methylpyrazolo[1,5-a]pyrimidine |
| 171 | 1-((7-(1-(4-Chlorobenzyl)piperidin-3-yl)-2-methylpyrazolo[1,5-a]pyrimidin-3-yl)methyl)piperidine-4-carboxamide |
| 172 | 1-((7-(1-(4-Chlorobenzyl)piperidin-3-yl)-2-methylpyrazolo[1,5-a]pyrimidin-3-yl)methyl)piperidine-4-carbonitrile |
| 173 | 4-((7-(1-(4-Chlorobenzyl)piperidin-3-yl)-2-methylpyrazolo[1,5-a]pyrimidin-3-yl)methyl)piperazin-2-one |
| 174 | 1-(4-((7-(1-(4-Chlorobenzyl)piperidin-3-yl)-2-methylpyrazolo[1,5-a]pyrimidin-3-yl)methyl)piperazin-1-yl)ethan-1-one |
| 175 | 7-(1-(4-Chlorobenzyl)piperidin-3-yl)-2-methyl-3-((4-(methylsulfonyl)piperazin-1-yl)methyl)pyrazolo[1,5-a]pyrimidine |
| 176 | 1-(3-(((7-(1-(4-Chlorobenzyl)piperidin-3-yl)-2-methylpyrazolo[1,5-a]pyrimidin-3-yl)methyl)amino)propyl)pyrrolidin-2-one |
| 177 | 1-(7-(1-(4-Chlorobenzyl)piperidin-3-yl)-2-methylpyrazolo[1,5-a]pyrimidin-3-yl)-N-((4-fluorotetrahydro-2H-pyran-4-yl)methyl)methanamine |
| 178 | N-((7-(1-(4-Chlorobenzyl)piperidin-3-yl)-2-methylpyrazolo[1,5-a]pyrimidin-3-yl)methyl)-2-(tetrahydro-2H-pyran-4-yl)ethan-1-amine |
| 179 | 1-(7-(1-(4-Chlorobenzyl)piperidin-3-yl)-2-methylpyrazolo[1,5-a]pyrimidin-3-yl)-N-((1-(methylsulfonyl)piperidin-4-yl)methyl)methanamine |
| 180 | 1-(4-((((7-(1-Benzylpiperidin-3-yl)-2-methylpyrazolo[1,5-a]pyrimidin-3-yl)methyl)amino)methyl)piperidin-1-yl)ethan-1-one |
| 181 | 1-(7-(1-(3-Fluorobenzyl)piperidin-3-yl)-2-methylpyrazolo[1,5-a]pyrimidin-3-yl)-N-((tetrahydro-2H-pyran-4-yl)methyl)methanamine |
| 182 | 1-(7-(1-(3,4-Difluorobenzyl)piperidin-3-yl)-2-methylpyrazolo[1,5-a]pyrimidin-3-yl)-N-((tetrahydro-2H-pyran-4-yl)methyl)methanamine |
| 183 | 4-((3-(2-Methyl-3-((((tetrahydro-2H-pyran-4-yl)methyl)amino)methyl)pyrazolo[1,5-a]pyrimidin-7-yl)piperidin-1-yl)methyl)benzonitrile |
| 184 | 1-(2-Methyl-7-(1-((6-(trifluoromethyl)pyridin-3-yl)methyl)piperidin-3-yl)pyrazolo[1,5-a]pyrimidin-3-yl)-N-((tetrahydro-2H-pyran-4-yl)methyl)methanamine |
| 185 | 1-(2-Methyl-7-(1-((tetrahydro-2H-pyran-4-yl)methyl)piperidin-3-yl)pyrazolo[1,5-a]pyrimidin-3-yl)-N-((tetrahydro-2H-pyran-4-yl)methyl)methanamine |
| 186 | 1-(7-(1-(2,4-Dichlorobenzyl)piperidin-3-yl)-2-methylpyrazolo[1,5-a]pyrimidin-3-yl)-N,N-dimethylmethanamine |
| 187 | 1-(7-(1-(4-Chlorobenzyl)piperidin-3-yl)-2-ethylpyrazolo[1,5-a]pyrimidin-3-yl)-N-((tetrahydro-2H-pyran-4-yl)methyl)methanamine |
| 188 | 1-(7-(1-(4-Chlorobenzyl)piperidin-3-yl)-2-cyclopropylpyrazolo[1,5-a]pyrimidin-3-yl)-N-((tetrahydro-2H-pyran-4-yl)methyl)methanamine |
| 189 | 1-(7-(1-(4-Chlorobenzyl)piperidin-3-yl)-2-methoxypyrazolo[1,5-a]pyrimidin-3-yl)-N-((tetrahydro-2H-pyran-4-yl)methyl)methanamine |
| 190 | 1-(2-Chloro-7-(1-(4-chlorobenzyl)piperidin-3-yl)pyrazolo[1,5-a]pyrimidin-3-yl)-N-((tetrahydro-2H-pyran-4-yl)methyl)methanamine |
| 191 | 1-(2-Chloro-7-(1-isopentylpiperidin-3-yl)pyrazolo[1,5-a]pyrimidin-3-yl)-N-((tetrahydro-2H-pyran-4-yl)methyl)methanamine |
| 192 | 1-(4-((((2-Chloro-7-(1-isopentylpiperidin-3-yl)pyrazolo[1,5-a]pyrimidin-3-yl)methyl)amino)methyl)piperidin-1-yl)ethan-1-one |
| 193 | (S)-1-(4-((((7-(1-(4-Chlorobenzyl)piperidin-3-yl)-2-methylpyrazolo[1,5-a]pyrimidin-3-yl)methyl)amino)methyl)piperidin-1-yl)ethan-1-one |
| 194 | (R)-1-(4-((((7-(1-(4-chlorobenzyl)piperidin-3-yl)-2-methylpyrazolo[1,5-a]pyrimidin-3-yl)methyl)amino)methyl)piperidin-1-yl)ethan-1-one |
| 195 | (R)-N-((7-((R)-1-(4-Chlorobenzyl)piperidin-3-yl)-2-methylpyrazolo[1,5-a]pyrimidin-3-yl)methyl)-1-phenylethan-1-amine |
| 196 | (R)-N-((7-((S)-1-(4-Chlorobenzyl)piperidin-3-yl)-2-methylpyrazolo[1,5-a]pyrimidin-3-yl)methyl)-1-phenylethan-1-amine |
| 197 | (S)-N-((7-((R)-1-(4-Chlorobenzyl)piperidin-3-yl)-2-methylpyrazolo[1,5-a]pyrimidin-3-yl)methyl)-1-phenylethan-1-amine |
| 198 | (S)-N-((7-((S)-1-(4-Chlorobenzyl)piperidin-3-yl)-2-methylpyrazolo[1,5-a]pyrimidin-3-yl)methyl)-1-phenylethan-1-amine |
| 199 | (S)-1-(7-(1-(4-Chlorobenzyl)piperidin-3-yl)-2-methylpyrazolo[1,5-a]pyrimidin-3-yl)-N-((tetrahydro-2H-pyran-4-yl)methyl)methanamine |
| 200 | (R)-1-(7-(1-(4-Chlorobenzyl)piperidin-3-yl)-2-methylpyrazolo[1,5-a]pyrimidin-3-yl)-N-((tetrahydro-2H-pyran-4-yl)methyl)methanamine |
| 201 | (+/−)-1-(7-((R/S)-1-(4-Chlorobenzyl)piperidin-3-yl)-2-methylpyrazolo[1,5-a]pyrimidin-3-yl)-N-(((S/R)-tetrahydrofuran-3-yl)methyl)methanamine |
| 202 | 1-(7-((R)-1-(4-Chlorobenzyl)piperidin-3-yl)-2-methylpyrazolo[1,5-a]pyrimidin-3-yl)-N-(((R)-tetrahydrofuran-3-yl)methyl)methanamine |
| 203 | 1-(7-((S)-1-(4-Chlorobenzyl)piperidin-3-yl)-2-methylpyrazolo[1,5-a]pyrimidin-3-yl)-N-(((S)-tetrahydrofuran-3-yl)methyl)methanamine |
| 204 | (S)-1-(7-(1-Benzylpiperidin-3-yl)-2-methylpyrazolo[1,5-a]pyrimidin-3-yl)-N-((tetrahydro-2H-pyran-4-yl)methyl)methanamine |

-continued

| EX | CHEMICAL NAME |
|---|---|
| 205 | (R)-1-(7-(1-Benzylpiperidin-3-yl)-2-methylpyrazolo[1,5-a]pyrimidin-3-yl)-N-((tetrahydro-2H-pyran-4-yl)methyl)methanamine |
| 206 | (S)-1-(7-(1-(4-Fluorobenzyl)piperidin-3-yl)-2-methylpyrazolo[1,5-a]pyrimidin-3-yl)-N-((tetrahydro-2H-pyran-4-yl)methyl)methanamine |
| 207 | (R)-1-(7-(1-(4-Fluorobenzyl)piperidin-3-yl)-2-methylpyrazolo[1,5-a]pyrimidin-3-yl)-N-((tetrahydro-2H-pyran-4-yl)methyl)methanamine |
| 208 | (S)-3-((3-(2-Methyl-3-((((tetrahydro-2H-pyran-4-yl)methyl)amino)methyl)pyrazolo[1,5-a]pyrimidin-7-yl)piperidin-1-yl)methyl)benzonitrile |
| 209 | (R)-3-((3-(2-Methyl-3-((((tetrahydro-2H-pyran-4-yl)methyl)amino)methyl)pyrazolo[1,5-alpyrimidin-7-yl)piperidin-1-yl)methyl)benzonitrile |
| 210 | (S)-1-(7-(1-(4-Chlorobenzyl)piperidin-3-yl)-2-methylpyrazolo[1,5-a]pyrimidin-3-yl)-N,N-dimethylmethanamine |
| 211 | (R)-1-(7-(1-(4-Chlorobenzyl)piperidin-3-yl)-2-methylpyrazolo[1,5-a]pyrimidin-3-yl)-N,N-dimethylmethanamine |
| 212 | (R)-1-(7-(1-(4-Chlorobenzyl)piperidin-3-yl)-2-methylpyrazolo[1,5-a]pyrimidin-3-yl)-N-methylmethanamine |
| 213 | (S)-1-(7-(1-(4-Chlorobenzyl)piperidin-3-yl)-2-methylpyrazolo[1,5-a]pyrimidin-3-yl)-N-methylmethanamine |
| 214 | ((S)-1-(7-(1-Benzylpiperidin-3-yl)-2-chloropyrazolo[1,5-a]pyrimidin-3-yl)-N-((tetrahydro-2H-pyran-4-yl)methyl)methanamine |
| 215 | ((R)-1-(7-(1-Benzylpiperidin-3-yl)-2-chloropyrazolo[1,5-a]pyrimidin-3-yl)-N-((tetrahydro-2H-pyran-4-yl)methyl)methanamine |
| 216 | (S)-1-(4-((((7-(1-Benzylpiperidin-3-yl)-2-chloropyrazolo[1,5-a]pyrimidin-3-yl)methyl)amino)methyl)piperidin-1-yl)ethan-1-one |
| 217 | (R)-1-(4-((((7-(1-benzylpiperidin-3-yl)-2-chloropyrazolo[1,5-a]pyrimidin-3-yl)methyl)amino)methyl)piperidin-1-yl)ethan-1-one |
| 218 | 4-((((7-(1-(4-Chlorobenzyl)piperidin-3-yl)-2-methylpyrazolo[1,5-a]pyrimidin-3-yl)methyl)amino)methyl)piperidine-1-carboxamide |
| 219 | (7-(1-(4-Chlorobenzyl)piperidin-3-yl)-2-methylpyrazolo[1,5-a]pyrimidin-3-yl)methanamine |
| 220 | 1-(7-(1-Benzylpiperidin-3-yl)-2-methylpyrazolo[1,5-a]pyrimidin-3-yl)-N-(((2R,6S)-2,6-dimethyltetrahydro-2H-pyran-4-yl)methyl)methanamine |
| 221 | (+/−)-1-(7-((R/S)-1-(4-Chlorobenzyl)piperidin-3-yl)-2-methylpyrazolo[1,5-a]pyrimidin-3-yl)-N-(((R/S)-2,2-dimethyltetrahydro-2H-pyran-4-yl)methyl)methanamine |
| 222 | (1-(7-((R)-1-(4-Chlorobenzyl)piperidin-3-yl)-2-methylpyrazolo[1,5-a]pyrimidin-3-yl)-N-(((S)-2,2-dimethyltetrahydro-2H-pyran-4-yl)methyl)methanamine |
| 223 | (1-(7-((S)-1-(4-Chlorobenzyl)piperidin-3-yl)-2-methylpyrazolo[1,5-a]pyrimidin-3-yl)-N-(((R)-2,2-dimethyltetrahydro-2H-pyran-4-yl)methyl)methanamine |
| 224 | (+/−)-(R/S)-N-((7-((R/S)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine |
| 225 | (S)-N-((7-((R)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine |
| 226 | (R)-N-((7-((S)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine |
| 227 | (R)-1-(7-(1-(4-Chlorobenzyl)piperidin-3-yl)-2-methylpyrazolo[1,5-a]pyrimidin-3-yl)-N-(cyclopropylmethyl)-N-methylmethanamine |
| 228 | (S)-1-(7-(1-(4-Chlorobenzyl)piperidin-3-yl)-2-methylpyrazolo[1,5-a]pyrimidin-3-yl)-N-(cyclopropylmethyl)-N-methylmethanamine |
| 229 | 1-(7-(1-(4-Chlorobenzyl)piperidin-3-yl)-2-methylpyrazolo[1,5-a]pyrimidin-3-yl)-N-(2,6-difluorobenzyl)-N-methylmethanamine |
| 230 | (4-((((7-(1-(4-Chlorobenzyl)piperidin-3-yl)-2-methylpyrazolo[1,5-a]pyrimidin-3-yl)methyl)(methyl)amino)methyl)phenyl)methanol |
| 231 | 1-(7-(1-(4-Chlorobenzyl)piperidin-3-yl)-2-methylpyrazolo[1,5-a]pyrimidin-3-yl)-N-methyl-N-((tetrahydro-2H-pyran-4-yl)methyl)methanamine |
| 232 | N-((7-(1-(4-Chlorobenzyl)piperidin-3-yl)-2-methylpyrazolo[1,5-a]pyrimidin-3-yl)methyl)-N-((tetrahydro-2H-pyran-4-yl)methyl)propan-2-amine |
| 233 | N-((7-(1-Benzylpiperidin-3-yl)-2-methylpyrazolo[1,5-a]pyrimidin-3-yl)methyl)-N-(((2R,6S)-2,6-dimethyltetrahydro-2H-pyran-4-yl)methyl)propan-2-amine |
| 234 | 1-(7-(1-Benzylpiperidin-3-yl)-2-methylpyrazolo[1,5-a]pyrimidin-3-yl)-N-(cyclopropyl-methyl)-N-methylmethanamine |
| 235 | N-((7-(1-(4-Chlorobenzyl)piperidin-3-yl)-2-methylpyrazolo[1,5-a]pyrimidin-3-yl)methyl)-2,2,2-trifluoro-N-((tetrahydro-2H-pyran-4-yl)methyl)ethan-1-amine |
| 236 | 2-(7-(1-(4-Chlorobenzyl)piperidin-3-yl)-2-methylpyrazolo[1,5-a]pyrimidin-3-yl)-N,N-dimethylethan-1-amine |
| 237 | 1-(7-(1-(4-Chlorobenzyl)piperidin-3-yl)-2,6-dimethylpyrazolo[1,5-a]pyrimidin-3-yl)-N-((tetrahydro-2H-pyran-4-yl)methyl)methanamine |
| 238 | 1-(7-(1-(4-Chlorobenzyl)piperidin-3-yl)-2,5-dimethylpyrazolo[1,5-a]pyrimidin-3-yl)-N-((tetrahydro-2H-pyran-4-yl)methyl)methanamine |
| 239 | (S)-1-(7-(1-(2-Fluorobenzyl)piperidin-3-yl)-2-methylpyrazolo[1,5-a]pyrimidin-3-yl)-N-((tetrahydro-2H-pyran-4-yl)methyl)methanamine |
| 240 | (S)-1-(7-(1-(2,4-Difluorobenzyl)piperidin-3-yl)-2-methylpyrazolo[1,5-a]pyrimidin-3-yl)-N-((tetrahydro-2H-pyran-4-yl)methyl)methanamine |
| 241 | (S)-1-(7-(1-(3,5-Difluorobenzyl)piperidin-3-yl)-2-methylpyrazolo[1,5-a]pyrimidin-3-yl)-N-((tetrahydro-2H-pyran-4-yl)methyl)methanamine |

-continued

| EX | CHEMICAL NAME |
|---|---|
| 242 | 1-(7-(1-(4-Methoxybenzyl)piperidin-3-yl)-2-methylpyrazolo[1,5-a]pyrimidin-3-yl)-N-((tetrahydro-2H-pyran-4-yl)methyl)methanamine |
| 243 | (R)-4-((((7-((S)-1-Benzylpiperidin-3-yl)-2-methylpyrazolo[1,5-a]pyrimidin-3-yl)methyl)amino)methyl)-1-methylpiperidin-2-one |
| 244 | (S)-4-((((7-((S)-1-Benzylpiperidin-3-yl)-2-methylpyrazolo[1,5-a]pyrimidin-3-yl)methyl)amino)methyl)-1-methylpiperidin-2-one |
| 245 | (R)-5-((((7-((S)-1-Benzylpiperidin-3-yl)-2-methylpyrazolo[1,5-a]pyrimidin-3-yl)methyl)amino)methyl)piperidin-2-one |
| 246 | (S)-5-((((7-((S)-1-Benzylpiperidin-3-yl)-2-methylpyrazolo[1,5-a]pyrimidin-3-yl)methyl)amino)methyl)piperidin-2-one |
| 247 | (S)-1-(4-((((7-(1-(3,4-Difluorobenzyl)piperidin-3-yl)-2-methylpyrazolo[1,5-a]pyrimidin-3-yl)methyl)amino)methyl)piperidin-1-yl)ethan-1-one |
| 248 | 1-(7-(1-Benzylpiperidin-3-yl)-2-methoxypyrazolo[1,5-a]pyrimidin-3-yl)-N-((tetrahydro-2H-pyran-4-yl)methyl)methanamine |
| 249 | 7-((1-(4-Chlorobenzyl)piperidin-3-yl)methyl)-2-methyl-3-(pyridin-4-yl)pyrazolo[1,5-a]pyrimidine |
| 250 | 7-((1-(3-Chlorobenzyl)piperidin-3-yl)methyl)-2-methyl-3-(pyridin-4-yl)pyrazolo[1,5-a]pyrimidine |
| 251 | 1-(7-((1-(4-Chlorobenzyl)piperidin-3-yl)methyl)-2-methylpyrazolo[1,5-a]pyrimidin-3-yl)-N,N-dimethylmethanamine |
| 252 | 1-(7-((1-(3-Chlorobenzyl)piperidin-3-yl)methyl)-2-methylpyrazolo[1,5-a]pyrimidin-3-yl)-N,N-dimethylmethanamine |
| 253 | 1-(7-(1-(4-Chlorobenzyl)azepan-3-yl)-2-methylpyrazolo[1,5-a]pyrimidin-3-yl)-N-((tetrahydro-2H-pyran-4-yl)methyl)methanamine |

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In the following the phrase "compound of the invention" is used. This is to be understood as any compound according to the invention as described above according to general Formulae (I), (I'), ($I^{2'}$), ($I^{2a'}$), ($I^{3'}$) or ($I^{3a'}$).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

For the sake of clarity the expression "a compound according to Formula (I), wherein e.g. $R_1$, $R_2$, $R_3$, $R_4$, $R_5$, $R_5'$, X, m, n and t are as defined below in the detailed description" would (just like the expression "a compound of Formula (I) as defined in any one of claims e.g. 1 to 8" found in the claims) refer to "a compound according to Formula (I)", wherein the definitions of the respective substituents $R_1$ etc. (also from the cited claims) are applied. In addition, this would also mean, though (especially in regards to the claims) that also one or more disclaimers or provisos defined in the description (or used in any of the cited claims like e.g. claim 1) would be applicable to define the respective compound. Thus, a disclaimer or a proviso found in e.g. claim 1 would be also used to define the compound "of Formula (I) as defined in any one of the corresponding related claims e.g. 1 to 8".

In general the processes are described below in the experimental part. The starting materials are commercially available or can be prepared by conventional methods.

A preferred embodiment of the invention is a process for the production of a compound according to Formula (I), wherein, if not defined otherwise, $R_1$, $R_2$, $R_3$, $R_4$, $R_5$, $R_5'$, X, m, n and t have the meanings defined in the description.

In a particular embodiment there is a process for the production of a compound according to Formula (I), said process comprises treating a compound of formula (VI) in which A is $-(CR_5R_5')_m-R_4$ and Y is an halogen atom,

VI

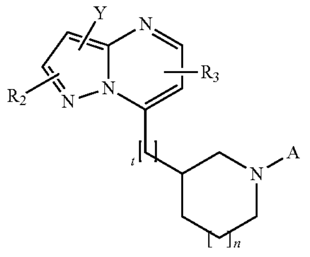

with a suitable boronic acid (or boronic ester) of formula (VII),

VII

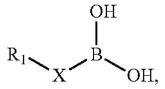

wherein $R_1$, $R_2$, $R_3$, $R_4$, $R_5$, $R_5'$, X, m, n and t have the meanings as defined in the description.

The reaction can be carried out in the presence of a suitable Pd catalyst, such as $Pd(PPh_3)_4$, with a suitable base, such as $K_2CO_3$ or $Na_2CO_3$, in a suitable solvent, such as mixtures of dimethoxyethane and water or mixtures of toluene, ethanol and water, at a suitable temperature, preferably heating. Alternatively, the reactions can be carried out under microwave heating.

In another particular embodiment there is a process for the production of a compound according to Formula (I), said process comprises alkylating a compound of formula (Ia) in which A is hydrogen, Ia

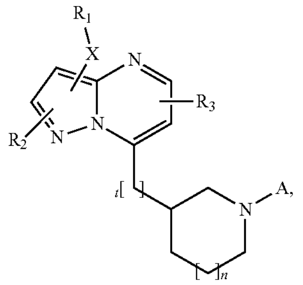

with a suitable alkylating reagent of formula XI,

Z-T XI wherein T is —$(CR_5R_5')_m$—$R_4$ and Z is a leaving group such as iodine, bromine, chlorine;

or alternatively by a reductive amination reaction with a suitable aldehyde of formula (XI), wherein Z is ═O;

wherein $R_1$, $R_2$, $R_3$, $R_4$, $R_5$, $R_5'$, X, m, n and t have the meanings as defined in the description.

In a particular embodiment there is a process for the production of a compound according to Formula (I), wherein $R_1$ is —$CH_2NR_6R_6'$, said process comprises reacting a compound of formula (VI) in which A is —$(CR_5R_5')_m$—$R_4$ and Y is an acid functionality,

VI

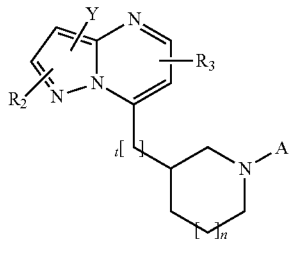

with a suitable amine of formula (IX)

IX

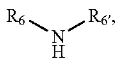

wherein and $R_2$, $R_3$, $R_4$, $R_5$, $R_5'$, $R_6$, $R_6'$, m, n and t have the meanings as defined in the description.

The reaction can be carried out in the presence of a suitable coupling agent, such as N-(3-dimethylaminopropyl)-N'-ethylcarbodiimide hydrochloride, in the presence of a base, such as triethylamine, in a suitable solvent, such as dimethylformamide, at a suitable temperature, preferably room temperature; followed by reduction using a suitable reducing agent, such as $AlH_3$, in a suitable solvent, such as tetrahydrofuran, at a suitable temperature, preferably between 0° C. and room temperature.

In a particular embodiment there is a process for the production of a compound according to Formula (I), wherein $R_1$ is —$CH_2NR_6R_6'$, said process comprises reacting a compound of formula (VI), in which A is —$(CR_5R_5')_m$—$R_4$ and Y is an halogen atom,

VI

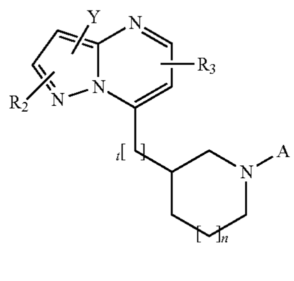

with a suitable potassium aminomethyltrifluoroborate salt of formula (X)

X

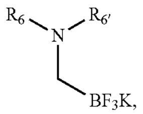

wherein $R_2$, $R_3$, $R_4$, $R_5$, $R_5'$, $R_6$, $R_6'$, m, n and t have the meanings as defined in the description.

The reaction can be carried out in the presence of a suitable Pd catalyst, such as allylpalladium(II) chloride dimer, with a suitable base, such as $K_3PO_4$, and a suitable phosphine ligand, such as dicyclohexyl(2',6'-dimethoxy-[1,1'-biphenyl]-2-yl)phosphine, in a suitable solvent, such as a mixture of dioxane and water, at a suitable temperature, preferably 100° C.

In a particular embodiment there is a process for the production of a compound according to Formula (I), wherein $R_1$ is —$CH_2NR_6R_6'$, said process comprises reacting a compound of formula (VIII) in which A is —$(CR_5R_5')_m$—$R_4$,

VIII

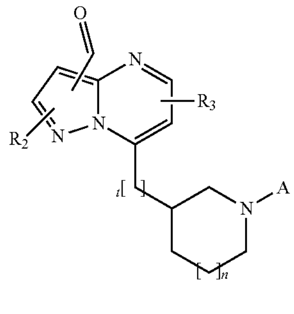

with a suitable amine of formula (IX)

IX

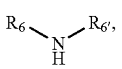

wherein $R_2$, $R_3$, $R_4$, $R_5$, $R_5'$, $R_6$, $R_6'$, m, n and t have the meanings as defined in the description.

The reaction can be carried out in the presence of a reducing reagent, such as sodium triacetoxyborohydride or sodium cyanoborohydride, in a suitable solvent, such as dichloromethane or methanol, optionally in the presence of an acid, preferably acetic acid, at a suitable temperature, preferably room temperature. Alternatively, the reactions can be carried out under microwave heating.

In a particular embodiment there is a process for the production of a compound according to Formula (I), wherein $R_1$ is —$CH_2NR_6R_6'$, said process comprises the alkylation of a derivative of Formula (Ib) in which A is hydrogen, Ib

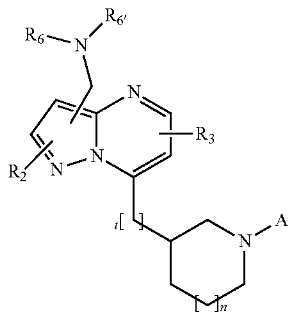

with a suitable alkylating reagent of formula (XI),

Z-T XI wherein T is —$(CR_5R_5')_m$—$R_4$ and Z is a leaving group such as iodine, bromine, chlorine;

or alternatively by a reductive amination reaction with a suitable aldehyde of formula XI, where Z is ═O;

wherein $R_2$, $R_3$, $R_4$, $R_5$, $R_5'$, $R_6$, $R_6'$, m, n and t have the meanings as defined in the description.

In a particular embodiment there is a process for the production of a compound according to Formula (I), said process comprises treating a compound of formula (VI) in which A is —$(CR_5R_5')_m$—$R_4$ and Y is an halogen atom,

VI

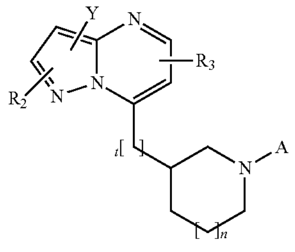

with a suitable boronic acid (or boronic ester) of formula (VII),

VII

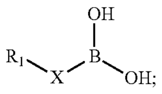

or said process comprises alkylating a compound of formula (Ia) in which A is hydrogen, Ia

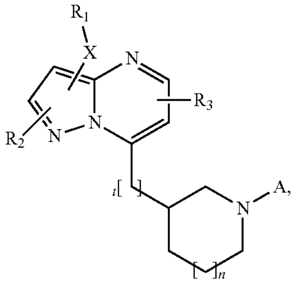

with a suitable alkylating reagent of formula (XI),

Z-T XI wherein T is —$(CR_5R_5')_m$—$R_4$ and Z is a leaving group such as iodine, bromine, chlorine;

or alternatively by a reductive amination reaction with a suitable aldehyde of formula XI, wherein Z is ═O;

and wherein $R_1$, $R_2$, $R_3$, $R_4$, $R_5$, $R_5'$, X, m, n and t have the meanings as defined in the description.

In a particular embodiment there is a process for the production of a compound according to Formula (I), wherein $R_1$ is —$CH_2NR_6R_6'$, said process comprises:

reacting a compound of formula (VI) in which A is —$(CR_5R_5')_m$—$R_4$ and Y is an acid functionality,

VI

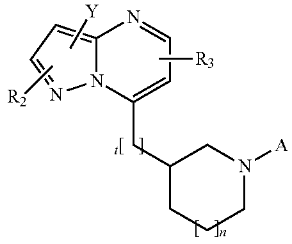

with a suitable amine of formula (IX)

IX

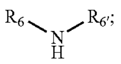

or reacting a compound of formula (VI), in which A is —$(CR_5R_5')_m$—$R_4$ and Y is an halogen atom,

VI

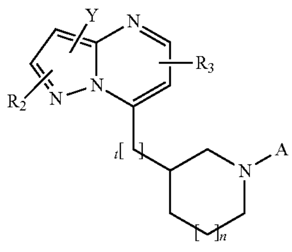

with a suitable potassium aminomethyltrifluoroborate salt of formula (X)

X

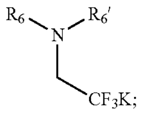

or reacting a compound of formula (VIII) in which A is $—(CR_5R_5')_m—R_4$,

VIII

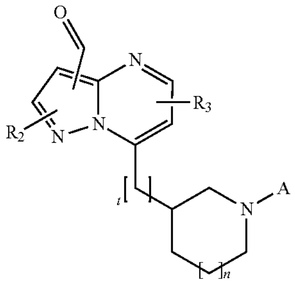

with a suitable amine of formula (IX)

IX

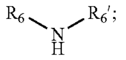

or alkylating a derivative of Formula (Ib) in which A is hydrogen,

Ib

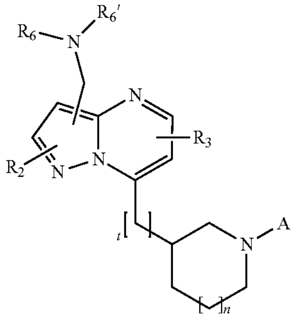

with a suitable alkylating reagent of formula (XI),

Z-T XI wherein T is $—(CR_5R_5')_m—R_4$ and Z is a leaving group such as iodine, bromine, chlorine;

or alternatively by a reductive amination reaction with a suitable aldehyde of formula (XI), where Z is =O;

wherein $R_2$, $R_3$, $R_4$, $R_5$, $R_5'$, $R_6$, $R_6'$, m, n and t have the meanings as defined in the description.

A particular embodiment of the invention refers to the use of a compound of Formula (Ia), Ia

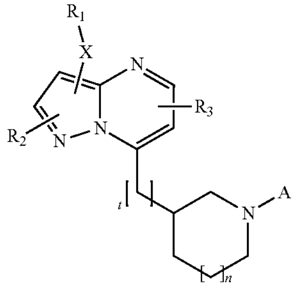

wherein $R_1$, $R_2$, $R_3$, X, n and t have the meaning as defined in the description, and A represents either hydrogen or a protecting group of the amino function (PG, such as benzyl or tert-butoxycarbonyl) for the preparation of compounds of Formula (I).

A particular embodiment of the invention refers to the use of a compound of Formula (Ib), Ib

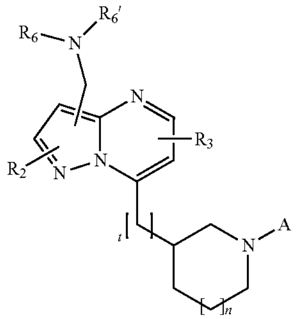

wherein $R_2$, $R_3$, $R_6$, $R_6'$, n and t have the meaning as defined in the description, and A represents either hydrogen or a protecting group of the amino function (PG, such as benzyl or tert-butoxycarbonyl) for the preparation of compounds of Formula (I).

A particular embodiment of the invention refers to the use of a compound of Formula (IIa), IIa

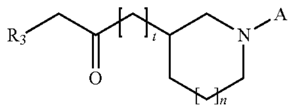

wherein $R_3$, n and t have the meaning as defined in the description, and A represents either hydrogen or a protecting group of the amino function (PG, such as benzyl or tert-butoxycarbonyl) for the preparation of compounds of Formula (I).

A particular embodiment of the invention refers to the use of a compound of Formula (IIb), IIb

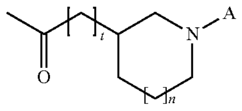

wherein n and t have the meaning as defined in the description, and A represents either hydrogen or a protecting group of the amino function (PG, such as benzyl or tert-butoxycarbonyl) for the preparation of compounds of Formula (I).

A particular embodiment of the invention refers to the use of a compound of Formula (IIIa), IIIa

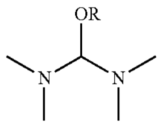

wherein R represents an alkyl group, for the preparation of compounds of Formula (I).

A particular embodiment of the invention refers to the use of a compound of Formula (IIIb), IIIb

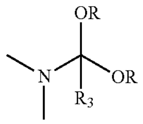

wherein $R_3$ has the meaning as defined in the description and R represents an alkyl group, for the preparation of compounds of Formula (I).

A particular embodiment of the invention refers to the use of a compound of Formula (IV),

IV

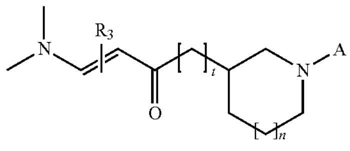

wherein $R_3$ has the meaning as defined in the description and A represents either hydrogen or a protecting group of the amino function (PG, such as benzyl or tert-butoxycarbonyl) for the preparation of compounds of Formula (I).

A particular embodiment of the invention refers to the use of a compound of Formula (V),

V

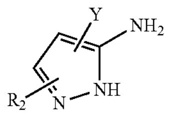

wherein $R_2$ has the meaning as defined in the description and Y represents a hydrogen, a halogen atom or an acid functionality, for the preparation of compounds of Formula (I).

A particular embodiment of the invention refers to the use of a compound of Formula (VI),

VI

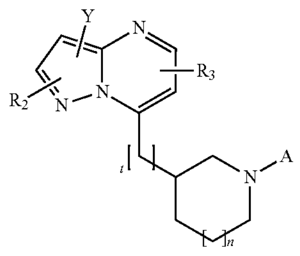

wherein $R_2$, $R_3$, n and t have the meaning as defined in the description, Y represents a hydrogen, a halogen atom or an acid functionality, and A represents either hydrogen or a protecting group of the amino function (PG, such as benzyl or tert-butoxycarbonyl) for the preparation of compounds of Formula (I).

A particular embodiment of the invention refers to the use of a compound of Formula (VII),

VII

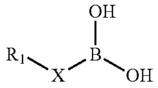

wherein $R_1$ has the meaning as defined in the description, for the preparation of compounds of Formula (I).

A particular embodiment of the invention refers to the use of a compound of Formula (VIII),

VIII

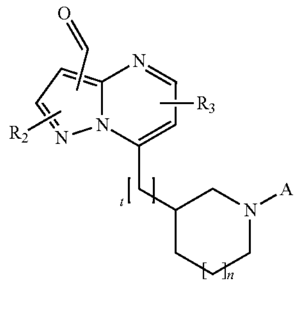

wherein $R_2$, $R_3$, n and t have the meaning as defined in the description, and A represents either hydrogen or a protecting group of the amino function (PG, such as benzyl or tert-butoxycarbonyl) for the preparation of compounds of Formula (I).

A particular embodiment of the invention refers to the use of a compound of Formula (IX),

IX

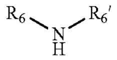

wherein $R_6$ and $R_6$' have the meaning as defined in the description, for the preparation of compounds of Formula (I).

A particular embodiment of the invention refers to the use of a compound of Formula (X),

X

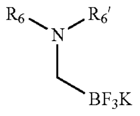

wherein $R_6$ and $R_6$' have the meaning as defined in the description, for the preparation of compounds of Formula (I).

A particular embodiment of the invention refers to the use of a compound of Formula (XI),

Z-T XI wherein T is $—C(R_5R_{5'})_mR_4$ and Z represents a halogen or an oxygen atom, and wherein $R_4$, $R_5$, $R_5$' and m have the meaning as defined in the description for the preparation of compounds of Formula (I).

A particular embodiment of the invention refers to the use of a compound of Formula (Ia), (Ib), (IIa), (IIb), (IIIa), (IIIb), (IV), (V), (VI), (VII), (VIII), (IX), (X) or (XI), Ia

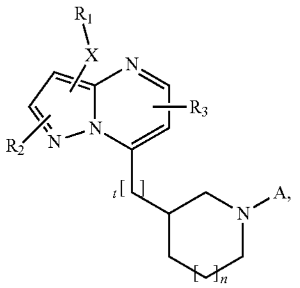

Ib

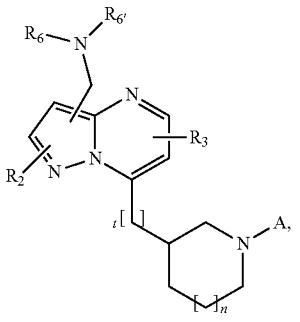

IIa

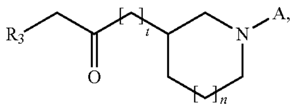

IIb

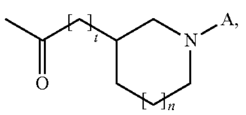

-continued

IIIa

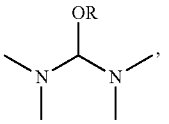

IIIb

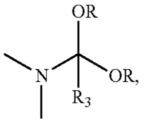

IV

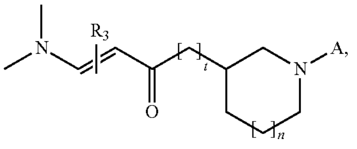

V

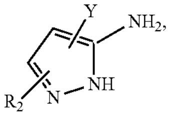

VI

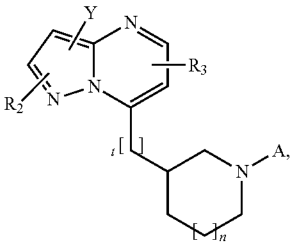

VII

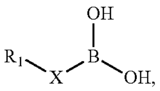

VIII

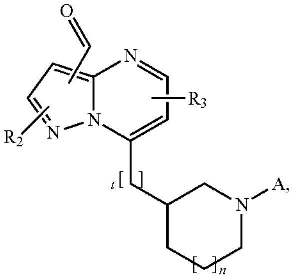

IX

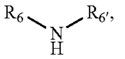

X

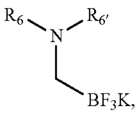

XI

Z—T

R represents an alkyl group, Y represents a hydrogen, a halogen atom or an acid functionality, A represents either hydrogen, $—C(R_5R_{5'})_mR_4$ or a protecting group of the amino function (PG, such as benzyl or tert-butoxycarbonyl), T represents the group $—C(R_5R_{5'})_m R_4$, and Z represents a halogen or an oxygen atom, and wherein $R_1$, $R_2$, $R_3$, $R_4$, $R_5$, $R_5$', $R_6$, $R_6$', X, m, n and t have the meaning as defined in the description, for the preparation of compounds of Formula (I).

A particular embodiment of the invention refers to the use of a compound of Formula (Ia), (Ib), (VI) or (VIII), Ia

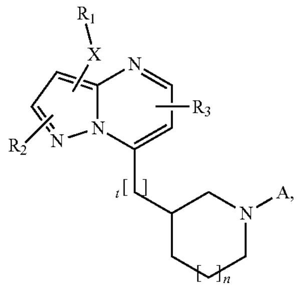

Ib

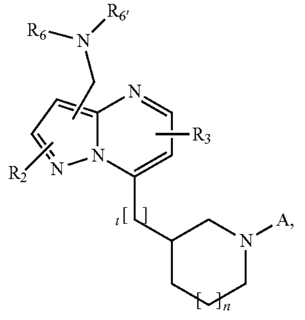

VI

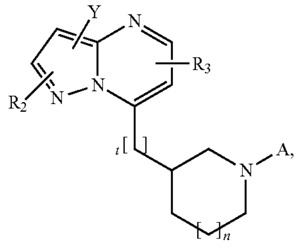

VIII

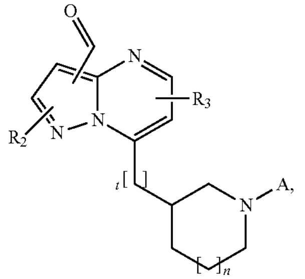

Y represents a hydrogen, a halogen atom or an acid functionality, A represents either hydrogen, —$C(R_5R_{5'})_mR_4$ or a protecting group of the amino function (such as benzyl or tert-butoxycarbonyl), and wherein $R_1$, $R_2$, $R_3$, $R_4$, $R_5$, $R_5'$, $R_6$, $R_6'$, X, m, n and t have the meaning as defined in the description, for the preparation of compounds of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules, etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula (I), or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general scope of the present invention.

General Experimental Part

Synthesis Description

The compounds of formula I may be prepared by the process described in Scheme 1, Scheme 1

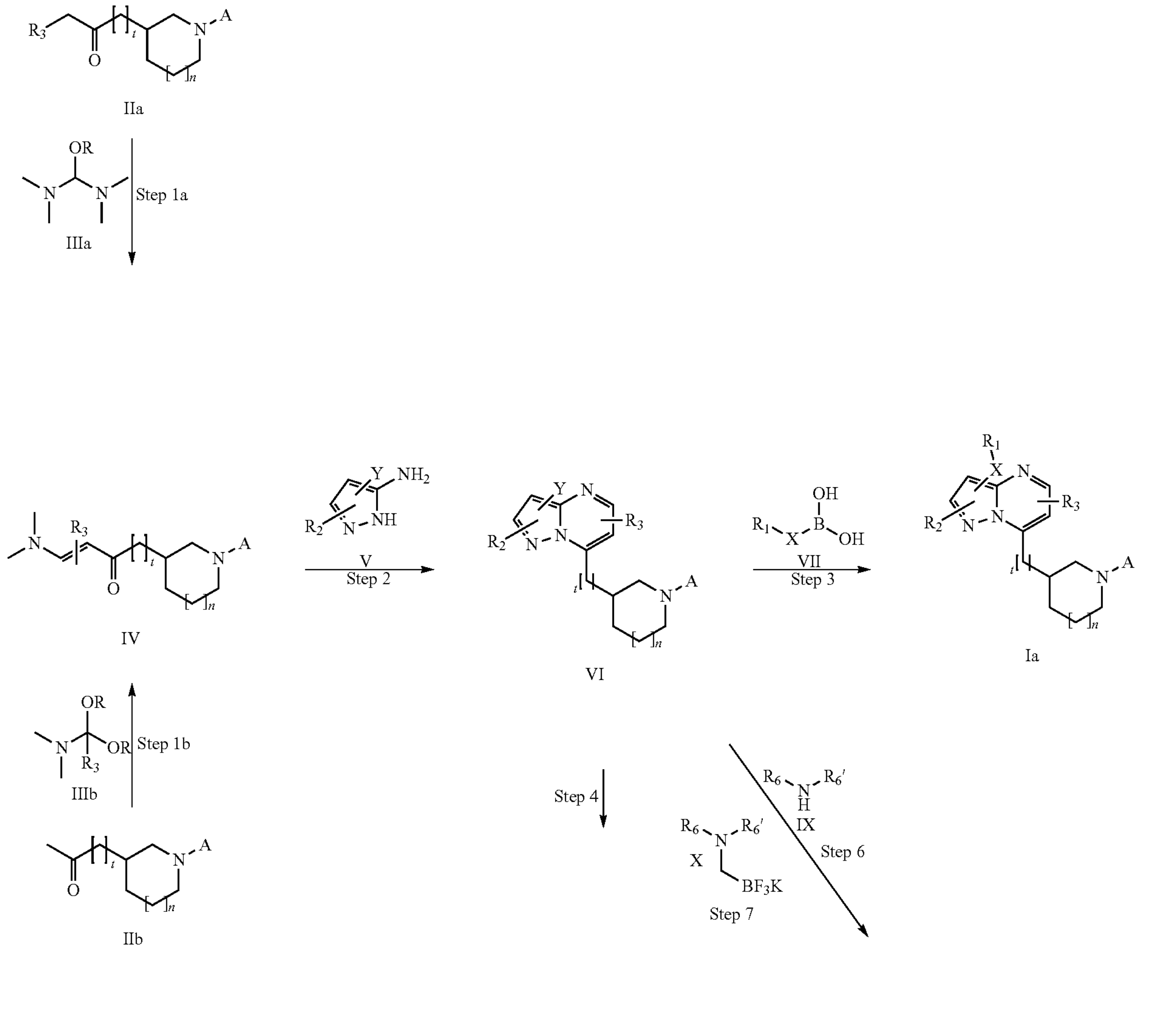

-continued

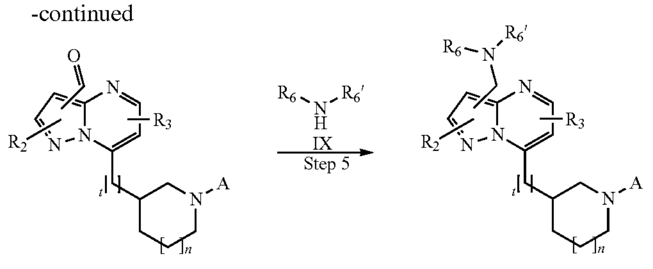

VIII Ib

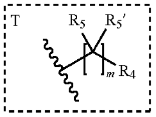

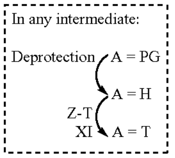

wherein $R_1$, $R_2$, $R_3$, $R_4$, $R_{5-5'}$, $R_{6-6'}$, X, m, n and t have the meanings as defined in the description, R represents an alkyl group, Y represents a hydrogen, a halogen atom or an acid functionality, A represents either hydrogen, a protecting group of the amino function (PG, such as benzyl or tert-butoxycarbonyl) or T, wherein T represents the group $C(R_5R_{5'})_mR_4$, and Z represents a halogen or an oxygen atom.

The process can be carried out as described below:

Step 1: A compound of formula IV can be prepared by treating a carbonyl derivative of formula IIa with a suitable alkoxy-N,N,N',N'-tetramethylmethanediamine derivative of formula IIIa (step 1a) or by treating a carbonyl derivative of formula IIb with a suitable 1,1-dialkoxy-1-N,N-dimethylalkylamine derivative of formula IIIb (step 1b) at a suitable temperature, preferably between 80° C. and 100° C.

Step 2: A compound of formula VI can be prepared by treating a compound of formula IV with a suitable 3-aminopyrazol derivative of formula V in a suitable solvent, such as acetic acid, at a suitable temperature, preferably between 50° C. and reflux temperature.

Step 3: A compound of formula Ia can be prepared by treating a compound of formula VI, in which Y is an halogen atom, with a suitable boronic acid (or boronic ester) of formula VII, in the presence of a suitable Pd catalyst, such as $Pd(PPh_3)_4$, with a suitable base, such as $K_2CO_3$ or $Na_2CO_3$, in a suitable solvent, such as mixtures of dimethoxyethane and water or mixtures of toluene, ethanol and water, at a suitable temperature, preferably heating. Alternatively, the reactions can be carried out under microwave heating.

Step 4: A compound of formula VIII can be prepared by treating a compound of formula VI, in which Y is a hydrogen atom, with $POCl_3$ in a suitable solvent, such as dimethylformamide, at a suitable temperature, preferably at 0° C. Alternatively, a compound of formula VIII can be prepared by treating a compound of formula VI, in which Y is an halogen atom, with (E)-4,4,5,5-tetramethyl-2-styryl-1,3,2-dioxaborolane in the presence of a suitable Pd catalyst, such as $Pd(dppf)Cl_2$, with a suitable base, such as $Na_2CO_3$, in a suitable solvent, such as mixtures of toluene, ethyl acetate and water, at a suitable temperature, preferably 90° C.; followed by treatment with a suitable oxidizing agent, such as $NaIO_4$, in the presence of a suitable catalyst, such as $OsO_4$, in in a suitable solvent, such as mixtures of acetone and water, at a suitable temperature, preferably room temperature.

Step 5: A compound of formula Ib can be prepared by treating a compound of formula VIII with a suitable amine of formula IX in the presence of a reducing reagent, such as sodium triacetoxyborohydride or sodium cyanoborohydride, in a suitable solvent, such as dichloromethane or methanol, optionally in the presence of an acid, preferably acetic acid, at a suitable temperature, preferably room temperature. Alternatively, the reactions can be carried out under microwave heating.

Step 6: Alternatively, a compound of formula Ib can be prepared by reacting a compound of formula VI, in which Y is an acid functionality, with a suitable amine of formula IX in the presence of a suitable coupling agent, such as N-(3-dimethylaminopropyl)-N'-ethylcarbodiimide hydrochloride, in the presence of a base, such as triethylamine, in a suitable solvent, such as dimethylformamide, at a suitable temperature, preferably room temperature; followed by reduction using a suitable reducing agent, such as $AlH_3$, in a suitable solvent, such as tetrahydrofuran, at a suitable temperature, preferably between 0° C. and room temperature.

Step 7: Alternatively, a compound of formula Ib can be prepared by reacting a compound of formula VI, in which Y is an halogen atom, with a suitable potassium aminomethyltrifluoroborate salt of formula X in the presence of a suitable Pd catalyst, such as allylpalladium(II) chloride dimer, with a suitable base, such as $K_3PO_4$, and a suitable phosphine ligand, such as dicyclohexyl(2',6'-dimethoxy-[1,1'-biphenyl]-2-yl)phosphine, in a suitable solvent, such as a mixture of dioxane and water, at a suitable temperature, preferably 100° C.

Additionally, the group $C(R_5R_{5'})_mR_4$ (T) can be incorporated at any step of the synthesis by converting a derivative where A is a protecting group, PG, to a derivative where A is H followed by a substitution reaction (see Scheme 1). The deprotection of PG may be carried out as follows:

When the protecting group is benzyl, the deprotection can be conducted in the presence of a suitable Pd catalyst, such as 10% Pd/C, with a suitable hydrogen source, such as ammonium formate, in a suitable solvent such as ethanol, at a suitable temperature such as 85° C.

When the protecting group is Boc (tert-butoxycarbonyl), the deprotection can be conducted by adding a solution of a strong acid such as HCl, in a suitable solvent such as diethyl ether, 1,4-dioxane or methanol, or with trifluoroacetic acid in dichloromethane.

The group T can then be introduced by means of any suitable reaction, such as:

An alkylation reaction with a suitable alkylating reagent of formula XI as shown in Scheme 1, where Z is a leaving group such as iodine, bromine, chlorine or alternatively an epoxide opening takes place; in a suitable solvent, such as acetonitrile, dichloromethane or dimethylacetamide; in the presence of an organic base, such as triethylamine or diisopropylethylamine, or an inorganic Lewis acid, such as $LiClO_4$; at a suitable temperature, comprised between room temperature and the reflux temperature, or alternatively, the reactions can be carried out under microwave heating.

A reductive amination reaction with a suitable aldehyde of formula XI, where Z is =O using the conditions described above in Step 5.

In addition, certain compounds of the present invention can also be obtained by functional group interconversion over compounds of formula Ia, Ib or any of the intermediates shown in Scheme 1. The following conversions are examples of transformations that may be carried out:

A halogen atom may be introduced using a suitable halogenating agent, such as NBS or NIS, in the presence of benzoyl peroxide, in a suitable solvent, such as carbon tetrachloride, at a suitable temperature, preferably 70° C.

A halogen atom may be converted to a hydroxyl group using a suitable borylating agent, such as bis(pinacolato)diboron, in the presence of a suitable Pd catalyst, such as $Pd(dppf)FeCl_2$, with a suitable base, such as KOAc, in a suitable solvent, such as dioxane, at a suitable temperature, preferably at 115° C.; followed by oxidation using a suitable oxidizing agent, such as hydrogen peroxide, in a suitable solvent, such as acetic acid, at a suitable temperature, preferably between 0° C. and room temperature.

A halogen atom may be converted to an alkylamino group using a suitable alkylamine in the presence of a suitable catalyst, such as $Pd_2dba_3$ or CuI, optionally in the presence of (S)-proline, with a suitable base, such as $KO^tBu$ or $K_2CO_3$, in a suitable solvent, such as toluene or dimethylsulfoxide, at a suitable temperature, preferably 100° C. Alternatively, the reactions can be carried out under microwave heating.

A halogen atom may be converted to a CN group using a suitable cyanide source, such as $K_4[Fe(CN)_6]\cdot 2H_2O$, in the presence of a suitable Pd catalyst, such as $Pd(OAc)_2$, and a suitable ligand, such as 1,1'-bis(diphenylphosphino)ferrocene, with a suitable base, such as $Na_2CO_3$, in a suitable solvent, such as N-methylpyrrolidone, at a suitable temperature, preferably 120° C. Alternatively, the reactions can be carried out under microwave heating.

A halogen atom may be converted to a pyrimidine ring using a suitable stannane reagent, such as tributyl (1-ethoxyvinyl)stannane, in the presence of a suitable Pd catalyst, such as $PdCl_2(PPh_3)_2$, in a suitable solvent, such as toluene, at a suitable temperature, preferably at 80° C.; followed by the conditions described in step 1a and by treatment with a suitable formimidamide source, such as formimidiamide acetate, at a suitable temperature, preferably 130° C.

A hydroxyl or an amino group may be alkylated using a suitable alkylating agent, such as an alkyl halide or an alkyl trifluoromethanesulfonate, in the presence of a base, such as triethylamine or NaH, in a suitable solvent, such as dichloromethane or dimethylformamide, at a suitable temperature, preferably between room temperature and 85° C.

A hydroxyl group may be arylated using a suitable aryl alcohol with a suitable coupling agent, such as diisopropyl azodicarboxylate, with a suitable phosphine, such as triphenylphosphine, in a suitable solvent, such as toluene, at a suitable temperature, preferably 100° C.

A double bond may be reduced using a suitable hydrogen source, such as hydrogen gas atmosphere, with a suitable Pd catalyst, such as $Pd(OH)_2$, in a suitable solvent, such as methanol, at a suitable temperature, preferably room temperature.

A carbonyl group may be reduced to alcohol using a suitable reducing agent, such as sodium borohydride, in a suitable solvent, such as tetrahydrofuran, at a suitable temperature, preferably between 0° C. and room temperature.

A carbonyl group may be converted to a nitroethyl group using nitromethane with a suitable base, such as methylamine, in a suitable solvent, such as methanol at a suitable temperature, preferably at 60° C.; followed by reduction using a suitable reducing agent, such as sodium borohydride, in a suitable solvent, such as methanol, at a suitable temperature, preferably room temperature.

A nitro group may be reduced to an amino group using a suitable reducing agent, such as Zn or hydrogen-Nickel Raney, optionally in the presence of $CaCl_2$, in a suitable solvent, such as methanol or mixtures of ethanol and water, at a suitable temperature, preferably between 40° C. and 80° C.

In some of the processes described above it may be necessary to protect the reactive or labile groups present with suitable protecting groups, such as for example acetyl, allyl, Alloc (allyloxycarbonyl), Boc (tert-butoxycarbonyl), or benzyl for the protection of amino groups, and common silyl protecting groups for the protection of the hydroxyl group. The procedures for the introduction and removal of these protecting groups are well known in the art and can be found thoroughly described in the literature.

In addition, a compound of formula I can be obtained in enantiopure form by resolution of a racemic mixture either by chiral preparative HPLC or by crystallization of a diastereomeric salt or co-crystal. Alternatively, the resolution step can be carried out at a previous stage, using any suitable intermediate.

The compounds of formula IIa, IIb, IIIa, IIIb, V, VII, IX, X and XI used in the methods disclosed above are commercially available or can be synthesized following common procedures described in the literature and exemplified in the synthesis of some intermediates.

EXAMPLES

The following abbreviations are used in the examples:

AcOH: acetic acid

ACN: acetonitrile

Anh: anhydrous

Aq: aqueous $Boc_2O$: di-tert-butyl dicarbonate
Chx: cyclohexane
Conc: concentrated
DCM: dichloromethane
DEA: diethylamine
DIAD: diisopropyl azodicarboxylate
DIPEA: N,N-diisopropylethylamine
DMA: N,N-dimethylacetamide
DME: dimethoxyethane
DMF: dimethylformamide
DMAP: dimethylaminopyridine
DMSO: dimethylsulfoxide
EDC·HCl: N-(3-dimethylaminopropyl)-N'-ethylcarbodiimide hydrochloride
$Et_2O$: diethyl ether
EtOAc: ethyl acetate
EtOH: ethanol
h: hour/s
HOBt: 1-hydroxybenzotriazole
HPLC: high performance liquid chromatography
iPrOH: isopropanol
LDA: lithium diisopropylamide
MeOH: methanol
MS: mass spectrometry
Min: minutes
MW: microwave
NBS: N-bromosuccinimide
NIS: N-iodosuccinimide
NMP: N-methyl-2-pyrrolidone
Quant: quantitative
Rt.: retention time
Rf: retention factor
r.t.: room temperature
Sat: saturated
Sol: solution
TEA: triethylamine
TFA: trifluoroacetic acid
THF: tetrahydrofuran
TLC: thin-layer chromatography
XPhos: 2-dicyclohexylphosphino-2',4',6'-triisopropylbiphenyl
Wt: weight The following methods were used to determine the HPLC-MS spectra:

Method A

Column Acquity UPLC BEH C18 2.1×50 mm, 1.7 μm; flow rate 0.61 mL/min; A: $NH_4HCO_3$ 10 mM; B: ACN; Gradient: 0.3 min in 98% A, 98% A to 5% A in 2.52 min, isocratic 1.02 min in 5% A.

Method B

Column Acquity UPLC BEH C18 2.1×50 mm, 1.7 μm, flow rate 0.60 mL/min; A: $NH_4HCO_3$10 mM, B: ACN; gradient: 0.3 min 90% A, 90% A to 5% A in 2.7 min, isocratic 0.7 min 5% A.

Method C

Column Aquity UPLC BEH C18 2.1×50 mm, 1.7 μm, flow rate 0.61 mL/min; A: $NH_4HCO_3$ 10 mM, B: ACN; gradient 0.3 min 98% A, 98% A to 0% A in 2.7 min; isocratic 2 min 0% A.

Method D

Column XBridge® Shield RP18 4.6×50 mm, 3.5 μm, flow rate 1.6 mL/min at 50° C.; A: 10 mM $NH_4HCO_3$/25% w/w $NH_4OH$ (99.8:0.12) pH 9, B: ACN; gradient 0.5 min 95% A, 95% to 0% A in 3.5 min; isocratic 1.5 min 0% A.

Method E

Column XBridge® Shield RP18 4.6×50 mm, 3.5 μm, flow rate 1.5 mL/min at 30° C.; A: 10 mM $NH_4HCO_3$/25% w/w $NH_4OH$ (99.8:0.12) pH 9, B: ACN; gradient 0.5 min 95% A, 95% to 0% A in 4.5 min; isocratic 1.5 min 0% A.

Method F

Column Acquity UPLC BEH C18 2.1×50 mm, 1.7 μm, flow rate 0.61 mL/min; A: $NH_4HCO_3$ 10 mM, B: ACN, C: MeOH+0.1% formic acid; gradient 0.3 min 98% A, 98% A to 0:95:5 A:B:C in 2.7 min; 0:95:5 A:B:C to 100% B in 0.1 min; isocratic 2 min 100% B.

Method G

Column Acquity UPLC BEH C18 2.1×50 mm, 1.7 m, flow rate 0.6 mL/min; $H_2O$+0.2% v/v $NH_3$, B: ACN; gradiente 95% A to 5% A in 4 min, 5% A to 0% A in 0.2 min, isocratic 0.48 min 0% A.

Method H

Column Aquity UPLC BEH C18 2.1×50 mm, 1.7 μm, flow rate 0.61 mL/min; A: $NH_4HCO_3$ 10 mM, B: ACN; gradient 0.3 min 98% A, 98% A to 100% B in 2.65 min; isocratic 2.05 min 100% B.

Method I

Column XBridge® Shield RP18 4.6×50 mm, 3.5 μm, flow rate 1.5 mL/min at 30° C.; A: 10 mM $NH_4HCO_3$/25% w/w $NH_4OH$ (99.8:0.12) pH 9, B: ACN; gradient 0.5 min 50% A, 50% to 5% A in 4.5 min; isocratic 1.5 min 5% A.

Method J

Column Acquity UPLC BEH C18 2.1×50 mm, 1.7 μm, flow rate 0.6 mL/min; $H_2O$+0.1% v/v TFA, B: ACN; gradient 95% A to 5% A in 4 min, 5% A to 0% A in 0.2 min, isocratic 0.48 min 0% A.

Method K

CHIRALPACK® IG-3 analytical column. 4.6×150 mm, 3 μm, flow rate 1.0 mL/min at 25° C.; A: 20 mM $NH_4HCO_3$/aq pH 9 (by DEA), B: ACN; isocratic 15 min: a) (20% A); b) (25% A); c) (30% A); d) (35% A); e) (40% A); f) (55% A); g) (60% A)

Method L

CHIRALPACK® IC-3 analytical column. 4.6×150 mm, 3 μm, flow rate 1.0 mL/min at 25° C.; A: 20 mM $NH_4HCO_3$/aq pH 9 (by DEA), B: ACN; isocratic 15 min 30% A.

Method M

CHIRALCEL® OJ-3R analytical column. 4.6×150 mm, 3 μm, flow rate 1.0 mL/min at 25° C.; A: 20 mM $NH_4HCO_3$/aq pH 9 (by DEA), B: ACN; isocratic 15 min 70% A.

Method N

Column Aquity UPLC BEH C18 2.1×50 mm, 1.7 μm, flow rate 0.61 mL/min; A: $NH_4HCO_3$ 10 mM pH 10.6, B: ACN; gradient 0.3 min 98% A, 98% A to 0% A in 2.7 min; isocratic 2 min 0% A.

SYNTHESIS OF EXAMPLES

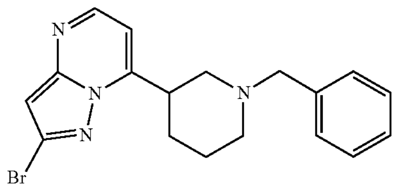 [SMILES: Brc1cc2nccc(C3CCCN(Cc4ccccc4)C3)n2n1]

Example 1. 7-(1-Benzylpiperidin-3-yl)-2-bromopyrazolo[1,5-a]pyrimidine

Step a. 1-(1-Benzylpiperidin-3-yl)-3-(dimethylamino)prop-2-en-1-one 1-(1-Benzylpiperidin-3-yl)ethanone (1.67 g, 7.7 mmol) and 1-tert-butoxy-N,N,N',N'-tetramethylmethanediamine (1.47 g, 8.5 mmol) were stirred at 80° C. during 16 h. The reaction mixture was cooled and evaporated to dryness under vacuum to give the title compound (1.96 g, Yield: 94%).

HPLC-MS (Method A): Rt: 1.44 min; ESI+-MS m/z: 273.2 (M+1).

Step b. Title Compound

5-Bromo-1H-pyrazol-3-amine (535 mg, 3.3 mmol) was added to a solution of the compound obtained in step a (900 mg, 3.3 mmol) in AcOH (10 mL) and the solution was stirred at 100° C. for 16 h. The mixture was cooled down and the solvent was evaporated under vacuum. 10% Aq NaOH was added and the product was extracted with EtOAc, the combined organic layers were washed with brine, dried over anh $Na_2SO_4$, filtered and concentrated to dryness. The crude product was purified by flash chromatography, silica gel, DCM:MeOH to give the title compound (612 mg, Yield: 50%).

HPLC-MS (Method A): Rt, 2.32 min; ESI+-MS m/z: 371 $[M+H]^+$.

This method was used for the preparation of examples 2-9 using suitable starting materials:

| STRUCTURE | EX | CHEMICAL NAME | Rt (min) | MS (M + H) | HPLC Method |
|---|---|---|---|---|---|
| 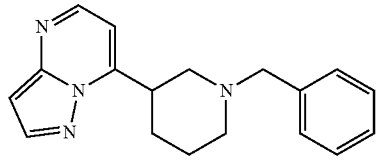 [SMILES: c1ccc(CN2CCCC(c3ccnc4ccnn34)C2)cc1] | 2 | 7-(1-Benzylpiperidin-3-yl)pyrazolo[1,5-a]pyrimidine | 1.91 | 293.2 | A |
| 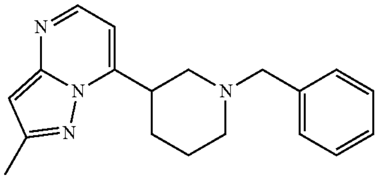 [SMILES: Cc1cc2nccc(C3CCCN(Cc4ccccc4)C3)n2n1] | 3 | 7-(1-Benzylpiperidin-3-yl)-2-methylpyrazolo[1,5-a]pyrimidine | 2.03 | 307.3 | A |
| 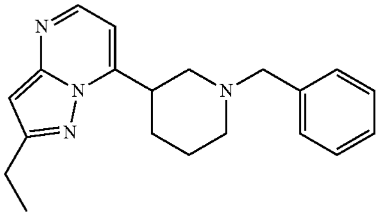 [SMILES: CCc1cc2nccc(C3CCCN(Cc4ccccc4)C3)n2n1] | 4 | 7-(1-Benzylpiperidin-3-yl)-2-ethylpyrazolo[1,5-a]pyrimidine | 2.24 | 321.2 | A |
| 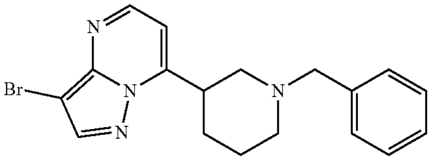 [SMILES: Brc1cnn2c(C3CCCN(Cc4ccccc4)C3)ccnc12] | 5 | 7-(1-Benzylpiperidin-3-yl)-3-bromopyrazolo[1,5-a]pyrimidine | 2.26 | 371 | A |
| 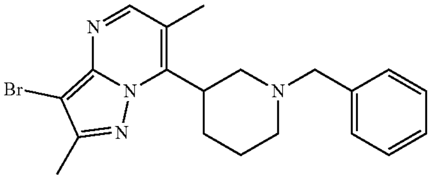 [SMILES: Cc1cnc2c(Br)c(C)nn2c1C1CCCN(Cc2ccccc2)C1] | 6 | 7-(1-Benzylpiperidin-3-yl)-3-bromo-2,6-dimethylpyrazolo[1,5-a]pyrimidine | 2.58 | 399 | A |
| 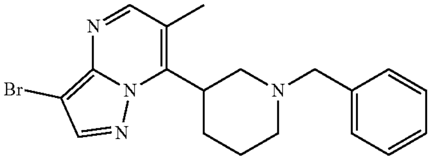 [SMILES: Cc1cnc2c(Br)cnn2c1C1CCCN(Cc2ccccc2)C1] | 7 | 7-(1-Benzylpiperidin-3-yl)-3-bromo-6-methylpyrazolo[1,5-a]pyrimidine | 2.40 | 385 | A |

-continued

| STRUCTURE | EX | CHEMICAL NAME | Rt (min) | MS (M + H) | HPLC Method |
|---|---|---|---|---|---|
| 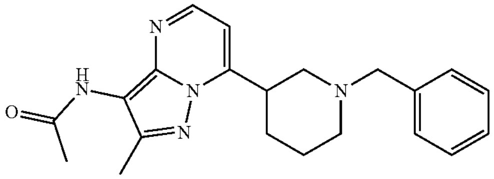 [SMILES: CC(=O)Nc1c(C)nn2c(C3CCCN(Cc4ccccc4)C3)ccnc12] | 8 | N-(7-(1-Benzylpiperidin-3-yl)-2-methylpyrazolo[1,5-a]pyrimidin-3-yl)acetamide | 1.92 | 364.2 | A |
| 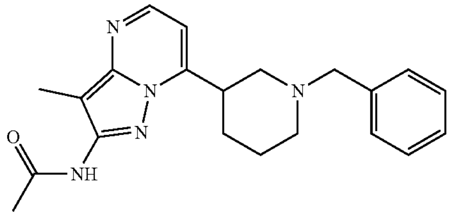 [SMILES: CC(=O)Nc1nn2c(C3CCCN(Cc4ccccc4)C3)ccnc2c1C] | 9 | N-(7-(1-Benzylpiperidin-3-yl)-3-methylpyrazolo[1,5-a]pyrimidin-2-yl)acetamide | 1.41 | 364.2 | A |

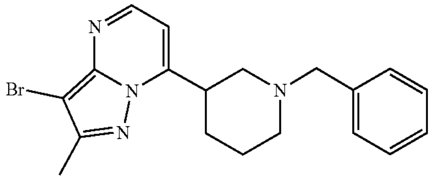 [SMILES: Cc1nn2c(C3CCCN(Cc4ccccc4)C3)ccnc2c1Br]

Example 10. 7-(1-Benzylpiperidin-3-yl)-3-bromo-2-methylpyrazolo[1,5-a]pyrimidine NBS (697 mg, 3.9 mmol) and benzoyl peroxide (94 mg, 0.4 mmol) were added to a solution of the compound obtained in example 3 (1.0 g, 3.3 mmol) in $CCl_4$ (150 mL) and the resulting mixture was heated at 70° C. for 16 h. After completion, the mixture was cooled down and the solvent was evaporated under vacuum. The residue was quickly filtered through a plug of silica with Chx:EtOAc (95:5) and concentrated to dryness. The crude product was purified by flash chromatography, silica gel, Chx:EtOAc to give the title compound (670 mg, Yield: 53%).

HPLC-MS (Method A): Rt, 2.39 min; ESI+-MS m/z: 385.1 $[M+H]^+$.

This method was used for the preparation of example 11 using suitable starting materials:

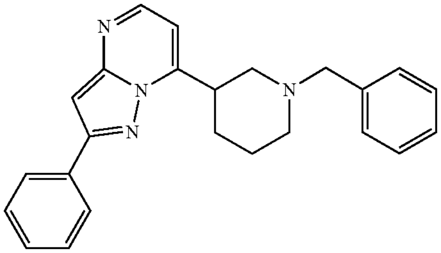

Example 12. 7-(1-Benzylpiperidin-3-yl)-2-phenylpyrazolo[1,5-a]pyrimidine

A MW tube was charged with the compound obtained in example 1 (200 mg, 0.54 mmol), phenylboronic acid (99 mg, 0.8 mmol), $K_2CO_3$ (223 mg, 1.6 mmol), $Pd(PPh_3)_4$ (12 mg, 0.01 mmol) and DME:$H_2O$ (1:1) (6 mL) and was degassed by means of bubbling argon for 5 min. The reaction mixture was heated under MW irradiation at 130° C. for 20 min. The suspension was diluted with EtOAc and washed with aq sat $NaHCO_3$ sol. The organic layer was dried over anh $Na_2SO_4$, filtered and solvent was removed under vacuum. The residue was purified by flash chromatography, silica gel, DCM:MeOH, to give the title compound (158 mg, Yield: 80%).

HPLC-MS (Method A): Rt, 2.56 min; ESI+-MS m/z: 369.3 $[M+H]^+$.

| STRUCTURE | EX | CHEMICAL NAME | Rt (min) | MS (M + H) | HPLC Method |
|---|---|---|---|---|---|
| 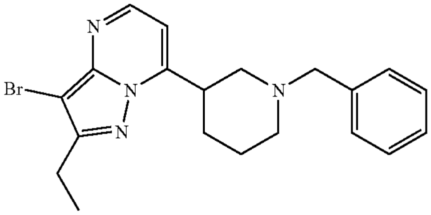 [SMILES: CCc1nn2c(C3CCCN(Cc4ccccc4)C3)ccnc2c1Br] | 11 | 7-(1-Benzylpiperidin-3-yl)-3-bromo-2-ethylpyrazolo[1,5-a]pyrimidine | 2.66 | 399.1 | C |

This method was used for the preparation of examples 13-60 using suitable starting materials:

| STRUCTURE | EX | CHEMICAL NAME | Rt (min) | MS (M + H) | HPLC Method |
|---|---|---|---|---|---|
| 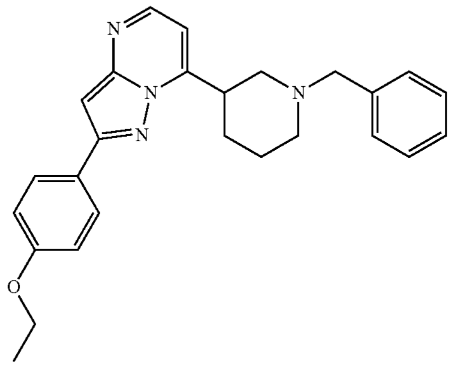 [SMILES: CCOc1ccc(-c2cc3nccc(C4CCCN(Cc5ccccc5)C4)n3n2)cc1] | 13 | 7-(1-Benzylpiperidin-3-yl)-2-(4-ethoxyphenyl)pyrazolo[1,5-a]pyrimidine | 2.64 | 413.3 | A |
| 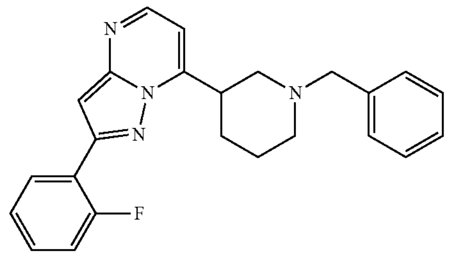 [SMILES: Fc1ccccc1-c1cc2nccc(C3CCCN(Cc4ccccc4)C3)n2n1] | 14 | 7-(1-Benzylpiperidin-3-yl)-2-(2-fluorophenyl)pyrazolo[1,5-a]pyrimidine | 2.62 | 387.3 | A |
| 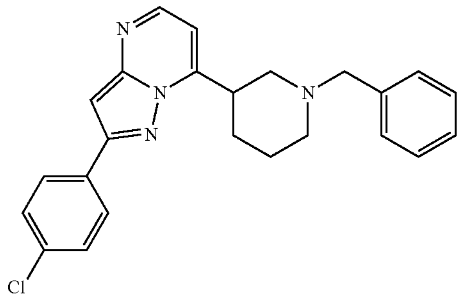 [SMILES: Clc1ccc(-c2cc3nccc(C4CCCN(Cc5ccccc5)C4)n3n2)cc1] | 15 | 7-(1-Benzylpiperidin-3-yl)-2-(4-chlorophenyl)pyrazolo[1,5-a]pyrimidine | 2.77 | 403.3 | A |
| 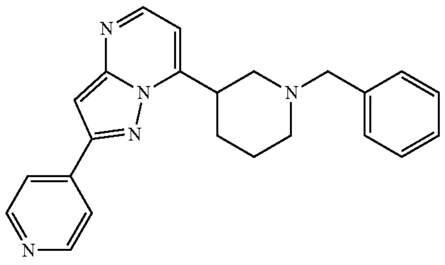 [SMILES: c1ccc(CN2CCCC(c3ccnc4cc(-c5ccncc5)nn34)C2)cc1] | 16 | 7-(1-Benzylpiperidin-3-yl)-2-(pyridin-4-yl)pyrazolo[1,5-a]pyrimidine | 2.06 | 370.3 | A |
| 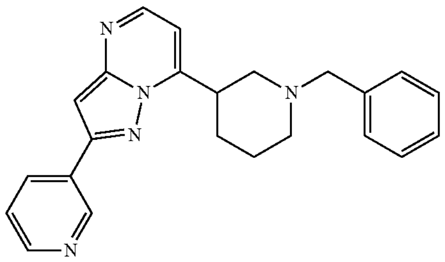 [SMILES: c1ccc(CN2CCCC(c3ccnc4cc(-c5cccnc5)nn34)C2)cc1] | 17 | 7-(1-Benzylpiperidin-3-yl)-2-(pyridin-3-yl)pyrazolo[1,5-a]pyrimidine | 2.06 | 370.3 | A |

-continued

| STRUCTURE | EX | CHEMICAL NAME | Rt (min) | MS (M + H) | HPLC Method |
|---|---|---|---|---|---|
| 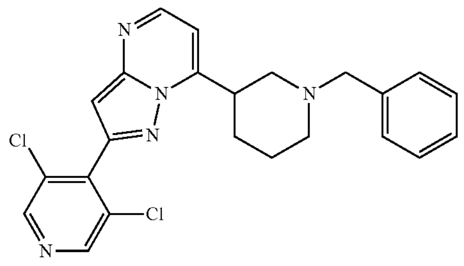 [SMILES: Clc1cncc(Cl)c1-c1cc2nccc(C3CCCN(Cc4ccccc4)C3)n2n1] | 18 | 7-(1-Benzylpiperidin-3-yl)-2-(3,5-dichloropyridin-4-yl)pyrazolo[1,5-a]pyrimidine | 2.48 | 438.3 | A |
| 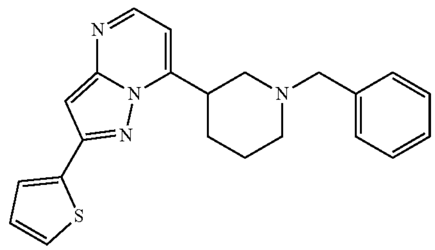 [SMILES: c1ccc(CN2CCCC(c3ccnc4cc(-c5cccs5)nn34)C2)cc1] | 19 | 7-(1-Benzylpiperidin-3-yl)-2-(thiophen-2-yl)pyrazolo[1,5-a]pyrimidine | 2.49 | 375.3 | A |
| 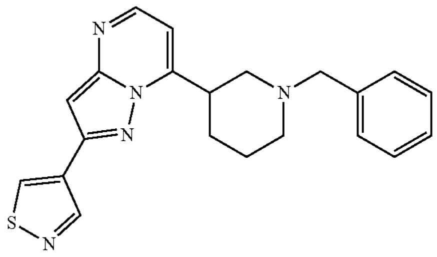 [SMILES: c1ccc(CN2CCCC(c3ccnc4cc(-c5cnsc5)nn34)C2)cc1] | 20 | 4-(7-(1-Benzylpiperidin-3-yl)pyrazolo[1,5-a]pyrimidin-2-yl)isothiazole | 2.22 | 376.2 | A |
| 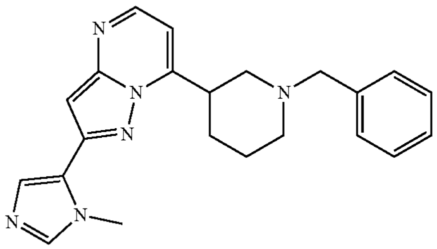 [SMILES: Cn1cncc1-c1cc2nccc(C3CCCN(Cc4ccccc4)C3)n2n1] | 21 | 7-(1-Benzylpiperidin-3-yl)-2-(1-methyl-1H-imidazol-5-yl)pyrazolo[1,5-a]pyrimidine | 1.83 | 373.3 | A |
| 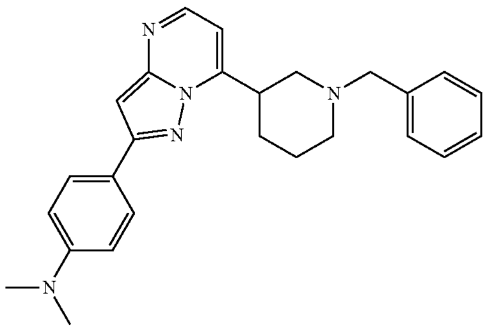 [SMILES: CN(C)c1ccc(-c2cc3nccc(C4CCCN(Cc5ccccc5)C4)n3n2)cc1] | 22 | 4-(7-(1-Benzylpiperidin-3-yl)pyrazolo[1,5-a]pyrimidin-2-yl)-N,N-dimethylaniline | 2.59 | 412.3 | A |

-continued

| STRUCTURE | EX | CHEMICAL NAME | Rt (min) | MS (M + H) | HPLC Method |
|---|---|---|---|---|---|
| 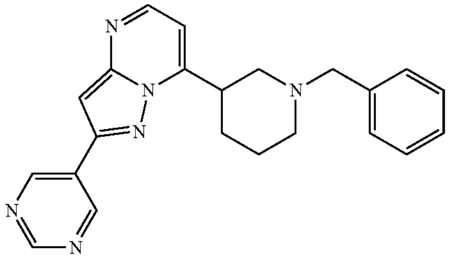 [SMILES: c1ccc(CN2CCCC(c3ccnc4cc(-c5cncnc5)nn34)C2)cc1] | 23 | 7-(1-Benzylpiperidin-3-yl)-2-(pyrimidin-5-yl)pyrazolo[1,5-a]pyrimidine | 1.90 | 371.2 | A |
| 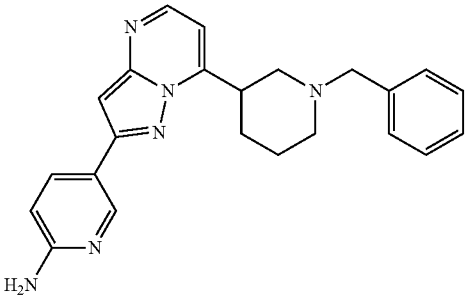 [SMILES: Nc1ccc(-c2cc3nccc(C4CCCN(Cc5ccccc5)C4)n3n2)cn1] | 24 | 5-(7-(1-Benzylpiperidin-3-yl)pyrazolo[1,5-a]pyrimidin-2-yl)pyridin-2-amine | 1.85 | 385.3 | A |
| 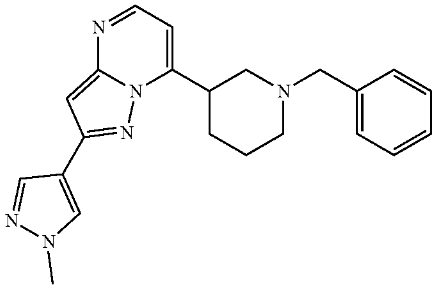 [SMILES: Cn1cc(-c2cc3nccc(C4CCCN(Cc5ccccc5)C4)n3n2)cn1] | 25 | 7-(1-Benzylpiperidin-3-yl)-2-(1-methyl-1H-pyrazol-4-yl)pyrazolo[1,5-a]pyrimidine | 1.88 | 373.2 | A |
| 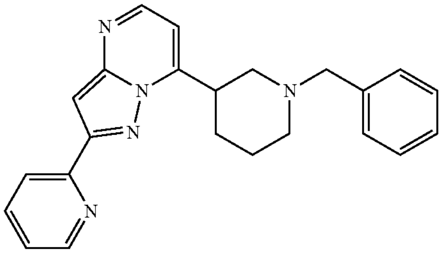 [SMILES: c1ccc(CN2CCCC(c3ccnc4cc(-c5ccccn5)nn34)C2)cc1] | 26 | 7-(1-Benzylpiperidin-3-yl)-2-(pyridin-2-yl)pyrazolo[1,5-a]pyrimidine | 2.11 | 370.2 | A |
| 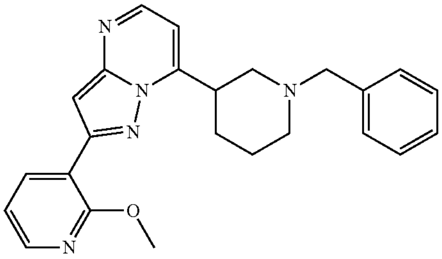 [SMILES: COc1ncccc1-c1cc2nccc(C3CCCN(Cc4ccccc4)C3)n2n1] | 27 | 7-(1-Benzylpiperidin-3-yl)-2-(2-methoxypyridin-3-yl)pyrazolo[1,5-a]pyrimidine | 2.45 | 400.1 | A |

-continued

| STRUCTURE | EX | CHEMICAL NAME | Rt (min) | MS (M + H) | HPLC Method |
|---|---|---|---|---|---|
| 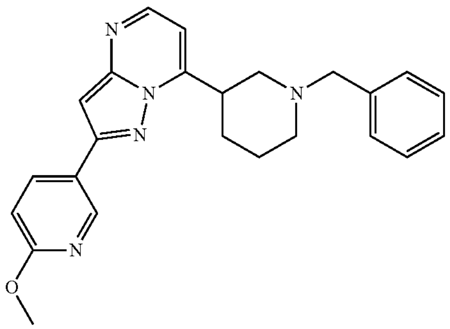 [SMILES: COc1ccc(-c2cc3nccc(C4CCCN(Cc5ccccc5)C4)n3n2)cn1] | 28 | 7-(1-Benzylpiperidin-3-yl)-2-(6-methoxypyridin-3-yl)pyrazolo[1,5-a]pyrimidine | 2.40 | 400.1 | A |
| 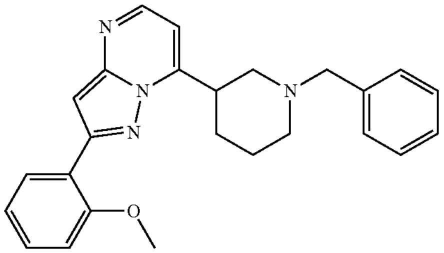 [SMILES: COc1ccccc1-c1cc2nccc(C3CCCN(Cc4ccccc4)C3)n2n1] | 29 | 7-(1-Benzylpiperidin-3-yl)-2-(2-methoxyphenyl)pyrazolo[1,5-a]pyrimidine | 2.54 | 399.2 | A |
| 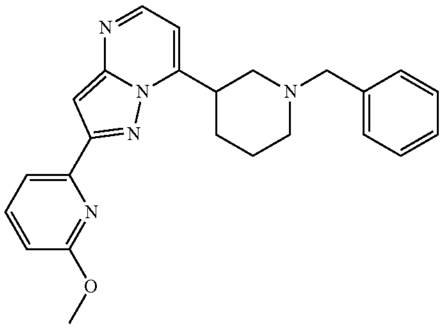 [SMILES: COc1cccc(-c2cc3nccc(C4CCCN(Cc5ccccc5)C4)n3n2)n1] | 30 | 7-(1-Benzylpiperidin-3-yl)-2-(6-methoxypyridin-2-yl)pyrazolo[1,5-a]pyrimidine | 2.53 | 400.1 | A |
| 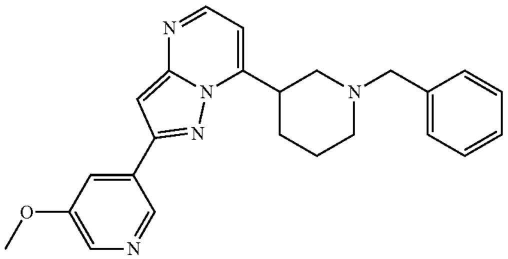 [SMILES: COc1cncc(-c2cc3nccc(C4CCCN(Cc5ccccc5)C4)n3n2)c1] | 31 | 7-(1-Benzylpiperidin-3-yl)-2-(5-methoxypyridin-3-yl)pyrazolo[1,5-a]pyrimidine | 2.41 | 400.2 | A |
| 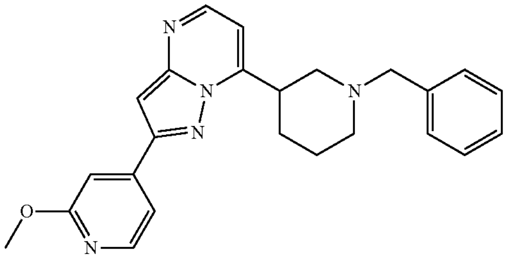 [SMILES: COc1cc(-c2cc3nccc(C4CCCN(Cc5ccccc5)C4)n3n2)ccn1] | 32 | 7-(1-Benzylpiperidin-3-yl)-2-(2-methoxypyridin-4-yl)pyrazolo[1,5-a]pyrimidine | 2.12 | 400.2 | A |

-continued

| STRUCTURE | EX | CHEMICAL NAME | Rt (min) | MS (M + H) | HPLC Method |
|---|---|---|---|---|---|
| 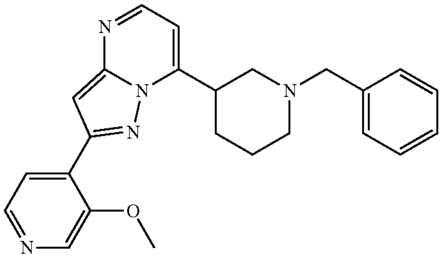 [SMILES: COc1cnccc1-c1cc2nccc(C3CCCN(Cc4ccccc4)C3)n2n1] | 33 | 7-(1-Benzylpiperidin-3-yl)-2-(3-methoxypyridin-4-yl)pyrazolo[1,5-a]pyrimidine | 2.12 | 400.2 | A |
| 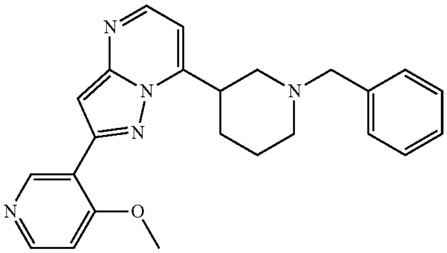 [SMILES: COc1ccncc1-c1cc2nccc(C3CCCN(Cc4ccccc4)C3)n2n1] | 34 | 7-(1-Benzylpiperidin-3-yl)-2-(4-methoxypyridin-3-yl)pyrazolo[1,5-a]pyrimidine | 1.98 | 400.2 | A |
| 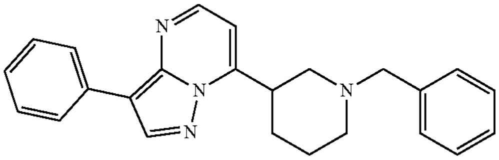 [SMILES: c1ccc(CN2CCCC(c3ccnc4c(-c5ccccc5)cnn34)C2)cc1] | 35 | 7-(1-Benzylpiperidin-3-yl)-3-phenylpyrazolo[1,5-a]pyrimidine | 2.59 | 369.1 | A |
| 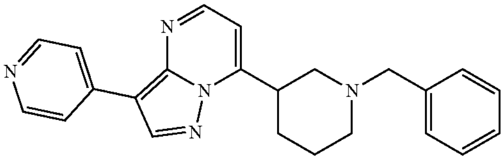 [SMILES: c1ccc(CN2CCCC(c3ccnc4c(-c5ccncc5)cnn34)C2)cc1] | 36 | 7-(1-Benzylpiperidin-3-yl)-3-(pyridin-4-yl)pyrazolo[1,5-a]pyrimidine | 2.13 | 370.1 | A |
| 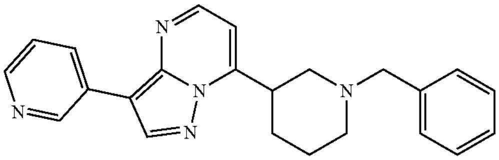 [SMILES: c1ccc(CN2CCCC(c3ccnc4c(-c5cccnc5)cnn34)C2)cc1] | 37 | 7-(1-Benzylpiperidin-3-yl)-3-(pyridin-3-yl)pyrazolo[1,5-a]pyrimidine | 2.12 | 370.1 | A |
| 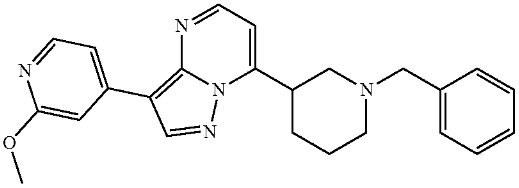 [SMILES: COc1cc(-c2cnn3c(C4CCCN(Cc5ccccc5)C4)ccnc23)ccn1] | 38 | 7-(1-Benzylpiperidin-3-yl)-3-(2-methoxypyridin-4-yl)pyrazolo[1,5-a]pyrimidine | 2.45 | 400.2 | A |
| 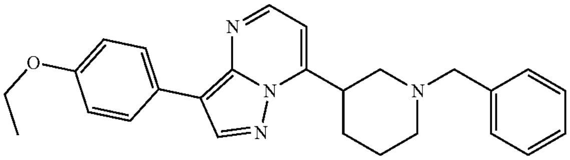 [SMILES: CCOc1ccc(-c2cnn3c(C4CCCN(Cc5ccccc5)C4)ccnc23)cc1] | 39 | 7-(1-Benzylpiperidin-3-yl)-3-(4-ethoxyphenyl)pyrazolo[1,5-a]pyrimidine | 2.69 | 413.2 | A |

-continued

| STRUCTURE | EX | CHEMICAL NAME | Rt (min) | MS (M + H) | HPLC Method |
|---|---|---|---|---|---|
| 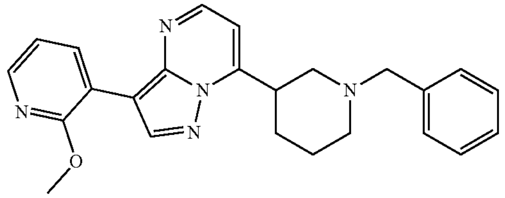 [SMILES: COc1ncccc1-c1cnn2c(C3CCCN(Cc4ccccc4)C3)ccnc12] | 40 | 7-(1-Benzylpiperidin-3-yl)-3-(2-methoxypyridin-3-yl)pyrazolo[1,5-a]pyrimidine | 2.55 | 400.2 | A |
| 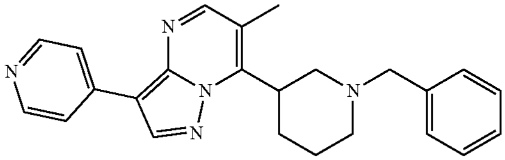 [SMILES: Cc1cnc2c(-c3ccncc3)cnn2c1C1CCCN(Cc2ccccc2)C1] | 41 | 7-(1-Benzylpiperidin-3-yl)-6-methyl-3-(pyridin-4-yl)pyrazolo[1,5-a]pyrimidine | 2.24 | 384.2 | A |
| 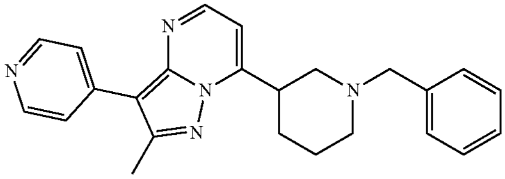 [SMILES: Cc1nn2c(C3CCCN(Cc4ccccc4)C3)ccnc2c1-c1ccncc1] | 42 | 7-(1-Benzylpiperidin-3-yl)-2-methyl-3-(pyridin-4-yl)pyrazolo[1,5-a]pyrimidine | 2.18 | 384.2 | A |
| 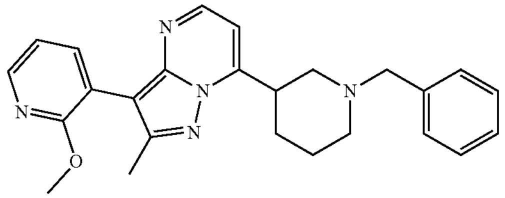 [SMILES: COc1ncccc1-c1c(C)nn2c(C3CCCN(Cc4ccccc4)C3)ccnc12] | 43 | 7-(1-Benzylpiperidin-3-yl)-3-(2-methoxypyridin-3-yl)-2-methylpyrazolo[1,5-a]pyrimidine | 2.35 | 414.2 | A |
| 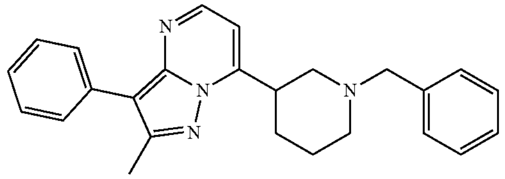 [SMILES: Cc1nn2c(C3CCCN(Cc4ccccc4)C3)ccnc2c1-c1ccccc1] | 44 | 7-(1-Benzylpiperidin-3-yl)-2-methyl-3-phenylpyrazolo[1,5-a]pyrimidine | 2.63 | 383.2 | A |
| 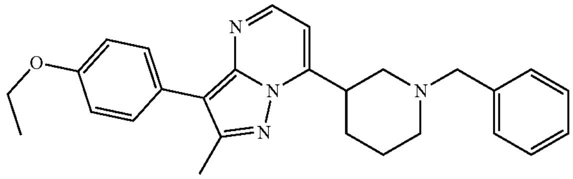 [SMILES: CCOc1ccc(-c2c(C)nn3c(C4CCCN(Cc5ccccc5)C4)ccnc23)cc1] | 45 | 7-(1-Benzylpiperidin-3-yl)-3-(4-ethoxyphenyl)-2-methylpyrazolo[1,5-a]pyrimidine | 2.70 | 427.2 | A |
| 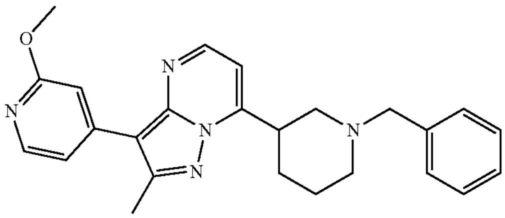 | 46 | 7-(1-Benzylpiperidin-3-yl)-3-(2-methoxypyridin-4-yl)-2-methylpyrazolo[1,5-a]pyrimidine | 2.50 | 414.1 | A |
| 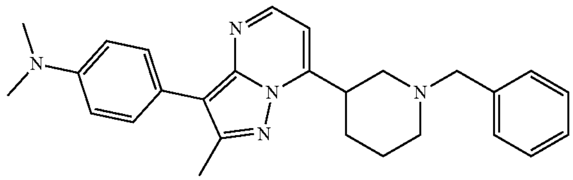 [SMILES: Cc1nn2c(C3CCCN(Cc4ccccc4)C3)ccnc2c1-c1ccc(N(C)C)cc1] | 47 | 4-(7-(1-Benzylpiperidin-3-yl)-2-methylpyrazolo[1,5-a]pyrimidin-3-yl)-N,N-dimethylaniline | 2.67 | 426.2 | A |

-continued

| STRUCTURE | EX | CHEMICAL NAME | Rt (min) | MS (M + H) | HPLC Method |
|---|---|---|---|---|---|
| 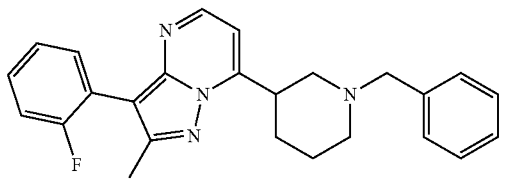 [SMILES: Cc1nn2c(C3CCCN(Cc4ccccc4)C3)ccnc2c1-c1ccccc1F] | 48 | 7-(1-Benzylpiperidin-3-yl)-3-(2-fluorophenyl)-2-methylpyrazolo[1,5-a]pyrimidine | 3.09 | 401.2 | B |
| 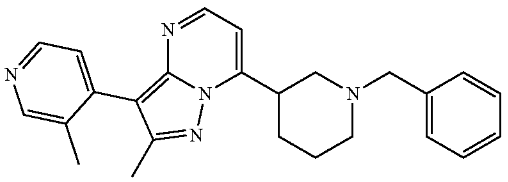 [SMILES: Cc1cnccc1-c1c(C)nn2c(C3CCCN(Cc4ccccc4)C3)ccnc12] | 49 | 7-(1-Benzylpiperidin-3-yl)-2-methyl-3-(3-methylpyridin-4-yl)pyrazolo[1,5-a]pyrimidine | 2.72 | 398.2 | B |
| 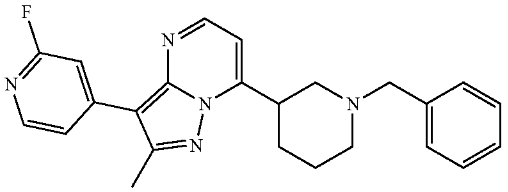 [SMILES: Cc1nn2c(C3CCCN(Cc4ccccc4)C3)ccnc2c1-c1ccnc(F)c1] | 50 | 7-(1-Benzylpiperidin-3-yl)-3-(2-fluoropyridin-4-yl)-2-methylpyrazolo[1,5-a]pyrimidine | 2.46 | 402.2 | A |
| 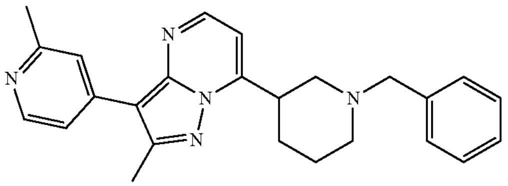 [SMILES: Cc1cc(-c2c(C)nn3c(C4CCCN(Cc5ccccc5)C4)ccnc23)ccn1] | 51 | 7-(1-Benzylpiperidin-3-yl)-2-methyl-3-(2-methylpyridin-4-yl)pyrazolo[1,5-a]pyrimidine | 2.25 | 398.3 | A |
| 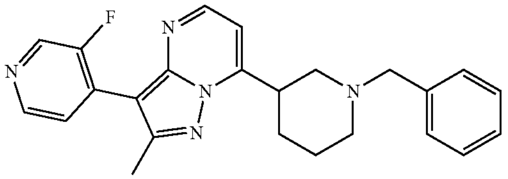 [SMILES: Cc1nn2c(C3CCCN(Cc4ccccc4)C3)ccnc2c1-c1ccncc1F] | 52 | 7-(1-Benzylpiperidin-3-yl)-3-(3-fluoropyridin-4-yl)-2-methylpyrazolo[1,5-a]pyrimidine | 2.22 | 402.2 | A |
| 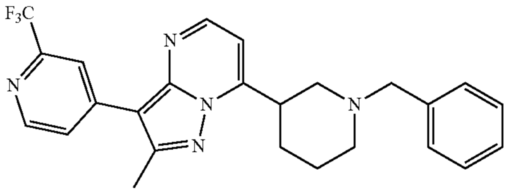 | 53 | 7-(1-Benzylpiperidin-3-yl)-2-methyl-3-(2-(trifluoromethyl)pyridin-4-yl)pyrazolo[1,5-a]pyrimidine | 2.63 | 452.2 | A |
| 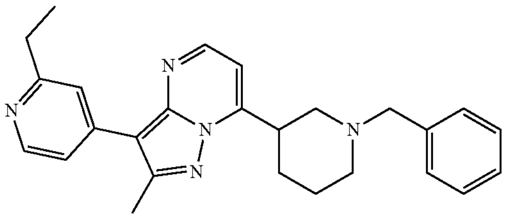 [SMILES: CCc1cc(-c2c(C)nn3c(C4CCCN(Cc5ccccc5)C4)ccnc23)ccn1] | 54 | 7-(1-Benzylpiperidin-3-yl)-3-(2-ethylpyridin-4-yl)-2-methylpyrazolo[1,5-a]pyrimidine | 2.41 | 412.3 | A |

-continued

| STRUCTURE | EX | CHEMICAL NAME | Rt (min) | MS (M + H) | HPLC Method |
|---|---|---|---|---|---|
| 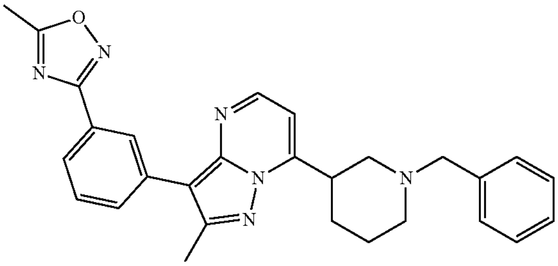 [SMILES: Cc1nc(-c2cccc(-c3c(C)nn4c(C5CCCN(Cc6ccccc6)C5)ccnc34)c2)no1] | 55 | 3-(3-(7-(1-Benzylpiperidin-3-yl)-2-methylpyrazolo[1,5-alpyrimidin-3-yl)phenyl)-5-methyl-1,2,4-oxadiazole | 2.62 | 465.2 | A |
| 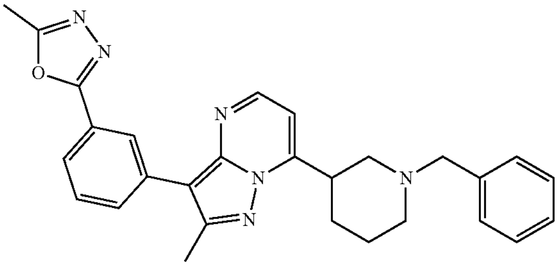 [SMILES: Cc1nnc(-c2cccc(-c3c(C)nn4c(C5CCCN(Cc6ccccc6)C5)ccnc34)c2)o1] | 56 | 2-(3-(7-(1-Benzylpiperidin-3-yl)-2-methylpyrazolo[1,5-a]pyrimidin-3-yl)phenyl)-5-methyl-1,3,4-oxadiazole | 2.85 | 465.3 | B |
| 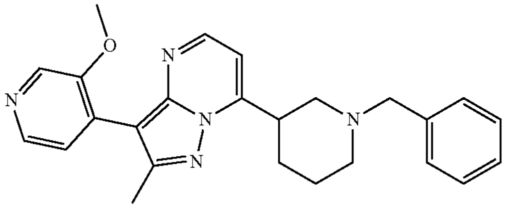 [SMILES: COc1cnccc1-c1c(C)nn2c(C3CCCN(Cc4ccccc4)C3)ccnc12] | 57 | 7-(1-Benzylpiperidin-3-yl)-3-(3-methoxypyridin-4-yl)-2-methylpyrazolo[1,5-a]pyrimidine | 2.13 | 414.3 | C |
| 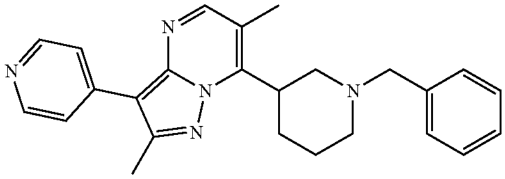 [SMILES: Cc1cnc2c(-c3ccncc3)c(C)nn2c1C1CCCN(Cc2ccccc2)C1] | 58 | 7-(1-Benzylpiperidin-3-yl)-2,6-dimethyl-3-(pyridin-4-yl)pyrazolo[1,5-a]pyrimidine | 2.35 | 398.2 | A |
| 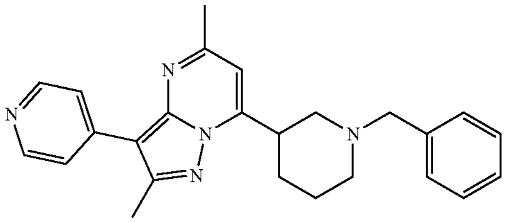 [SMILES: Cc1cc(C2CCCN(Cc3ccccc3)C2)n2nc(C)c(-c3ccncc3)c2n1] | 59 | 7-(1-Benzylpiperidin-3-yl)-2,5-dimethyl-3-(pyridin-4-yl)pyrazolo[1,5-a]pyrimidine | 2.34 | 398.3 | A |
| 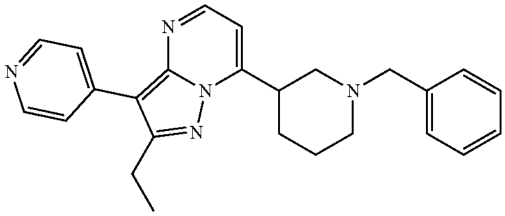 [SMILES: CCc1nn2c(C3CCCN(Cc4ccccc4)C3)ccnc2c1-c1ccncc1] | 60 | 7-(1-Benzylpiperidin-3-yl)-2-ethyl-3-(pyridin-4-yl)pyrazolo[1,5-a]pyrimidine | 2.80 | 398.4 | B |

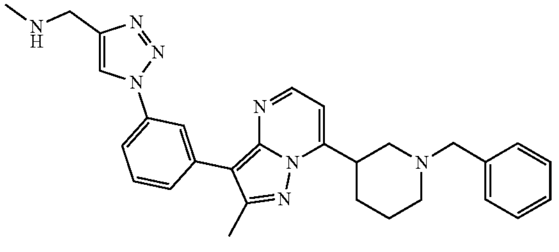 [SMILES: CNCc1cn(-c2cccc(-c3c(C)nn4c(C5CCCN(Cc6ccccc6)C5)ccnc34)c2)nn1]

Example 61. 1-(1-(3-(7-(1-Benzylpiperidin-3-yl)-2-methylpyrazolo[1,5-a]pyrimidin-3-yl)phenyl)-1H-1,2,3-triazol-4-yl)-N-methylmethanamine Step a. tert-Butyl ((1-(3-bromophenyl)-1H-1,2,3-triazol-4-yl)methyl)(methyl)carbamate TEA (0.92 mL, 6.6 mmol) and di-tert-butyl dicarbonate (450 mg, 2.1 mmol) were added in portions to a solution of 1-(1-(3-bromophenyl)-1H-1,2,3-triazol-4-yl)-N-methyl-methanamine hydrochloride (500 mg, 1.6 mmol) in DCM (5 mL) and the reaction mixture was stirred at r.t. for 16 h. The resulting mixture was washed with aq sat $NaHCO_3$ sol, water and brine. The organic layer was dried over anh $Na_2SO_4$, filtered and concentrated to give the title compound (735 mg, Yield: Quant.).

HPLC-MS (Method A): Rt: 2.11 min; ESI+-MS m/z: 367.1 (M+1).

Step b. (3-(4-(((tert-Butoxycarbonyl)(methyl)amino)methyl)-1H-1,2,3-triazol-1-yl)phenyl)boronic acid To a solution of the compound obtained in step a (580 mg, 1.6 mmol), bis(pinacolato)diboron (802 mg, 3.2 mmol) and KOAc (465 mg, 4.7 mmol) in anh DMSO (25 mL), Pd(dppf)Fe·$Cl_2$ (115 mg, 0.16 mmol) was added under argon atmosphere, and the mixture was heated at 90° C. for 16 h. The mixture was dissolved with an EtOAc:$Et_2O$ (1:1) mixture and washed with aq sat $NaHCO_3$ sol. The organic layer was dried over anh $Na_2SO_4$, filtered and solvent was removed under vacuum. The crude product was purified by flash chromatography, silica gel, Chx:EtOAc to give the title compound (690 mg, Yield: Quant.).

HPLC-MS (Method A): Rt: 1.52 min; ESI+-MS m/z: 333.1 (M+1).

Step c. tert-Butyl ((1-(3-(7-(1-benzylpiperidin-3-yl)-2-methylpyrazolo[1,5-a]pyrimidin-3-yl)phenyl)-1H-1,2,3-triazol-4-yl)methyl)(methyl)carbamate Starting from the compound obtained in example 10 (70 mg, 0.18 mmol) and the compound obtained in step b (90 mg, 0.27 mmol) and following the procedure described in example 12, the title compound was obtained (58 mg, Yield: 44%).

HPLC-MS (Method A): Rt: 2.71 min; ESI+-MS m/z: 593.5 (M+1).

Step d. Title Compound

TFA (0.5 mL) was added to a solution of the compound obtained in step c (58 mg, 0.08 mmol) in DCM (5 mL) and the mixture was stirred at r.t. for 16 h. The reaction mixture was basified with aq sat $NaHCO_3$ sol and the mixture was extracted with DCM. The combined organic layers were washed with brine, dried over anh $Na_2SO_4$, filtered and concentrated to dryness. The crude product was purified by flash chromatography, silica gel, DCM:MeOH to give the title compound (22 mg, Yield: 57%).

HPLC-MS (Method A): Rt, 2.06 min; ESI+-MS m/z: 493.3 $[M+H]^+$.

This method was used for the preparation of example 62 using suitable starting materials:

| STRUCTURE | EX | CHEMICAL NAME | Rt (min) | MS (M + H) | HPLC Method |
|---|---|---|---|---|---|
| 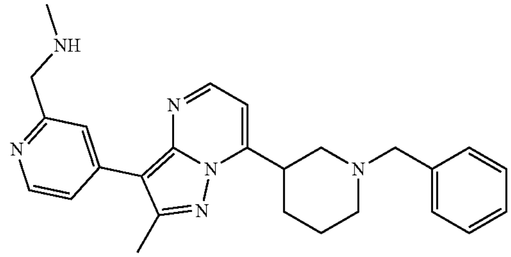 [SMILES: CNCc1cc(-c2c(C)nn3c(C4CCCN(Cc5ccccc5)C4)ccnc23)ccn1] | 62 | 1-(4-(7-(1-Benzylpiperidin-3-yl)-2-methylpyrazolo[1,5-a]pyrimidin-3-yl)pyridin-2-yl)-N-methylmethanamine | 1.89 | 427.3 | A |

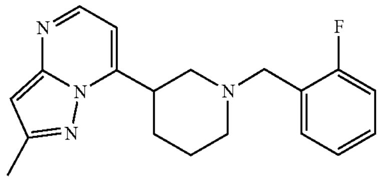 [SMILES: Cc1cc2nccc(C3CCCN(Cc4ccccc4F)C3)n2n1]

Example 63. 7-(1-(2-Fluorobenzyl)piperidin-3-yl)-2-methylpyrazolo[1,5-a]pyrimidine Step a. 2-Methyl-7-(piperidin-3-yl)pyrazolo[1,5-a]pyrimidine A Radley tube was charged with the compound obtained in example 3 (100 mg, 0.32 mmol), ammonium formate (72 mg, 1.1 mmol), 10% Pd/C (34 mg, 0.03 mmol) and EtOH (10 mL) and the reaction mixture was stirred at 85° C. for 2 h. The suspension was filtered through Celite and the solvent was removed under vacuum to give the title compound (70 mg, Yield: 99%).

HPLC-MS (Method A): Rt: 0.92 min; ESI+-MS m/z: 217.1 (M+1).

Step b. Title Compound

A MW tube was charged with the compound obtained in step a (75 mg, 0.35 mmol), 2-fluorobenzaldehyde (47 mg, 0.38 mmol), $NaBH_3CN$ (65 mg, 1 mmol) and MeOH (3 mL) and the mixture was heated under MW irradiation at 120° C. for 20 min. The reaction mixture was concentrated under reduced pressure and the residue was diluted with EtOAc and washed with aq sat $NaHCO_3$ sol. The organic layer was dried over anh $Na_2SO_4$, filtered and solvent was removed under vacuum. The residue was purified by flash chromatography, silica gel, DCM:MeOH, to give the title compound (41 mg, Yield: 36%).

HPLC-MS (Method A): Rt, 2.06 min; ESI+-MS m/z: 325.2 $[M+H]^+$.

This method was used for the preparation of examples 64-77 using suitable starting materials:

| STRUCTURE | EX | CHEMICAL NAME | Rt (min) | MS (M + H) | HPLC Method |
|---|---|---|---|---|---|
| 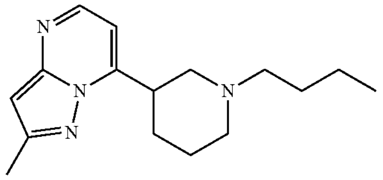 [SMILES: CCCCN1CCCC(c2ccnc3cc(C)nn23)C1] | 64 | 7-(1-Butylpiperidin-3-yl)-2-methylpyrazolo[1,5-a]pyrimidine | 1.85 | 273.3 | A |
| 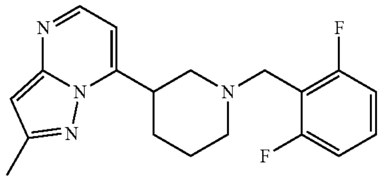 [SMILES: Cc1cc2nccc(C3CCCN(Cc4c(F)cccc4F)C3)n2n1] | 65 | 7-(1-(2,6-Difluorobenzyl)piperidin-3-yl)-2-methylpyrazolo[1,5-a]pyrimidine | 2.05 | 343.2 | A |
| 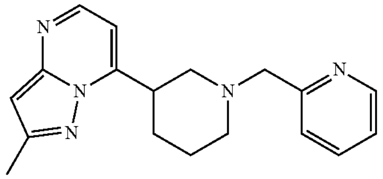 [SMILES: Cc1cc2nccc(C3CCCN(Cc4ccccn4)C3)n2n1] | 66 | 2-Methyl-7-(1-(pyridin-2-ylmethyl)piperidin-3-yl)pyrazolo[1,5-a]pyrimidine | 1.48 | 308.3 | A |
| 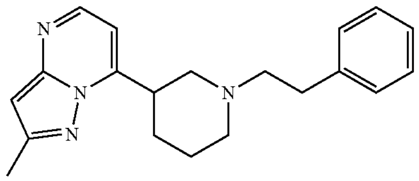 [SMILES: Cc1cc2nccc(C3CCCN(CCc4ccccc4)C3)n2n1] | 67 | 2-Methyl-7-(1-phenethylpiperidin-3-yl)pyrazolo[1,5-a]pyrimidine | 2.06 | 321.3 | A |
| 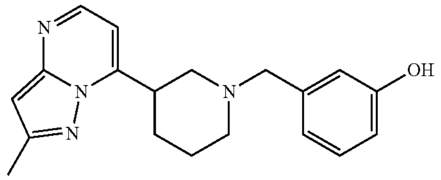 [SMILES: Cc1cc2nccc(C3CCCN(Cc4cccc(O)c4)C3)n2n1] | 68 | 3-((3-(2-Methylpyrazolo[1,5-a]pyrimidin-7-yl)piperidin-1-yl)methyl)phenol | 1.62 | 323.3 | A |
| 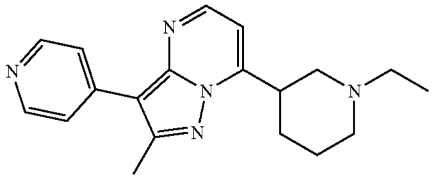 [SMILES: CCN1CCCC(c2ccnc3c(-c4ccncc4)c(C)nn23)C1] | 69 | 7-(1-Ethylpiperidin-3-yl)-2-methyl-3-(pyridin-4-yl)pyrazolo[1,5-a]pyrimidine | 1.55 | 322.1 | A |
| 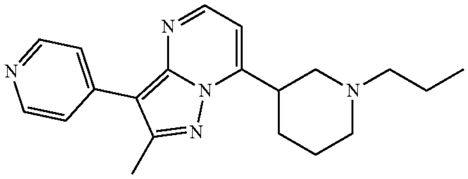 [SMILES: CCCN1CCCC(c2ccnc3c(-c4ccncc4)c(C)nn23)C1] | 70 | 2-Methyl-7-(1-propylpiperidin-3-yl)-3-(pyridin-4-yl)pyrazolo[1,5-a]pyrimidine | 1.83 | 336.2 | A |

-continued

| STRUCTURE | EX | CHEMICAL NAME | Rt (min) | MS (M + H) | HPLC Method |
|---|---|---|---|---|---|
| 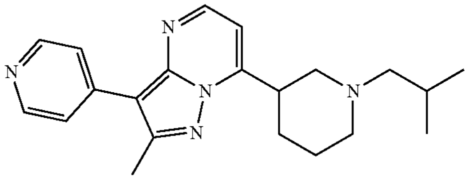 [SMILES: Cc1nn2c(C3CCCN(CC(C)C)C3)ccnc2c1-c1ccncc1] | 71 | 7-(1-Isobutylpiperidin-3-yl)-2-methyl-3-(pyridin-4-yl)pyrazolo[1,5-a]pyrimidine | 2.31 | 350.2 | A |
| 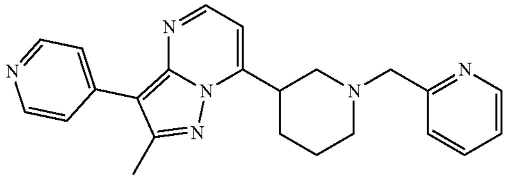 [SMILES: Cc1nn2c(C3CCCN(Cc4ccccn4)C3)ccnc2c1-c1ccncc1] | 72 | 2-Methyl-7-(1-(pyridin-2-ylmethyl)piperidin-3-yl)-3-(pyridin-4-yl)pyrazolo[1,5-a]pyrimidine | 1.66 | 385.2 | A |
| 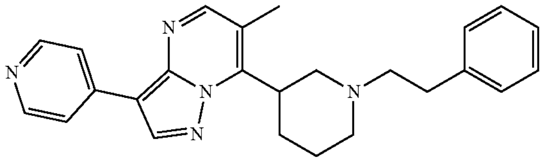 [SMILES: Cc1cnc2c(-c3ccncc3)cnn2c1C1CCCN(CCc2ccccc2)C1] | 73 | 6-Methyl-7-(1-phenethylpiperidin-3-yl)-3-(pyridin-4-yl)pyrazolo[1,5-a]pyrimidine | 2.19 | 398.2 | A |
| 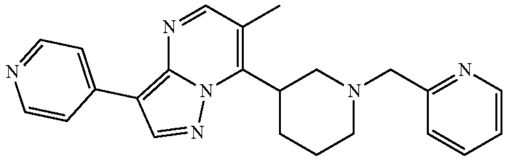 [SMILES: Cc1cnc2c(-c3ccncc3)cnn2c1C1CCCN(Cc2ccccn2)C1] | 74 | 6-Methyl-7-(1-(pyridin-2-ylmethyl)piperidin-3-yl)-3-(pyridin-4-yl)pyrazolo[1,5-a]pyrimidine | 1.70 | 385.3 | A |
| 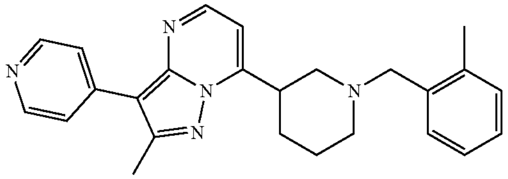 [SMILES: Cc1ccccc1CN1CCCC(c2ccnc3c(-c4ccncc4)c(C)nn23)C1] | 75 | 2-methyl-7-(1-(2-methylbenzyl)piperidin-3-yl)-3-(pyridin-4-yl)pyrazolo[1,5-a]pyrimidine | 2.39 | 398.3 | C |
| 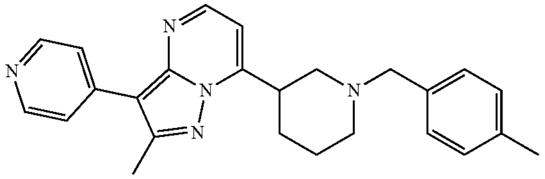 [SMILES: Cc1ccc(CN2CCCC(c3ccnc4c(-c5ccncc5)c(C)nn34)C2)cc1] | 76 | 2-Methyl-7-(1-(4-methylbenzyl)piperidin-3-yl)-3-(pyridin-4-yl)pyrazolo[1,5-a]pyrimidine | 2.38 | 398.3 | C |

-continued

| STRUCTURE | EX | CHEMICAL NAME | Rt (min) | MS (M + H) | HPLC Method |
|---|---|---|---|---|---|
| 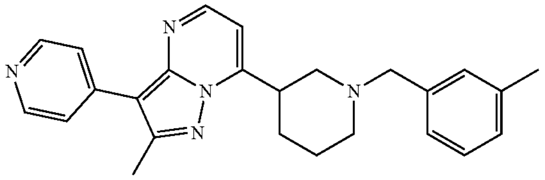 [SMILES: Cc1cccc(CN2CCCC(c3ccnc4c(-c5ccncc5)c(C)nn34)C2)c1] | 77 | 2-Methyl-7-(1-(3-methylbenzyl)piperidin-3-yl)-3-(pyridin-4-yl)pyrazolo[1,5-a]pyrimidine | 2.39 | 398.3 | C |

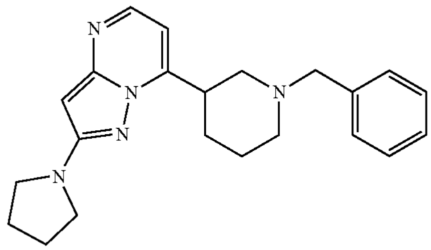 [SMILES: c1ccc(CN2CCCC(c3ccnc4cc(N5CCCC5)nn34)C2)cc1]

Example 78. 7-(1-Benzylpiperidin-3-yl)-2-(pyrrolidin-1-yl)pyrazolo[1,5-a]pyrimidine A schlenk flask was charged with the compound obtained in example 1 (125 mg, 0.33 mmol), pyrrolidine (0.05 mL, 0.67 mmol), XPhos (16 mg, 0.034 mmol), $Pd_2dba_3$ (15 mg, 0.0044 mmol) and $KO^tBu$ (113 mg, 1 mmol) and was evacuated and backfilled with argon. Toluene (4 mL), degassed by means of bubbling argon for 5 min, was added and the reaction mixture was heated at 100° C. for 16 h. The reaction mixture was concentrated under reduced pressure and the residue was diluted with EtOAc and washed with aq sat $NaHCO_3$ sol. The organic layer was dried over anh $Na_2SO_4$, filtered and the solvent was removed under vacuum. The residue was purified by flash chromatography, silica gel, Chx:EtOAc, to give the title compound (16 mg, Yield: 13%).

HPLC-MS (Method A): Rt, 2.42 min; ESI+–MS m/z: 362.3 $[M+H]^+$.

This method was used for the preparation of example 79 using suitable starting materials:

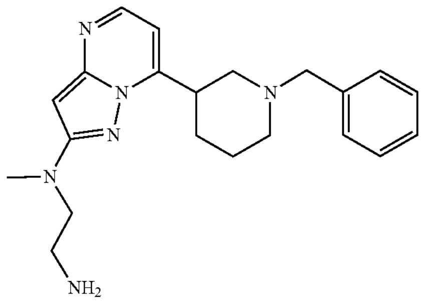

Example 80. $N^1$-(7-(1-Benzylpiperidin-3-yl)pyrazolo[1,5-a]pyrimidin-2-yl)-$N^1$-methylethane-1,2-diamine Step a. tert-Butyl (2-((7-(1-benzylpiperidin-3-yl)pyrazolo[1,5-a]pyrimidin-2-yl)(methyl)amino)ethyl)carbamate Starting from the compound obtained in example 1 (350 mg, 0.94 mmol) and tert-butyl (2-(methylamino)ethyl)carbamate (197 mg, 1.13 mmol) and following the procedure described in example 78, the title compound was obtained (77 mg, Yield: 17%).

HPLC-MS (Method A): Rt: 2.36 min; ESI+–m/z: 465.2 (M+1).

| STRUCTURE | EX | CHEMICAL NAME | Rt (min) | MS (M + H) | HPLC Method |
|---|---|---|---|---|---|
| 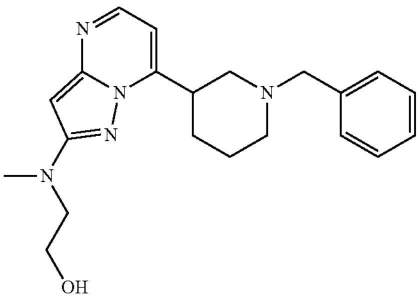 [SMILES: CN(CCO)c1cc2nccc(C3CCCN(Cc4ccccc4)C3)n2n1] | 79 | 2-((7-(1-Benzylpiperidin-3-yl)pyrazolo[1,5-a]pyrimidin-2-yl)(methyl)amino)ethanol | 1.83 | 366.4 | A |

Step b. Title Compound

Starting from the compound obtained in step a (89 mg, 0.2 mmol) and following the procedure described in step d of example 61, the title compound was obtained (72 mg, Yield: 98%).

HPLC-MS (Method A): Rt, 1.68 min; ESI+-MS m/z: 356.3 $[M+H]^+$.

This method was used for the preparation of examples 81-83 using suitable starting materials:

| STRUCTURE | EX | CHEMICAL NAME | Rt (min) | MS (M + H) | HPLC Method |
|---|---|---|---|---|---|
| 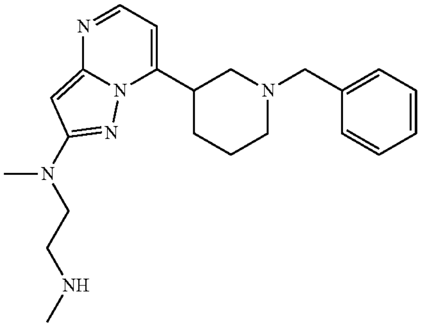 [SMILES: CNCCN(C)c1cc2nccc(C3CCCN(Cc4ccccc4)C3)n2n1] | 81 | $N^1$-(7-(1-Benzylpiperidin-3-yl)pyrazolo[1,5-a]pyrimidin-2-yl)-$N^1$,$N^2$-dimethylethane-1,2-diamine | 1.62 | 379.2 | A |
| 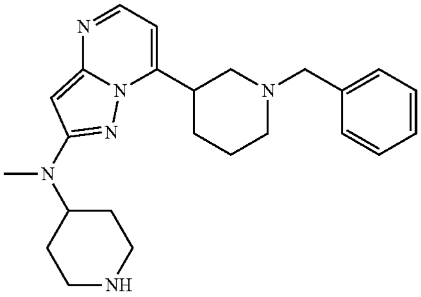 [SMILES: CN(c1cc2nccc(C3CCCN(Cc4ccccc4)C3)n2n1)C1CCNCC1] | 82 | 7-(1-Benzylpiperidin-3-yl)-N-methyl-N-(piperidin-4-yl)pyrazolo[1,5-a]pyrimidin-2-amine | 1.65 | 405.2 | A |
| 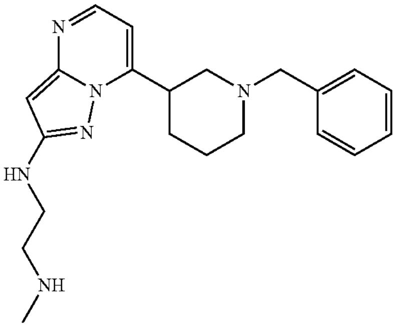 [SMILES: CNCCNc1cc2nccc(C3CCCN(Cc4ccccc4)C3)n2n1] | 83 | $N^1$-(7-(1-Benzylpiperidin-3-yl)pyrazolo[1,5-a]pyrimidin-2-yl)-$N^2$-methylethane-1,2-diamine | 1.54 | 365.2 | A |

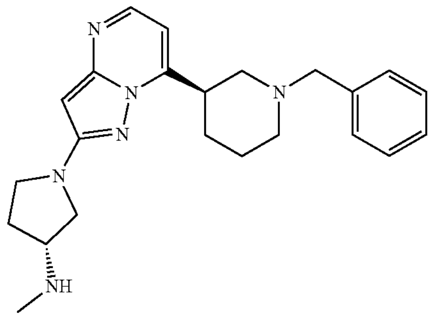

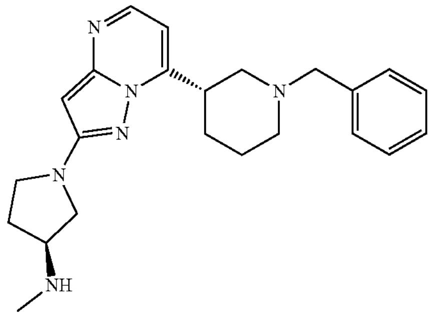

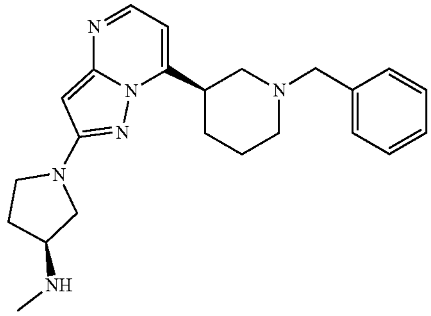

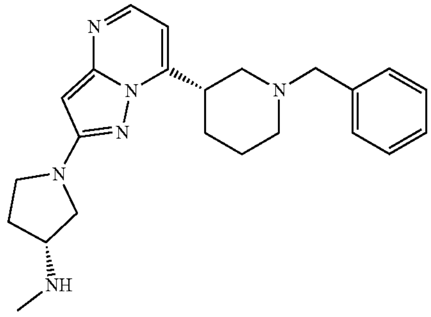

Examples 84, 85, 86 and 87. (R)-1-(7-((R)-1-Benzylpiperidin-3-yl)pyrazolo[1,5-a]pyrimidin-2-yl)-N-methylpyrrolidin-3-amine, (S)-1-(7-((S)-1-benzylpiperidin-3-yl)pyrazolo[1,5-a]pyrimidin-2-yl)-N-methylpyrrolidin-3-amine, (S)-1-(7-((R)-1-benzylpiperidin-3-yl)pyrazolo[1,5-a]pyrimidin-2-yl)-N-methylpyrrolidin-3-amine and (R)-1-(7-((S)-1-benzylpiperidin-3-yl)pyrazolo[1,5-a]pyrimidin-2-yl)-N-methylpyrrolidin-3-amine Starting from 1-(7-(1-benzylpiperidin-3-yl)pyrazolo[1,5-a]pyrimidin-2-yl)-N-methylpyrrolidin-3-amine, obtained following a similar procedure to that described in example 80, a chiral preparative HPLC [Column Chiralpak IA 20×250 mm, 5 μm; temperature: r.t.; eluent: n-Heptane/DCM/EtOH/$Et_2NH$ 70/28/2/0.1 v/v/v/v; flow rate: 13 mL/min; Rt1: 11.9 min; Rt2: 13.2 min; Rt3:13.7 min; Rt4: 13.9 min] was carried out to give the title compounds.

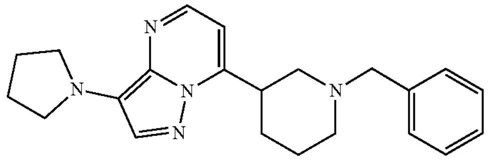 [SMILES: c1ccc(CN2CCCC(c3ccnc4c(N5CCCC5)cnn34)C2)cc1]

Example 88. 7-(1-Benzylpiperidin-3-yl)-3-(pyrrolidin-1-yl)pyrazolo[1,5-a]pyrimidine Step a. 7-(1-Benzylpiperidin-3-yl)-3-iodopyrazolo[1,5-a]pyrimidine Starting from 4-iodo-1H-pyrazol-3-amine (153 mg, 0.73 mmol) and following the procedure described in step b of example 1, the title compound was obtained (170 mg, Yield: 55%).

HPLC-MS (Method A): Rt: 2.35 min; ESI+-MS m/z: 419.0 (M+1).

Step b. Title Compound

A MW tube was charged with the compound obtained in step a (80 mg, 0.19 mmol), pyrrolidine (0.06 mL, 0.76 mmol), CuI (14 mg, 0.077 mmol), (S)-proline (8 mg, 0.077 mmol), $K_2CO_3$ (53 mg, 0.38 mmol) and DMSO (2 mL) and the mixture was degassed by means of bubbling argon for 5 min and heated under MW irradiation at 100° C. for 3 h. The mixture was dissolved with EtOAc:$Et_2O$ (1:1) and was washed with aq sat $NaHCO_3$ sol. The organic layer was dried over anh $Na_2SO_4$, filtered and the solvent was removed under vacuum. The crude product was purified by flash chromatography, silica gel, Chx:EtOAc to give the title compound (10 mg, Yield: 14%).

HPLC-MS (Method B): Rt, 2.81 min; ESI+-MS m/z: 362.4 $[M+H]^+$.

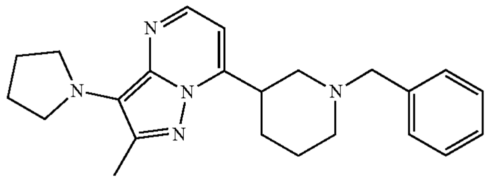 [SMILES: Cc1nn2c(C3CCCN(Cc4ccccc4)C3)ccnc2c1N1CCCC1]

Example 89. 7-(1-Benzylpiperidin-3-yl)-2-methyl-3-(pyrrolidin-1-yl)pyrazolo[1,5-a]pyrimidine Step a. 7-(1-Benzylpiperidin-3-yl)-3-iodo-2-methylpyrazolo[1,5-a]pyrimidine Starting from the compound obtained in example 3 (415 mg, 1.35 mmol) and NIS (426 mg, 1.9 mmol) and following the procedure described in example 10, the title compound was obtained (434 mg, Yield: 74%).

HPLC-MS (Method A): Rt: 2.46 min; ESI+-MS m/z: 433.1 (M+1).

Step b. Title Compound

Starting from the compound obtained in step a (243 mg, 0.56 mmol) and following the procedure described in step b of example 88, the title compound was obtained (10 mg, Yield: 5%).

HPLC-MS (Method A): Rt, 1.59 min; ESI+-MS m/z: 406.4 $[M+H]^+$.

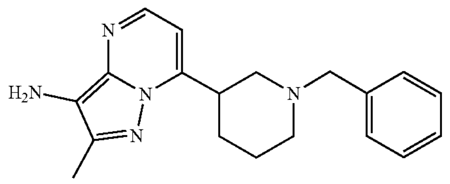 [SMILES: Cc1nn2c(C3CCCN(Cc4ccccc4)C3)ccnc2c1N]

Example 90. 7-(1-Benzylpiperidin-3-yl)-2-methylpyrazolo[1,5-a]pyrimidin-3-amine

A solution of the compound obtained in example 8 in conc HCl (3 mL) was stirred at 90° C. for 6 h. The reaction mixture was cooled to r.t. and basified with 10% aq sat $NaHCO_3$ sol and the mixture was extracted with DCM. The combined organic layers were washed with brine, dried over anh $Na_2SO_4$, filtered and concentrated to dryness. The crude product was purified by flash chromatography, silica gel, DCM:MeOH to give the title compound (43 mg, Yield: 40%).

HPLC-MS (Method A): Rt, 2.94 min; ESI+-MS m/z: 320.4 $[M+H]^+$.

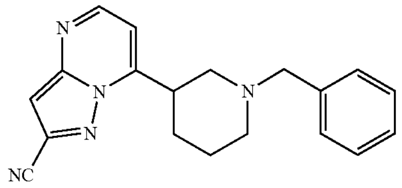 [SMILES: N#Cc1cc2nccc(C3CCCN(Cc4ccccc4)C3)n2n1]

Example 91. 7-(1-Benzylpiperidin-3-yl)pyrazolo[1,5-a]pyrimidine-2-carbonitrile

A schlenk flask was charged with the compound obtained in example 1 (90 mg, 0.24 mmol), $K_4[Fe(CN)_6]$-$2H_2O$ (24 mg, 0.06 mmol), 1,1'-bis(diphenylphosphino)ferrocene (28 mg, 0.05 mmol), $Pd(OAc)_2$ (2 mg, 0.006 mmol) and $Na_2CO_3$ (26 mg, 0.24 mmol) and was evacuated and backfilled with argon. NMP (2 mL), degassed by means of bubbling argon for 5 min, was added and the reaction mixture was heated at 120° C. for 16 h. The reaction mixture was diluted with EtOAc and washed with aq sat $NaHCO_3$ sol. The organic layer was dried over anh $Na_2SO_4$, filtered and solvent was removed under vacuum. The residue was purified by flash chromatography, silica gel, Chx:EtOAc, to give the title compound (8 mg, Yield: 10%).

HPLC-MS (Method A): Rt, 2.16 min; ESI+-MS m/z: 318.2 $[M+H]^+$.

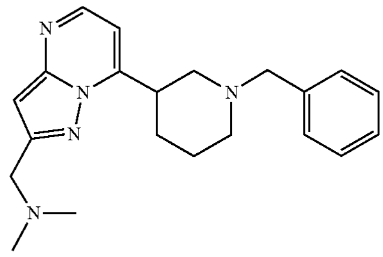 [SMILES: CN(C)Cc1cc2nccc(C3CCCN(Cc4ccccc4)C3)n2n1]

Example 92. 1-(7-(1-Benzylpiperidin-3-yl)pyrazolo[1,5-a]pyrimidin-2-yl)-N,N-dimethylmethanamine Step a. 7-(1-Benzylpiperidin-3-yl)pyrazolo[1,5-a]pyrimidine-2-carboxylic acid Starting from 3-amino-1H-pyrazole-5-carboxylic acid (93 mg, 0.73 mmol) and following the procedure described in step b of example 1, the title compound was obtained (94 mg, Yield: 38%).

HPLC-MS (Method A): Rt: 1.19 min; ESI+-MS m/z: 337.2 (M+1).

Step b. 7-(1-Benzylpiperidin-3-yl)-N,N-dimethylpyrazolo[1,5-a]pyrimidine-2-carboxamide Dimethylamine hydrochloride (170 mg, 2.1 mmol), TEA (0.58 mL, 4.1 mmol), EDC-HCl (398 mg, 2.1 mmol), DMAP (13 mg, 0.1 mmol) and HOBt (281 mg, 2.1 mmol) were added to a solution of the compound obtained in step a (350 mg, 0.77 mmol) in DMF (15 mL) and the reaction was stirred at r.t. for 16 h. The mixture was dissolved with EtOAc:$Et_2O$ (1:1) and was washed with aq sat $NaHCO_3$ sol. The organic layer was dried over anh $Na_2SO_4$, filtered and solvent was removed under vacuum. The crude product was purified by flash chromatography, silica gel, DCM:MeOH to give the title compound (320 mg, Yield: 74%).

HPLC-MS (Method A): Rt: 1.78 min; ESI+-MS m/z: 364.1 (M+1).

Step c. Title Compound

To a 1 M solution of $AlH_3$ in THF (4.4 mL, 4.4 mmol) at 0° C., a solution of the compound obtained in step b (320 mg, 0.88 mmol) in THF (4 mL) was added and the mixture was stirred at 0° C. for 90 min. After this time, water was added dropwise and the mixture was extracted with EtOAc. The organic layer was dried over anh $Na_2SO_4$, filtered and solvent was removed under vacuum. The crude product was purified by flash chromatography, silica gel, DCM:MeOH to give the title compound (30 mg, Yield: 10%).

HPLC-MS (Method A): Rt, 1.80 min; ESI+-MS m/z: 350.2 $[M+H]^+$.

This method was used for the preparation of examples 93 and 94 using suitable starting materials:

| STRUCTURE | EX | CHEMICAL NAME | Rt (min) | MS (M + H) | HPLC Method |
|---|---|---|---|---|---|
| 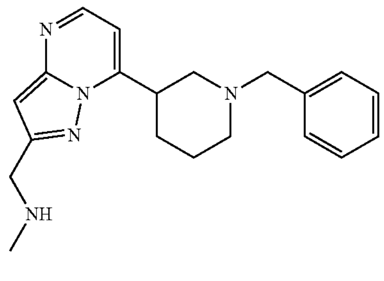 [SMILES: CNCc1cc2nccc(C3CCCN(Cc4ccccc4)C3)n2n1] | 93 | 1-(7-(1-Benzylpiperidin-3-yl)pyrazolo[1,5-a]pyrimidin-2-yl)-N-methylmethanamine | 1.54 | 336.1 | A |
| 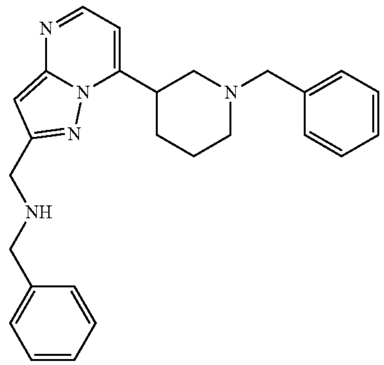 [SMILES: c1ccc(CNCc2cc3nccc(C4CCCN(Cc5ccccc5)C4)n3n2)cc1] | 94 | N-Benzyl-1-(7-(1-benzylpiperidin-3-yl)pyrazolo[1,5-a]pyrimidin-2-yl)methanamine | 2.19 | 412.2 | A |

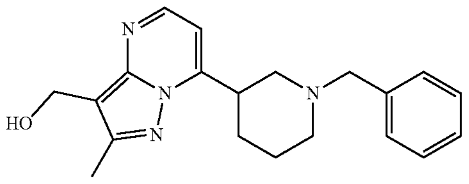 [SMILES: Cc1nn2c(C3CCCN(Cc4ccccc4)C3)ccnc2c1CO]

Example 95. (7-(1-Benzylpiperidin-3-yl)-2-methylpyrazolo[1,5-a]pyrimidin-3-yl)methanol Step a. 7-(1-Benzylpiperidin-3-yl)-2-methylpyrazolo[1,5-a]pyrimidine-3-carbaldehyde To a solution of the compound obtained in example 3 (50 mg, 0.16 mmol) in DMF (2 mL), $POCl_3$ (46 μL, 0.5 mmol) was added and the resulting mixture was stirred at r.t. for 16 h. The reaction mixture was cooled to 0° C. and the excess of $POCl_3$ was quenched by the addition of ice. The resulting solution was neutralized with 1 M aq NaOH, diluted with water and extracted with DCM. The organic layer was dried over anh $Na_2SO_4$, filtered and solvent was removed under vacuum to give the title compound (63 mg, Yield: Quant.).

HPLC-MS (Method A): Rt: 2.00 min; ESI+-MS m/z: 335.1 (M+1).

Step b. Title Compound $NaBH_4$ (7 mg, 0.2 mmol) was added to a solution of the compound obtained in step a (63 mg, 0.19 mmol) in THF (4 mL) and the mixture was stirred at r.t. for 16 h. The reaction mixture was cooled to 0° C. and water was slowly added. The residue was extracted with DCM, the organic layer was dried over anh $Na_2SO_4$, filtered and the solvent was removed under vacuum. The crude product was purified by flash chromatography, silica gel, Chx:EtOAc to give the title compound (12 mg, Yield: 19%).

HPLC-MS (Method A): Rt, 1.68 min; ESI+-MS m/z: 337.2 $[M+H]^+$.

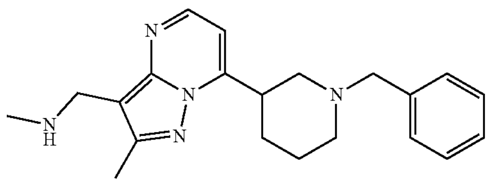 [SMILES: CNCc1c(C)nn2c(C3CCCN(Cc4ccccc4)C3)ccnc12]

Example 96. 1-(7-(1-Benzylpiperidin-3-yl)-2-methylpyrazolo[1,5-a]pyrimidin-3-yl)-N-methylmethanamine Starting from the compound obtained in step a of example 95 (80 mg, 0.24 mmol) in a 2 M solution of methylamine in THF (0.7 mL, 1.4 mmol) and following the procedure described in step b of example 63, the title compound was obtained (41 mg, Yield: 49%).

HPLC-MS (Method A): Rt, 1.46 min; ESI+-MS m/z: 350.1 $[M+H]^+$.

This method was used for the preparation of examples 97-99 using suitable starting materials:

| STRUCTURE | EX | CHEMICAL NAME | Rt (min) | MS (M + H) | HPLC Method |
|---|---|---|---|---|---|
| 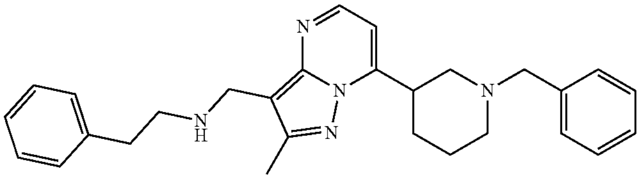 [SMILES: Cc1nn2c(C3CCCN(Cc4ccccc4)C3)ccnc2c1CNCCc1ccccc1] | 97 | N-((7-(1-Benzylpiperidin-3-yl)-2-methylpyrazolo[1,5-a]pyrimidin-3-yl)methyl)-2-phenylethanamine | 2.16 | 440.2 | A |
| 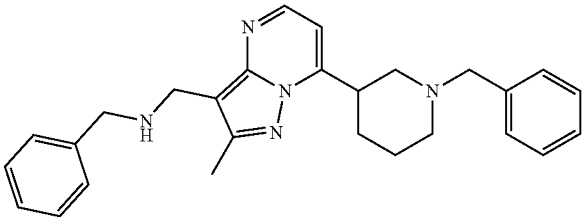 [SMILES: Cc1nn2c(C3CCCN(Cc4ccccc4)C3)ccnc2c1CNCc1ccccc1] | 98 | N-Benzyl-1-(7-(1-benzylpiperidin-3-yl)-2-methylpyrazolo[1,5-a]pyrimidin-3-yl)methanamine | 2.23 | 426.2 | A |
| 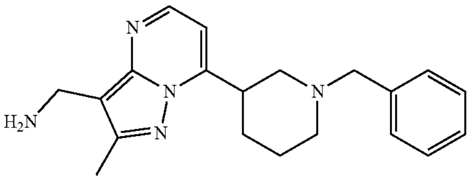 [SMILES: Cc1nn2c(C3CCCN(Cc4ccccc4)C3)ccnc2c1CN] | 99 | (7-(1-Benzylpiperidin-3-yl)-2-methylpyrazolo[1,5-a]pyrimidin-3-yl)methanamine | 1.85 | 334.2 | B |

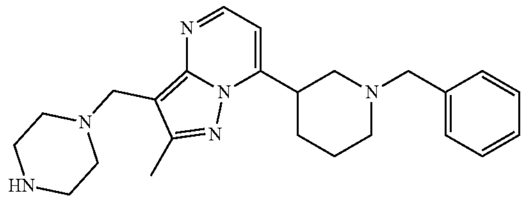 [SMILES: Cc1nn2c(C3CCCN(Cc4ccccc4)C3)ccnc2c1CN1CCNCC1]

Example 100. 7-(1-Benzylpiperidin-3-yl)-2-methyl-3-(piperazin-1-ylmethyl)pyrazolo[1,5-a]pyrimidine Step a. tert-Butyl 4-((7-(1-benzylpiperidin-3-yl)-2-methylpyrazolo[1,5-a]pyrimidin-3-yl)methyl)piperazine-1-carboxylate Starting from the compound obtained in step a of example 95 (100 mg, 0.3 mmol) and tert-butyl piperazine-1-carboxylate (278 mg, 1.5 mmol) and following the procedure described in step b of example 63, the title compound was obtained (123 mg, Yield: 81%).

HPLC-MS (Method A): Rt: 2.47 min; ESI+-MS m/z: 505.3 (M+1).

Step b. Title Compound

Starting from the compound obtained in step a (123 mg, 0.24 mmol) and following the procedure described in step d of example 61, the title compound was obtained (59 mg, Yield: 60%).

HPLC-MS (Method A): Rt, 1.55 min; ESI+-MS m/z: 405.3 $[M+H]^+$.

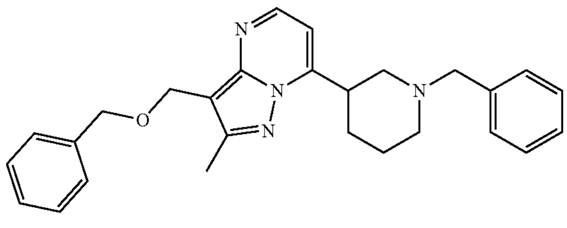 [SMILES: Cc1nn2c(C3CCCN(Cc4ccccc4)C3)ccnc2c1COCc1ccccc1]

Example 101. 3-((Benzyloxy)methyl)-7-(1-benzylpiperidin-3-yl)-2-methylpyrazolo[1,5-a]pyrimidine NaH (60% in mineral oil) (13 mg, 0.33 mmol) was added to a solution of the compound obtained in example 95 (45 mg, 0.13 mmol) in DMF (4 mL) and the reaction was stirred at 0° C. for 30 min. Then, benzyl bromide (32 μL, 0.27 mmol) was added and the mixture was stirred 16 h at 85° C. The mixture was dissolved with EtOAc:$Et_2O$ (1:1) and washed with brine. The organic layer was dried over anh $Na_2SO_4$, filtered and solvent was removed under vacuum. The crude product was purified by flash chromatography, silica gel, Chx:EtOAc to give the title compound (22 mg, Yield: 38%).

HPLC-MS (Method A): Rt, 2.53 min; ESI+-MS m/z: 427.2 $[M+H]^+$.

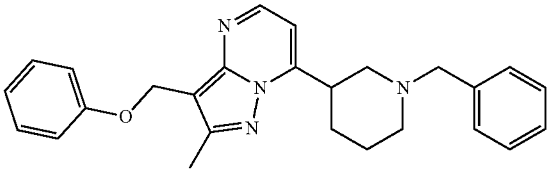 [SMILES: Cc1nn2c(C3CCCN(Cc4ccccc4)C3)ccnc2c1COc1ccccc1]

Example 102. 7-(1-Benzylpiperidin-3-yl)-2-methyl-3-(phenoxymethyl)pyrazolo[1,5-a]pyrimidine DIAD (60 μL, 0.31 mmol) was added to a solution of the compound obtained in example 95 (80 mg, 0.24 mmol), phenol (29 mg, 0.31 mmol) and $PPh_3$ (81 mg, 0.31 mmol) in toluene (10 mL) and the mixture was stirred at 100° C. for 16 h. The reaction was quenched with water, diluted with EtOAc and washed with brine. The organic layer was dried over anh $Na_2SO_4$, filtered and the solvent was removed under vacuum. The crude product was purified by flash chromatography, silica gel, DCM:MeOH to give the title compound (21 mg, Yield: 21%).

HPLC-MS (Method A): Rt, 2.18 min; ESI+-MS m/z: 413.3 $[M+H]^+$.

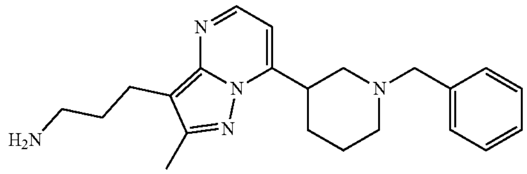 [SMILES: Cc1nn2c(C3CCCN(Cc4ccccc4)C3)ccnc2c1CCCN]

Example 103. 3-(7-(1-Benzylpiperidin-3-yl)-2-methylpyrazolo[1,5-a]pyrimidin-3-yl)propan-1-amine Step a. tert-Butyl (3-(7-(1-benzylpiperidin-3-yl)-2-methylpyrazolo[1,5-a]pyrimidin-3-yl)allyl)carbamate A schlenk flask was charged with the compound obtained in example 10 (360 mg, 0.93 mmol), tert-butyl (3-(4,4,5,5-tetramethyl-1,3,2-dioxaborolan-2-yl)allyl)carbamate (291 mg, 1 mmol), $Pd(PPh_3)_4$ (108 mg, 0.09 mmol) and $Na_2CO_3$ (198 mg, 1.9 mmol) and then was evacuated and backfilled with argon. A mixture of toluene:EtOH:$H_2O$ (3:1:1) (4 mL), degassed by means of bubbling argon for 5 min, was added and the reaction mixture was heated at 80° C. for 16 h. The suspension was diluted with EtOAc and washed with aq sat $NaHCO_3$ sol and brine. The organic layer was dried over anh $Na_2SO_4$, filtered and solvent was removed under vacuum. The residue was purified by flash chromatography, silica gel, Chx:Acetone, to give the title compound (56 mg, Yield: 13%).

HPLC-MS (Method A): Rt: 2.46 min; ESI+-MS m/z: 462.2 (M+1).

Step b. tert-Butyl (3-(7-(1-benzylpiperidin-3-yl)-2-methylpyrazolo[1,5-a]pyrimidin-3-yl)propyl)carbamate $Pd(OH)_2$ (27 mg, 0.2 mmol) was added to a solution of the compound obtained in step a (90 mg, 0.2 mmol) in MeOH (4 mL) and the solution was stirred under $H_2$ atmosphere during 16 h. The suspension was filtered through Celite and the solvent was removed under vacuum. The residue was purified by flash chromatography, silica gel, DCM:MeOH, to give the title compound (25 mg, Yield: 28%).

HPLC-MS (Method B): Rt: 2.89 min; ESI+-MS m/z: 464.3 (M+1).

Step c. Title Compound

Starting from the compound obtained in step b (25 mg, 0.05 mmol) and following the procedure described in step d of example 61, the title compound was obtained (3 mg, Yield: 11%).

HPLC-MS (Method A): Rt, 1.56 min; ESI+-MS m/z: 364.2 $[M+H]^+$.

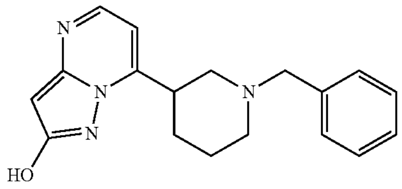 [SMILES: Oc1cc2nccc(C3CCCN(Cc4ccccc4)C3)n2n1]

Examples 104 and 105. 7-(1-Benzylpiperidin-3-yl)pyrazolo[1,5-a]pyrimidin-2-ol

Step a. (7-(1-Benzylpiperidin-3-yl)pyrazolo[1,5-a]pyrimidin-2-yl)boronic acid

To a solution of the compound obtained in example 1 (50 mg, 0.13 mmol), bis(pinacolato)diboron (51 mg, 0.2 mmol) and KOAc (39 mg, 0.4 mmol) in anh dioxane (5 mL) under argon atmosphere, Pd(dppf)Fe·$Cl_2$ (6 mg, 0.008 mmol) was added and the mixture was heated at 115° C. for 16 h. The reaction was quenched with brine, diluted with EtOAc and washed with brine. The organic layer was dried over anh $Na_2SO_4$, filtered and the solvent was removed under vacuum to give the title compound (70 mg, Yield: Quant).

HPLC-MS (Method C): Rt: 1.56 min; ESI+-MS m/z: 337.2 (M+1).

Step b. Title Compound

To a solution of the compound obtained in step a (50 mg, 0.15 mmol) in AcOH (3 mL) at 0° C., $H_2O_2$ (9 μL, 0.33 mmol) was added. The solution was stirred at this temperature for 30 min and allowed to warm to r.t. during 16 h more. The reaction mixture was filtered through Celite and the solvent was removed under vacuum. The residue was purified by flash chromatography, silica gel, DCM:MeOH, to give the title compound (10 mg, Yield: 22%).

HPLC-MS (Method C): Rt, 1.43 min; ESI+-MS m/z: 309.2 $[M+H]^+$.

This method was also used for the preparation of example 105.

| STRUCTURE | EX | CHEMICAL NAME | Rt (min) | MS (M + H) | HPLC Method |
|---|---|---|---|---|---|
| 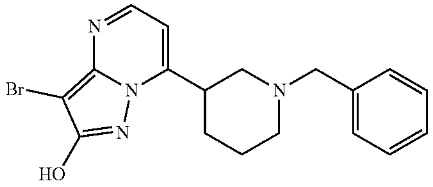 [SMILES: Oc1nn2c(C3CCCN(Cc4ccccc4)C3)ccnc2c1Br] | 105 | 7-(1-Benzylpiperidin-3-yl)-3-bromopyrazolo[1,5-a]pyrimidin-2-ol | 1.31 | 387.2 | C |

Examples 106, 107, 108 and 109. (S)-2-((R)-3-(2-Methyl-3-(pyridin-4-yl)pyrazolo[1,5-a]pyrimidin-7-yl)piperidin-1-yl)-2-phenylethanol, (S)-2-((S)-3-(2-methyl-3-(pyridin-4-yl)pyrazolo[1,5-a]pyrimidin-7-yl)piperidin-1-yl)-2-phenylethanol, (R)-2-((S)-3-(2-methyl-3-(pyridin-4-yl)pyrazolo[1,5-a]pyrimidin-7-yl)piperidin-1-yl)-2-phenylethanol and (R)-2-((R)-3-(2-methyl-3-(pyridin-4-yl)pyrazolo[1,5-a]pyrimidin-7-yl)piperidin-1-yl)-2-phenylethanol

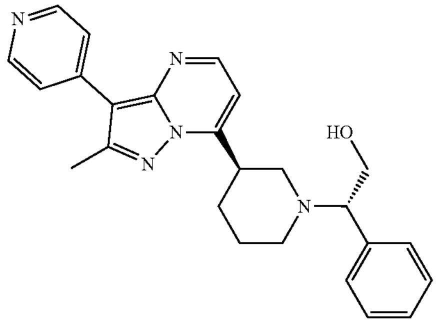

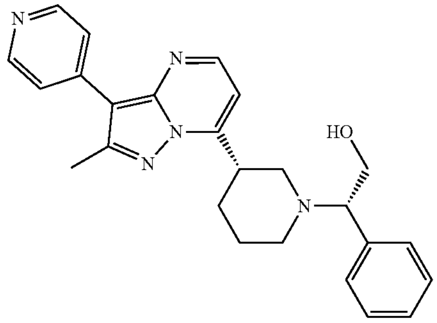

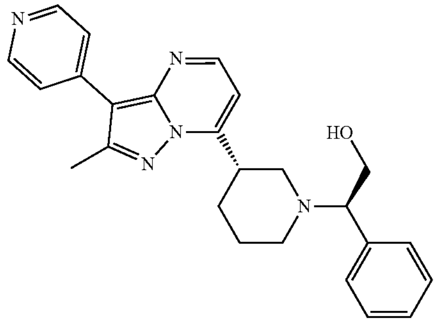

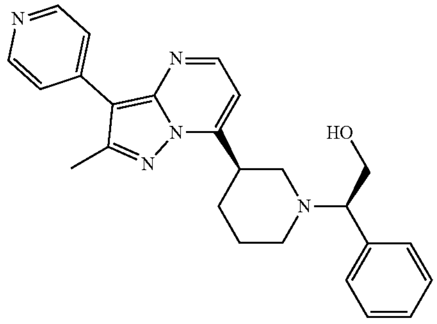

Step a. 2-Methyl-7-(piperidin-3-yl)-3-(pyridin-4-yl)pyrazolo[1,5-a]pyrimidine

Starting from the compound obtained in example 42 (154 mg, 0.4 mmol) and following the procedure described in step a. of example 63, the title compound was obtained (120 mg, Yield: Quant).

HPLC-MS (Method C): Rt: 1.12 min; ESI+-MS m/z: 294.1 (M+1).

Step b. 2-(3-(2-Methyl-3-(pyridin-4-yl)pyrazolo[1,5-a]pyrimidin-7-yl)piperidin-1-yl)-2-phenylethanol To a solution of 2-phenyloxirane (45 mg, 0.37 mmol) in ACN (2 mL), $LiClO_4$ (79 mg, 0.75 mmol) was added and the suspension was stirred until complete solution of the salts. Then, a solution of the compound obtained in step a (45 mg, 0.37 mmol) in ACN (0.5 mL) was added and the solution was stirred at 80° C. for 16 h. The suspension was diluted with EtOAc and washed with aq sat $NaHCO_3$ sol and brine. The organic layer was dried over anh $Na_2SO_4$, filtered and solvent was removed under vacuum. The residue was purified by flash chromatography, silica gel, Chx:EtOAc, to give the title compound (34 mg, Yield: 23%).

HPLC-MS (Method C): Rt: 1.95 min; ESI+-MS m/z: 414.3 (M+1).

Step c. Title Compounds

Starting from the compound obtained in step b, a chiral preparative HPLC [Column LUX C3 21.2×250 mm, 5 μm; temperature: 40° C.; eluent: MeOH/EtOH/$NH_3$ 70/30/0.1 v/v/v; flow rate: 50 mL/min; Rt1: 2.02 min; Rt2: 2.15 min; Rt3: 2.84; Rt4: 3.83 min] was carried out to give the title compounds.

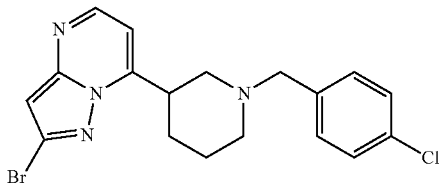 [SMILES: Clc1ccc(CN2CCCC(c3ccnc4cc(Br)nn34)C2)cc1]

Example 110. 2-Bromo-7-(1-(4-chlorobenzyl)piperidin-3-yl)pyrazolo[1,5-a]pyrimidine Step a. tert-Butyl 3-acetylpiperidine-1-carboxylate To a 0° C. cooled solution of 1-(tert-butyl) 3-ethyl piperidine-1,3-dicarboxylate (5 g, 19.43 mmol), and N,O-dimethylhydroxylamine hydrochloride (2.27 g, 23.32 mmol) in anh THF (69 mL) and under argon atmosphere, methylmagnesium chloride (3 M in THF, 35.6 mL, 107 mmol) was added dropwise. The reaction was allowed to warm up to r.t. for 16 h. Then the solution was quenched with aq sat $NH_4Cl$ sol at 0° C. The aq layer was extracted with EtOAc and the combined organic extracts were washed with brine, dried over $MgSO_4$, filtered and concentrated to give the title compound as a light brown oil (4.19 g, Yield: 95%).

HPLC-MS (Method E): Rt.: 3.33 min; ESI+MS: m/z 254.0 $[M+H]^+$.

Step b. tert-Butyl (E)-3-(3-(dimethylamino)acryloyl)piperidine-1-carboxylate

A solution of the compound obtained in step a (4.15 g, 18.28 mmol) and 1-tert-butoxy-N,N,N',N'-tetramethylmethanediamine (3.82 mL, 21.93 mmol) were mixed in a sealed reactor under argon and the mixture was stirred at 100° C. for 16 h. The reaction mixture was concentrated to dryness under reduced pressure to give the title compound as a brown oil (5.50 g). This compound was used in the next step without further purification.

HPLC-MS (Method E): Rt.: 2.63 min; ESI+MS: m/z 283.3 $[M+H]^+$.

Step c. tert-Butyl 3-(2-bromopyrazolo[1,5-a]pyrimidin-7-yl)piperidine-1-carboxylate To a solution of the compound obtained in step b (3.2 g, 11.33 mmol) in glacial AcOH (48 mL), 5-bromo-1H-pyrazol-3-amine (2.01 mg, 12.47 mmol) was added. The reaction mixture was stirred at 50° C. for 9 h. The solvent was evaporated and the residue was purified by flash chromatography, silica gel, hexane/EtOAc as eluents to give the title compound as a brown foam (2.85 g, Yield: 66%).

HPLC-MS (Method D): Rt.: 2.98 min; ESI+MS: m/z 381.1 $[M+H]^+$.

Step d. 2-Bromo-7-(piperidin-3-yl)pyrazolo[1,5-a]pyrimidine hydrochloride

The compound obtained in step c (1.04 g, 2.73 mmol) was treated with HCl (4 M in dioxane, 13.64 mL, 54.6 mmol). A yellow precipitate appeared just after the addition. The reaction mixture was stirred for 1.5 h, then the solvent was evaporated to give the title compound as a yellow solid (960 mg) which was used in the next step without further purification.

HPLC-MS (Method E): Rt.: 2.25 min; ESI+MS: m/z 281.0 $[M+H]^+$.

Step e. Title Compound

To a solution of the compound obtained in step d (80 mg, 0.25 mmol) in anh MeOH (2 mL) TEA (0.07 mL, 0.50 mmol) was added and the solution was stirred for 5 min. 4-Chlorobenzaldehyde (53.1 mg, 0.38 mmol) and AcOH (0.012 mL, 0.2 mmol) were added to the solution followed by sodium cyanotrihydroborate (31.7 mg, 0.50 mmol) and the reaction mixture was stirred at r.t. for 16 h. Then, solvent was evaporated and the reaction mixture was dissolved with DCM and poured into aq sat $NaHCO_3$ sol, the organic layer was separated and the aq layer was extracted with DCM. The combined organic extracts were washed with brine, dried over anh $Na_2SO_4$ and filtered. Solvent was evaporated and the residue was purified by flash chromatography, silica gel, DCM:MeOH as eluents to give the title compound as a yellow solid (81 mg, Yield: 78%).

HPLC-MS (Method D): Rt.: 3.43 min; ESI+MS: m/z 405.0 $[M+H]^+$.

This method was used for the preparation of examples 111-113 using suitable starting materials:

| STRUCTURE | EX | CHEMICAL NAME | Rt (min) | MS (M + H) | HPLC Method |
|---|---|---|---|---|---|
| 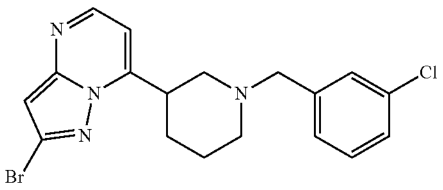 [SMILES: Clc1cccc(CN2CCCC(c3ccnc4cc(Br)nn34)C2)c1] | 111 | 2-Bromo-7-(1-(3-chlorobenzyl)piperidin-3-yl)pyrazolo[1,5-a]pyrimidine | 3.45 | 405.0 | D |
| 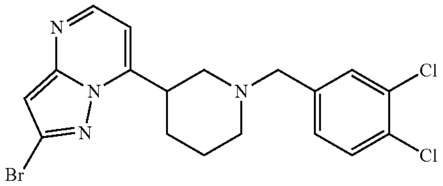 [SMILES: Clc1ccc(CN2CCCC(c3ccnc4cc(Br)nn34)C2)cc1Cl] | 112 | 2-Bromo-7-(1-(3,4-dichlorobenzyl)piperidin-3-yl)pyrazolo[1,5-a]pyrimidine | 3.65 | 439.0 | D |

-continued

| STRUCTURE | EX | CHEMICAL NAME | Rt (min) | MS (M + H) | HPLC Method |
|---|---|---|---|---|---|
| 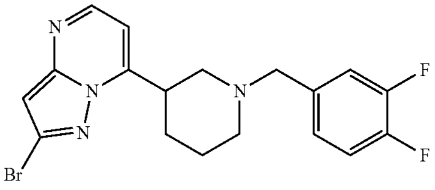 [SMILES: Fc1ccc(CN2CCCC(c3ccnc4cc(Br)nn34)C2)cc1F] | 113 | 2-Bromo-7-(1-(3,4-difluorobenzyl)piperidin-3-yl)pyrazolo[1,5-a]pyrimidine | 3.32 | 407.1 | D |

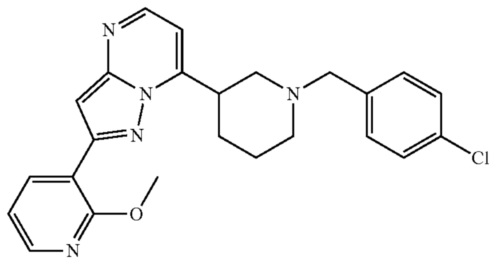

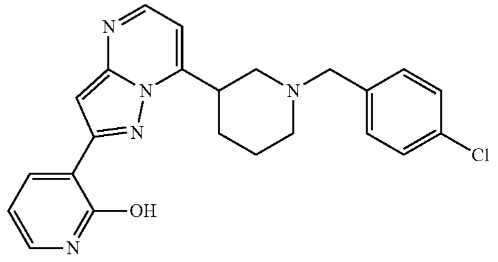

Examples 114 and 115. 7-(1-(4-Chlorobenzyl)piperidin-3-yl)-2-(2-methoxypyridin-3-yl)pyrazolo[1,5-a]pyrimidine and 3-(7-(1-(4-chlorobenzyl)piperidin-3-yl)pyrazolo[1,5-a]pyrimidin-2-yl)pyridin-2-ol Step a. tert-Butyl 3-(2-(2-methoxypyridin-3-yl)pyrazolo[1,5-a]pyrimidin-7-yl)piperidine-1-carboxylate A sealed tube was charged with the compound obtained in step c of example 110 (1.67 g, 4.38 mmol), (2-methoxypyridin-3-yl)boronic acid (1.00 g, 6.57 mmol), $K_2CO_3$ (1.81 g, 13.14 mmol), $Pd(PPh_3)_4$ (500 mg, 0.44 mmol) and DME:$H_2O$ (3:1, 26 mL). The reaction mixture was degassed by argon for 5 min and heated at 100° C. for 16 h. The suspension was diluted with EtOAc and the organic layer was separated, washed with aq sat $Na_2CO_3$ sol, dried over anh $Na_2SO_4$, filtered and concentrated under vacuum. The residue was purified by flash chromatography, silica gel, DCM:MeOH, to give the title compound as a brown foam (1.28 g, Yield: 71%).

HPLC-MS (Method E): Rt.: 3.83 min; ESI+MS: m/z 410.2 $[M+H]^+$.

Step b. 2-(2-Methoxypyridin-3-yl)-7-(piperidin-3-yl)pyrazolo[1,5-a]pyrimidine hydrochloride and 3-(7-(piperidin-3-yl)pyrazolo[1,5-a]pyrimidin-2-yl)pyridin-2-ol hydrochloride Starting from the compound obtained in step a (790 mg, 1.92 mmol) and following the procedure described in step d of example 110, the title compounds were obtained as a 1:1 mixture (400 mg). This mixture was used in the next step without further purification.

HPLC-MS (Method D): Rt.: 1.45 min; ESI+MS: m/z 296.1 $[M+H]^+$ and Rt.: 2.03 min; ESI+MS: m/z 310.1 $[M+H]^+$ respectively.

Step c. Title Compounds

To a solution of the mixture of compounds obtained in step b (200 mg, 0.57 mmol) in anh DMA (3 mL) TEA (0.24 mL, 1.73 mmol) was added and the solution was stirred for 5 min. 1-Chloro-4-(chloromethyl)benzene (93.1 mg, 0.57 mmol) was added and the reaction mixture was stirred at 70° C. for 16 h. The reaction mixture was allowed to cool down to r.t. and was poured into aq sat $NaHCO_3$ sol and DCM, the organic layer was separated and the aq layer was extracted with DCM. The combined organic extracts were washed with brine, dried over anh $Na_2SO_4$ and filtered. Solvent was evaporated and the residue was purified by flash chromatography, silica gel, DCM:MeOH as eluents to give the title compounds as yellow solids (69 mg, Yield: 26% and 52 mg, Yield: 20% respectively).

HPLC-MS (Method D): Rt.: 3.60 min; ESI+ MS: m/z 434.1 $[M+H]^+$ and Rt.: 2.73 min; ESI+MS: m/z 420.1 $[M+H]^+$ respectively.

This method was used for the preparation of examples 116-119 using suitable starting materials:

| STRUCTURE | EX | CHEMICAL NAME | Rt (min) | MS (M + H) | HPLC Method |
|---|---|---|---|---|---|
| 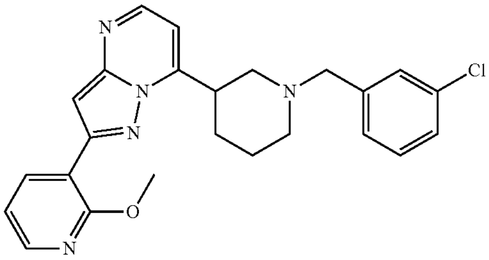 [SMILES: COc1ncccc1-c1cc2nccc(C3CCCN(Cc4cccc(Cl)c4)C3)n2n1] | 116 | 7-(1-(3-Chlorobenzyl)piperidin-3-yl)-2-(2-methoxypyridin-3-yl)pyrazolo[1,5-a]pyrimidine | 3.62 | 434.1 | D |
| 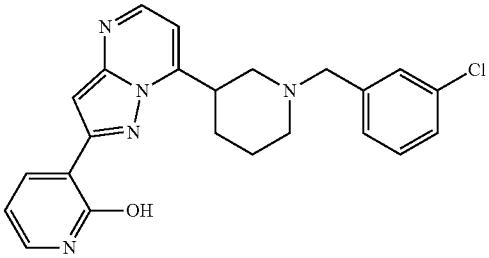 [SMILES: Oc1ncccc1-c1cc2nccc(C3CCCN(Cc4cccc(Cl)c4)C3)n2n1] | 117 | 3-(7-(1-(3-Chlorobenzyl)piperidin-3-yl)pyrazolo[1,5-a]pyrimidin-2-yl)pyridin-2-ol | 2.75 | 420.1 | D |
| 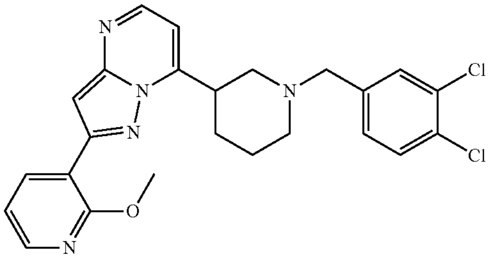 [SMILES: COc1ncccc1-c1cc2nccc(C3CCCN(Cc4ccc(Cl)c(Cl)c4)C3)n2n1] | 118 | 7-(1-(3,4-Dichlorobenzyl)piperidin-3-yl)-2-(2-methoxypyridin-3-yl)pyrazolo[1,5-a]pyrimidine | 4.77 | 468.1 | E |
| 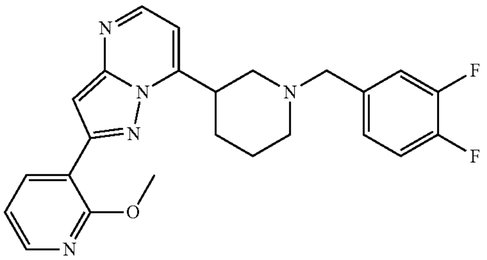 [SMILES: COc1ncccc1-c1cc2nccc(C3CCCN(Cc4ccc(F)c(F)c4)C3)n2n1] | 119 | 7-(1-(3,4-Difluorobenzyl)piperidin-3-yl)-2-(2-methoxypyridin-3-yl)pyrazolo[1,5-a]pyrimidine | 4.30 | 436.1 | E |

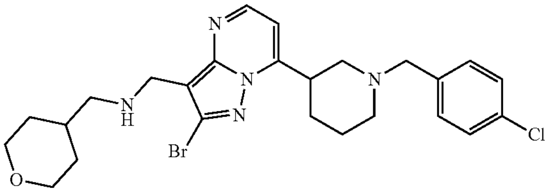 [SMILES: Clc1ccc(CN2CCCC(c3ccnc4c(CNCC5CCOCC5)c(Br)nn34)C2)cc1]

Example 120. 1-(2-Bromo-7-(1-(4-chlorobenzyl)piperidin-3-yl)pyrazolo[1,5-a]pyrimidin-3-yl)-N-((tetrahydro-2H-pyran-4-yl)methyl)methanamine Step a. 2-Bromo-7-(1-(4-chlorobenzyl)piperidin-3-yl)pyrazolo[1,5-a]pyrimidine-3-carbaldehyde To a solution of the compound obtained in example 110 (175 mg, 0.43 mmol) in DMF (1.1 mL), $POCl_3$ (0.11 mL, 1.19 mmol) was added and the reaction mixture was stirred at r.t. for 16 h. After that time, the reaction mixture was cooled down to 0° C. and ice-water was added carefully, the mixture was basified with 2N NaOH to pH 11. The resulting suspension was extracted with EtOAc. The combined organic extracts were washed with brine, dried over anh $Na_2SO_4$, filtered and concentrated to obtain the title compound as a brown solid (175 mg, Yield: 75%).

HPLC-MS (Method E): Rt.: 3.82 min; ESI+MS: m/z 433.0 $[M+H]^+$.

Step b. Title Compound

Starting from the compound obtained in step a (175 mg, 0.40 mmol) and (tetrahydro-2H-pyran-4-yl)methanamine (116 mg, 1.0 mmol) and following the procedure described in step e of example 110, the title compound was obtained (60 mg, Yield: 27%).

HPLC-MS (Method E): Rt.: 4.02 min; ESI+MS: m/z 532.1 $[M+H]^+$.

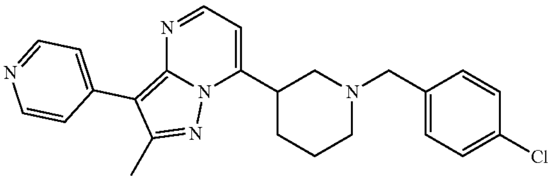 [SMILES: Cc1nn2c(C3CCCN(Cc4ccc(Cl)cc4)C3)ccnc2c1-c1ccncc1]

Example 121. 7-(1-(4-Chlorobenzyl)piperidin-3-yl)-2-methyl-3-(pyridin-4-yl)pyrazolo[1,5-a]pyrimidine Step a. tert-Butyl 3-(3-bromo-2-methylpyrazolo[1,5-a]pyrimidin-7-yl)piperidine-1-carboxylate Starting from the compound obtained in step b of example 110 (2 g, 7.08 mmol) and 4-bromo-5-methyl-1H-pyrazol-3-amine (1.37 g, 7.79 mmol) and following the procedure described in step c of example 110, the title compound was obtained as a brown foam (2.04 g, Yield: 73%).

HPLC-MS (Method E): Rt.: 3.75 min; ESI+MS: m/z 395.1 $[M+H]^+$.

Step b. tert-Butyl 3-(2-methyl-3-(pyridin-4-yl)pyrazolo[1,5-a]pyrimidin-7-yl)piperidine-1-carboxylate Starting from the compound obtained in step a (1.2 g, 3.04 mmol) and 4-(4,4,5,5-tetramethyl-1,3,2-dioxaborolan-2-yl)pyridine (0.93 g, 4.55 mmol) and following the procedure described in step a of examples 114 and 115, the title compound was obtained as a brown solid (1.78 g, Yield: 58%).

HPLC-MS (Method E): Rt.: 3.37 min; ESI+MS: m/z 394.2 $[M+H]^+$.

Step c. 2-Methyl-7-(piperidin-3-yl)-3-(pyridin-4-yl)pyrazolo[1,5-a]pyrimidine dihydrochloride Starting from the compound obtained in step b (0.70 g, 1.78 mmol) and following the procedure described in step d of example 110, the title compound was obtained as a yellow solid (650 mg).

HPLC-MS (Method E): Rt.: 2.17 min; ESI+MS: m/z 294.1 $[M+H]^+$.

Step d. Title Compound

Starting from the compound obtained in step c (80 mg, 0.21 mmol) and following the procedure described in step e of example 110, the title compound was obtained (61.8 mg, Yield: 65%).

HPLC-MS (Method D): Rt.: 3.30 min; ESI+MS: m/z 418.1 $[M+H]^+$.

This method was used for the preparation of examples 122-133 using suitable starting materials:

| STRUCTURE | EX | CHEMICAL NAME | Rt (min) | MS (M + H) | HPLC Method |
|---|---|---|---|---|---|
| 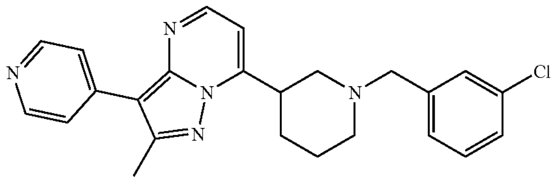 [SMILES: Cc1nn2c(C3CCCN(Cc4cccc(Cl)c4)C3)ccnc2c1-c1ccncc1] | 122 | 7-(1-(3-Chlorobenzyl)piperidin-3-yl)-2-methyl-3-(pyridin-4-yl)pyrazolo[1,5-a]pyrimidine | 4.03 | 418.1 | E |
| 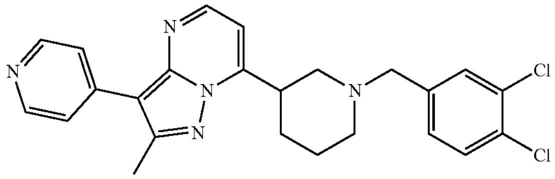 [SMILES: Cc1nn2c(C3CCCN(Cc4ccc(Cl)c(Cl)c4)C3)ccnc2c1-c1ccncc1] | 123 | 7-(1-(3,4-Dichlorobenzyl)piperidin-3-yl)-2-methyl-3-(pyridin-4-yl)pyrazolo[1,5-a]pyrimidine | 4.33 | 452.1 | E |
| 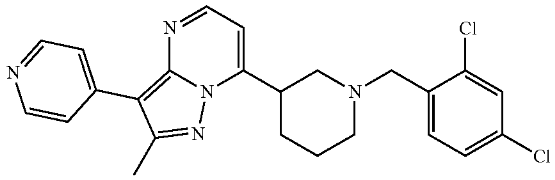 | 124 | 7-(1-(2,4-Dichlorobenzyl)piperidin-3-yl)-2-methyl-3-(pyridin-4-yl)pyrazolo[1,5-a]pyrimidine | 4.53 | 452.1 | E |
| 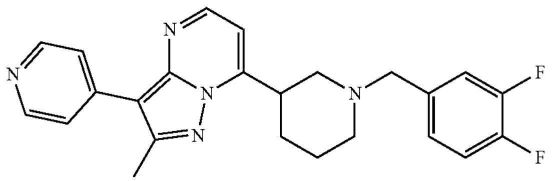 [SMILES: Cc1nn2c(C3CCCN(Cc4ccc(F)c(F)c4)C3)ccnc2c1-c1ccncc1] | 125 | 7-(1-(3,4-Difluorobenzyl)piperidin-3-yl)-2-methyl-3-(pyridin-4-yl)pyrazolo[1,5-a]pyrimidine | 3.85 | 420.1 | E |

-continued

| STRUCTURE | EX | CHEMICAL NAME | Rt (min) | MS (M + H) | HPLC Method |
|---|---|---|---|---|---|
| 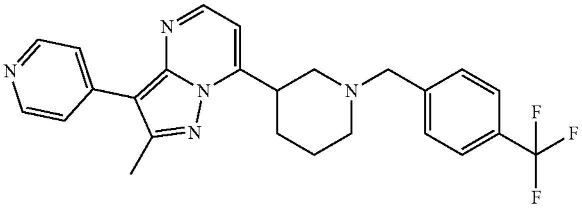 [SMILES: Cc1nn2c(C3CCCN(Cc4ccc(C(F)(F)F)cc4)C3)ccnc2c1-c1ccncc1] | 126 | 2-Methyl-3-(pyridin-4-yl)-7-(1-(4-(trifluoromethyl)benzyl)piperidin-3-yl)pyrazolo[1,5-a]pyrimidine | 4.07 | 452.2 | E |
| 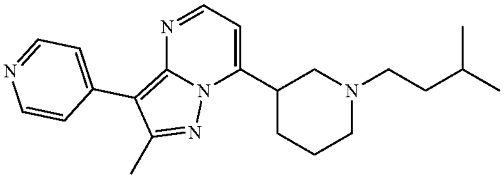 [SMILES: Cc1nn2c(C3CCCN(CCC(C)C)C3)ccnc2c1-c1ccncc1] | 127 | 7-(1-Isopentylpiperidin-3-yl)-2-methyl-3-(pyridin-4-yl)pyrazolo[1,5-a]pyrimidine | 3.70 | 364.2 | E |
| 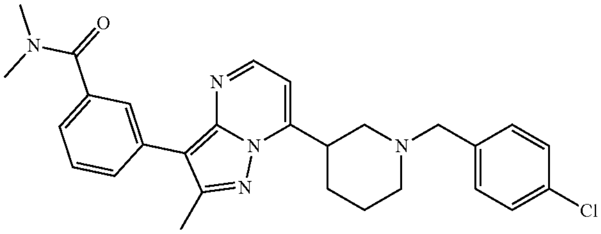 [SMILES: Cc1nn2c(C3CCCN(Cc4ccc(Cl)cc4)C3)ccnc2c1-c1cccc(C(=O)N(C)C)c1] | 128 | 3-(7-(1-(4-Chlorobenzyl)piperidin-3-yl)-2-methylpyrazolo[1,5-a]pyrimidin-3-yl)-N,N-dimethylbenzamide | 3.95 | 488.2 | E |
| 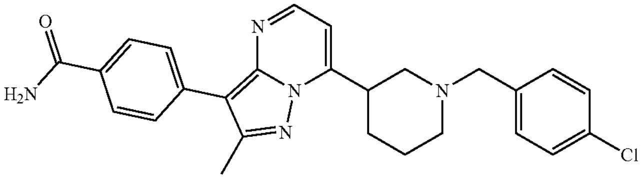 [SMILES: Cc1nn2c(C3CCCN(Cc4ccc(Cl)cc4)C3)ccnc2c1-c1ccc(C(N)=O)cc1] | 129 | 4-(7-(1-(4-Chlorobenzyl)piperidin-3-yl)-2-methylpyrazolo[1,5-a]pyrimidin-3-yl)benzamide | 3.62 | 460.1 | E |
| 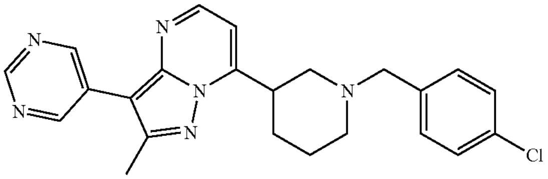 [SMILES: Cc1nn2c(C3CCCN(Cc4ccc(Cl)cc4)C3)ccnc2c1-c1cncnc1] | 130 | 7-(1-(4-Chlorobenzyl)piperidin-3-yl)-2-methyl-3-(pyrimidin-5-yl)pyrazolo[1,5-a]pyrimidine | 3.73 | 419.1 | E |
| 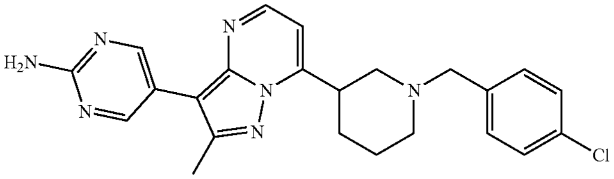 [SMILES: Cc1nn2c(C3CCCN(Cc4ccc(Cl)cc4)C3)ccnc2c1-c1cnc(N)nc1] | 131 | 5-(7-(1-(4-Chlorobenzyl)piperidin-3-yl)-2-methylpyrazolo[1,5-a]pyrimidin-3-yl)pyrimidin-2-amine | 3.47 | 434.1 | E |

-continued

| STRUCTURE | EX | CHEMICAL NAME | Rt (min) | MS (M + H) | HPLC Method |
|---|---|---|---|---|---|
| 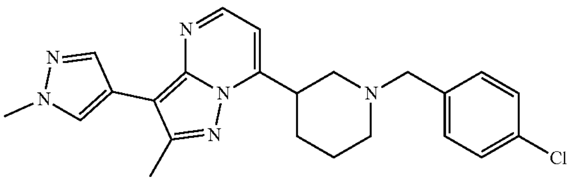 [SMILES: Cc1nn2c(C3CCCN(Cc4ccc(Cl)cc4)C3)ccnc2c1-c1cnn(C)c1] | 132 | 7-(1-(4-Chlorobenzyl)piperidin-3-yl)-2-methyl-3-(1-methyl-1H-pyrazol-4-yl)pyrazolo[1,5-a]pyrimidine | 3.80 | 421.1 | E |
| 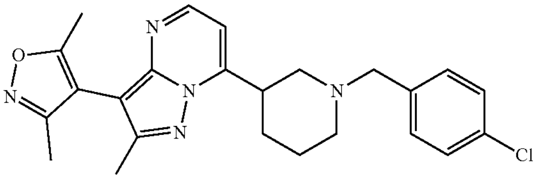 [SMILES: Cc1noc(C)c1-c1c(C)nn2c(C3CCCN(Cc4ccc(Cl)cc4)C3)ccnc12] | 133 | 4-(7-(1-(4-Chlorobenzyl)piperidin-3-yl)-2-methylpyrazolo[1,5-a]pyrimidin-3-yl)-3,5-dimethylisoxazole | 4.03 | 436.1 | E |

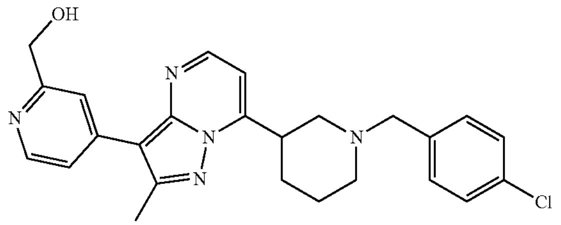 [SMILES: Cc1nn2c(C3CCCN(Cc4ccc(Cl)cc4)C3)ccnc2c1-c1ccnc(CO)c1]

Example 134. (4-(7-(1-(4-Chlorobenzyl)piperidin-3-yl)-2-methylpyrazolo[1,5-a]pyrimidin-3-yl)pyridin-2-yl)methanol Step a. 4-Bromo-2-(((tert-butyldimethylsilyl)oxy)methyl)pyridine To a stirred solution of (4-bromopyridin-2-yl)methanol (400 mg, 2.13 mmol) in DMF (8 mL), imidazole (290 mg, 4.25 mmol) and tert-butyldimethylchlorosilane (321 mg, 2.13 mmol) were added. The reaction mixture was stirred at r.t. for 16 h. Then, the mixture was diluted with EtOAc and the organic layer washed with water and brine, dried over anh $Na_2SO_4$, filtered and concentrated under vacuum. The residue was purified by flash chromatography, silica gel, hexane:EtOAc, to give the title compound as a brown foam (514 mg, Yield: 80%).

HPLC-MS (Method E): Rt.: 3.15 min; ESI+MS: m/z 302.0 $[M+H]^+$.

Step b. 2-(((tert-Butyldimethylsilyl)oxy)methyl)-4-(4,4,5,5-tetramethyl-1,3,2-dioxaborolan-2-yl)pyridine To a solution of the compound obtained in step a (514 mg, 1.7 mmol) in dioxane (10 mL), 4,4,4',4',5,5,5',5'-octamethyl-2,2'-bi(1,3,2-dioxaborolane) (518 mg, 2.04 mmol), $PdCl_2$(dppf)-$CH_2Cl_2$ adduct (139 mg, 0.17 mmol) and potassium acetate (501 mg, 5.10 mmol) were added. The reaction mixture was degassed by argon for 5 min, and heated at 100° C. for 16 h. Then, the reaction mixture was filtered over double paper filter, the black solid on the filter was washed with EtOAc. The filtrate was concentrated under vacuum and the residue was triturated and sonicated in hexane for 30 min. The black suspension was filtered again over double paper filter and the black solid on the filter washed with hexane. The filtrate was concentrated to give 830 mg of a brown oil which was used in the next step without further purification.

HPLC-MS (Method E): Rt.: 3.23 min; ESI+MS: m/z 268 $[M+H]^+$.

Step c. tert-Butyl 3-(3-(2-(((tert-butyldimethylsilyl)oxy)methyl)pyridin-4-yl)-2-methylpyrazolo[1,5-a]pyrimidin-7-yl)piperidine-1-carboxylate Starting from the compound obtained in step b (200 mg, 0.5 mmol) and following the procedure described in step a of example 114, the title compound was obtained (125 mg, Yield: 46%).

HPLC-MS (Method E): Rt.: 4.78 min; ESI+MS: m/z 539.1 $[M+H]^+$.

Step d. (4-(2-Methyl-7-(piperidin-3-yl)pyrazolo[1,5-a]pyrimidin-3-yl)pyridin-2-yl)methanol dihydrochloride Starting from the compound obtained in step c (110 mg, 0.20 mmol) and following the procedure described in step d of example 110, the title compound was obtained (76 mg, Yield: 94%) after evaporation of the solvent, trituration and sonication of the solid in hexane, filtration and drying under vacuum.

HPLC-MS (Method E): Rt.: 2.13 min; ESI+MS: m/z 324.1 $[M+H]^+$.

Step e. Title Compound

Starting from the compound obtained in step d (75 mg, 0.18 mmol) and following the procedure described in step e of example 110, the title compound was obtained (28 mg, Yield: 32%).

HPLC-MS (Method E): Rt.: 3.53 min; ESI+MS: m/z 448.1 $[M+H]^+$.

This method was used for the preparation of example 135 using suitable starting materials:

| STRUCTURE | EX | CHEMICAL NAME | Rt (min) | MS (M + H) | HPLC Method |
|---|---|---|---|---|---|
| 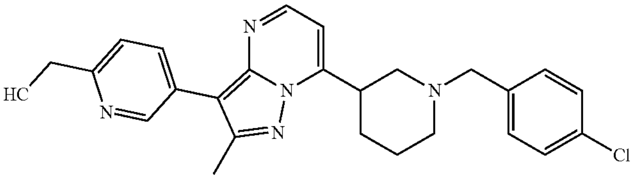 [SMILES: CCc1ccc(-c2c(C)nn3c(C4CCCN(Cc5ccc(Cl)cc5)C4)ccnc23)cn1] | 135 | (5-(7-(1-(4-Chlorobenzyl)piperidin-3-yl)-2-methylpyrazolo[1,5-a]pyrimidin-3-yl)pyridin-2-yl)methanol | 3.47 | 448.1 | E |

This method (steps b-e) was used for the preparation of examples 136-138 using suitable starting materials:

| STRUCTURE | EX | CHEMICAL NAME | Rt (min) | MS (M + H) | HPLC Method |
|---|---|---|---|---|---|
| 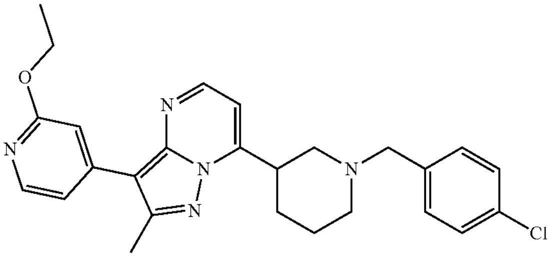 [SMILES: CCOc1cc(-c2c(C)nn3c(C4CCCN(Cc5ccc(Cl)cc5)C4)ccnc23)ccn1] | 136 | 7-(1-(4-Chlorobenzyl)piperidin-3-yl)-3-(2-ethoxypyridin-4-yl)-2-methylpyrazolo[1,5-a]pyrimidine | 4.65 | 462.1 | E |
| 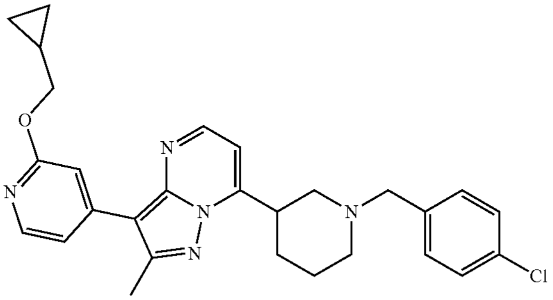 [SMILES: Cc1nn2c(C3CCCN(Cc4ccc(Cl)cc4)C3)ccnc2c1-c1ccnc(OCC2CC2)c1] | 137 | 7-(1-(4-Chlorobenzyl)piperidin-3-yl)-3-(2-(cyclopropylmethoxy)pyridin-4-yl)-2-methylpyrazolo[1,5-a]pyrimidine | 4.83 | 488.2 | E |
| 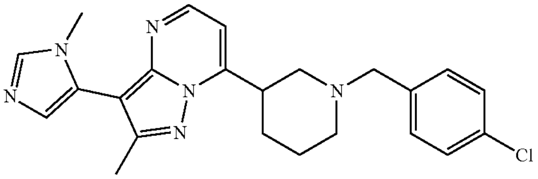 [SMILES: Cc1nn2c(C3CCCN(Cc4ccc(Cl)cc4)C3)ccnc2c1-c1cncn1C] | 138 | 7-(1-(4-Chlorobenzyl)piperidin-3-yl)-2-methyl-3-(1-methyl-1H-imidazol-5-yl)pyrazolo[1,5-a]pyrimidine | 3.42 | 421.1 | E |

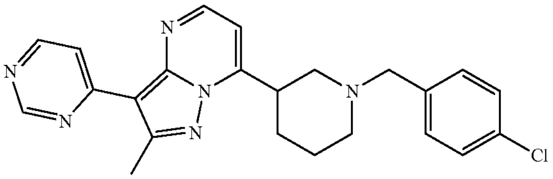 [SMILES: Cc1nn2c(C3CCCN(Cc4ccc(Cl)cc4)C3)ccnc2c1-c1ccncn1]

Example 139. 7-(1-(4-Chlorobenzyl)piperidin-3-yl)-2-methyl-3-(pyrimidin-4-yl)pyrazolo[1,5-a]pyrimidine

Step a. tert-Butyl 3-(3-acetyl-2-methylpyrazolo[1,5-a]pyrimidin-7-yl)piperidine-1-carboxylate To a solution of the compound obtained in step a of example 121 (1 g, 2.53 mmol) in toluene (3 mL), tributyl (1-ethoxyvinyl)stannane (1.70 mL, 5.06 mmol) and bis (triphenylphosphine)palladium (II) chloride (178 mg, 0.253 mmol) were added. The reaction mixture was heated at 80° C. for 24 h. After this time, solvent was evaporated and the residue was purified by flash chromatography, silica gel, hexane:EtOAc, to give the title compound as a brown foam (721 mg, Yield: 80%).

HPLC-MS (Method E): Rt.: 3.43 min; ESI+MS: m/z 359.2 [M+H]+.

Step b. tert-Butyl (E)-3-(3-(3-(dimethylamino)acryloyl)-2-methylpyrazolo[1,5-a]pyrimidin-7-yl)piperidine-1-carboxylate The compound obtained in step a (721 mg, 2.01 mmol) and 1-tert-butoxy-N,N,N',N'-tetramethylmethanediamine (2 mL, 9.69 mmol) were stirred at 100° C. in a sealed reactor under argon for 3 h. The reaction mixture was concentrated to dryness under reduced pressure to give the title compound as a brown oil (832 mg, Yield: Quant).

HPLC-MS (Method E): Rt.: 3.00 min; ESI+MS: m/z 414.2 $[M+H]^+$.

Step c. tert-Butyl 3-(2-methyl-3-(pyrimidin-4-yl) pyrazolo[1,5-a]pyrimidin-7-yl)piperidine-1-carboxylate The compound obtained in step b (397 mg, 0.96 mmol) and formimidamide acetate (198 mg, 1.92 mmol) were stirred at 130° C. in a sealed reactor under argon for 2 h. After this time, the reaction mixture was purified by flash chromatography, silica gel, DCM:MeOH, to give the title compound as a brown foam (100 mg, Yield: 26%).

HPLC-MS (Method E): Rt.: 3.55 min; ESI+MS: m/z 395.2 $[M+H]^+$.

Step d. 2-Methyl-7-(piperidin-3-yl)-3-(pyrimidin-4-yl)pyrazolo[1,5-a]pyrimidine hydrochloride Starting from the compound obtained in step c (100 mg, 0.25 mmol) and following the procedure described in step d of example 110, the title compound was obtained (93 mg). This compound was used in the next step without further purification.

HPLC-MS (Method E): Rt.: 2.28 min; ESI+MS: m/z 295.1 $[M+H]^+$.

Step e. Title Compound

Starting from the compound obtained in step d (93 mg, 0.25 mmol) and following the procedure described in step e of example 110, the title compound was obtained (39 mg, Yield: 33%).

HPLC-MS (Method E): Rt.: 4.22 min; ESI+MS: m/z 419.1 $[M+H]^+$.

This method was used for the preparation of example 140 using suitable starting materials:

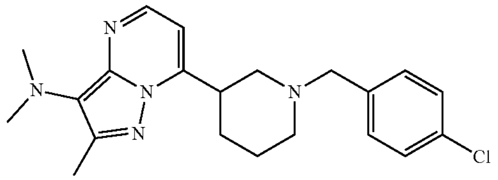 [SMILES: Cc1nn2c(C3CCCN(Cc4ccc(Cl)cc4)C3)ccnc2c1N(C)C]

Example 141. 7-(1-(4-Chlorobenzyl)piperidin-3-yl)-N,N,2-trimethylpyrazolo[1,5-a]pyrimidin-3-amine Step a. N-(5-Methyl-1H-pyrazol-3-yl)acetamide 5-Methyl-1H-pyrazol-3-amine (2.69 g, 27.7 mmol) was dissolved in water (24 mL), followed by the slow addition of sodium bicarbonate (6.98 g, 83.0 mmol), to which acetic anhydride (5 mL, 53.0 mmol) was added dropwise. The reaction mixture was heated at reflux for 16 h. The suspension was cooled down, filtered and the resulting solid was washed with water. The final compound was observed to be partially soluble in water, the aq phase was concentrated as well, and both solids were combined and dried under vacuum to give the title compound (1.89 g, Yield: 49%).

HPLC-MS (Method E): Rt.: 1.10 min; ESI+MS: m/z 140.0 $[M+H]^+$.

Step b. N-(5-Methyl-4-nitro-1H-pyrazol-3-yl)acetamide

Sulfuric acid (9.7 mL, 180 mmol) was cooled down to 0° C. and the compound obtained in step a (1.0 g, 7.19 mmol) was slowly added. Then fuming nitric acid (0.48 mL, 10.78 mmol) was added dropwise. The reaction mixture was stirred at 0° C. for 30 min. The solution was poured into ice and a solid precipitated off. The solid was filtered through a sintered funnel and dried under vacuum to give the title compound (1.89 g, Yield: 49%).

HPLC-MS (Method E): Rt.: 1.42 min; ESI+MS: m/z 185.0 $[M+H]^+$.

Step c. 5-Methyl-4-nitro-1H-pyrazol-3-amine hydrochloride

The compound obtained in step b (1.03 g, 5.59 mmol) and 6M HCl (6 mL, 36 mmol) were heated at 100° C. for 2 h. After this time, solvent was evaporated to give the title compound (793 mg). This compound was used in the next step without further purification.

HPLC-MS (Method E): Rt.: 1.38 min; ESI+MS: m/z 143.1 $[M+H]^+$.

| STRUCTURE | EX | CHEMICAL NAME | Rt (min) | MS (M + H) | HPLC Method |
|---|---|---|---|---|---|
| 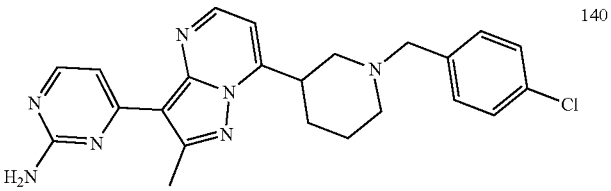 | 140 | 4-(7-(1-(4-Chlorobenzyl)piperidin-3-yl)-2-methylpyrazolo[1,5-a]pyrimidin-3-yl)pyrimidin-2-amine | 3.83 | 434.1 | E |

Step d. tert-Butyl 3-(2-methyl-3-nitropyrazolo[1,5-a]pyrimidin-7-yl)piperidine-1-carboxylate Starting from the compound obtained in step c (793 mg, 5.59 mmol) and following the procedure described in step c of example 110, the title compound was obtained (1.89 g, Yield: 94%).

HPLC-MS (Method E): Rt.: 3.23 min; ESI+MS: m/z 362.1 $[M+H]^+$.

Step e. tert-Butyl 3-(3-amino-2-methylpyrazolo[1,5-a]pyrimidin-7-yl)piperidine-1-carboxylate To a solution of the compound obtained in step d (1.89 g, 5.23 mmol) in EtOH (31 mL), zinc (10.26 g, 157 mmol) and calcium chloride (0.29 g, 2.61 mmol) dissolved in the minimum amount of water were added. The reaction mixture was refluxed for 2 h. After this time, the suspension was filtered through a pad of Celite and the solid was washed with hot EtOH. The filtrate was concentrated and the residue was purified by flash chromatography, silica gel, EtOAc: $MeOH:NH_3$, to give the title compound (864 mg, Yield: 50%).

HPLC-MS (Method E): Rt.: 2.65 min; ESI+MS: m/z 332.2 $[M+H]^+$.

Step f. tert-Butyl 3-(3-(dimethylamino)-2-methylpyrazolo[1,5-a]pyrimidin-7-yl)piperidine-1-carboxylate Starting from the compound obtained in step e (576 mg, 1.74 mmol) and 37% aq formaldehyde (0.39 mL, 5.21 mmol) and following the procedure described in step e of example 110, the title compound was obtained (1.89 g, Yield: 94%).

HPLC-MS (Method E): Rt.: 3.35 min; ESI+MS: m/z 360.2 $[M+H]^+$.

Step g. N,N,2-trimethyl-7-(piperidin-3-yl)pyrazolo[1,5-a]pyrimidin-3-amine hydrochloride Starting from the compound obtained in step f (674 mg, 1.87 mmol) and following the procedure described in step d of example 110, the title compound was obtained (623 mg). This compound was used in the next step without further purification.

HPLC-MS (Method E): Rt.: 1.83 min; ESI+MS: m/z 260.1 $[M+H]^+$.

Step h. Title Compound

Starting from the compound obtained in step g (242 mg, 0.93 mmol) and following the procedure described in step e of example 110, the title compound was obtained (225 mg, Yield: 62%).

HPLC-MS (Method E): Rt.: 3.97 min; ESI+MS: m/z 384.1 $[M+H]^+$.

This method was used for the preparation of example 142 using suitable starting materials:

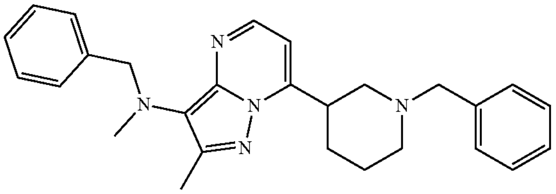

Example 143. N-Benzyl-7-(1-benzylpiperidin-3-yl)-N,2-dimethylpyrazolo[1,5-a]pyrimidin-3-amine Step a. tert-Butyl 3-(3-((tert-butoxycarbonyl)amino)-2-methylpyrazolo[1,5-a]pyrimidin-7-yl)piperidine-1-carboxylate To a solution of the compound obtained in step e of example 141 (288 mg, 0.86 mmol) in DCM (5 mL), TEA (0.18 mL, 1.30 mmol) and $Boc_2O$ (284 mg, 1.30 mmol) were added and the reaction mixture was stirred at r.t. for 16 h. The resulting mixture was diluted with aq sat $NaHCO_3$ sol. The organic layer was separated and washed with brine, dried over anh $Na_2SO_4$, filtered and concentrated to give the title compound (375 mg).

HPLC-MS (Method E): Rt.: 3.47 min; ESI+MS: m/z 432.2 $[M+H]^+$.

Step b. tert-Butyl 3-(3-((tert-butoxycarbonyl)(methyl)amino)-2-methylpyrazolo[1,5-a]pyrimidin-7-yl)piperidine-1-carboxylate To a 0° C. cooled solution of the compound obtained in step a (390 mg, 0.90 mmol) in DMF (3 mL), sodium hydride (60% wt in mineral oil, 54 mg, 1.35 mmol) was added under argon and the resulting mixture was stirred for 20 min, followed by the addition of iodomethane (0.11 mL, 1.80 mmol), the reaction mixture was stirred at r.t. for 2 h. After this time, still starting material remained, the reactants were added again at 0° C. and the reaction mixture was left stirring at r.t. for 16 h. Then, the reaction mixture was concentrated under vacuum and the residue was treated with EtOAc and aq sat $NaHCO_3$ sol. The organic layer was separated and washed with brine, dried over anh $Na_2SO_4$, filtered and concentrated to give the title compound (330 mg).

HPLC-MS (Method E): Rt.: 3.73 min; ESI+MS: m/z 446.2 $[M+H]^+$.

Step c. N,2-Dimethyl-7-(piperidin-3-yl)pyrazolo[1,5-a]pyrimidin-3-amine hydrochloride Starting from the compound obtained in step b (330 mg, 0.74 mmol) and following the procedure described in step d of example 110, the title compound was obtained (623 mg).

| STRUCTURE | EX | CHEMICAL NAME | Rt (min) | MS (M + H) | HPLC Method |
|---|---|---|---|---|---|
| 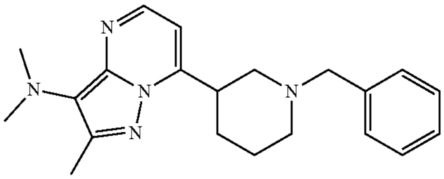 [SMILES: Cc1nn2c(C3CCCN(Cc4ccccc4)C3)ccnc2c1N(C)C] | 142 | 7-(1-Benzylpiperidin-3-yl)-N,N,2-trimethylpyrazolo[1,5-a]pyrimidin-3-amine | 3.60 | 350.1 | E |

HPLC-MS (Method E): Rt.: 1.85 min; ESI+MS: m/z 246.1 $[M+H]^+$.

Step d. Title Compound

Starting from the compound obtained in step c (236 mg, 0.74 mmol) and benzaldehyde (0.22 mL, 2.22 mmol) and following the procedure described in step e of example 110, the title compound was obtained (24 mg, Yield: 7%).

HPLC-MS (Method E): Rt.: 4.45 min; ESI+MS: m/z 426.2 $[M+H]^+$.

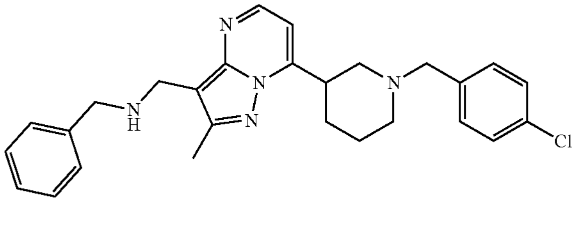 [SMILES: Cc1nn2c(C3CCCN(Cc4ccc(Cl)cc4)C3)ccnc2c1CNCc1ccccc1]

Example 144. N-Benzyl-1-(7-(1-(4-chlorobenzyl)piperidin-3-yl)-2-methylpyrazolo[1,5-a]pyrimidin-3-yl)methanamine Step a. tert-Butyl 3-(2-methylpyrazolo[1,5-a]pyrimidin-7-yl)piperidine-1-carboxylate Starting from the compound obtained in step b of example 110 (2.0 g, 7.08 mmol) and 5-methyl-1H-pyrazol-3-amine (0.75 g, 7.79 mmol) and following the procedure described in step c of example 110, the title compound was obtained (2.1 g, Yield: 93%).

HPLC-MS (Method E): Rt.: 3.22 min; ESI+MS: m/z 317.1 $[M+H]^+$.

Step b. 2-Methyl-7-(piperidin-3-yl)pyrazolo[1,5-a]pyrimidine hydrochloride

Starting from the compound obtained in step a (600 mg, 1.89 mmol) and following the procedure described in step d of example 110, the title compound was obtained (403 mg). This compound was used in the next step without further purification.

HPLC-MS (Method E): Rt.: 1.98 min; ESI+MS: m/z 217.1 $[M+H]^+$.

Step c. 7-(1-(4-Chlorobenzyl)piperidin-3-yl)-2-methylpyrazolo[1,5-a]pyrimidine

Starting from the compound obtained in step b (403 mg, 1.60 mmol) and following the procedure described in step e of example 110, the title compound was obtained (379 mg Yield: 68%).

HPLC-MS (Method E): Rt.: 3.78 min; ESI+MS: m/z 341.1 $[M+H]^+$.

Step d. 7-(1-(4-Chlorobenzyl)piperidin-3-yl)-2-methylpyrazolo[1,5-a]pyrimidine-3-carbaldehyde Starting from the compound obtained in step c (409 mg, 1.09 mmol) and following the procedure described in step a of example 120, the title compound was obtained (379 mg Yield: 98%).

HPLC-MS (Method E): Rt.: 3.72 min; ESI+MS: m/z 389.1 $[M+H]^+$.

Step e. Title Compound

Starting from the compound obtained in step d (200 mg, 0.54 mmol) and phenylmethanamine (0.17 mL, 1.62 mmol) and following the procedure described in step e of example 110, the title compound was obtained (63 mg, Yield: 25%).

HPLC-MS (Method E): Rt.: 4.23 min; ESI+MS: m/z 460.2 $[M+H]^+$.

This method was used for the preparation of examples 145-192 using suitable starting materials:

| STRUCTURE | EX | CHEMICAL NAME | Rt (min) | MS (M + H) | HPLC Method |
|---|---|---|---|---|---|
| 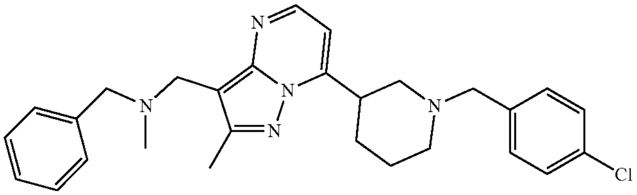 [SMILES: Cc1nn2c(C3CCCN(Cc4ccc(Cl)cc4)C3)ccnc2c1CN(C)Cc1ccccc1] | 145 | N-Benzyl-1-(7-(1-(4-chlorobenzyl)piperidin-3-yl)-2-methylpyrazolo[1,5-a]pyrimidin-3-yl)-N-methylmethanamine | 4.60 | 474.2 | E |
| 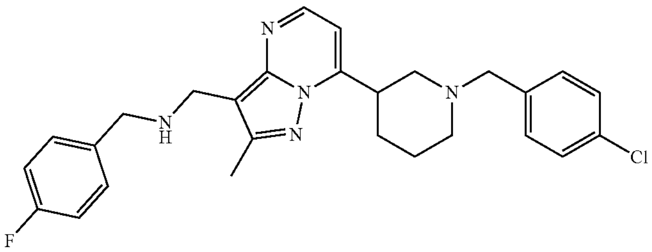 [SMILES: Cc1nn2c(C3CCCN(Cc4ccc(Cl)cc4)C3)ccnc2c1CNCc1ccc(F)cc1] | 146 | 1-(7-(1-(4-Chlorobenzyl)piperidin-3-yl)-2-methylpyrazolo[1,5-a]pyrimidin-3-yl)-N-(4-fluorobenzyl)methanamine | 4.23 | 478.2 | E |

-continued

| STRUCTURE | EX | CHEMICAL NAME | Rt (min) | MS (M + H) | HPLC Method |
|---|---|---|---|---|---|
| 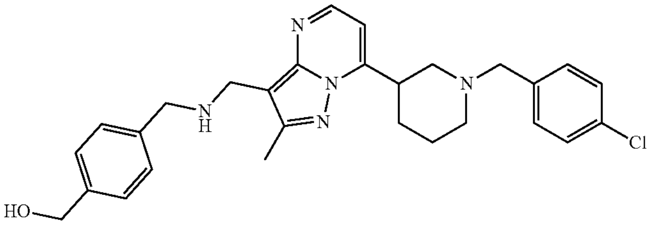 [SMILES: Cc1nn2c(C3CCCN(Cc4ccc(Cl)cc4)C3)ccnc2c1CNCc1ccc(CO)cc1] | 147 | (4-((((7-(1-(4-Chlorobenzyl)piperidin-3-yl)-2-methylpyrazolo[1,5-a]pyrimidin-3-yl)methyl)amino)methyl)phenyl)methanol | 3.52 | 490.2 | E |
| 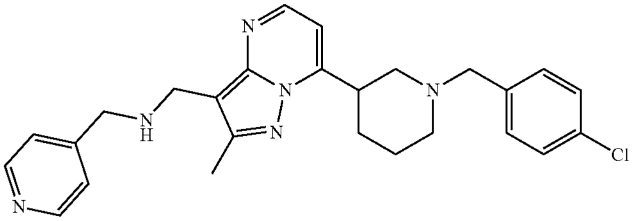 [SMILES: Cc1nn2c(C3CCCN(Cc4ccc(Cl)cc4)C3)ccnc2c1CNCc1ccncc1] | 148 | 1-(7-(1-(4-Chlorobenzyl)piperidin-3-yl)-2-methylpyrazolo[1,5-a]pyrimidin-3-yl)-N-(pyridin-4-ylmethyl)methanamine | 3.35 | 461.2 | E |
| 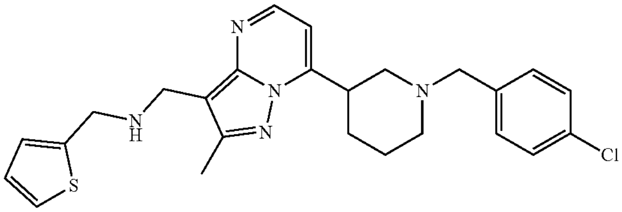 [SMILES: Cc1nn2c(C3CCCN(Cc4ccc(Cl)cc4)C3)ccnc2c1CNCc1cccs1] | 149 | 1-(7-(1-(4-Chlorobenzyl)piperidin-3-yl)-2-methylpyrazolo[1,5-a]pyrimidin-3-yl)-N-(thiophen-2-ylmethyl)methanamine | 4.15 | 466.1 | E |
| 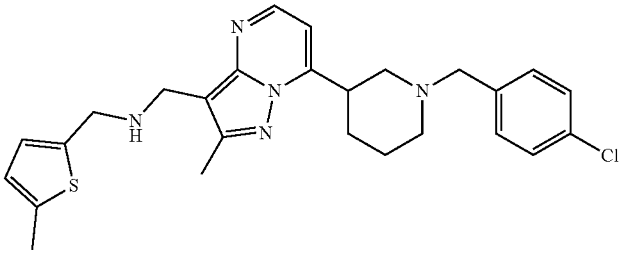 [SMILES: Cc1ccc(CNCc2c(C)nn3c(C4CCCN(Cc5ccc(Cl)cc5)C4)ccnc23)s1] | 150 | 1-(7-(1-(4-Chlorobenzyl)piperidin-3-yl)-2-methylpyrazolo[1,5-a]pyrimidin-3-yl)-N-((5-methylthiophen-2-yl)methyl)methanamine | 4.33 | 480.1 | E |
| 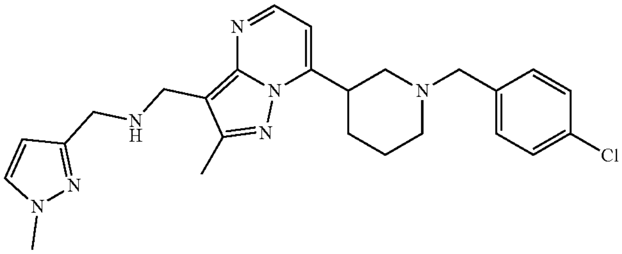 [SMILES: Cc1nn2c(C3CCCN(Cc4ccc(Cl)cc4)C3)ccnc2c1CNCc1ccn(C)n1] | 151 | 1-(7-(1-(4-Chlorobenzyl)piperidin-3-yl)-2-methylpyrazolo[1,5-a]pyrimidin-3-yl)-N-((1-methyl-1H-pyrazol-3-yl)methyl)methanamine | 3.57 | 464.2 | E |
| 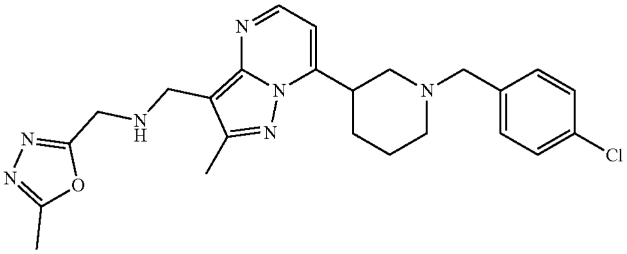 [SMILES: Cc1nnc(CNCc2c(C)nn3c(C4CCCN(Cc5ccc(Cl)cc5)C4)ccnc23)o1] | 152 | 1-(7-(1-(4-Chlorobenzyl)piperidin-3-yl)-2-methylpyrazolo[1,5-a]pyrimidin-3-yl)-N-((5-methyl-1,3,4-oxadiazol-2-yl)methyl)methanamine | 3.05 | 466.2 | E |

-continued

| STRUCTURE | EX | CHEMICAL NAME | Rt (min) | MS (M + H) | HPLC Method |
|---|---|---|---|---|---|
| 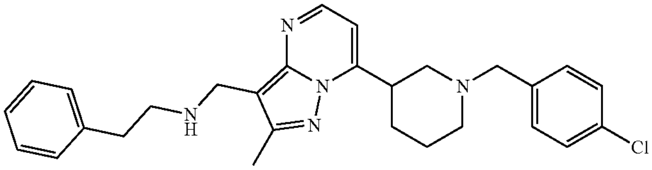 [SMILES: Cc1nn2c(C3CCCN(Cc4ccc(Cl)cc4)C3)ccnc2c1CNCCc1ccccc1] | 153 | N-((7-(1-(4-Chlorobenzyl)piperidin-3-yl)-2-methylpyrazolo[1,5-a]pyrimidin-3-yl)methyl)-2-phenylethan-1-amine | 4.23 | 474.1 | E |
| 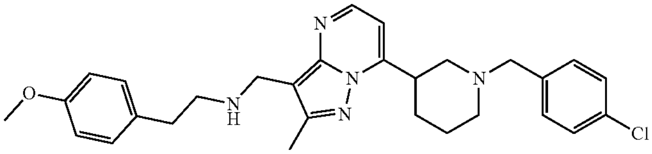 [SMILES: COc1ccc(CCNCc2c(C)nn3c(C4CCCN(Cc5ccc(Cl)cc5)C4)ccnc23)cc1] | 154 | N-((7-(1-(4-Chlorobenzyl)piperidin-3-yl)-2-methylpyrazolo[1,5-a]pyrimidin-3-yl)methyl)-2-(4-methoxyphenyl)ethan-1-amine | 4.47 | 504.2 | E |
| 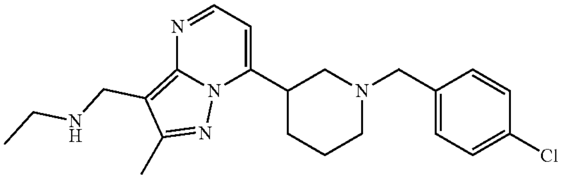 [SMILES: CCNCc1c(C)nn2c(C3CCCN(Cc4ccc(Cl)cc4)C3)ccnc12] | 155 | N-((7-(1-(4-Chlorobenzyl)piperidin-3-yl)-2-methylpyrazolo[1,5-a]pyrimidin-3-yl)methyl)ethanamine | 4.00 | 398.2 | E |
| 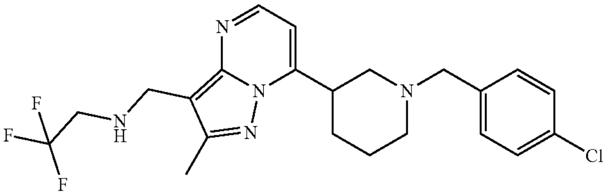 [SMILES: Cc1nn2c(C3CCCN(Cc4ccc(Cl)cc4)C3)ccnc2c1CNCC(F)(F)F] | 156 | N-((7-(1-(4-Chlorobenzyl)piperidin-3-yl)-2-methylpyrazolo[1,5-a]pyrimidin-3-yl)methyl)-2,2,2-trifluoroethan-1-amine | 3.98 | 452.1 | E |
| 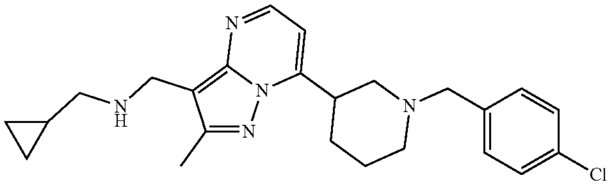 [SMILES: Cc1nn2c(C3CCCN(Cc4ccc(Cl)cc4)C3)ccnc2c1CNCC1CC1] | 157 | 1-(7-(1-(4-Chlorobenzyl)piperidin-3-yl)-2-methylpyrazolo[1,5-a]pyrimidin-3-yl)-N-(cyclopropylmethyl) methanamine | 4.50 | 424.2 | E |
| 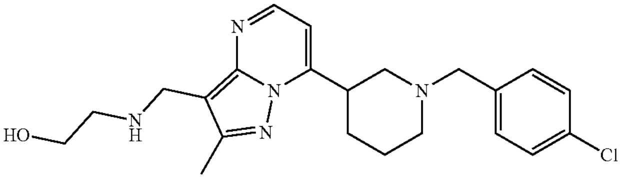 [SMILES: Cc1nn2c(C3CCCN(Cc4ccc(Cl)cc4)C3)ccnc2c1CNCCO] | 158 | 2-(((7-(1-(4-Chlorobenzyl)piperidin-3-yl)-2-methylpyrazolo[1,5-a]pyrimidin-3-yl)methyl)amino)ethan-1-ol | 3.38 | 414.2 | E |
| 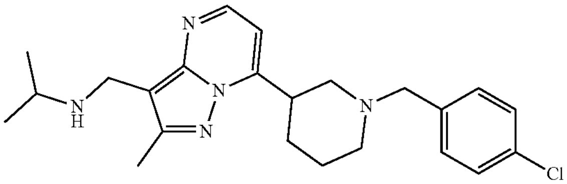 [SMILES: Cc1nn2c(C3CCCN(Cc4ccc(Cl)cc4)C3)ccnc2c1CNC(C)C] | 159 | N-((7-(1-(4-Chlorobenzyl)piperidin-3-yl)-2-methylpyrazolo[1,5-a]pyrimidin-3-yl)methyl)propan-2-amine | 2.72 | 412.2 | I |
| 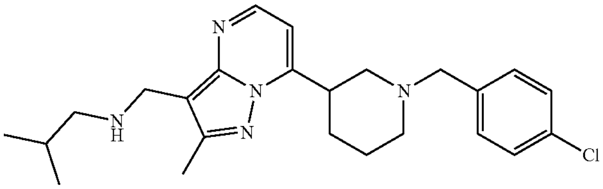 [SMILES: Cc1nn2c(C3CCCN(Cc4ccc(Cl)cc4)C3)ccnc2c1CNCC(C)C] | 160 | N-((7-(1-(4-Chlorobenzyl)piperidin-3-yl)-2-methylpyrazolo[1,5-a]pyrimidin-3-yl)methyl)-2-methylpropan-1-amine | 2.88 | 425.2 | I |

-continued

| STRUCTURE | EX | CHEMICAL NAME | Rt (min) | MS (M + H) | HPLC Method |
|---|---|---|---|---|---|
| 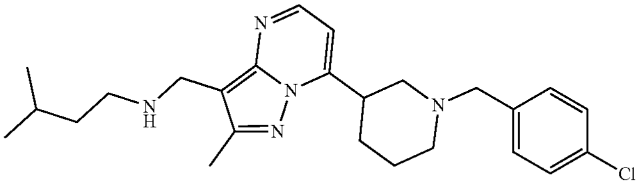 [SMILES: Cc1nn2c(C3CCCN(Cc4ccc(Cl)cc4)C3)ccnc2c1CNCCC(C)C] | 161 | N-((7-(1-(4-Chlorobenzyl)piperidin-3-yl)-2-methylpyrazolo[1,5-a]pyrimidin-3-yl)methyl)-3-methylbutan-1-amine | 3.82 | 440.2 | I |
| 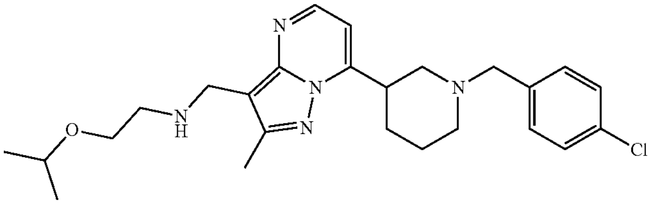 [SMILES: Cc1nn2c(C3CCCN(Cc4ccc(Cl)cc4)C3)ccnc2c1CNCCOC(C)C] | 162 | N-((7-(1-(4-Chlorobenzyl)piperidin-3-yl)-2-methylpyrazolo[1,5-a]pyrimidin-3-yl)methyl)-2-isopropoxyethan-1-amine | 4.32 | 456.2 | E |
| 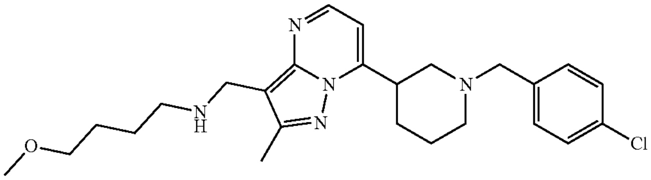 [SMILES: COCCCCNCc1c(C)nn2c(C3CCCN(Cc4ccc(Cl)cc4)C3)ccnc12] | 163 | N-((7-(1-(4-Chlorobenzyl)piperidin-3-yl)-2-methylpyrazolo[1,5-a]pyrimidin-3-yl)methyl)-4-methoxybutan-1-amine | 3.28 | 456.2 | I |
| 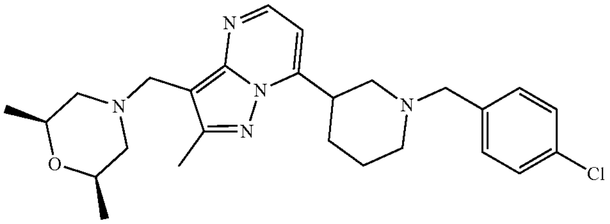 [SMILES: Cc1nn2c(C3CCCN(Cc4ccc(Cl)cc4)C3)ccnc2c1CN1C[C@@H](C)O[C@@H](C)C1] | 164 | (2S,6R)-4-((7-(1-(4-Chlorobenzyl)piperidin-3-yl)-2-methylpyrazolo[1,5-a]pyrimidin-3-yl)methyl)-2,6-dimethylmorpholine | 3.28 | 468.2 | E |
| 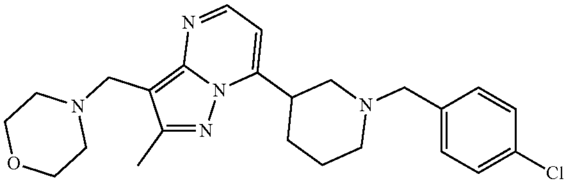 [SMILES: Cc1nn2c(C3CCCN(Cc4ccc(Cl)cc4)C3)ccnc2c1CN1CCOCC1] | 165 | 4-((7-(1-(4-Chlorobenzyl)piperidin-3-yl)-2-methylpyrazolo[1,5-a]pyrimidin-3-yl)methyl)morpholine | 3.50 | 440.2 | E |
| 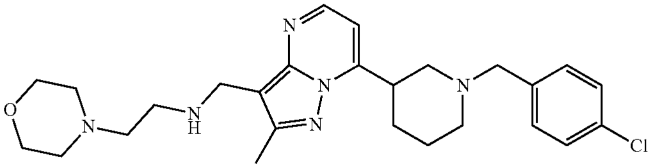 | 166 | N-((7-(1-(4-Chlorobenzyl)piperidin-3-yl)-2-methylpyrazolo[1,5-a]pyrimidin-3-yl)methyl)-2-morpholinoethan-1-amine | 4.15 | 483.2 | E |
| 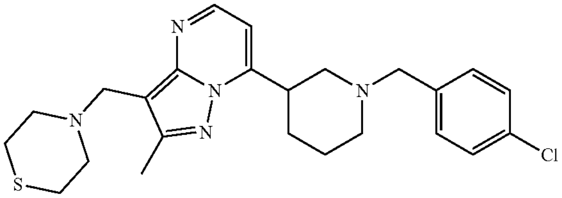 [SMILES: Cc1nn2c(C3CCCN(Cc4ccc(Cl)cc4)C3)ccnc2c1CN1CCSCC1] | 167 | 4-((7-(1-(4-Chlorobenzyl)piperidin-3-yl)-2-methylpyrazolo[1,5-a]pyrimidin-3-yl)methyl)thiomorpholine | 4.05 | 456.1 | E |

-continued

| STRUCTURE | EX | CHEMICAL NAME | Rt (min) | MS (M + H) | HPLC Method |
|---|---|---|---|---|---|
| 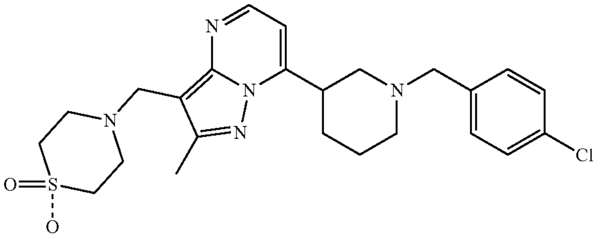 | 168 | 4-((7-(1-(4-Chlorobenzyl)piperidin-3-yl)-2-methylpyrazolo[1,5-a]pyrimidin-3-yl)methyl)thiomorpholine 1,1-dioxide | 3.38 | 488.1 | E |
| 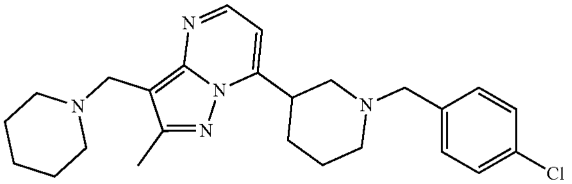 [SMILES: Cc1nn2c(C3CCCN(Cc4ccc(Cl)cc4)C3)ccnc2c1CN1CCCCC1] | 169 | 7-(1-(4-Chlorobenzyl)piperidin-3-yl)-2-methyl-3-(piperidin-1-ylmethyl)pyrazolo[1,5-a]pyrimidine | 4.70 | 438.2 | E |
| 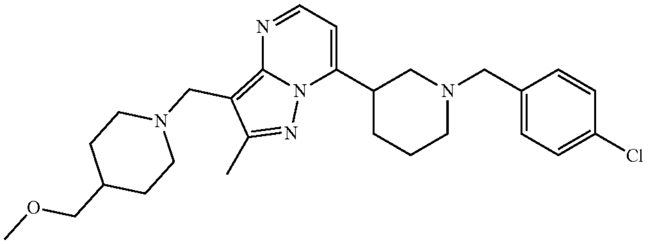 [SMILES: COCC1CCN(Cc2c(C)nn3c(C4CCCN(Cc5ccc(Cl)cc5)C4)ccnc23)CC1] | 170 | 7-(1-(4-Chlorobenzyl)piperidin-3-yl)-3-((4-(methoxymethyl)piperidin-1-yl)methyl)-2-methylpyrazolo[1,5-a]pyrimidine | 4.70 | 482.2 | E |
| 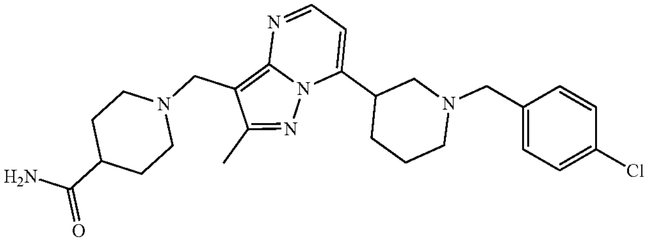 [SMILES: Cc1nn2c(C3CCCN(Cc4ccc(Cl)cc4)C3)ccnc2c1CN1CCC(C(N)=O)CC1] | 171 | 1-((7-(1-(4-Chlorobenzyl)piperidin-3-yl)-2-methylpyrazolo[1,5-a]pyrimidin-3-yl)methyl)piperidine-4-carboxamide | 3.07 | 481.2 | E |
| 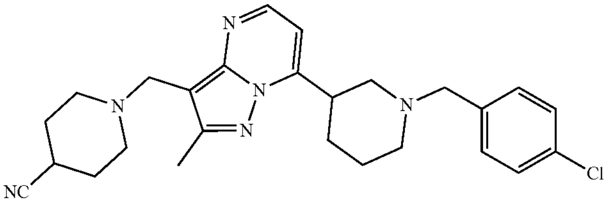 [SMILES: Cc1nn2c(C3CCCN(Cc4ccc(Cl)cc4)C3)ccnc2c1CN1CCC(C#N)CC1] | 172 | 1-((7-(1-(4-Chlorobenzyl)piperidin-3-yl)-2-methylpyrazolo[1,5-a]pyrimidin-3-yl)methyl)piperidine-4-carbonitrile | 3.73 | 463.2 | E |
| 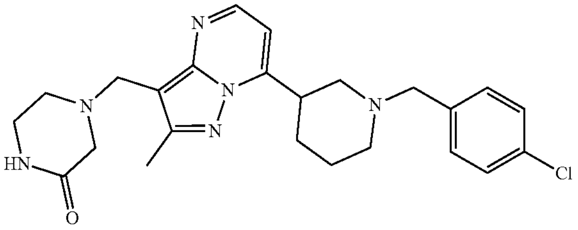 [SMILES: Cc1nn2c(C3CCCN(Cc4ccc(Cl)cc4)C3)ccnc2c1CN1CCNC(=O)C1] | 173 | 4-((7-(1-(4-Chlorobenzyl)piperidin-3-yl)-2-methylpyrazolo[1,5-alpyrimidin-3-yl)methyl)piperazin-2-one | 2.95 | 453.2 | E |

-continued

| STRUCTURE | EX | CHEMICAL NAME | Rt (min) | MS (M + H) | HPLC Method |
|---|---|---|---|---|---|
| 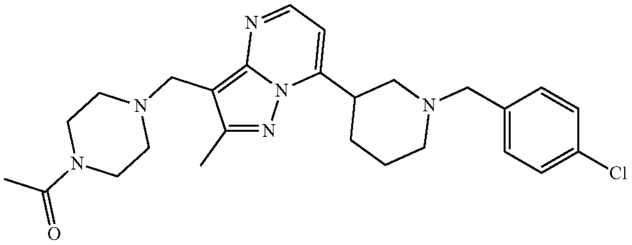 [SMILES: CC(=O)N1CCN(Cc2c(C)nn3c(C4CCCN(Cc5ccc(Cl)cc5)C4)ccnc23)CC1] | 174 | 1-(4-((7-(1-(4-Chlorobenzyl)piperidin-3-yl)-2-methylpyrazolo[1,5-a]pyrimidin-3-yl)methyl)piperazin-1-yl)ethan-1-one | 3.15 | 481.2 | E |
| 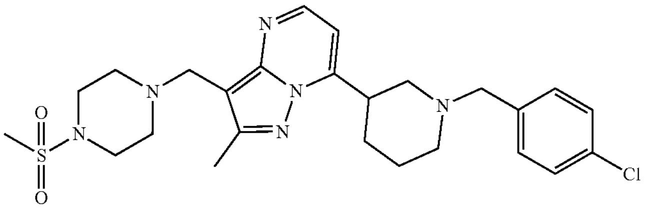 [SMILES: Cc1nn2c(C3CCCN(Cc4ccc(Cl)cc4)C3)ccnc2c1CN1CCN(S(C)(=O)=O)CC1] | 175 | 7-(1-(4-Chlorobenzyl)piperidin-3-yl)-2-methyl-3-((4-(methylsulfonyl)piperazin-1-yl)methyl)pyrazolo[1,5-a]pyrimidine | 3.50 | 517.2 | E |
| 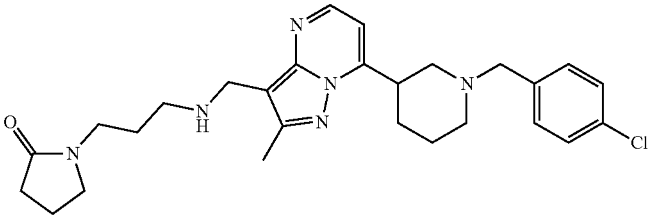 [SMILES: Cc1nn2c(C3CCCN(Cc4ccc(Cl)cc4)C3)ccnc2c1CNCCCN1CCCC1=O] | 176 | 1-(3-(((7-(1-(4-Chlorobenzyl)piperidin-3-yl)-2-methylpyrazolo[1,5-a]pyrimidin-3-yl)methyl)amino)propyl) pyrrolidin-2-one | 4.20 | 495.2 | E |
| 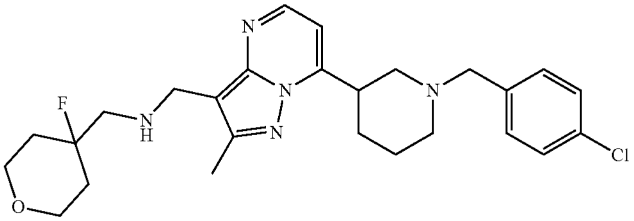 [SMILES: Cc1nn2c(C3CCCN(Cc4ccc(Cl)cc4)C3)ccnc2c1CNCC1(F)CCOCC1] | 177 | 1-(7-(1-(4-Chlorobenzyl)piperidin-3-yl)-2-methylpyrazolo[1,5-a]pyrimidin-3-yl)-N-((4-fluorotetrahydro-2H-pyran-4-yl)methyl)methanamine | 3.63 | 486.2 | E |
| 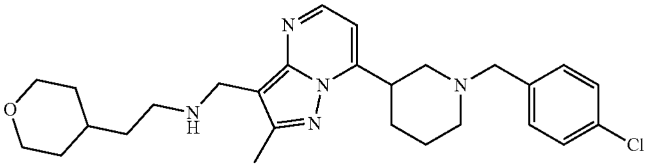 [SMILES: Cc1nn2c(C3CCCN(Cc4ccc(Cl)cc4)C3)ccnc2c1CNCCC1CCOCC1] | 178 | N-((7-(1-(4-Chlorobenzyl)piperidin-3-yl)-2-methylpyrazolo[1,5-a]pyrimidin-3-yl)methyl)-2-(tetrahydro-2H-pyran-4-yl)ethan-1-amine | 2.97 | 482.2 | I |
| 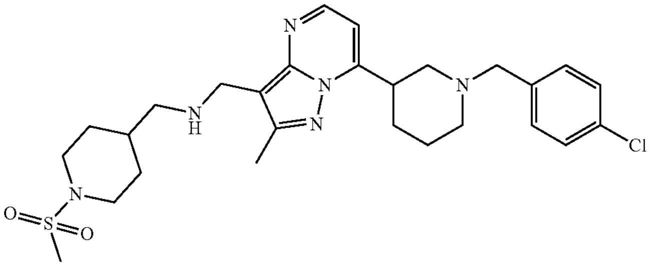 [SMILES: Cc1nn2c(C3CCCN(Cc4ccc(Cl)cc4)C3)ccnc2c1CNCC1CCN(S(C)(=O)=O)CC1] | 179 | 1-(7-(1-(4-Chlorobenzyl)piperidin-3-yl)-2-methylpyrazolo[1,5-a]pyrimidin-3-yl)-N-((1-(methylsulfonyl)piperidin-4-yl)methyl)methanamine | 3.93 | 546.1 | E |

-continued

| STRUCTURE | EX | CHEMICAL NAME | Rt (min) | MS (M + H) | HPLC Method |
|---|---|---|---|---|---|
| 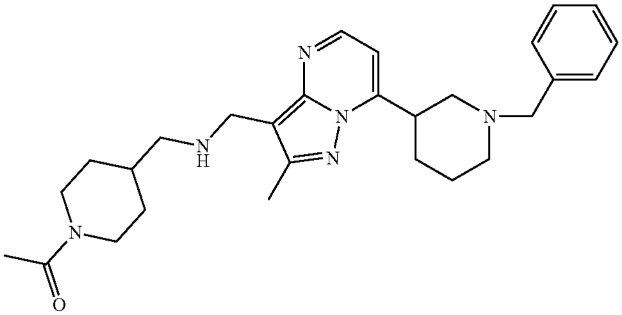 [SMILES: CC(=O)N1CCC(CNCc2c(C)nn3c(C4CCCN(Cc5ccccc5)C4)ccnc23)CC1] | 180 | 1-(4-((((7-(1-Benzylpiperidin-3-yl)-2-methylpyrazolo[1,5-a]pyrimidin-3-yl)methyl)amino)methyl) piperidin-1-yl)ethan-1-one | 2.50 | 476.1 | D |
| 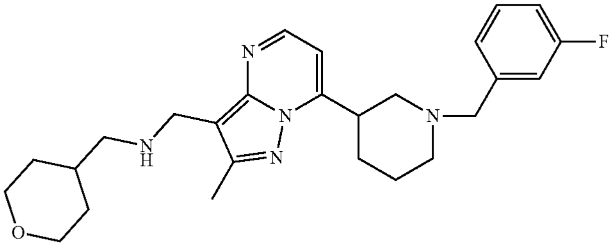 [SMILES: Cc1nn2c(C3CCCN(Cc4cccc(F)c4)C3)ccnc2c1CNCC1CCOCC1] | 181 | 1-(7-(1-(3-Fluorobenzyl)piperidin-3-yl)-2-methylpyrazolo[1,5-a]pyrimidin-3-yl)-N-((tetrahydro-2H-pyran-4-yl)methyl)methanamine | 4.15 | 452.2 | E |
| 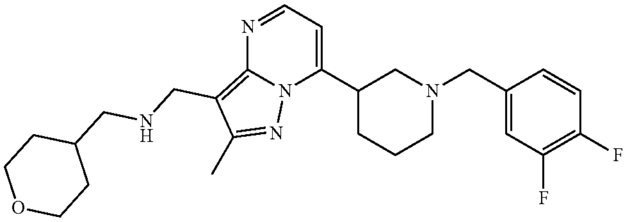 [SMILES: Cc1nn2c(C3CCCN(Cc4ccc(F)c(F)c4)C3)ccnc2c1CNCC1CCOCC1] | 182 | 1-(7-(1-(3,4-Difluorobenzyl)piperidin-3-yl)-2-methylpyrazolo[1,5-a]pyrimidin-3-yl)-N-((tetrahydro-2H-pyran-4-yl)methyl)methanamine | 1.87 | 470.2 | I |
| 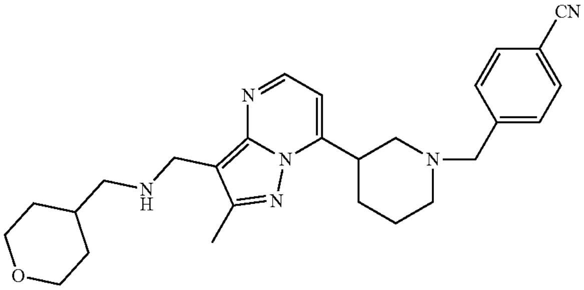 [SMILES: Cc1nn2c(C3CCCN(Cc4ccc(C#N)cc4)C3)ccnc2c1CNCC1CCOCC1] | 183 | 4-((3-(2-Methyl-3-((((tetrahydro-2H-pyran-4-yl)methyl)amino)methyl) pyrazolo[1,5-a]pyrimidin-7-yl)piperidin-1-yl)methyl)benzonitrile | 1.60 | 459.2 | I |
| 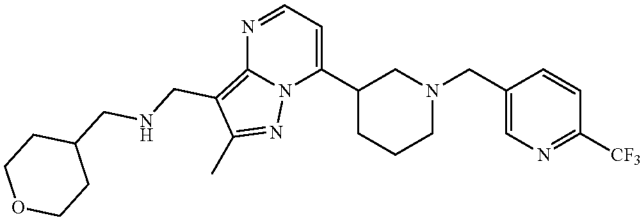 [SMILES: Cc1nn2c(C3CCCN(Cc4ccc(C(F)(F)F)nc4)C3)ccnc2c1CNCC1CCOCC1] | 184 | 1-(2-Methyl-7-(1-((6-(trifluoromethyl)pyridin-3-yl)methyl)piperidin-3-yl)pyrazolo[1,5-a]pyrimidin-3-yl)-N-((tetrahydro-2H-pyran-4-yl)methyl)methanamine | 3.53 | 503.2 | E |

-continued

| STRUCTURE | EX | CHEMICAL NAME | Rt (min) | MS (M + H) | HPLC Method |
|---|---|---|---|---|---|
| 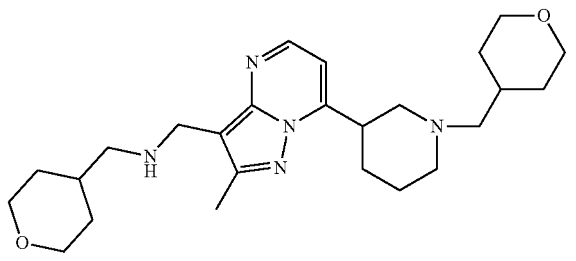 [SMILES: Cc1nn2c(C3CCCN(CC4CCOCC4)C3)ccnc2c1CNCC1CCOCC1] | 185 | 1-(2-Methyl-7-(1-((tetrahydro-2H-pyran-4-yl)methyl)piperidin-3-yl)pyrazolo[1,5-a]pyrimidin-3-yl)-N-((tetrahydro-2H-pyran-4-yl)methyl)methanamine | 3.02 | 442.3 | E |
| 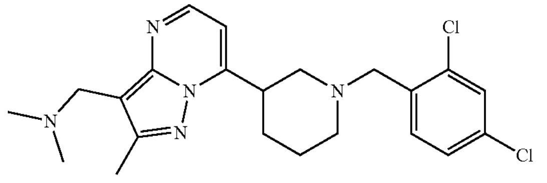 [SMILES: Cc1nn2c(C3CCCN(Cc4ccc(Cl)cc4Cl)C3)ccnc2c1CN(C)C] | 186 | 1-(7-(1-(2,4-Dichlorobenzyl)piperidin-3-yl)-2-methylpyrazolo[1,5-a]pyrimidin-3-yl)-N,N-dimethylmethanamine | 4.52 | 432.2 | I |
| 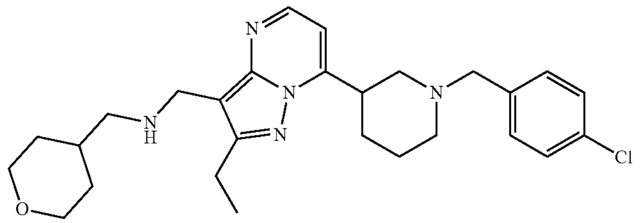 [SMILES: CCc1nn2c(C3CCCN(Cc4ccc(Cl)cc4)C3)ccnc2c1CNCC1CCOCC1] | 187 | 1-(7-(1-(4-Chlorobenzyl)piperidin-3-yl)-2-ethylpyrazolo[1,5-a]pyrimidin-3-yl)-N-((tetrahydro-2H-pyran-4-yl)methyl)methanamine | 4.37 | 482.2 | E |
| 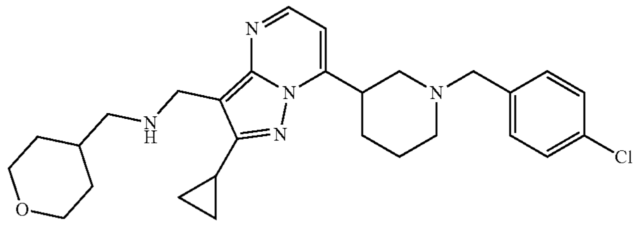 [SMILES: Clc1ccc(CN2CCCC(c3ccnc4c(CNCC5CCOCC5)c(C5CC5)nn34)C2)cc1] | 188 | 1-(7-(1-(4-Chlorobenzyl)piperidin-3-yl)-2-cyclopropylpyrazolo[1,5-a]pyrimidin-3-yl)-N-((tetrahydro-2H-pyran-4-yl)methyl)methanamine | 3.08 | 494.2 | I |
| 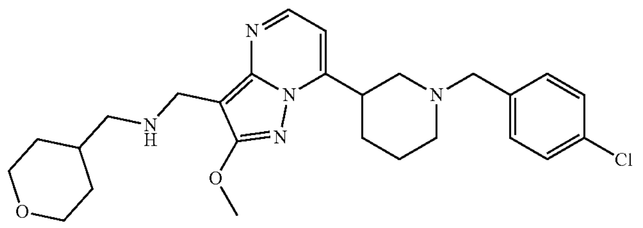 [SMILES: COc1nn2c(C3CCCN(Cc4ccc(Cl)cc4)C3)ccnc2c1CNCC1CCOCC1] | 189 | 1-(7-(1-(4-Chlorobenzyl)piperidin-3-yl)-2-methoxypyrazolo[1,5-a]pyrimidin-3-yl)-N-((tetrahydro-2H-pyran-4-yl)methyl)methanamine | 2.95 | 484.2 | I |
| 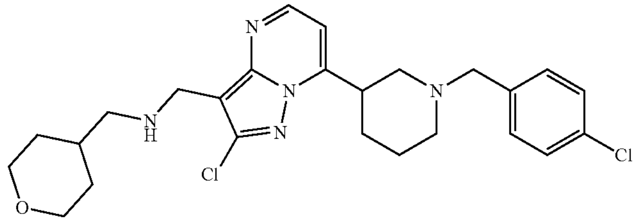 [SMILES: Clc1ccc(CN2CCCC(c3ccnc4c(CNCC5CCOCC5)c(Cl)nn34)C2)cc1] | 190 | 1-(2-Chloro-7-(1-(4-chlorobenzyl)piperidin-3-yl)pyrazolo[1,5-a]pyrimidin-3-yl)-N-((tetrahydro-2H-pyran-4-yl)methyl)methanamine | 3.98 | 488.1 | E |

-continued

| STRUCTURE | EX | CHEMICAL NAME | Rt (min) | MS (M + H) | HPLC Method |
|---|---|---|---|---|---|
| 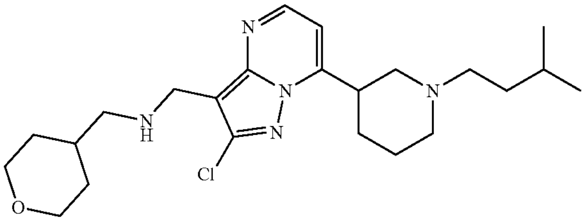 [SMILES: CC(C)CCN1CCCC(c2ccnc3c(CNCC4CCOCC4)c(Cl)nn23)C1] | 191 | 1-(2-Chloro-7-(1-isopentylpiperidin-3-yl)pyrazolo[1,5-a]pyrimidin-3-yl)-N-((tetrahydro-2H-pyran-4-yl)methyl)methanamine | 3.93 | 434.2 | E |
| 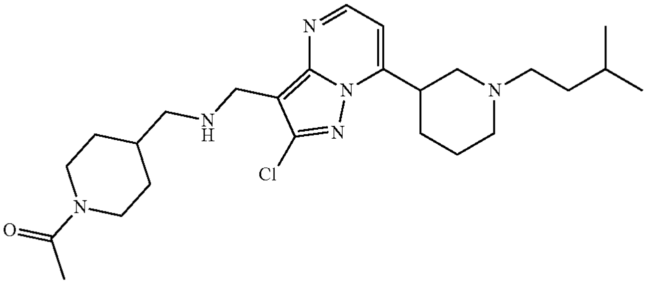 [SMILES: CC(=O)N1CCC(CNCc2c(Cl)nn3c(C4CCCN(CCC(C)C)C4)ccnc23)CC1] | 192 | 1-(4-((((2-chloro-7-(1-isopentylpiperidin-3-yl)pyrazolo[1,5-a]pyrimidin-3-yl)methyl)amino)methyl)piperidin-1-yl)ethan-1-one | 3.52 | 475.2 | E |

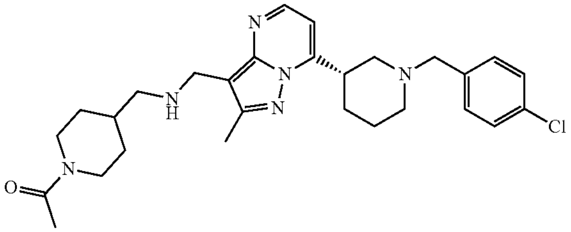

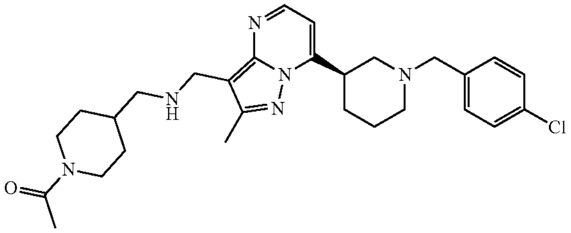

Examples 193 and 194. (S)-1-(4-((((7-(1-(4-Chlorobenzyl)piperidin-3-yl)-2-methylpyrazolo[1,5-a]pyrimidin-3-yl)methyl)amino)methyl)piperidin-1-yl)ethan-1-one and (R)-1-(4-((((7-(1-(4-chlorobenzyl)piperidin-3-yl)-2-methylpyrazolo[1,5-a]pyrimidin-3-yl)methyl)amino)methyl)piperidin-1-yl)ethan-1-one Starting from 1-(4-((((7-(1-(4-chlorobenzyl)piperidin-3-yl)-2-methylpyrazolo[1,5-a]pyrimidin-3-yl)methyl)amino)methyl)piperidin-1-yl)ethan-1-one, obtained following a similar procedure to that described in example 144, a chiral preparative HPLC [Column Chiralpak AD-H 20×250 mm, 5 μm; temperature: r.t.; eluent: n-Heptane/EtOH/$Et_2NH$ 70/30/0.1 v/v/v flow rate 14 mL/min; Rt1: 21.1 min; Rt2: 24.0 min] was carried out to give the title compounds.

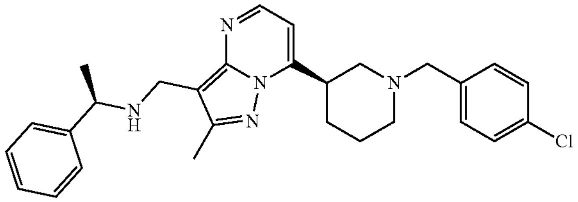

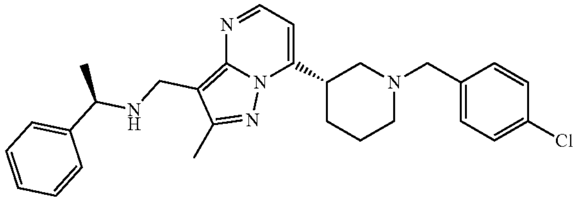

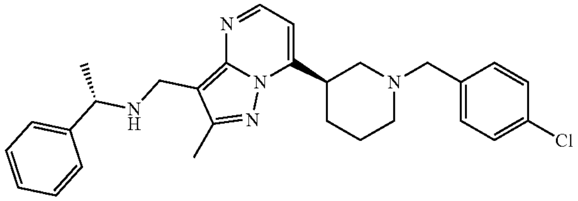

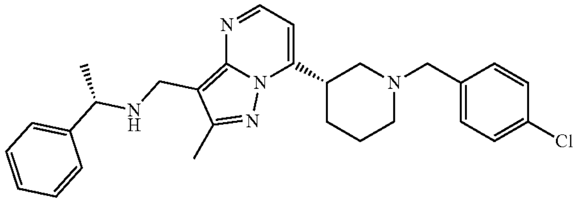

Examples 195, 196, 197 and 198. (R)—N-((7-((R)-1-(4-Chlorobenzyl)piperidin-3-yl)-2-methylpyrazolo[1,5-a]pyrimidin-3-yl)methyl)-1-phenylethan-1-amine, (R)—N-((7-((S)-1-(4-chlorobenzyl)piperidin-3-yl)-2-methylpyrazolo[1,5-a]pyrimidin-3-yl)methyl)-1-phenylethan-1-amine, (S)—N-((7-((R)-1-(4-chlorobenzyl)piperidin-3-yl)-2-methylpyrazolo[1,5-a]pyrimidin-3-yl)methyl)-1-phenylethan-1-amine and (S)—N-((7-((S)-1-(4-chlorobenzyl)piperidin-3-yl)-2-methylpyrazolo[1,5-a]pyrimidin-3-yl)methyl)-1-phenylethan-1-amine Starting from N-((7-(1-(4-chlorobenzyl)piperidin-3-yl)-2-methylpyrazolo[1,5-a]pyrimidin-3-yl)methyl)-1-phenylethanamine, obtained following a similar procedure to that described in example 144, two chiral preparative HPLC [Column Chiralpak AD-H 20×250 mm, 5 μm; temperature: r.t.; eluent: n-Heptane/EtOH/$Et_2NH$ 95/5/0.02 v/v/v; flow rate: 20 mL/min; Rt1: 6.9 min: Rt2: 8.2 min and Column Chiralpak AD-H 20×250 mm, 5 μm; temperature: r.t.; eluent: n-Heptane/EtOH/$Et_2NH$ 90/10/0.03 v/v/v; flow rate: 20 mL/min; Rt1: 7.2 min: Rt2: 9.3 min] were carried out to give the title compounds.

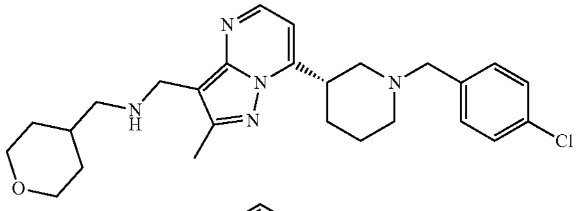

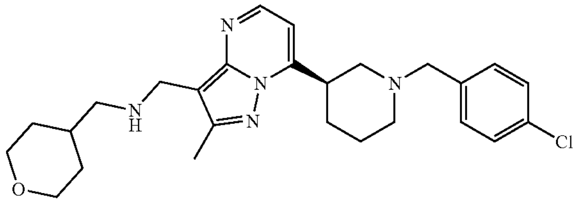

Examples 199 and 200. (S)-1-(7-(1-(4-Chlorobenzyl)piperidin-3-yl)-2-methylpyrazolo[1,5-a]pyrimidin-3-yl)-N-((tetrahydro-2H-pyran-4-yl)methyl)methanamine and (R)-1-(7-(1-(4-chlorobenzyl)piperidin-3-yl)-2-methylpyrazolo[1,5-a]pyrimidin-3-yl)-N-((tetrahydro-2H-pyran-4-yl)methyl)methanamine Starting from 1-(7-(1-(4-chlorobenzyl)piperidin-3-yl)-2-methylpyrazolo[1,5-a]pyrimidin-3-yl)-N-((tetrahydro-2H-pyran-4-yl)methyl)methanamine, obtained following a similar procedure to that described in example 144, a chiral preparative HPLC [Column Reprosil AMS 20×250 mm, 5 μm; temperature: 40° C.; eluent: MeOH/$CO_2$/$NH_3$ 20/80/0.2 v/v/v/; flow rate: 50 mL/min; Rt1: 3.19; Rt2: 3.65] was carried out to give the title compounds.

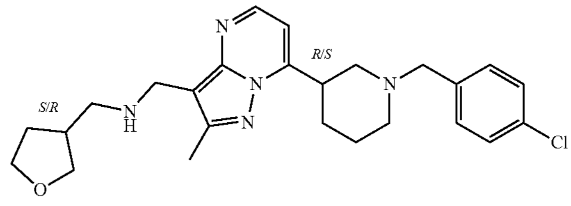

-continued

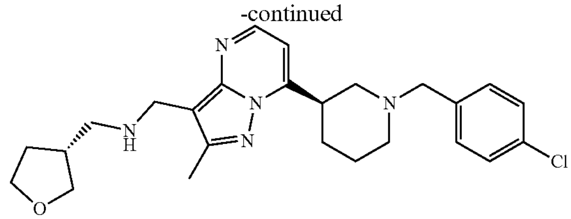

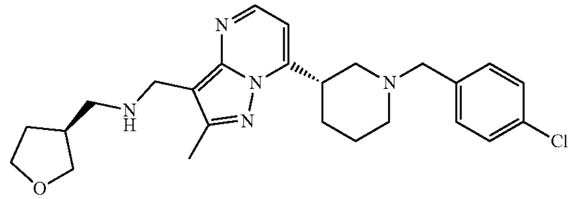

Examples 201, 202 and 203. (+/−)-1-(7-((R/S)-1-(4-Chlorobenzyl)piperidin-3-yl)-2-methylpyrazolo[1,5-a]pyrimidin-3-yl)-N—(((S/R)-tetrahydrofuran-3-yl)methyl)methanamine, 1-(7-((R)-1-(4-chlorobenzyl)piperidin-3-yl)-2-methylpyrazolo[1,5-a]pyrimidin-3-yl)-N—(((R)-tetrahydrofuran-3-yl)methyl)methanamine and 1-(7-((S)-1-(4-chlorobenzyl)piperidin-3-yl)-2-methylpyrazolo[1,5-a]pyrimidin-3-yl)-N—(((S)-tetrahydrofuran-3-yl)methyl)methanamine Starting from 1-(7-(1-(4-chlorobenzyl)piperidin-3-yl)-2-methylpyrazolo[1,5-a]pyrimidin-3-yl)-N-((tetrahydrofuran-3-yl)methyl)methanamine, obtained following a similar procedure to that described in example 144, a chiral preparative HPLC [Column LUX C3 21.1×250 mm, 5 μm; temperature: r.t.; eluent: ACN/$NH_3$ 100/0.2 v/v; flow rate: 13 mL/min; Rt1: 3.9 min; Rt2: 4.65 min; Rt3: 5.38 min] was carried out to give the title compounds.

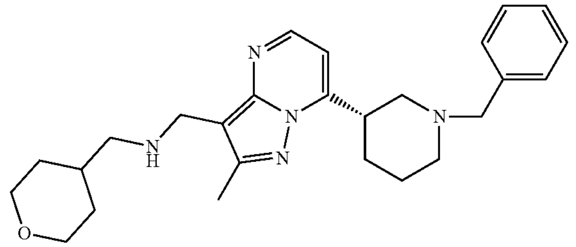

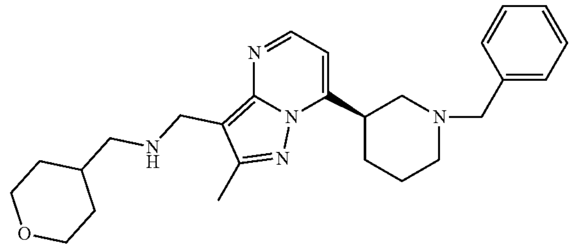

Examples 204 and 205. (S)-1-(7-(1-Benzylpiperidin-3-yl)-2-methylpyrazolo[1,5-a]pyrimidin-3-yl)-N-((tetrahydro-2H-pyran-4-yl)methyl)methanamine and (R)-1-(7-(1-benzylpiperidin-3-yl)-2-methylpyrazolo[1,5-a]pyrimidin-3-yl)-N-((tetrahydro-2H-pyran-4-yl)methyl)methanamine Starting from 1-(7-(1-benzylpiperidin-3-yl)-2-methylpyrazolo[1,5-a]pyrimidin-3-yl)-N-((tetrahydro-2H-pyran- 4-yl)methyl)methanamine, obtained following a similar procedure to that described in example 144, a chiral preparative HPLC [Column Chiralpak AD-H 20×250 mm, 5 μm; temperature: r.t.; eluent: n-Heptane/EtOH/$Et_2NH$ 85/15/0.05 v/v/v; flow rate: 12 mL/min; Rt1: 11.7; Rt2: 13.8 min] was carried out to give the title compounds.

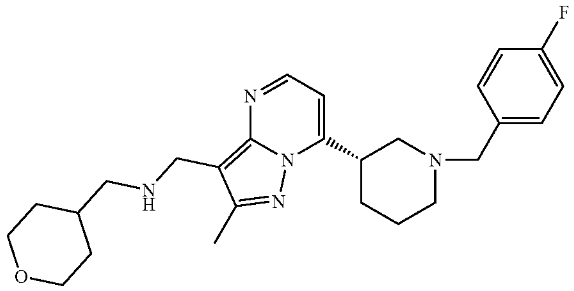

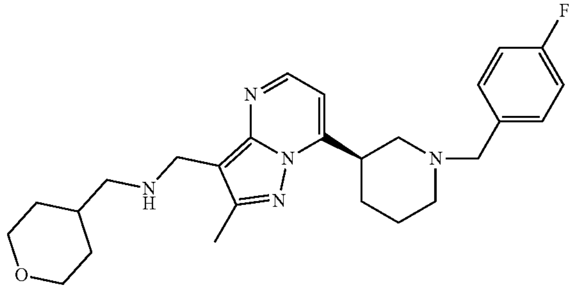

Examples 206 and 207. (S)-1-(7-(1-(4-Fluorobenzyl)piperidin-3-yl)-2-methylpyrazolo[1,5-a]pyrimidin-3-yl)-N-((tetrahydro-2H-pyran-4-yl)methyl) methanamine and (R)-1-(7-(1-(4-fluorobenzyl) piperidin-3-yl)-2-methylpyrazolo[1,5-a]pyrimidin-3-yl)-N-((tetrahydro-2H-pyran-4-yl)methyl) methanamine Starting from 1-(7-(1-(4-fluorobenzyl)piperidin-3-yl)-2-methylpyrazolo[1,5-a]pyrimidin-3-yl)-N-((tetrahydro-2H-pyran-4-yl)methyl)methanamine, obtained following a similar procedure to that described in example 144, a chiral preparative HPLC [Column Chiralpak AD-H 20×250 mm, 5 μm; temperature: r.t.; eluent: n-Heptane/EtOH/$Et_2NH$ 95/5/0.4 v/v/v; flow rate: 14 mL/min; Rt1: 32.5 min; Rt2: 36.1 min] was carried out to give the title compounds.

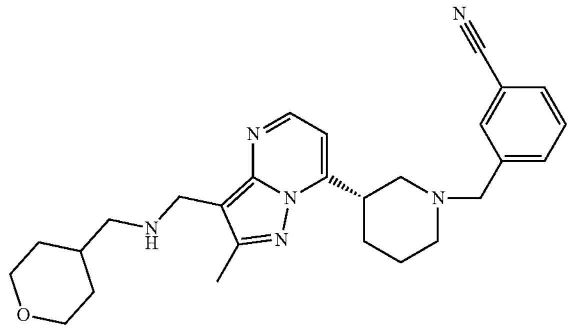

-continued

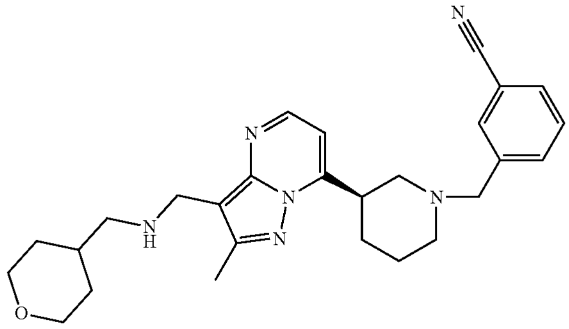

Examples 208 and 209. (S)-3-((3-(2-Methyl-3-((((tetrahydro-2H-pyran-4-yl)methyl)amino)methyl) pyrazolo[1,5-a]pyrimidin-7-yl)piperidin-1-yl) methyl)benzonitrile and (R)-3-((3-(2-methyl-3-((((tetrahydro-2H-pyran-4-yl)methyl)amino)methyl) pyrazolo[1,5-a]pyrimidin-7-yl)piperidin-1-yl) methyl)benzonitrile Starting from 3-((3-(2-methyl-3-((((tetrahydro-2H-pyran-4-yl)methyl)amino)methyl) pyrazolo[1,5-a]pyrimidin-7-yl) piperidin-1-yl)methyl)benzonitrile, obtained following a similar procedure to that described in example 144, a chiral preparative HPLC [Column Chiralpak AD-H 20×250 mm, 5 μm: temperature: r.t.; eluent: n-Heptane/EtOH/$Et_2NH$ 70/30/0.1 v/v/v; flow rate: 12 mL/min; Rt1: 15.1 min; Rt2: 17.6 min] was carried out to give the title compounds.

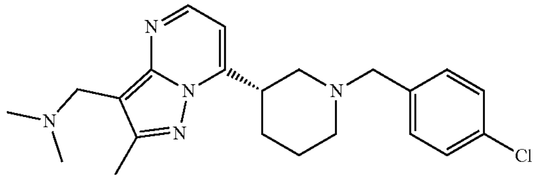

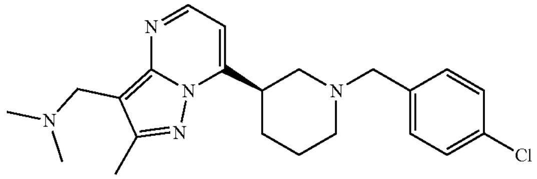

Examples 210 and 211. (S)-17-(1-(4-Chlorobenzyl) piperidin-3-yl)-2-methylpyrazolo[1,5-a]pyrimidin-3-yl)-N,N-dimethylmethanamine and (R)-1-(7-(1-(4-chlorobenzyl)piperidin-3-yl)-2-methylpyrazolo[1,5-a]pyrimidin-3-yl)-N,N-dimethylmethanamine Starting from 1-(7-(1-(4-chlorobenzyl)piperidin-3-yl)-2-methylpyrazolo[1,5-a]pyrimidin-3-yl)-N,N-dimethylmethanamine, obtained following a similar procedure to that described in example 144, a chiral preparative HPLC [Column Chiralcel OJ 20×250 mm; 5 μm; temperature: r.t.; eluent: n-Heptane/EtOH/Et2NH 90/10/0.03 v/v/v; flow rate: 15 mL/min; Rt1: 6.1 min; Rt2: 7.5 min] was carried out to give the title compounds.

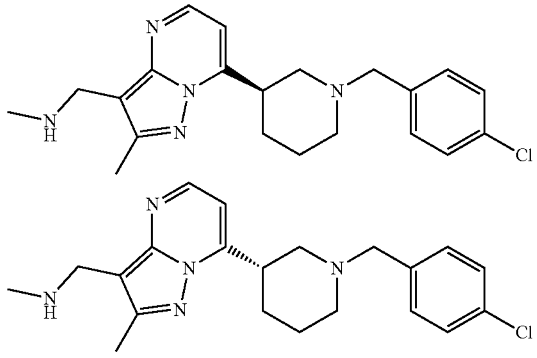

Examples 212 and 213. (R)-1-(7-(1-(4-Chlorobenzyl)piperidin-3-yl)-2-methylpyrazolo[1,5-a]pyrimidin-3-yl)-N-methylmethanamine and (S)-1-(7-(1-(4-chlorobenzyl)piperidin-3-yl)-2-methylpyrazolo[1,5-a]pyrimidin-3-yl)-N-methylmethanamine Starting from 1-(7-(1-(4-chlorobenzyl)piperidin-3-yl)-2-methylpyrazolo[1,5-a]pyrimidin-3-yl)-N-methylmethanamine, obtained following a similar procedure to that described in example 144, a chiral preparative HPLC [Column LUX C3 21.2×250, 5 μm; temperature: r.t.; eluent MeOH/$NH_3$ 100/0.2 v/v; flow rate: 21 mL/min; Rt1: 2.7 min; Rt2: 2.98 min] was carried out to give the title compounds.

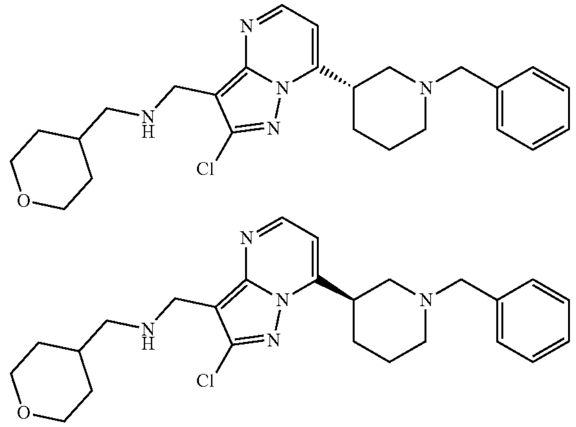

Examples 214 and 215. ((S)-1-(7-(1-Benzylpiperidin-3-yl)-2-chloropyrazolo[1,5-a]pyrimidin-3-yl)-N-((tetrahydro-2H-pyran-4-yl)methyl)methanamine and ((R)-1-(7-(1-benzylpiperidin-3-yl)-2-chloropyrazolo[1,5-a]pyrimidin-3-yl)-N-((tetrahydro-2H-pyran-4-yl)methyl)methanamine Starting from 1-(7-(1-benzylpiperidin-3-yl)-2-chloropyrazolo[1,5-a]pyrimidin-3-yl)-N-((tetrahydro-2H-pyran-4-yl)methyl)methanamine, obtained following a similar procedure to that described in example 144, a chiral preparative HPLC [Column Chiralpak AD-H 20×250 mm; 5 μm; temperature: r.t.; eluent n-Heptane/EtOH/$Et_2NH$ 80/20/0.1 v/v/v; flow rate: 11 mL/min; Rt1: 13.23 min; Rt2: 16.2 min] was carried out to give the title compounds.

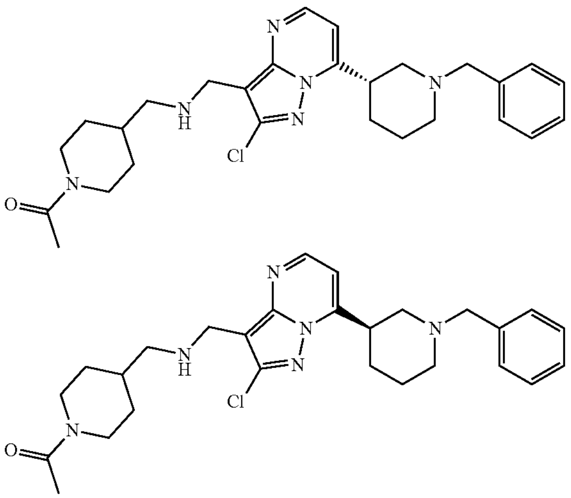

Examples 216 and 217. (S)-1-(4-((((7-(1-Benzylpiperidin-3-yl)-2-chloropyrazolo[1,5-a]pyrimidin-3-yl)methyl)amino)methyl)piperidin-1-yl)ethan-1-one and (R)-1-(4-((((7-(1-benzylpiperidin-3-yl)-2-chloropyrazolo[1,5-a]pyrimidin-3-yl)methyl)amino)methyl)piperidin-1-yl)ethan-1-one Starting from 1-(4-((((7-(1-benzylpiperidin-3-yl)-2-chloropyrazolo[1,5-a]pyrimidin-3-yl)methyl)amino)methyl)piperidin-1-yl)ethanone, obtained following a similar procedure to that described in example 144, a chiral preparative HPLC [Column Chiralpak AD-H 20×250 mm; 5 μm; temperature: r.t.; eluent n-Heptane/EtOH/$Et_2NH$ 80/20/0.1 v/v/v; flow rate: 12 mL/min; Rt1: 15.8 min; Rt2: 18.4 min] was carried out to give the title compounds.

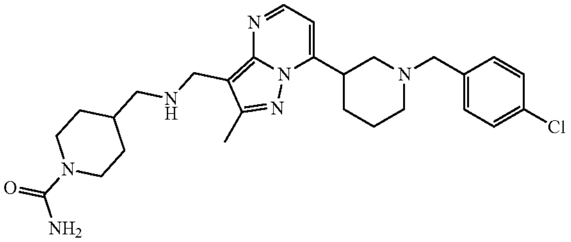 [SMILES: Cc1nn2c(C3CCCN(Cc4ccc(Cl)cc4)C3)ccnc2c1CNCC1CCN(C(N)=O)CC1]

Example 218. 4-((((7-(1-(4-Chlorobenzyl)piperidin-3-yl)-2-methylpyrazolo[1,5-a]pyrimidin-3-yl)methyl)amino)methyl)piperidine-1-carboxamide Step a. tert-Butyl ((1-(tosylcarbamoyl)piperidin-4-yl)methyl)carbamate To a 0° C. cooled solution of tert-butyl (piperidin-4-ylmehtyl)carbamate (500 mg, 2.33 mmol) in anh DCM (16 mL) 4-methylbenzenesulfonyl isocyanate (0.5 mL, 3.29 mmol) was added dropwise under argon atmosphere. The reaction mixture was left to reach r.t. and stirred for 16 h. Then, the reaction mixture was quenched with pH 5 buffer sodium acetate/AcOH sol and brine. The aq layer was extracted with DCM and the combined organic extracts were dried over $MgSO_4$, filtered and concentrated. The residue was purified by flash chromatography, silica gel, DCM:MeOH, to give the title compound as an oil (461 mg, Yield: 48%).

HPLC-MS (Method E): Rt.: 2.05 min; ESI+MS: m/z 410.1 $[M+H]^+$.

Step b. tert-Butyl ((1-carbamoylpiperidin-4-yl)methyl)carbamate

Sodium (155 mg, 6.74 mmol) and naphthalene (860 mg, 6.71 mmol) in anh THF (67 mL) was stirred under argon atmosphere for 2 h until it turned to a dark green solution, then this solution was cooled down to −78° C. and the compound obtained in step a (460 mg, 1.18 mmol) in anhydrous THF (22 mL) was added dropwise (30 min addition). The reaction mixture was stirred at −78° C. for 1.5 h and then allowed to reach r.t. and stirred for an additional 1.5 h at this temperature. After this time the reaction mixture was cooled down to −78° C. and quenched carefully with MeOH. Then the solution was allowed to reach r.t and the solvent was evaporated. This residue was partitioned between DCM and aq sat $NaHCO_3$ sol and the aq layer was extracted with DCM. The combined organic extracts were dried over $MgSO_4$, filtered and concentrated. The residue was purified by flash chromatography, silica gel, DCM:MeOH, to give the title compound as an oil (150 mg, Yield: 52%).

HPLC-MS (Method E): Rt.: 2.10 min; ESI+MS: m/z 258.1 $[M+H]^+$.

Step c. 4-(Aminomethyl)piperidine-1-carboxamide hydrochloride

Starting from the compound obtained in step b (150 mg, 0.58 mmol) and following the procedure described in step d of example 110, the title compound was obtained (113 mg).

HPLC-MS (Method E): Rt.: 0.92 min; ESI+MS: m/z 158.1 $[M+H]^+$.

Step d. Title Compound

Starting from the compound obtained in step c (113 mg, 0.58 mmol) and the compound obtained in step d of example 144 (128 mg, 0.35 mmol) and following the procedure described in step e of example 110, the title compound was obtained (14 mg, Yield: 8%).

HPLC-MS (Method E): Rt.: 3.82 min; ESI+MS: m/z 510.2 $[M+H]^+$.

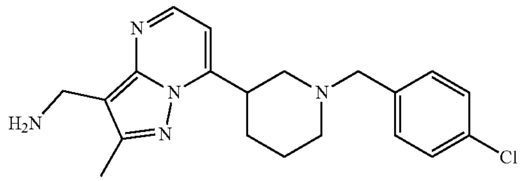 [SMILES: Cc1nn2c(C3CCCN(Cc4ccc(Cl)cc4)C3)ccnc2c1CN]

Example 219. (7-(1-(4-Chlorobenzyl)piperidin-3-yl)-2-methylpyrazolo[1,5-a]pyrimidin-3-yl)methanamine Step a. N-((7-(1-(4-Chlorobenzyl)piperidin-3-yl)-2-methylpyrazolo[1,5-a]pyrimidin-3-yl)methyl)prop-2-en-1-amine Starting from the compound obtained in step d of example 144 (1.08 g, 2.93 mmol) and prop-2-en-1-amine (0.44 mL, 5.86 mmol) and following the procedure described in step e of example 110, the title compound was obtained (863 mg, Yield: 71%).

HPLC-MS (Method E): Rt.: 4.20 min; ESI+MS: m/z 410.2 $[M+H]^+$.

Step b. Title Compound

To a solution of the compound obtained in step a (863 mg, 2.10 mmol) in anh DCM (50 mL), $Pd(OAc)_2$ (47 mg, 0.20 mmol), $PPh_3$ (165 mg, 0.62 mmol) and 1,3-dimethylpyrimidine-2,4,6 (1H, 3H, 5H)-trione (888 mg, 5.69 mmol) were added. The resulting mixture was stirred at r.t under argon atmosphere for 16 h. Then, the reaction mixture was quenched with aq sat $NaHCO_3$ sol and the aq layer was extracted with DCM. The combined organic extracts were dried over $MgSO_4$, filtered and evaporated. The residue was purified by flash chromatography, silica gel, DCM:MeOH:$NH_3$, to give the title compound as a solid (517 mg, Yield: 63%).

HPLC-MS (Method E): Rt.: 4.43 min; ESI+MS: m/z 370.1 $[M+H]^+$.

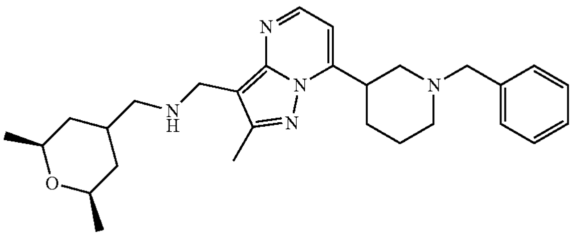 [SMILES: Cc1nn2c(C3CCCN(Cc4ccccc4)C3)ccnc2c1CNCC1C[C@@H](C)O[C@@H](C)C1]

Example 220. 1-(7-(1-Benzylpiperidin-3-yl)-2-methylpyrazolo[1,5-a]pyrimidin-3-yl)-N-(((2R,6S)-2,6-dimethyltetrahydro-2H-pyran-4-yl)methyl)methanamine Step a. (2R,6S)-4-(Methoxymethylene)-2,6-dimethyltetrahydro-2H-pyran To a 0° C. cooled solution of LDA (2 M in THF, 4.4 mL, 8.80 mmol) a solution of (methoxymethyl)diphenylphosphine oxide (1.92 g, 7.80 mmol) in anh THF (30 mL) was added. The resulting red solution was cooled to −40° C., and another solution of (2R,6S)-2,6-dimethyltetrahydro-4H-pyran-4-one (250 mg, 1.95 mmol) in anh THF (10 mL) was added. The resulting brown suspension was stirred at −40° C. for 30 min and then warmed up to 40° C. for 16 h under argon atmosphere. Then, the reaction mixture was cooled down to r.t and quenched with water. Then, brine was added to this solution and the aqueous layer was extracted with EtOAc. The combined organic extracts were dried over $MgSO_4$, filtered and concentrated. The residue was purified by flash chromatography, silica gel, hexane/EtOAc, to give the title compound as an oil (141 mg, Yield: 46%).

Step b. (2R,6S)-2,6-Dimethyltetrahydro-2H-pyran-4-carbaldehyde

To a solution of the compound obtained in step a (140 mg, 0.89 mmol) in ACN (1 mL), 2 M HCl (1.4 mL, 2.80 mmol) was added. The mixture was stirred at r.t for 5 h. The reaction mixture was diluted with 2 M HCl and the aq layer was extracted with DCM. The combined organic extracts were dried over $MgSO_4$, filtered and concentrated under low pressure and low temperature to avoid distillation of the product since it seemed to have a low boiling point. This gave the tittle compound (120 mg) that was used in the next step without further purification.

Step c. Title Compound

Starting from the compound obtained in step b (43 mg, 0.3 mmol) and (7-(1-benzylpiperidin-3-yl)-2-methylpyrazolo[1,5-a]pyrimidin-3-yl)methanamine (obtained following the procedure described in example 219) (150 mg, 0.44 mmol) and following the procedure described in step e of example 110, the title compound was obtained (118 mg, Yield: 85%).

HPLC-MS (Method E): Rt.: 4.50 min; ESI+MS: m/z 462.3 $[M+H]^+$.

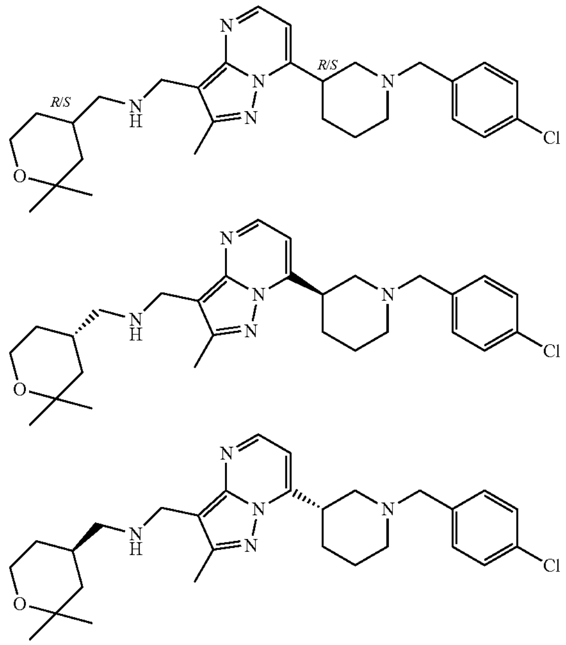

Examples 221, 222 and 223. (+/−)-1-(7-((R/S)-1-(4-Chlorobenzyl)piperidin-3-yl)-2-methylpyrazolo[1,5-a]pyrimidin-3-yl)-N—(((R/S)-2,2-dimethyltetrahydro-2H-pyran-4-yl)methyl)methanamine, (1-(7-((R)-1-(4-chlorobenzyl)piperidin-3-yl)-2-methylpyrazolo[1,5-a]pyrimidin-3-yl)-N—(((S)-2,2-dimethyltetrahydro-2H-pyran-4-yl)methyl) methanamine and (1-(7-((S)-1-(4-chlorobenzyl) piperidin-3-yl)-2-methylpyrazolo[1,5-a]pyrimidin-3-yl)-N—(((R)-2,2-dimethyltetrahydro-2H-pyran-4-yl) methyl)methanamine Starting from 1-(7-(1-(4-chlorobenzyl)piperidin-3-yl)-2-methylpyrazolo[1,5-a]pyrimidin-3-yl)-N-((2,2-dimethyltetrahydro-2H-pyran-4-yl)methyl)methanamine, obtained following a similar procedure to that described in example 220, a chiral preparative HPLC [Column LUX A1 21.2×250 mm; 5 μm; temperature: r.t.; eluent n-Heptane/iPrOH/$NH_3$ 80/20/0.5 v/v/v; flow rate: 21 mL/min; Rt1: 5.64 min; Rt2: 6.35; Rt3: 7.37 min] was carried out to give the title compounds.

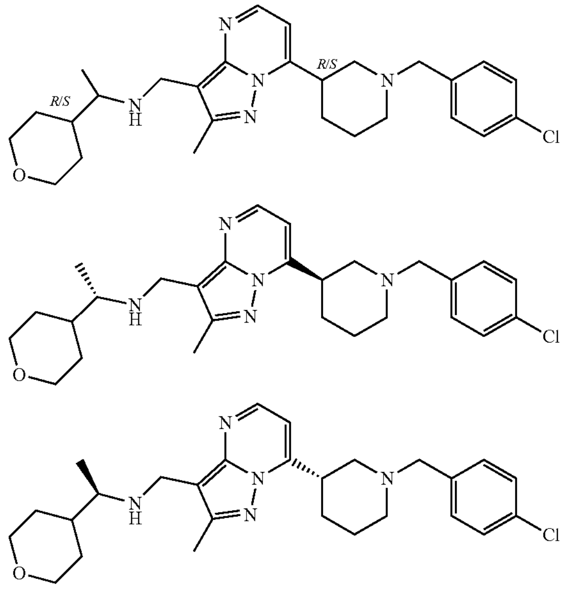

Examples 224, 225 and 226. (+/−)-(R/S)—N-((7-((R/S)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine, (S)—N-((7-((R)-1-(4-chlorobenzyl)piperidin-3-yl)-2-methylpyrazolo[1,5-a]pyrimidin-3-yl)methyl)-1-(tetrahydro-2H-pyran-4-yl)ethan-1-amine and (R)—N-((7-((S)-1-(4-chlorobenzyl)piperidin-3-yl)-2-methylpyrazolo[1,5-a]pyrimidin-3-yl)methyl)-1-(tetrahydro-2H-pyran-4-yl)ethan-1-amine Starting from N-((7-(1-(4-chlorobenzyl)piperidin-3-yl)-2-methylpyrazolo[1,5-a]pyrimidin-3-yl)methyl)-1-(tetrahydro-2H-pyran-4-yl)ethanamine, obtained following a similar procedure to that described in example 220, a chiral preparative HPLC [Column LUX C4 21.2×250 mm; 5 μm; temperature: r.t.; eluent ACN/$Et_2NH$ 100/1 v/v; flow rate: 21 mL/min; Rt1: 7.58 min; Rt2: 8.39; Rt3: 12.03 min] was carried out to give the title compounds.

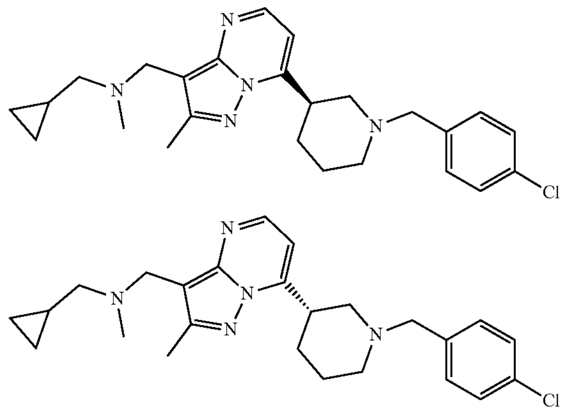

Examples 227 and 228. (R)-1-(7-(1-(4-Chlorobenzyl)piperidin-3-yl)-2-methylpyrazolo[1,5-a]pyrimidin-3-yl)-N-(cyclopropylmethyl)-N-methylmethanamine and (S)-1-(7-(1-(4-chlorobenzyl)piperidin-3-yl)-2-methylpyrazolo[1,5-a]pyrimidin-3-yl)-N-(cyclopropylmethyl)-N-methylmethanamine Step a. 1-(7-(1-(4-chlorobenzyl)piperidin-3-yl)-2-methylpyrazolo[1,5-a]pyrimidin-3-yl)-N-(cyclopropylmethyl)-N-methylmethanamine Starting from the compound obtained in example 157 (685 mg, 1.6 mmol) and paraformaldehyde (976 mg, 32.5 mmol) and following the procedure described in step e of example 110, the title compound was obtained (314 mg, Yield: 43%).

HPLC-MS (Method E): Rt.: 5.15 min; ESI+MS: m/z 438.0 $[M+H]^+$.

Step b. Title Compounds

Starting from the compound obtained in step a, a chiral preparative HPLC [Column Chiralcel OJ 20×250 mm; 5 μm; temperature: r.t.; eluent n-Heptane/EtOH/$Et_2NH$ 98/2/0.01 v/v/v; flow rate: 19 mL/min; Rt1: 7.6 min; Rt2: 11.1 min] was carried out to give the title compounds.

This method (step a) was used for the preparation of examples 229-234 using suitable starting materials:

| STRUCTURE | EX | CHEMICAL NAME | Rt (min) | MS (M + H) | HPLC Method |
|---|---|---|---|---|---|
| 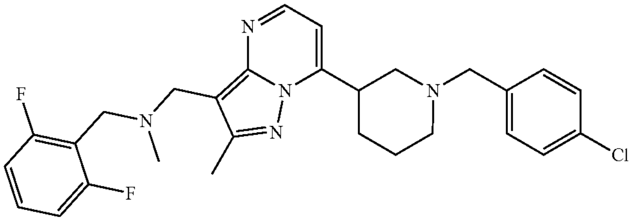 [SMILES: Cc1nn2c(C3CCCN(Cc4ccc(Cl)cc4)C3)ccnc2c1CN(C)Cc1c(F)cccc1F] | 229 | 1-(7-(1-(4-Chlorobenzyl)piperidin-3-yl)-2-methylpyrazolo[1,5-a]pyrimidin-3-yl)-N-(2,6-difluorobenzyl)-N-methylmethanamine | 4.55 | 510.2 | E |
| 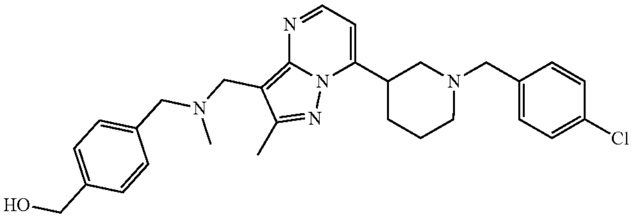 [SMILES: Cc1nn2c(C3CCCN(Cc4ccc(Cl)cc4)C3)ccnc2c1CN(C)Cc1ccc(CO)cc1] | 230 | (4-((((7-(1-(4-Chlorobenzyl)piperidin-3-yl)-2-methylpyrazolo[1,5-a]pyrimidin-3-yl)methyl)(methyl)amino)methyl)phenyl)methanol | 3.88 | 504.2 | E |
| 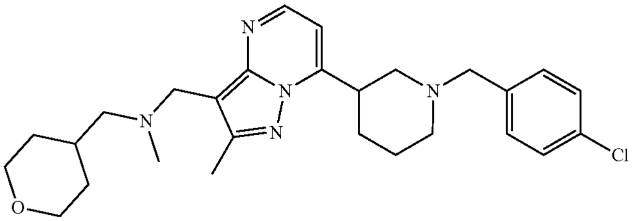 [SMILES: Cc1nn2c(C3CCCN(Cc4ccc(Cl)cc4)C3)ccnc2c1CN(C)CC1CCOCC1] | 231 | 1-(7-(1-(4-Chlorobenzyl)piperidin-3-yl)-2-methylpyrazolo[1,5-a]pyrimidin-3-yl)-N-methyl-N-((tetrahydro-2H-pyran-4-yl)methyl)methanamine | 4.18 | 482.2 | E |
| 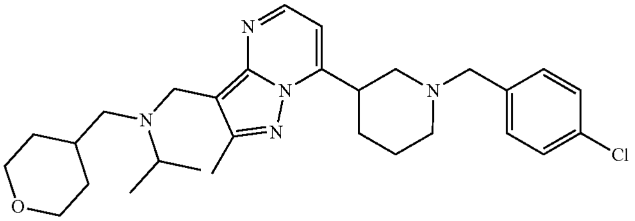 [SMILES: Cc1nn2c(C3CCCN(Cc4ccc(Cl)cc4)C3)ccnc2c1CN(CC1CCOCC1)C(C)C] | 232 | N-((7-(1-(4-Chlorobenzyl)piperidin-3-yl)-2-methylpyrazolo[1,5-a]pyrimidin-3-yl)methyl)-N-((tetrahydro-2H-pyran-4-yl)methyl)propan-2-amine | 4.85 | 510.2 | E |
| 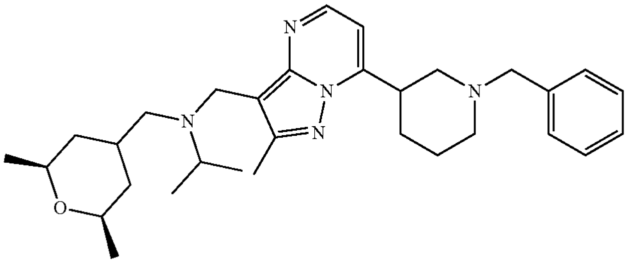 [SMILES: Cc1nn2c(C3CCCN(Cc4ccccc4)C3)ccnc2c1CN(CC1C[C@@H](C)O[C@@H](C)C1)C(C)C] | 233 | N-((7-(1-Benzylpiperidin-3-yl)-2-methylpyrazolo[1,5-a]pyrimidin-3-yl)methyl)-N-(((2R,6S)-2,6-dimethyltetrahydro-2H-pyran-4-yl)methyl)propan-2-amine | 5.00 | 504.2 | E |

-continued

| STRUCTURE | EX | CHEMICAL NAME | Rt (min) | MS (M + H) | HPLC Method |
|---|---|---|---|---|---|
| 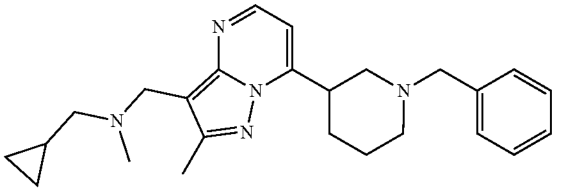 [SMILES: Cc1nn2c(C3CCCN(Cc4ccccc4)C3)ccnc2c1CN(C)CC1CC1] | 234 | 1-(7-(1-Benzylpiperidin-3-yl)-2-methylpyrazolo[1,5-a]pyrimidin-3-yl)-N-(cyclopropylmethyl)-N-methylmethanamine | 4.80 | 404.2 | E |

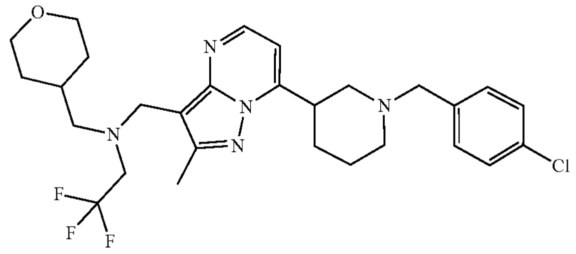 [SMILES: Cc1nn2c(C3CCCN(Cc4ccc(Cl)cc4)C3)ccnc2c1CN(CC1CCOCC1)CC(F)(F)F]

Example 235. N-((7-(1-(4-Chlorobenzyl)piperidin-3-yl)-2-methylpyrazolo[1,5-a]pyrimidin-3-yl)methyl)-2,2,2-trifluoro-N-((tetrahydro-2H-pyran-4-yl)methyl)ethan-1-amine To a solution of 1-(7-(1-(4-chlorobenzyl)piperidin-3-yl)-2-methylpyrazolo[1,5-a]pyrimidin-3-yl)-N-((tetrahydro-2H-pyran-4-yl)methyl)methanamine (obtained following the procedure described in example 144) (60 mg, 0.12 mmol) in DCM (4 mL), TEA (0.04 mL, 0.28 mmol) and 2,2,2-trifluoroethyl trifluoromethanesulfonate (0.14 mL, 1.0 mmol) were added and the reaction mixture was stirred under argon atmosphere at r.t. for 4 days. The reaction mixture was poured into water and the aq layer was extracted with DCM. The combined organic extracts were dried over $MgSO_4$, filtered and concentrated to give the title compound as an oil (58.6 mg, Yield: 74%).

HPLC-MS (Method E): Rt.: 4.52 min; ESI+MS: m/z 550.2 $[M+H]^+$.

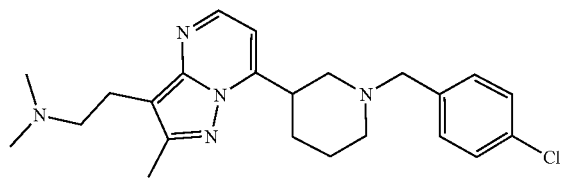 [SMILES: Cc1nn2c(C3CCCN(Cc4ccc(Cl)cc4)C3)ccnc2c1CCN(C)C]

Example 236. 2-(7-(1-(4-Chlorobenzyl)piperidin-3-yl)-2-methylpyrazolo[1,5-a]pyrimidin-3-yl)-N,N-dimethylethan-1-amine Step a. (E)-7-(1-(4-Chlorobenzyl)piperidin-3-yl)-2-methyl-3-(2-nitrovinyl)pyrazolo[1,5-a]pyrimidine To a solution of the compound obtained in step d of example 144 (500 mg, 1.35 mmol) in MeOH (10 mL), potassium acetate (532 mg, 5.42 mmol), methylamine hydrochloride (252 mg, 3.73 mmol) and nitromethane (0.08 mL, 1.49 mmol) were added. The reaction mixture was stirred under argon atmosphere at r.t for 60 h. Then, it was poured into water and a solid precipitated off. The solid was filtered, washed with water and dried over vacuum to give the title compound as a yellow solid (392 mg, Yield: 70%). This solid was used in the next step without further purification.

HPLC-MS (Method E): Rt.: 4.40 min; ESI+MS: m/z 412.2 $[M+H]^+$.

Step b. 7-(1-(4-Chlorobenzyl)piperidin-3-yl)-2-methyl-3-(2-nitroethyl)pyrazolo[1,5-a]pyrimidine To a solution of the compound obtained in step a (343 mg, 0.83 mmol) in MeOH (10 mL), sodium borohydride (98 mg, 2.58 mmol) was slowly added portionwise to the solution at r.t. The reaction mixture was stirred under nitrogen atmosphere for 45 min. The solvent was evaporated and the residue was diluted with a mixture of EtOAc, aq sat $NaHCO_3$ sol and brine. The aq layer was extracted with EtOAc, the combined organic extracts were dried over $MgSO_4$, filtered and concentrated to give the title compound as a solid (328 mg, Yield: 95%). This solid was used in the next step without further purification.

HPLC-MS (Method E): Rt.: 3.93 min; ESI+MS: m/z 414.2 $[M+H]^+$.

Step c. 2-(7-(1-(4-Chlorobenzyl)piperidin-3-yl)-2-methylpyrazolo[1,5-a]pyrimidin-3-yl)ethan-1-amine To a solution of the compound obtained in step b (328 mg, 0.79 mmol) in MeOH (10 mL), Nickel Raney (46.5 mg, 0.79 mmol) was added and the reaction mixture was stirred under hydrogen atmosphere at 40° C. for 16 h. Then it was filtered through a pad of Celite and the solvent was evaporated to give the title compound as an oil (298 mg, Yield: 98%). This compound was used in the next step without further purification.

HPLC-MS (Method E): Rt.: 5.06 min; ESI+MS: m/z 384.1 $[M+H]^+$.

Step d. Title Compound

Starting from the compound obtained in step c (135 mg, 0.35 mmol) and following the procedure described in examples 227 and 228, the title compound was obtained (72 mg, Yield: 49%).

HPLC-MS (Method E): Rt.: 4.27 min; ESI+MS: m/z 412.2 $[M+H]^+$.

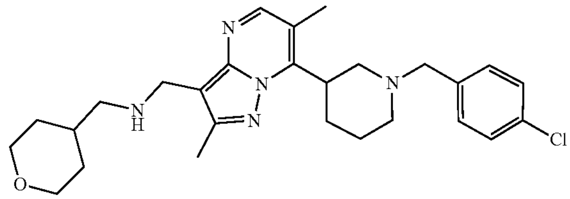 [SMILES: Cc1cnc2c(CNCC3CCOCC3)c(C)nn2c1C1CCCN(Cc2ccc(Cl)cc2)C1]

Example 237. 1-(7-(1-(4-Chlorobenzyl)piperidin-3-yl)-2,6-dimethylpyrazolo[1,5-a]pyrimidin-3-yl)-N-((tetrahydro-2H-pyran-4-yl)methyl)methanamine Step a. tert-Butyl 3-propionylpiperidine-1-carboxylate To a 0° C. stirring solution of 1-(tert-butyl) 3-ethyl piperidine-1,3-dicarboxylate (2.06 g, 8.0 mmol), and N,O-dimethylhydroxylamine hydrochloride (273 mg, 8.95 mmol) in dry THF (21 mL) and under argon atmosphere, ethylmagnesium chloride (2 M in THF, 23.0 mL, 46.0 mmol) was added dropwise. The reaction was allowed to warm up to r.t. for 3 h. Then the solution was quenched with aq sat $NH_4Cl$ sol at 0° C. The aq layer was extracted with EtOAc and the combined organic extracts were washed with brine, dried over anh $Na_2SO_4$, filtered and concentrated to give the title compound (1.90 g, Yield: 98%) as a light brown oil.

HPLC-MS (Method E): Rt.: 3.17 min; ESI+MS: m/z 242.0 $[M+H]^+$.

Step b. tert-Butyl (Z)-3-(3-(dimethylamino)-2-methylacryloyl)piperidine-1-carboxylate Starting from the compound obtained in step a (600 mg, 2.48 mmol) and following the procedure described in step b of example 110, the title compound was obtained (735 mg).

HPLC-MS (Method E): Rt.: 2.87 min; ESI+MS: m/z 297.1 $[M+H]^+$.

Step c. Title Compound

Starting from the compound obtained in step b (735 mg, 2.48 mmol) and following the procedure described in example 144, the title compound was obtained (29 mg, Yield: 29% for 5 steps).

HPLC-MS (Method I): Rt.: 2.50 min; ESI+MS: m/z 482.2 $[M+H]^+$.

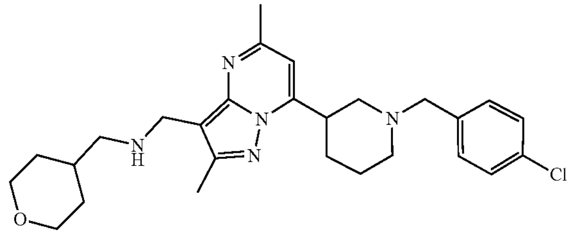 [SMILES: Cc1cc(C2CCCN(Cc3ccc(Cl)cc3)C2)n2nc(C)c(CNCC3CCOCC3)c2n1]

Example 238. 1-(7-(1-(4-Chlorobenzyl)piperidin-3-yl)-2,5-dimethylpyrazolo[1,5-a]pyrimidin-3-yl)-N-((tetrahydro-2H-pyran-4-yl)methyl)methanamine Step a. tert-Butyl (E)-3-(3-(dimethylamino)but-2-enoyl)piperidine-1-carboxylate Starting from the compound obtained step a of example 110 (250 mg, 1.10 mmol) and 1,1-dimethoxy-N,N-dimethylethan-1-amine (176 mg, 1.32 mmol) and following the procedure described in step b of example 110, the title compound was obtained (308 mg).

HPLC-MS (Method E): Rt.: 2.87 min; ESI+MS: m/z 297.1 $[M+H]^+$.

Step b. Title Compound

Starting from the compound obtained in step a (308 mg, 1.03 mmol) and following the procedure described in example 144, the title compound was obtained (80 mg, Yield: 14% for 6 steps).

HPLC-MS (Method I): Rt.: 2.97 min; ESI+MS: m/z 482.2 $[M+H]^+$.

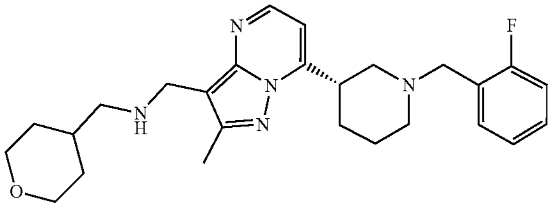 [SMILES: Cc1nn2c([C@H]3CCCN(Cc4ccccc4F)C3)ccnc2c1CNCC1CCOCC1]

Example 239. (S)-1-(7-(1-(2-Fluorobenzyl)piperidin-3-yl)-2-methylpyrazolo[1,5-a]pyrimidin-3-yl)-N-((tetrahydro-2H-pyran-4-yl)methyl)methanamine Step a. tert-Butyl (S)-3-acetylpiperidine-1-carboxylate To a 0° C. stirring solution of 1-(tert-butyl) 3-ethyl (S)-piperidine-1,3-dicarboxylate (5 g, 19.43 mmol), and N,O-dimethylhydroxylamine hydrochloride (2.27 g, 23.32 mmol) in dry THF (40 mL), methylmagnesium chloride (3 M in THF, 35.6 mL, 107 mmol) was added dropwise under argon atmosphere. The reaction mixture was allowed to stir at 0° C. for 1 h. Then the solution was quenched with aq sat $NH_4Cl$ sol at 0° C. The aq layer was extracted with EtOAc and the combined organic extracts were washed with brine, dried over $MgSO_4$, filtered and concentrated to give the title compound (4.18 g, Yield: 95%) as a light yellow oil.

HPLC-MS (Method K (f)): Rt.: 3.83 min; ESI+MS: m/z 228.0 $[M+H]^+$.

Step b. tert-Butyl (S,E)-3-(3-(dimethylamino)acryloyl)piperidine-1-carboxylate

The compound obtained in step a (2.01 g, 8.84 mmol) and 1-tert-butoxy-N,N,N',N'-tetramethylmethanediamine (1.83 mL, 8.84 mmol) were mixed in a sealed reactor under argon and the mixture were stirred at 100° C. for 30 min. After this time the reaction mixture was immediately cooled down to 0° C. for 15 min and then concentrated to dryness under reduced pressure to give the title compound as a yellow oil (2.49 g).

HPLC-MS (Method K (f)): Rt.: 4.98 min; ESI+MS: m/z 283.3 $[M+H]^+$.

Step c. tert-Butyl (S)-3-(2-bromopyrazolo[1,5-a]pyrimidin-7-yl)piperidine-1-carboxylate A solution of the compound obtained in step b (2.50 g, 8.84 mmol) was dissolved in glacial AcOH (15 mL) and 5-bromo-1H-pyrazol-3-amine (1.56 g, 8.84 mmol) was added. The reaction mixture was stirred at 50° C. for 7 h. The solvent was evaporated and the residue was purified by flash chromatography, silica gel, hexane/EtOAc as eluents to give the title compound as a yellow sticky solid (2.45 g, Yield: 70%).

HPLC-MS (Method L): Rt.: 7.68 min; ESI+MS: m/z 396.1 $[M+H]^+$.

Step d. tert-Butyl (S,E)-3-(2-methyl-3-styrylpyrazolo[1,5-a]pyrimidin-7-yl)piperidine-1-carboxylate A solution of the compound obtained in step c (2.49 g, 6.30 mmol), (E)-4,4,5,5-tetramethyl-2-styryl-1,3,2-dioxaborolane (2.90 g, 12.60 mmol), $Pd(dppf)Cl_2$ (140 mg, 0.17 mmol) and aq sodium carbonate sol (2 M, 10.7 mL, 21.42 mmol) in toluene/EtOAc (2:1, 21 mL) was degassed by means of bubbling argon and stirred at 90° C. for 16 h. The reaction mixture was diluted with EtOAc, The organic layer was washed with aq sat $Na_2CO_3$ sol, brine, dried over anh $Na_2SO_4$, filtered and concentrated. The residue was purified by flash chromatography, silica gel, DCM as eluent to give the title compound as a yellow oil (647 mg, Yield: 24%).

HPLC-MS (Method K (b)): Rt.: 7.07 min; ESI+MS: m/z 419.1 $[M+H]^+$.

Step e. (S,E)-2-Methyl-7-(piperidin-3-yl)-3-styrylpyrazolo[1,5-a]pyrimidine hydrochloride Starting from the compound obtained in step d (647 mg, 1.54 mmol) and following the procedure described in step d of example 110, the title compound was obtained (549 mg). This compound was used in the next step without further purification.

Step f. (S,E)-7-(1-(2-Fluorobenzyl)piperidin-3-yl)-2-methyl-3-styrylpyrazolo[1,5-a]pyrimidine The compound obtained in step e (175 mg, 0.49 mmol) was dissolved in dry DCM (8 mL) and TEA (0.2 mL, 1.48 mmol) was added at r.t. To this solution 2-fluorobenzaldehyde (0.1 mL, 0.99 mmol) and AcOH (0.003 mL, 0.49 mmol) were added, after 5 min of shaking, sodium triacetoxyhydroborate (218 mg, 1 mmol) was added to the solution and the reaction mixture was left at r.t. for 16 h. Then, the reaction mixture was diluted with DCM, the organic layer was washed with aq sat $Na_2CO_3$ sol, then dried over anh $Na_2SO_4$ and filtered. Solvent was evaporated and the residue was purified by flash chromatography, silica gel, DCM:MeOH as eluents to give the title compound as a yellow oil (150 mg, Yield: 67% for 2 steps).

HPLC-MS (Method K (a)): Rt.: 7.78 min; ESI+MS: m/z 427.1 $[M+H]^+$.

Step g. (S)-7-(1-(2-Fluorobenzyl)piperidin-3-yl)-2-methylpyrazolo[1,5-a]pyrimidine-3-carbaldehyde To a solution of the compound obtained in step f (145 mg, 0.4 mmol) in acetone/water (6:1, 7 mL), $NaIO_4$ (218 mg, 1.02 mmol) and $OsO_4$ (10 mg, 0.04 mmol) were added consecutively at r.t. After the $OsO_4$ addition, the yellow solution became black and a light brown solid precipitated off. The resulting mixture was stirred at r.t. for 2 h, then, it was filtered through a fritted glass funnel, the grey solid washed with EtOAc. Then organic phase was washed with aq sat $Na_2CO_3$ sol, brine and dried over anh $Na_2SO_4$, filtered and concentrated. The residue was purified by flash chromatography, silica gel, DCM:MeOH as eluents to give the title compound as a yellow solid (55 mg, Yield: 45%). This yellow solid was precipitated in the minimum amount of MeOH then filtered, the solid washed with the minimum amount of MeOH, then with hexane and dried under vacuum to obtain the title compound with an ee>90%.

HPLC-MS (Method K (d)): Rt.: 5.53 min; ESI+MS: m/z 353.1 $[M+H]^+$.

Step h. Title Compound

To a solution of the compound obtained in step g (50 mg, 0.14 mmol) in dry MeOH (2 mL) tetrahydro-2H-pyran-4-yl methanamine (24.0 mg, 0.21 mmol) and drops of AcOH were added. The reaction mixture was left shaking at r.t. for 15 min, sodium cyanotrihydroborate (9.0 mg, 0.14 mmol) was added and the reaction mixture was stirred at r.t. for 3 h. Then, solvent was evaporated and the reaction mixture was dissolved with DCM and poured into aq sat $NaHCO_3$ sol, the organic layer was separated and the aq layer was extracted with DCM. The combined organic extracts were washed with brine, dried over anh $Na_2SO_4$ and filtered. Solvent was evaporated and the residue was purified by flash chromatography, silica gel, DCM:MeOH as eluents to give the title compound (53 mg, Yield: 79%).

HPLC-MS (Method M): Rt.: 12.77 min; ESI+MS: m/z 452.2 $[M+H]^+$.

This method was used for the preparation of examples 240-242 using suitable starting materials:

| STRUCTURE | EX | CHEMICAL NAME | Rt (min) | MS (M + H) | HPLC Method |
|---|---|---|---|---|---|
| 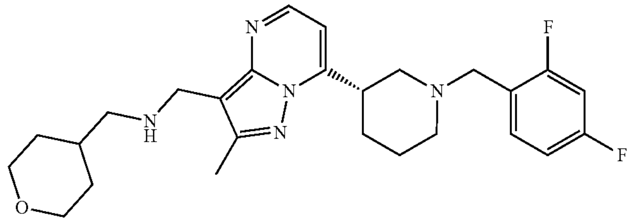 [SMILES: Cc1nn2c([C@H]3CCCN(Cc4ccc(F)cc4F)C3)ccnc2c1CNCC1CCOCC1] | 240 | (S)-1-(7-(1-(2,4-Difluorobenzyl)piperidin-3-yl)-2-methylpyrazolo[1,5-a]pyrimidin-3-yl)-N-((tetrahydro-2H-pyran-4-yl)methyl)methanamine | 4.18 | 470.2 | E |

-continued

| STRUCTURE | EX | CHEMICAL NAME | Rt (min) | MS (M + H) | HPLC Method |
|---|---|---|---|---|---|
| 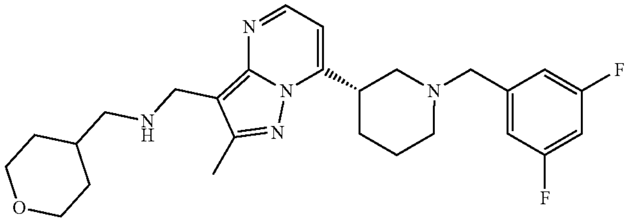 [SMILES: Cc1nn2c([C@H]3CCCN(Cc4cc(F)cc(F)c4)C3)ccnc2c1CNCC1CCOCC1] | 241 | (S)-1-(7-(1-(3,5-Difluorobenzyl)piperidin-3-yl)-2-methylpyrazolo[1,5-a]pyrimidin-3-yl)-N-((tetrahydro-2H-pyran-4-yl)methyl)methanamine | 4.47 | 470.2 | E |
| 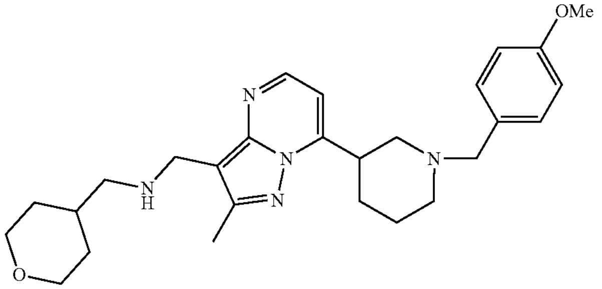 [SMILES: COc1ccc(CN2CCCC(c3ccnc4c(CNCC5CCOCC5)c(C)nn34)C2)cc1] | 242 | 1-(7-(1-(4-Methoxybenzyl)piperidin-3-yl)-2-methylpyrazolo[1,5-a]pyrimidin-3-yl)-N-((tetrahydro-2H-pyran-4-yl)methyl)methanamine | 3.98 | 464.2 | E |

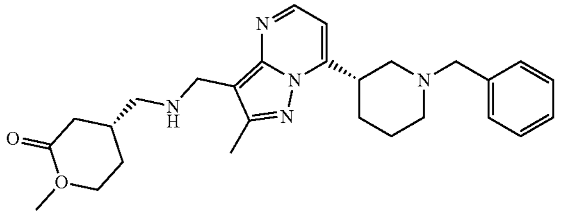

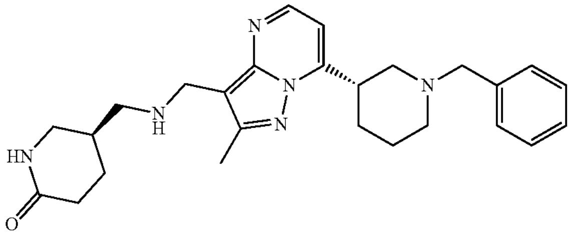

Examples 243 and 244. (R)-4-((((7-((S)-1-Benzylpiperidin-3-yl)-2-methylpyrazolo[1,5-a]pyrimidin-3-yl)methyl)amino)methyl)-1-methylpiperidin-2-one, (S)-4-((((7-((S)-1-Benzylpiperidin-3-yl)-2-methylpyrazolo[1,5-a]pyrimidin-3-yl)methyl)amino)methyl)-1-methylpiperidin-2-one Starting from 4-((((7-((S)-1-benzylpiperidin-3-yl)-2-methylpyrazolo[1,5-a]pyrimidin-3-yl)methyl)amino)methyl)-1-methylpiperidin-2-one, obtained following a similar procedure to that described in example 239, a chiral preparative HPLC [Column Chiralpak AD-H 20×250 mm; 5 μm; temperature: r.t.; eluent n-Heptane/EtOH/$Et_2NH$ 70/30/0.1 v/v/v; flow rate: 12 mL/min; Rt1: 13.7 min; Rt2: 17.2 min] was carried out to give the title compounds.

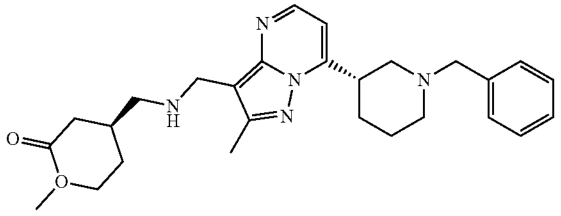

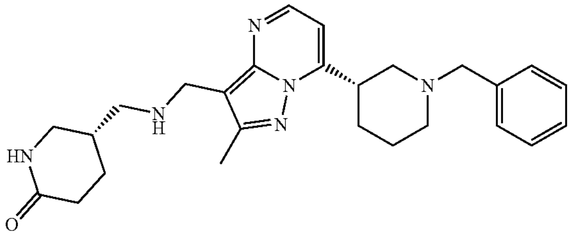

Examples 245 and 246. (R)-5-((((7-((S)-1-Benzylpiperidin-3-yl)-2-methylpyrazolo[1,5-a]pyrimidin-3-yl)methyl)amino)methyl)piperidin-2-one and (S)-5-((((7-((S)-1-Benzylpiperidin-3-yl)-2-methylpyrazolo[1,5-a]pyrimidin-3-yl)methyl)amino)methyl)piperidin-2-one Starting from 5-((((7-(1-benzylpiperidin-3-yl)-2-methylpyrazolo[1,5-a]pyrimidin-3-yl)methyl)amino)methyl)piperidin-2-one, obtained following a similar procedure to that described in example 239, a chiral preparative HPLC [Column Chiralpak IB 20×250 mm; 5 μm; temperature: r.t.; eluent n-Heptane/EtOH/$Et_2NH$ 80/20/0.1 v/v/v; flow rate: 12 mL/min; Rt1: 19.8 min; Rt2: 27.3 min] was carried out to give the title compounds.

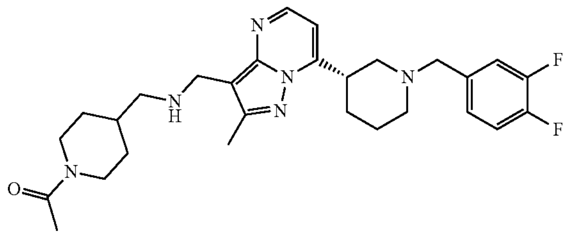 [SMILES: CC(=O)N1CCC(CNCc2c(C)nn3c([C@H]4CCCN(Cc5ccc(F)c(F)c5)C4)ccnc23)CC1]

Example 247. (S)-1-(4-((((7-(1-(3,4-Difluorobenzyl)piperidin-3-yl)-2-methylpyrazolo[1,5-a]pyrimidin-3-yl)methyl)amino)methyl)piperidin-1-yl)ethan-1-one Method 1:

Step a. Ethyl (S)-1-(3,4-difluorobenzyl)piperidine-3-carboxylate

To a solution of ethyl (S)-piperidine-3-carboxylate (6.10 g, 38.80 mmol) in dry DCM (130 mL) cooled at 0° C., DIPEA (10.13 mL, 58.2 mmol) was added dropwise under argon atmosphere, followed by 4-(bromomethyl)-1,2-difluorobenzene (4.96 mL, 38.80 mmol). The reaction mixture was allowed to warm up to r.t. and stirred for 16 h. The organic layer washed with aq sat $Na_2CO_3$ sol and brine. Then it was dried over anh $Na_2SO_4$ and concentrated. The residue was purified by flash chromatography, silica gel, hexane:EtOAc as eluents to give the title compound as a yellow oil (9.65 g, Yield: 83%).

HPLC-MS (Method K (b)): Rt.: 4.58 min; ESI+MS: m/z 284.0 $[M+H]^+$.

Step b. (S)-1-(1-(3,4-Difluorobenzyl)piperidin-3-yl)ethan-1-one

Starting from the compound obtained in step a (5.20 g, 18.35 mmol) and following the procedure described in step a of example 239, the title compound was obtained as a light brown oil (4.61 g). This compound was used in the next step without further purification.

HPLC-MS (Method K (g)): Rt.: 13.03 min; ESI+MS: m/z 254.0 $[M+H]^+$.

Step c. (S,E)-1-(1-(3,4-Difluorobenzyl)piperidin-3-yl)-3-(dimethylamino)prop-2-en-1-one Starting from the compound obtained in step b (3.39 g, 13.38 mmol) and following the procedure described in step b of example 239, the title compound was obtained as a brown oil (4.10 g). This compound was used in the next step without further purification.

HPLC-MS (Method K (e)): Rt.: 5.28 min; ESI+MS: m/z 309.0 $[M+H]^+$.

Step d. (S)-3-Bromo-7-(1-(3,4-difluorobenzyl)piperidin-3-yl)-2-methylpyrazolo[1,5-a]pyrimidine Starting from the compound obtained in step c (4.10 g, 13.30 mmol) and following the procedure described in step c of example 239, the title compound was obtained as a thick brown oil (3.20 g, Yield: 55% for 3 steps).

HPLC-MS (Method K (c)): Rt.: 5.57 min; ESI+MS: m/z 421.0 $[M+H]^+$.

Step e. (S,E)-7-(1-(3,4-Difluorobenzyl)piperidin-3-yl)-2-methyl-3-styrylpyrazolo[1,5-a]pyrimidine Starting from the compound obtained in step d (2.16 g, 5.13 mmol) and following the procedure described in step d of example 239, the title compound was obtained as a yellow sticky solid (1.94 g, Yield: 80%).

HPLC-MS (Method K(a)): Rt.: 7.02 min; ESI+MS: m/z 445.1 $[M+H]^+$.

Step f. (S)-7-(1-(3,4-Difluorobenzyl)piperidin-3-yl)-2-methylpyrazolo[1,5-a]pyrimidine-3-carbaldehyde Starting from the compound obtained in step e (1.94 g, 4.36 mmol) and following the procedure described in step g of example 239, the title compound was obtained as a white solid (500 mg, Yield: 31%).

HPLC-MS (Method K(d)): Rt.: 5.60 min; ESI+MS: m/z 3715.1 $[M+H]^+$.

Step g. Title Compound

Starting from the compound obtained in step f (500 mg, 1.35 mmol) and 1-(4-aminomethyl)piperidin-1-yl)ethan-1-one and following the procedure described in step h of example 239, the title compound was obtained as a sticky brown solid (434 mg, Yield: 62%).

HPLC-MS (Method E): Rt.: 3.10 min; ESI+MS: m/z 511.2 $[M+H]^+$.

Method 2:

Step a. Piperidin-4-ylmethanol hydrochloride

Starting from tert-butyl 4-(hydroxymethyl)piperidine-1-carboxylate (1.0 g, 4.64 mmol) and following the procedure step d of example 110, the title compound was obtained (704 mg). This compound was used in the next step without further purification.

Step b. 1-(4-(Hydroxymethyl)piperidin-1-yl)ethan-1-one

To a solution of the compound obtained in step a (704 mg, 4.64 mmol) in acetone (16 mL), $K_2CO_3$ (1.6 g, 11.6 mmol) was added followed by dropwise addition of acetic anhydride (0.52 mL, 5.57 mmol). The reaction mixture was stirred at r.t. for 3 h. Then, it was filtered through a plug of Celite, and the resulting white solid was washed with acetone several times. The combined filtrates were then concentrated under reduced pressure. The residue was purified by flash chromatography, silica gel, DCM:MeOH as eluents to give the title compound as a yellow oil (600 mg, Yield: 82%).

HPLC-MS (Method E): Rt.: 1.00 min; ESI+MS: m/z 158.0 $[M+H]^+$.

Step c. 1-Acetylpiperidine-4-carbaldehyde

To a 0° C. solution of the compound obtained in step b (600 mg, 3.82 mmol) in chloroform (13 mL), Dess-Martin Periodinane (1.78 g, 4.20 mmol) was added under argon atmosphere, and the reaction mixture was allowed to warm up to r.t and stirred for 2 h. Then, the resulting suspension was filtered through a plug of Celite, and the resulting white solid was washed with chloroform several times. The combined filtrates were then concentrated under reduced pressure. The residue was dissolved in DCM and MP-carbonate resin (loading 3.5 mmol/g, 3.2 g, 11.46 mmol) was added to the solution and the reaction mixture was stirred for 3 h. Then, it was filtered through a fritted glass funnel and the resulting filtrate was concentrated under vacuum to give the desired title compound as a colourless oil (238 mg, Yield: 40%). This compound must be kept in the freezer under argon atmosphere for short times as it is an unstable compound.

HPLC-MS (Method E): Rt.: 0.87 min; ESI+MS: m/z 156.0 $[M+H]^+$.

Step d. tert-Butyl (S)-((7-(1-(3,4-difluorobenzyl)piperidin-3-yl)-2-methylpyrazolo[1,5-a]pyrimidin-3-yl)methyl)carbamate To a solution of the compound obtained in step d (method 1) of example 247 (839 mg, 1.99 mmol) in a mixture of dioxane/water (5:1.5, 12 mL), potassium (((tert-butoxycarbonyl)amino)methyl)trifluoroborate (944 mg, 3.98 mmol), dicyclohexyl(2',6'-dimethoxy-[1,1'-biphenyl]-2-yl)phosphine (327 mg, 0.8 mmol), $K_3PO_4$ (3.38 g, 15.93 mmol) and allylpaladium(II) chloride dimer (61 mg, 0.17 mmol) were added, the resulting mixture was degassed by argon for 5 min and heated at 100° C. for 16 h. Then, it was cooled down to r.t and filtered through a double paper filter, the resulting solid was washed with EtOAc several times, and the combined filtrates were concentrated to dryness under vacuum. The residue was purified by flash chromatography, silica gel, DCM:MeOH as eluents to give the title compound as an orange solid (556 mg, Yield: 59%).

HPLC-MS (Method E): Rt.: 3.92 min; ESI+MS: m/z 472.1 $[M+H]^+$.

Step e. (S)-(7-(1-(3,4-Difluorobenzyl)piperidin-3-yl)-2-methylpyrazolo[1,5-a]pyrimidin-3-yl)methanamine dihydrochloride Starting from the compound obtained in step d (455 mg, 0.96 mmol) and following the procedure described in step d of example 110, the title compound was obtained (358 mg). This compound was used in the next step without further purification.

HPLC-MS (Method E): Rt.: 4.40 min; ESI+MS: m/z 372.0 $[M+H]^+$.

Step f. Title Compound

To a solution of the compound obtained in step e (398 mg, 1.07 mmol) in dry MeOH (14 mL), TEA (0.37 mL, 2.68 mmol) was added, followed by dropwise addition of the aldehyde obtained in step c (145 mg, 0.91 mmol) in dry MeOH (1 mL) and a few drops of AcOH. After vigorously stirring for 10 min, sodium cyanotrihydroborate (67.30 mg, 1.07 mmol) was added under argon atmosphere, the reaction mixture was stirred at r.t. for 3 h. Then, solvent was evaporated under reduced pressure, the resulting residue was partitioned between DCM (30 mL) and aq sat $NaHCO_3$ sol. The organic layer was separated, washed with aq sat $NaHCO_3$ sol, dried over $MgSO_4$, filtered and concentrated under vacuum. The residue was purified by preparative HPLC (XBridge $C_{18}$ column and 10 mM $NH_4HCO_3$/25% w/w $NH_4OH$ (99.8:0.12):ACN as eluents) to give the title compound as a colourless oil (180 mg, Yield: 32%).

HPLC-MS (Method E): Rt.: 3.10 min; ESI+MS: m/z 511.2 $[M+H]^+$.

This method (2) was used for the preparation of example 248 using suitable starting materials:

| STRUCTURE | EX | CHEMICAL NAME | Rt (min) | MS (M + H) | HPLC Method |
|---|---|---|---|---|---|
| 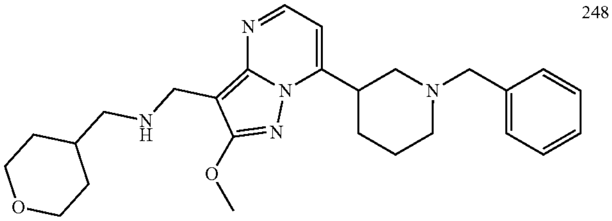 | 248 | 1-(7-(1-Benzylpiperidin-3-yl)-2-methoxypyrazolo[1,5-a]pyrimidin-3-yl)-N-((tetrahydro-2H-pyran-4-yl)methyl)methanamine | 4.82 | 450.2 | E |

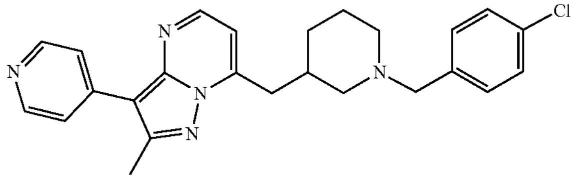 [SMILES: Cc1nn2c(CC3CCCN(Cc4ccc(Cl)cc4)C3)ccnc2c1-c1ccncc1]

Example 249. 7-((1-(4-Chlorobenzyl)piperidin-3-yl)methyl)-2-methyl-3-(pyridin-4-yl)pyrazolo[1,5-a]pyrimidine Step a. tert-Butyl 3-(2-(methoxy(methyl)amino)-2-oxoethyl)piperidine-1-carboxylate To a solution of 2-(1-(tert-butoxycarbonyl)piperidin-3-yl)acetic acid (2 g, 8.22 mmol) in DCM (60 mL) cooled at 0° C., N,O-dimethylhydroxylamine (653 mg, 10.69 mmol), EDC·HCl (2.36 g, 12.33 mmol), HOBt (1.89 g, 12.33 mmol) and TEA (4.6 mL, 32.9 mmol) were sequentially added and the reaction mixture was allowed to warm up to r.t and stirred for 16 h. Then, it was partitioned between DCM and 2 N HCl. The organic layer was separated, washed with 2 N HCl. 1 N NaOH, brine, dried over anh $Na_2SO_4$, filtered and concentrated under vacuum to give the title compound as a colourless viscous oil (1.70 g, Yield: 72%). This compound was used in the next step without further purification.

HPLC-MS (Method E): Rt.: 2.83 min; ESI+MS: m/z 287.1 $[M+H]^+$.

Step b. tert-Butyl 3-(2-oxopropyl)piperidine-1-carboxylate

To a 0° C. stirring solution of the compound obtained in step a (1.7 g, 5.94 mmol) in anh THF (15 mL), methylmagnesium chloride (3 M in THF, 3.0 mL, 9 mmol) was added dropwise under argon atmosphere. The reaction was allowed to warm up to r.t and stirred for 2 h. Then, the reaction mixture was partitioned between $Et_2O$ and 2 N HCl. The organic layer was separated, washed with brine, dried over anh $Na_2SO_4$, filtered and concentrated under vacuum to give the title compound as a colourless oil (1.32 g, Yield: 92%). This compound was used in the next step without further purification.

HPLC-MS (Method E): Rt.: 3.00 min; ESI+MS: m/z 242.1 $[M+H]^+$.

Step c. tert-Butyl (E)-3-(4-(dimethylamino)-2-oxobut-3-en-1-yl)piperidine-1-carboxylate Starting from the compound obtained in step b (1.32 g, 5.47 mmol) and following the procedure described in step b of example 110, the title compound was obtained (1.62 g). This compound was used in the next step without further purification.

HPLC-MS (Method E): Rt.: 2.67 min; ESI+MS: m/z 297.0 $[M+H]^+$.

Step d. tert-Butyl 3-((3-bromo-2-methylpyrazolo[1,5-a]pyrimidin-7-yl)methyl)piperidine-1-carboxylate Starting from the compound obtained in step c (800 mg, 2.7 mmol) and following the procedure described in step a of example 121, the title compound was obtained (640 mg, Yield: 57%).

HPLC-MS (Method E): Rt.: 3.73 min; ESI+MS: m/z 409.1 $[M+H]^+$.

Step e. tert-Butyl 3-((2-methyl-3-(pyridin-4-yl)pyrazolo[1,5-a]pyrimidin-7-yl)methyl)piperidine-1-carboxylate Starting from the compound obtained in step d (220 mg, 0.53 mmol) and following the procedure described in step a of example 114, the title compound was obtained (123 mg, Yield: 55%).

HPLC-MS (Method E): Rt.: 3.42 min; ESI+MS: m/z 408.1 $[M+H]^+$.

Step f. 2-Methyl-7-(piperidin-3-ylmethyl)-3-(pyridin-4-yl)pyrazolo[1,5-a]pyrimidine dihydrochloride Starting from the compound obtained in step e (123 mg, 0.30 mmol) and following the procedure described in step d of example 110, the title compound was obtained (104 mg). This compound was used in the next step without further purification.

HPLC-MS (Method E): Rt.: 2.47 min; ESI+MS: m/z 308.0 $[M+H]^+$.

Step g. Title Compound

Starting from the compound obtained in step f (120 mg, 0.35 mmol) and following the procedure described in step e of example 110, the title compound was obtained (90 mg, Yield: 59%).

HPLC-MS (Method E): Rt.: 3.98 min; ESI+MS: m/z 432.1 $[M+H]^+$.

This method was used for the preparation of example 250 using suitable starting materials:

| STRUCTURE | EX | CHEMICAL NAME | Rt (min) | MS (M + H) | HPLC Method |
|---|---|---|---|---|---|
| 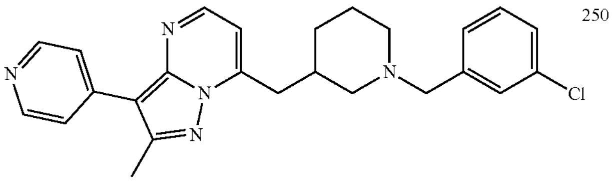 | 250 | 7-((1-(3-Chlorobenzyl)piperidin-3-yl)methyl)-2-methyl-3-(pyridin-4-yl)pyrazolo[1,5-a]pyrimidine | 3.98 | 432.1 | E |

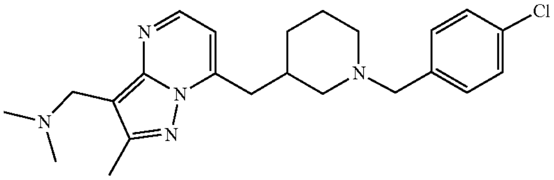 [SMILES: Cc1nn2c(CC3CCCN(Cc4ccc(Cl)cc4)C3)ccnc2c1CN(C)C]

Example 251. 1-(7-((1-(4-Chlorobenzyl)piperidin-3-yl)methyl)-2-methylpyrazolo[1,5-a]pyrimidin-3-yl)-N,N-dimethylmethanamine Step a. tert-Butyl 3-((2-methylpyrazolo[1,5-a]pyrimidin-7-yl)methyl)piperidine-1-carboxylate Starting from the compound obtained in step c of example 249, (2.15 g, 7.25 mmol) and following the procedure described in step a of example 144, the title compound was obtained (1.5 g. Yield: 60%).

HPLC-MS (Method E): Rt.: 3.20 min; ESI+MS: m/z 331.0 $[M+H]^+$.

Step b. 2-Methyl-7-(piperidin-3-ylmethyl)pyrazolo[1,5-a]pyrimidine hydrochloride Starting from the compound obtained in step a (1.0 g, 3.03 mmol) and following the procedure described in step d of example 110, the title compound was obtained (807 mg). This compound was used in the next step without further purification.

HPLC-MS (Method E): Rt.: 2.12 min; ESI+MS: m/z 231.0 $[M+H]^+$.

Step c. 7-((1-(4-Chlorobenzyl)piperidin-3-yl) methyl)-2-methylpyrazolo[1,5-a]pyrimidine Starting from the compound obtained in step b (420 mg, 1.57 mmol) and following the procedure described in step e of example 110, the title compound was obtained (245 mg, Yield: 59%).

HPLC-MS (Method E): Rt.: 3.77 min; ESI+MS: m/z 355.1 $[M+H]^+$.

Step d. 7-((1-(4-Chlorobenzyl)piperidin-3-yl) methyl)-2-methylpyrazolo[1,5-a]pyrimidine-3-carb-aldehyde Starting from the compound obtained in step c (345 mg, 0.97 mmol) and following the procedure described in step a of example 120, the title compound was obtained (290 mg, Yield: 54%).

HPLC-MS (Method E): Rt.: 3.70 min; ESI+MS: m/z 383.1 $[M+H]^+$.

Step e. Title Compound

Starting from the compound obtained in step d (290 mg, 0.75 mmol) and dimethylamine (0.94 mL, 1.89 mmol) and following the procedure described in step e of example 110, the title compound was obtained (31 mg, Yield: 8%).

HPLC-MS (Method I): Rt.: 2.95 min; ESI+MS: m/z 412.2 $[M+H]^+$.

This method was used for the preparation of examples 252 and 253 using suitable starting materials:

| STRUCTURE | EX | CHEMICAL NAME | Rt (min) | MS (M + H) | HPLC Method |
|---|---|---|---|---|---|
| 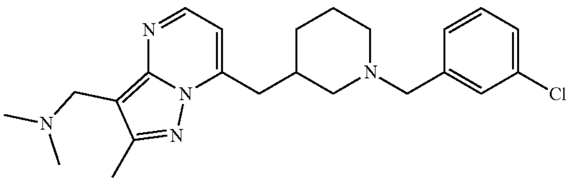 [SMILES: Cc1nn2c(CC3CCCN(Cc4cccc(Cl)c4)C3)ccnc2c1CN(C)C] | 252 | 1-(7-((1-(3-Chlorobenzyl)piperidin-3-yl)methyl)-2-methylpyrazolo[1,5-a]pyrimidin-3-yl)-N,N-dimethylmethanamine | 3.10 | 412.2 | I |
| 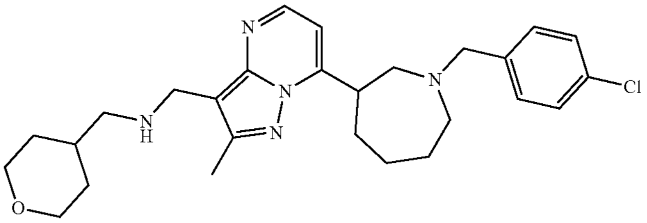 [SMILES: Cc1nn2c(C3CCCCN(Cc4ccc(Cl)cc4)C3)ccnc2c1CNCC1CCOCC1] | 253 | 1-(7-(1-(4-Chlorobenzyl)azepan-3-yl)-2-methylpyrazolo[1,5-a]pyrimidin-3-yl)-N-((tetrahydro-2H-pyran-4-yl)methyl)methanamine | 3.02 | 482.1 | I |

Biological Activity

Pharmacological Study

Human $\alpha_2\delta$-1 Subunit of $Ca_v2.2$ Calcium Channel Assay

Human $\alpha_2\delta$-1 enriched membranes (2.5 μg) were incubated with 15 nM of radiolabeled $[^3H]$-Gabapentin in assay buffer containing Hepes-KOH 10 mM, pH 7.4. NSB (non specific binding) was measured by adding 10 μM pregabalin. The binding of the test compound was measured at either one concentration (% inhibition at 1 or 10 μM) or five different concentrations to determine affinity values (Ki). After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 h and 30 μL of scintillation cocktail were added to each well before radioactivity reading. Readings were performed in a Trilux 1450 Microbeta radioactive counter (Perkin Elmer).

Human $\sigma_1$ Receptor Radioligand Assay

Transfected HEK-293 membranes (7 μg) were incubated with 5 nM of $[^3H](+)$-pentazocine in assay buffer containing Tris-HCl 50 mM at pH 8. NBS (non-specific binding) was measured by adding 10 μM haloperidol. The binding of the test compound was measured at either one concentration (% inhibition at 1 or 10 μM) or five different concentrations to determine affinity values (Ki). Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail.

Results

As this invention is aimed at providing a compound or a chemically related series of compounds which act as dual ligands of the $\alpha_2\delta$ subunit of voltage-gated calcium channels and the $\sigma_1$ receptor it is a very preferred embodiment in which the compounds are selected which act as dual ligands of the $\alpha_2\delta$ subunit of voltage-gated calcium channels and the $\sigma_1$-receptor and especially compounds which have a binding expressed as $K_i$ responding to the following scales:

$K_i(\sigma_1)$ is preferably <1000 nM, more preferably <500 nM, even more preferably <100 nM.

$K_i(\alpha_2\delta\text{-}1)$ is preferably <10000 nM, more preferably <5000 nM, or even more preferably <500 nM.

The following scale has been adopted for representing the binding to 61-receptor expressed as $K_i$:

$+K_i\ (\sigma_1)>1000$ nM $++500\ \text{nM}<=K_i(\sigma_1)<=1000$ nM $+++K_i(\sigma_1)<500$ nM Preferably, when $K_i\ (\sigma_1)>1000$ nM, the following scale has been adopted for representing the binding to the σ1-receptor:

$+K_i\ (\sigma_1)>1000$ nM or inhibition ranges between 1% and 50%.

The following scale has been adopted for representing the binding to the $\alpha_2\delta$-1 subunit of voltage-gated calcium channels expressed as $K_i$:

+$K_i(\alpha_2\delta\text{-}1)>5000$ nM

++500 nM<=$K_i(\alpha_2\delta\text{-}1)<=5000$ nM

+++$K_i(\alpha_2\delta\text{-}1)<500$ nM

Preferably, when $K_i(\alpha_2\delta\text{-}1)>5000$ nM, the following scale has been adopted for representing the binding to the $\alpha_2\delta$-1 subunit of voltage-gated calcium channels:

+$K_i(\alpha_2\delta\text{-}1)>5000$ nM or inhibition ranges between 1% and 50%

Table of Examples with Binding to the $\sigma_1$ Receptor and the $\alpha_2\delta$-1 Subunit of the Voltage-Gated Calcium Channel All compounds prepared in the present application exhibit binding to the $\alpha_2\delta$-1 subunit of voltage-gated calcium channels and to the $\sigma_1$ receptor, in particular the following binding results are shown:

| Example | α2δ binding | σ-1 binding |
|---|---|---|
| 1 | ++ | ++ |
| 2 | ++ | + |
| 3 | ++ | ++ |
| 4 | ++ | +++ |
| 5 | ++ | +++ |
| 6 | ++ | + |
| 7 | + | + |
| 8 | + | + |
| 9 | + | + |
| 10 | ++ | +++ |
| 11 | ++ | +++ |
| 12 | + | ++ |
| 13 | + | + |
| 14 | ++ | ++ |
| 15 | + | + |
| 16 | ++ | + |
| 17 | ++ | ++ |
| 18 | ++ | ++ |
| 19 | ++ | + |
| 20 | ++ | + |
| 21 | ++ | + |
| 22 | ++ | + |
| 23 | ++ | + |
| 24 | ++ | + |
| 25 | + | + |
| 26 | +++ | + |
| 27 | ++ | ++ |
| 28 | ++ | + |
| 29 | ++ | + |
| 30 | + | + |
| 31 | ++ | + |
| 32 | + | + |
| 33 | ++ | + |
| 34 | ++ | + |
| 35 | + | ++ |
| 36 | ++ | ++ |
| 37 | ++ | + |
| 38 | ++ | + |
| 39 | + | + |
| 40 | ++ | + |
| 41 | ++ | + |
| 42 | ++ | + |
| 43 | ++ | + |
| 44 | + | + |
| 45 | + | ++ |
| 46 | ++ | + |
| 47 | + | + |
| 48 | + | + |
| 49 | + | + |
| 50 | ++ | + |
| 51 | ++ | ++ |
| 52 | ++ | + |
| 53 | ++ | + |
| 54 | ++ | + |
| 55 | ++ | + |
| 56 | ++ | + |

-continued

| Example | α2δ binding | σ-1 binding |
|---|---|---|
| 57 | ++ | + |
| 58 | ++ | + |
| 59 | ++ | + |
| 60 | ++ | + |
| 61 | ++ | + |
| 62 | ++ | + |
| 63 | + | + |
| 64 | + | +++ |
| 65 | ++ | + |
| 66 | + | + |
| 67 | + | + |
| 68 | + | + |
| 69 | + | + |
| 70 | + | + |
| 71 | + | + |
| 72 | ++ | + |
| 73 | + | +++ |
| 74 | ++ | + |
| 75 | ++ | + |
| 76 | ++ | ++ |
| 77 | + | + |
| 78 | + | ++ |
| 79 | + | + |
| 80 | ++ | + |
| 81 | ++ | + |
| 82 | ++ | + |
| 83 | ++ | + |
| 84 | ++ | + |
| 85 | + | + |
| 86 | ++ | + |
| 87 | ++ | + |
| 88 | + | ++ |
| 89 | ++ | ++ |
| 90 | + | + |
| 91 | ++ | + |
| 92 | ++ | + |
| 93 | ++ | + |
| 94 | ++ | + |
| 95 | + | + |
| 96 | ++ | + |
| 97 | ++ | +++ |
| 98 | ++ | +++ |
| 99 | ++ | + |
| 100 | ++ | + |
| 101 | + | +++ |
| 102 | + | + |
| 103 | ++ | + |
| 106 | + | + |
| 107 | + | + |
| 108 | + | + |
| 109 | ++ | + |
| 110 | + | ++ |
| 111 | + | + |
| 112 | + | + |
| 113 | ++ | + |
| 114 | + | + |
| 115 | + | + |
| 116 | + | + |
| 117 | + | + |
| 118 | + | + |
| 119 | + | + |
| 120 | +++ | +++ |
| 121 | ++ | ++ |
| 122 | ++ | + |
| 123 | ++ | + |
| 124 | + | ++ |
| 125 | ++ | + |
| 126 | + | + |
| 127 | + | +++ |
| 128 | + | + |
| 129 | + | + |
| 130 | ++ | + |
| 131 | + | + |
| 132 | ++ | + |
| 133 | + | + |
| 134 | + | ++ |
| 135 | + | + |

-continued

| Example | α2δ binding | σ-1 binding |
|---|---|---|
| 136 | + | + |
| 137 | + | + |
| 138 | + | + |
| 139 | + | + |
| 140 | ++ | + |
| 141 | + | +++ |
| 142 | + | + |
| 143 | + | ++ |
| 144 | ++ | +++ |
| 145 | ++ | +++ |
| 146 | ++ | +++ |
| 147 | + | +++ |
| 148 | ++ | +++ |
| 149 | ++ | +++ |
| 150 | ++ | +++ |
| 151 | ++ | +++ |
| 152 | + | ++ |
| 153 | ++ | +++ |
| 154 | ++ | ++ |
| 155 | ++ | +++ |
| 156 | + | ++ |
| 157 | ++ | +++ |
| 158 | ++ | +++ |
| 159 | ++ | +++ |
| 160 | ++ | +++ |
| 161 | ++ | +++ |
| 162 | ++ | +++ |
| 163 | +++ | +++ |
| 164 | ++ | ++ |
| 165 | + | ++ |
| 166 | ++ | +++ |
| 167 | ++ | +++ |
| 168 | ++ | ++ |
| 169 | ++ | +++ |
| 170 | +++ | +++ |
| 171 | ++ | +++ |
| 172 | + | +++ |
| 173 | + | + |
| 174 | ++ | + |
| 175 | + | + |
| 176 | ++ | + |
| 177 | ++ | +++ |
| 178 | ++ | +++ |
| 179 | ++ | ++ |
| 180 | ++ | +++ |
| 181 | ++ | +++ |
| 182 | +++ | +++ |
| 183 | + | +++ |
| 184 | + | +++ |
| 185 | + | + |
| 186 | + | +++ |
| 187 | +++ | +++ |
| 188 | +++ | +++ |
| 189 | +++ | +++ |
| 190 | +++ | +++ |
| 191 | + | +++ |
| 192 | + | +++ |
| 193 | +++ | +++ |
| 194 | ++ | +++ |
| 195 | ++ | +++ |
| 196 | + | +++ |
| 197 | ++ | +++ |
| 198 | +++ | +++ |
| 199 | +++ | +++ |
| 200 | + | +++ |
| 201 | + | +++ |
| 202 | +++ | +++ |
| 203 | ++ | +++ |
| 204 | ++ | +++ |
| 205 | + | +++ |
| 206 | +++ | +++ |
| 207 | + | +++ |
| 208 | + | +++ |
| 209 | + | +++ |
| 210 | ++ | +++ |
| 210 | ++ | +++ |
| 211 | + | +++ |

-continued

| Example | α2δ binding | σ-1 binding |
|---|---|---|
| 212 | + | +++ |
| 213 | ++ | +++ |
| 214 | ++ | +++ |
| 215 | + | +++ |
| 216 | +++ | +++ |
| 216 | +++ | +++ |
| 217 | + | ++ |
| 217 | + | +++ |
| 218 | ++ | ++ |
| 219 | ++ | ++ |
| 220 | ++ | ++ |
| 221 | +++ | +++ |
| 222 | + | +++ |
| 223 | + | +++ |
| 224 | ++ | +++ |
| 225 | + | +++ |
| 226 | ++ | +++ |
| 227 | + | +++ |
| 228 | +++ | +++ |
| 229 | ++ | ++ |
| 230 | ++ | +++ |
| 231 | ++ | +++ |
| 232 | + | +++ |
| 233 | + | ++ |
| 234 | ++ | +++ |
| 235 | + | ++ |
| 236 | ++ | +++ |
| 237 | +++ | +++ |
| 238 | ++ | +++ |
| 239 | + | +++ |
| 240 | ++ | +++ |
| 241 | + | +++ |
| 242 | + | +++ |
| 243 | ++ | + |
| 244 | ++ | + |
| 245 | ++ | + |
| 246 | ++ | + |
| 247 | +++ | +++ |
| 248 | ++ | ++ |
| 249 | + | +++ |
| 250 | + | ++ |
| 251 | + | +++ |
| 252 | + | +++ |
| 253 | + | +++ |

The invention claimed is:

1. A compound of Formula (I):

(I)

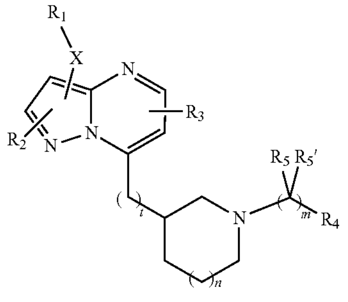

or a pharmaceutically acceptable salt or stereoisomer thereof, wherein:

X is a bond, $-(CH_2)_p-$, $-(CH_2)_p-NR_x-(CH_2)_q-$, $-(CH_2)_p-NR_x-CH(CH_3)-$, or $-(CH_2)_p-O-(CH_2)_q-$;

$R_x$ is H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more substituents independently selected from the group consisting of halogen, CN, $NR_{13}R_{13'}$, O(haloalkyl), and $OR_{13}$;

each $R_{13}$ is independently H or $C_{1-6}$ alkyl;

each $R_{13'}$ is independently H or $C_{1-6}$ alkyl;

$R_1$ is H, halogen, CN, $C_{1-6}$ alkyl, $C_{2-6}$ alkenyl, $C_{2-6}$ alkynyl, $NR_6R_{6'}$, $OR_6$, cycloalkyl, heterocyclyl, or aryl;

wherein the $C_{1-6}$ alkyl, $C_{2-6}$ alkenyl, or $C_{2-6}$ alkynyl is optionally substituted with one or more substituents independently selected from the group consisting of halogen, CN, $NR_{11}R_{11'}$, O(haloalkyl), and $OR_{11}$; and wherein the cycloalkyl, heterocyclyl, or aryl is optionally substituted with one or more substituents independently selected from the group consisting of halogen, CN, $NO_2$, $C_{1-6}$ alkyl, haloalkyl, alkyl(cycloalkyl), $(CH_2)_rNR_{11}R_{11'}$, $(CH_2)_rOR_{11}$, $C(CH_3)_2OR_{11}$, $C(O)R_{11}$, $C(O)NR_{11}R_{11'}$, $C(O)OR_{11}$, $NR_{11}C(O)R_{11'}$, $NR_{11}C(O)NR_{11'}R_{11''}$, $NR_{11}S(O)_2R_{11'}$, $NR_{11}S(O)_2NR_{11'}R_{11''}$, O(haloalkyl), $OCH_2CH_2OR_{11}$, =O, $SR_{11}$, $S(O)R_{11}$, $S(O)_2R_{11}$, $S(O)_2NR_{11}R_{11'}$, and heterocyclyl;

$R_6$ is H, $C_{1-6}$ alkyl, alkyl(cycloalkyl), alkyl(heterocyclyl), alkyl(aryl), $C_{2-6}$ alkenyl, $C_{2-6}$ alkynyl, O(haloalkyl), cycloalkyl, heterocyclyl, or aryl;

wherein the $C_{1-6}$ alkyl, $C_{2-6}$ alkenyl, or $C_{2-6}$ alkynyl is optionally substituted with one or more substituents independently selected from the group consisting of halogen, CN, $NR_{13}R_{13'}$, O(haloalkyl), and $OR_{13}$; and wherein the cycloalkyl of alkyl(cycloalkyl), heterocyclyl of alkyl(heterocyclyl), aryl of alkyl(aryl), cycloalkyl, heterocyclyl, or aryl is optionally substituted with one or more substituents independently selected from the group consisting of halogen, CN, $NO_2$, $C_{1-6}$ alkyl, haloalkyl, alkyl (cycloalkyl), $(CH_2)_rNR_{14}R_{14'}$, $(CH_2)_rOR_{14}$, $C(CH_3)_2OR_{14}$, $C(O)R_{14}$, $C(O)NR_{14}R_{14'}$, $C(O)OR_{14}$, $NR_{14}C(O)R_{14'}$, $NR_{14}C(O)NR_{14'}R_{14''}$, $NR_{14}S(O)_2R_{14'}$, $NR_{14}S(O)_2NR_{14'}R_{14''}$, O(haloalkyl), $OCH_2CH_2OR_{14}$, =O, $SR_{14}$, $S(O)R_{14}$, $S(O)_2R_{14}$, $S(O)_2NR_{14}R_{14'}$, and heterocyclyl;

each $R_{14}$ is independently H, $C_{1-6}$ alkyl, cycloalkyl, heterocyclyl, or aryl;

each $R_{14'}$ is independently H, $C_{1-6}$ alkyl, cycloalkyl, heterocyclyl, or aryl;

each $R_{14''}$ is independently H, $C_{1-6}$ alkyl, cycloalkyl, heterocyclyl, or aryl;

$R_{6'}$ is H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more substituents independently selected from the group consisting of halogen, CN, $NR_{13}R_{13'}$, O(haloalkyl), and $OR_{13}$; or $R_6$ and $R_{6'}$, taken together with the nitrogen atom to which they are attached, form a heterocyclyl, wherein the heterocyclyl is optionally substituted with one or more substituents independently selected from the group consisting of halogen, CN, $NO_2$, $C_{1-6}$ alkyl, haloalkyl, alkyl(cycloalkyl), $(CH_2)_rNR_{14}R_{14'}$, $(CH_2)_rOR_{14}$, $C(CH_3)_2OR_{14}$, $C(O)R_{14}$, $C(O)NR_{14}R_{14'}$, $C(O)OR_{14}$, $NR_{14}C(O)R_{14'}$, $NR_{14}C(O)NR_{14'}R_{14''}$, $NR_{14}S(O)_2R_{14'}$, $NR_{14}S(O)_2NR_{14'}R_{14''}$, O(haloalkyl), $OCH_2CH_2OR_{14}$, =O, $SR_{14}$, $S(O)R_{14}$, $S(O)_2R_{14}$, $S(O)_2NR_{14}R_{14'}$, and heterocyclyl;

each $R_{11}$ is independently H, $C_{1-6}$ alkyl, alkyl(cycloalkyl), alkyl(heterocyclyl), alkyl(aryl), cycloalkyl, heterocyclyl, or aryl;

each $R_{11'}$ is independently H, $C_{1-6}$ alkyl, alkyl(cycloalkyl), alkyl(heterocyclyl), alkyl(aryl), cycloalkyl, heterocyclyl, or aryl;

each $R_{11''}$ is independently H, $C_{1-6}$ alkyl, alkyl(cycloalkyl), alkyl(heterocyclyl), alkyl(aryl), cycloalkyl, heterocyclyl, or aryl;

$R_2$ is H, halogen, $C_{1-6}$ alkyl, alkyl(cycloalkyl), $C_{2-6}$ alkenyl, $C_{2-6}$ alkynyl, $OR_7$, O(haloalkyl), or cycloalkyl;

wherein the $C_{1-6}$ alkyl, $C_{2-6}$ alkenyl, or $C_{2-6}$ alkynyl is optionally substituted with one or more substituents independently selected from the group consisting of halogen, CN, $NR_{21}R_{21'}$, O(haloalkyl), and $OR_{21}$; and wherein the cycloalkyl of alkyl(cycloalkyl) or cycloalkyl is optionally substituted with one or more substituents independently selected from the group consisting of halogen, CN, $NO_2$, $C_{1-6}$ alkyl, haloalkyl, $(CH_2)_rNR_{21}R_{21'}$, $(CH_2)_rOR_{21}$, $C(CH_3)_2OR_{21}$, $C(O)R_{21}$, $C(O)NR_{21}R_{21'}$, $C(O)OR_{21}$, $NR_{21}C(O)R_{21'}$, $NR_{21}C(O)NR_{21'}R_{21''}$, $NR_{21}S(O)_2R_{21'}$, $NR_{21}S(O)_2NR_{21'}R_{21''}$, O(haloalkyl), $OCH_2CH_2OR_{21}$, =O, $SR_{21}$, $S(O)R_{21}$, $S(O)_2R_{21}$, and $S(O)_2NR_{21}R_{21'}$;

$R_7$ is H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more substituents independently selected from the group consisting of halogen, CN, $NR_{13}R_{13'}$, O(haloalkyl), and $OR_{13}$;

each $R_{21}$ is independently H or $C_{1-6}$ alkyl;

each $R_{21'}$ is independently H or $C_{1-6}$ alkyl;

each $R_{21''}$ is independently H or $C_{1-6}$ alkyl;

$R_3$ is H, halogen, $C_{1-6}$ alkyl, $C_{2-6}$ alkenyl, $C_{2-6}$ alkynyl, $OR_8$, or O(haloalkyl), wherein the $C_{1-6}$ alkyl, $C_{2-6}$ alkenyl, or $C_{2-6}$ alkynyl is optionally substituted with one or more substituents independently selected from the group consisting of halogen, CN, $NR_{31}R_{31'}$, O(haloalkyl), and $OR_{31}$;

$R_8$ is H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more substituents independently selected from the group consisting of halogen, CN, $NR_{13}R_{13'}$, O(haloalkyl), and $OR_{13}$;

each $R_{31}$ is independently H or $C_{1-6}$ alkyl;

each $R_{31'}$ is independently H or $C_{1-6}$ alkyl;

$R_4$ is $C_{1-6}$ alkyl, $C_{2-6}$ alkenyl, $C_{2-6}$ alkynyl, cycloalkyl, heterocyclyl, or aryl;

wherein the $C_{1-6}$ alkyl, $C_{2-6}$ alkenyl, or $C_{2-6}$ alkynyl is optionally substituted with one or more substituents independently selected from the group consisting of halogen, CN, $NR_{41}R_{41'}$, O(haloalkyl), and $OR_{41}$; and wherein the cycloalkyl, heterocyclyl, or aryl is optionally substituted with one or more substituents independently selected from the group consisting of halogen, CN, $NO_2$, $C_{1-6}$ alkyl, haloalkyl, $(CH_2)_rNR_{41}R_{41'}$, $(CH_2)_rOR_{41}$, $C(CH_3)_2OR_{41}$, $C(O)R_{41}$, $C(O)NR_{41}R_{41'}$, $C(O)OR_{41}$, $NR_{41}C(O)R_{41'}$, $NR_{41}C(O)NR_{41'}R_{41''}$, $NR_{41}S(O)_2R_{41'}$, $NR_{41}S(O)_2NR_{41'}R_{41''}$, O(haloalkyl), $OCH_2CH_2OR_{41}$, =O, $SR_{41}$, $S(O)R_{41}$, $S(O)_2R_{41}$, and $S(O)_2NR_{41}R_{41'}$;

each $R_{41}$ is independently H or $C_{1-6}$ alkyl;

each $R_{41'}$ is independently H or $C_{1-6}$ alkyl;

each $R_{41''}$ is independently H or $C_{1-6}$ alkyl;

$R_5$ is H, $C_{1-6}$ alkyl, $C_{2-6}$ alkenyl, $C_{2-6}$ alkynyl, or O(haloalkyl), wherein the $C_{1-6}$ alkyl, $C_{2-6}$ alkenyl, or $C_{2-6}$ alkynyl is optionally substituted with one or more substituents independently selected from the group consisting of halogen, CN, $NR_{51}R_{51'}$, O(haloalkyl), and $OR_{51}$;

$R_{5'}$ is H, $C_{1-6}$ alkyl, $C_{2-6}$ alkenyl, $C_{2-6}$ alkynyl, or O(haloalkyl), wherein the $C_{1-6}$ alkyl, $C_{2-6}$ alkenyl, or $C_{2-6}$ alkynyl is optionally substituted with one or more substituents independently selected from the group consisting of halogen, CN, $NR_{51}R_{51'}$, O(haloalkyl), and $OR_{51}$;

each $R_{51}$ is independently H or $C_{1-6}$ alkyl;

each $R_{51'}$ is independently H or $C_{1-6}$ alkyl;

m is 1, 2, 3, or 4;

n is 1 or 2;

p is 0, 1, 2, 3, or 4;

q is 0, 1, 2, 3, or 4;

each r is independently 0, 1, 2, or 3; and t is 0 or 1;

with the proviso that the following compound is excluded:

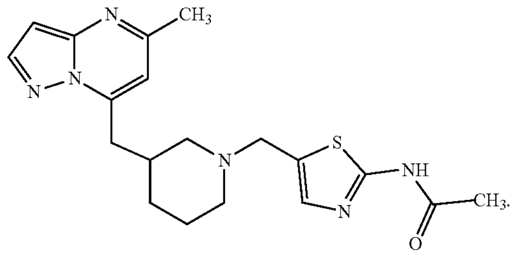 [SMILES: CC(=O)Nc1ncc(CN2CCCC(Cc3cc(C)nc4ccnn34)C2)s1]

2. The compound according to claim 1, or a pharmaceutically acceptable salt or stereoisomer thereof, wherein $R_4$ is phenyl, wherein the phenyl is optionally substituted with one or more substituents independently selected from the group consisting of halogen, CN, $NO_2$, $C_{1-6}$ alkyl, haloalkyl, $(CH_2)_rNR_{41}R_{41'}$, $(CH_2)_rOR_{41}$, $C(CH_3)_2OR_{41}$, $C(O)R_{41}$, $C(O)NR_{41}R_{41'}$, $C(O)OR_{41}$, $NR_{41}C(O)R_{41'}$, $NR_{41}C(O)NR_{41'}R_{41''}$, $NR_{41}S(O)_2R_{41'}$, $NR_{41}S(O)_2NR_{41'}R_{41''}$, O(haloalkyl), $OCH_2CH_2OR_{41}$, =O, $SR_{41}$, $S(O)R_{41}$, $S(O)_2R_{41}$, and $S(O)_2NR_{41}R_{41'}$.

3. The compound according to claim 1, or a pharmaceutically acceptable salt or stereoisomer thereof, wherein:

n is 1; and t is 0.

4. The compound according to claim 1, wherein the compound is of Formula (I'):

(I')

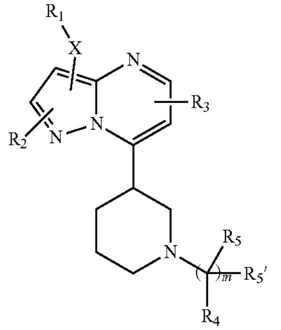

or a pharmaceutically acceptable salt or stereoisomer thereof.

5. The compound according to claim 1, wherein the compound is of Formula ($I^{2'}$):

($I^{2'}$)

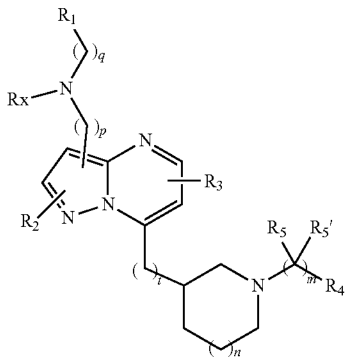

or a pharmaceutically acceptable salt or stereoisomer thereof.

6. The compound according to claim 1, wherein the compound is of Formula ($I^{3'}$):

($I^{3'}$)

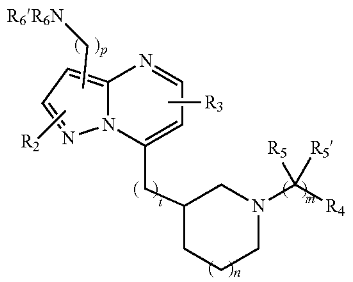

or a pharmaceutically acceptable salt or stereoisomer thereof.

7. The compound according to claim 1, wherein the compound is selected from the group consisting of:

7-(1-Benzylpiperidin-3-yl)-2-bromopyrazolo[1,5-a]pyrimidine, 7-(1-Benzylpiperidin-3-yl)pyrazolo[1,5-a]pyrimidine, 7-(1-Benzylpiperidin-3-yl)-2-methylpyrazolo[1,5-a]pyrimidine, 7-(1-Benzylpiperidin-3-yl)-2-ethylpyrazolo[1,5-a]pyrimidine, 7-(1-Benzylpiperidin-3-yl)-3-bromopyrazolo[1,5-a]pyrimidine, 7-(1-Benzylpiperidin-3-yl)-3-bromo-2,6-dimethylpyrazolo[1,5-a]pyrimidine, 7-(1-Benzylpiperidin-3-yl)-3-bromo-6-methylpyrazolo[1,5-a]pyrimidine, 7-(1-Benzylpiperidin-3-yl)-3-bromo-2-methylpyrazolo[1,5-a]pyrimidine, 7-(1-Benzylpiperidin-3-yl)-3-bromo-2-ethylpyrazolo[1,5-a]pyrimidine, 7-(1-Benzylpiperidin-3-yl)-2-phenylpyrazolo[1,5-a]pyrimidine, 7-(1-Benzylpiperidin-3-yl)-2-(4-ethoxyphenyl)pyrazolo[1,5-a]pyrimidine, 7-(1-Benzylpiperidin-3-yl)-2-(2-fluorophenyl)pyrazolo[1,5-a]pyrimidine,
7-(1-Benzylpiperidin-3-yl)-2-(4-chlorophenyl)pyrazolo[1,5-a]pyrimidine,
7-(1-Benzylpiperidin-3-yl)-2-(pyridin-4-yl)pyrazolo[1,5-a]pyrimidine,
7-(1-Benzylpiperidin-3-yl)-2-(pyridin-3-yl)pyrazolo[1,5-a]pyrimidine,
7-(1-Benzylpiperidin-3-yl)-2-(3,5-dichloropyridin-4-yl)pyrazolo[15-a]pyrimidine,
7-(1-Benzylpiperidin-3-yl)-2-(thiophen-2-yl)pyrazolo[1,5-a]pyrimidine,
4-(7-(1-Benzylpiperidin-3-yl)pyrazolo[1,5-a]pyrimidin-2-yl)isothiazole,
7-(1-Benzylpiperidin-3-yl)-2-(1-methyl-1H-imidazol-5-yl)pyrazolo[1,5-a]pyrimidine,
4-(7-(1-Benzylpiperidin-3-yl)pyrazolo[1,5-a]pyrimidin-2-yl)-N,N-dimethylaniline,
7-(1-Benzylpiperidin-3-yl)-2-(pyrimidin-5-yl)pyrazolo[1,5-a]pyrimidine,
5-(7-(1-Benzylpiperidin-3-yl)pyrazolo[1,5-a]pyrimidin-2-yl)pyridin-2-amine,
7-(1-Benzylpiperidin-3-yl)-2-(1-methyl-1H-pyrazol-4-yl)pyrazolo[1,5-a]pyrimidine,
7-(1-Benzylpiperidin-3-yl)-2-(pyridin-2-yl)pyrazolo[1,5-a]pyrimidine,
7-(1-Benzylpiperidin-3-yl)-2-(2-methoxypyridin-3-yl)pyrazolo[1,5-a]pyrimidine,
7-(1-Benzylpiperidin-3-yl)-2-(6-methoxypyridin-3-yl)pyrazolo[1,5-a]pyrimidine,
7-(1-Benzylpiperidin-3-yl)-2-(2-methoxyphenyl)pyrazolo[1,5-a]pyrimidine,
7-(1-Benzylpiperidin-3-yl)-2-(6-methoxypyridin-2-yl)pyrazolo[1,5-a]pyrimidine,
7-(1-Benzylpiperidin-3-yl)-2-(5-methoxypyridin-3-yl)pyrazolo[1,5-a]pyrimidine,
7-(1-Benzylpiperidin-3-yl)-2-(2-methoxypyridin-4-yl)pyrazolo[1,5-a]pyrimidine,
7-(1-Benzylpiperidin-3-yl)-2-(3-methoxypyridin-4-yl)pyrazolo[1,5-a]pyrimidine,
7-(1-Benzylpiperidin-3-yl)-2-(4-methoxypyridin-3-yl)pyrazolo[1,5-a]pyrimidine,
7-(1-Benzylpiperidin-3-yl)-3-phenylpyrazolo[1,5-a]pyrimidine,
7-(1-Benzylpiperidin-3-yl)-3-(pyridin-4-yl)pyrazolo[1,5-a]pyrimidine,
7-(1-Benzylpiperidin-3-yl)-3-(pyridin-3-yl)pyrazolo[1,5-a]pyrimidine,
7-(1-Benzylpiperidin-3-yl)-3-(2-methoxypyridin-4-yl)pyrazolo[1,5-a]pyrimidine,
7-(1-Benzylpiperidin-3-yl)-3-(4-ethoxyphenyl)pyrazolo[1,5-a]pyrimidine,
7-(1-Benzylpiperidin-3-yl)-3-(2-methoxypyridin-3-yl)pyrazolo[1,5-a]pyrimidine,
7-(1-Benzylpiperidin-3-yl)-6-methyl-3-(pyridin-4-yl)pyrazolo[1,5-a]pyrimidine,
7-(1-Benzylpiperidin-3-yl)-2-methyl-3-(pyridin-4-yl)pyrazolo[1,5-a]pyrimidine,
7-(1-Benzylpiperidin-3-yl)-3-(2-methoxypyridin-3-yl)-2-methylpyrazolo[1,5-a]pyrimidine,
7-(1-Benzylpiperidin-3-yl)-2-methyl-3-phenylpyrazolo[1,5-a]pyrimidine,
7-(1-Benzylpiperidin-3-yl)-3-(4-ethoxyphenyl)-2-methylpyrazolo[1,5-a]pyrimidine,
7-(1-Benzylpiperidin-3-yl)-3-(2-methoxypyridin-4-yl)-2-methylpyrazolo[1,5-a]pyrimidine,
4-(7-(1-Benzylpiperidin-3-yl)-2-methylpyrazolo[1,5-a]pyrimidin-3-yl)-N,N-dimethylaniline,
7-(1-Benzylpiperidin-3-yl)-3-(2-fluorophenyl)-2-methylpyrazolo[1,5-a]pyrimidine,
7-(1-Benzylpiperidin-3-yl)-2-methyl-3-(3-methylpyridin-4-yl)pyrazolo[1,5-a]pyrimidine,
7-(1-Benzylpiperidin-3-yl)-3-(2-fluoropyridin-4-yl)-2-methylpyrazolo[1,5-a]pyrimidine,
7-(1-Benzylpiperidin-3-yl)-2-methyl-3-(2-methylpyridin-4-yl)pyrazolo[1,5-a]pyrimidine,
7-(1-Benzylpiperidin-3-yl)-3-(3-fluoropyridin-4-yl)-2-methylpyrazolo[1,5-a]pyrimidine,
7-(1-Benzylpiperidin-3-yl)-2-methyl-3-(2-(trifluoromethyl)pyridin-4-yl)pyrazolo[1,5-a]pyrimidine,
7-(1-Benzylpiperidin-3-yl)-3-(2-ethylpyridin-4-yl)-2-methylpyrazolo[1,5-a]pyrimidine,
3-(3-(7-(1-Benzylpiperidin-3-yl)-2-methylpyrazolo[1,5-a]pyrimidin-3-yl)phenyl)-5-methyl-1,2,4-oxadiazole,
2-(3-(7-(1-Benzylpiperidin-3-yl)-2-methylpyrazolo[1,5-a]pyrimidin-3-yl)phenyl)-5-methyl-1,3,4-oxadiazole,
7-(1-Benzylpiperidin-3-yl)-3-(3-methoxypyridin-4-yl)-2-methylpyrazolo[1,5-a]pyrimidine,
7-(1-Benzylpiperidin-3-yl)-2,6-dimethyl-3-(pyridin-4-yl)pyrazolo[1,5-a]pyrimidine,
7-(1-Benzylpiperidin-3-yl)-2,5-dimethyl-3-(pyridin-4-yl)pyrazolo[1,5-a]pyrimidine,
7-(1-Benzylpiperidin-3-yl)-2-ethyl-3-(pyridin-4-yl)pyrazolo[1,5-a]pyrimidine,
1-(1-(3-(7-(1-Benzylpiperidin-3-yl)-2-methylpyrazolo[1,5-a]pyrimidin-3-yl)phenyl)-1H-1,2,3-triazol-4-yl)-N-methylmethanamine,
1-(4-(7-(1-Benzylpiperidin-3-yl)-2-methylpyrazolo[1,5-a]pyrimidin-3-yl)pyridin-2-yl)-N-methylmethanamine,
7-(1-(2-Fluorobenzyl)piperidin-3-yl)-2-methylpyrazolo[1,5-a]pyrimidine,
7-(1-Butylpiperidin-3-yl)-2-methylpyrazolo[1,5-a]pyrimidine,
7-(1-(2,6-Difluorobenzyl)piperidin-3-yl)-2-methylpyrazolo[1,5-a]pyrimidine,
2-Methyl-7-(1-(pyridin-2-ylmethyl)piperidin-3-yl)pyrazolo[1,5-a]pyrimidine,
2-Methyl-7-(1-phenethylpiperidin-3-yl)pyrazolo[1,5-a]pyrimidine,
3-((3-(2-Methylpyrazolo[1,5-a]pyrimidin-7-yl)piperidin-1-yl)methyl)phenol,
7-(1-Ethylpiperidin-3-yl)-2-methyl-3-(pyridin-4-yl)pyrazolo[1,5-a]pyrimidine,
2-Methyl-7-(1-propylpiperidin-3-yl)-3-(pyridin-4-yl)pyrazolo[1,5-a]pyrimidine,
7-(1-Isobutylpiperidin-3-yl)-2-methyl-3-(pyridin-4-yl)pyrazolo[1,5-a]pyrimidine,
2-Methyl-7-(1-(pyridin-2-ylmethyl)piperidin-3-yl)-3-(pyridin-4-yl)pyrazolo[1,5-a]pyrimidine,
6-Methyl-7-(1-phenethylpiperidin-3-yl)-3-(pyridin-4-yl)pyrazolo[1,5-a]pyrimidine,
6-Methyl-7-(1-(pyridin-2-ylmethyl)piperidin-3-yl)-3-(pyridin-4-yl)pyrazolo[1,5-a]pyrimidine,
2-Methyl-7-(1-(2-methylbenzyl)piperidin-3-yl)-3-(pyridin-4-yl)pyrazolo[1,5-a]pyrimidine,
2-Methyl-7-(1-(4-methylbenzyl)piperidin-3-yl)-3-(pyridin-4-yl)pyrazolo[1,5-a]pyrimidine,
2-Methyl-7-(1-(3-methylbenzyl)piperidin-3-yl)-3-(pyridin-4-yl)pyrazolo[1,5-a]pyrimidine,
7-(1-Benzylpiperidin-3-yl)-2-(pyrrolidin-1-yl)pyrazolo[1,5-a]pyrimidine,
2-((7-(1-Benzylpiperidin-3-yl)pyrazolo[1,5-a]pyrimidin-2-yl)(methyl)amino)ethanol, $N^1$-(7-(1-Benzylpiperidin-3-yl)pyrazolo[1,5-a]pyrimidin-2-yl)-$N^1$-methylethane-1,2-diamine $N^1$-(7-(1-Benzylpiperidin-3-yl)pyrazolo[1,5-a]pyrimidin-2-yl)-$N^1$,$N^2$-dimethylethane-1,2-diamine, 7-(1-Benzylpiperidin-3-yl)-N-methyl-N-(piperidin-4-yl)pyrazolo[1,5-a]pyrimidin-2-amine, $N^1$-(7-(1-Benzylpiperidin-3-yl)pyrazolo[1,5-a]pyrimidin-2-yl)-$N^2$-methylethane-1,2-diamine, (R)-1-(7-((R)-1-Benzylpiperidin-3-yl)pyrazolo[1,5-a]pyrimidin-2-yl)-N-methylpyrrolidin-3-amine, (S)-1-(7-((S)-1-Benzylpiperidin-3-yl)pyrazolo[1,5-a]pyrimidin-2-yl)-N-methylpyrrolidin-3-amine, (S)-1-(7-((R)-1-Benzylpiperidin-3-yl)pyrazolo[1,5-a]pyrimidin-2-yl)-N-methylpyrrolidin-3-amine, (R)-1-(7-((S)-1-Benzylpiperidin-3-yl)pyrazolo[1,5-a]pyrimidin-2-yl)-N-methylpyrrolidin-3-amine, 7-(1-Benzylpiperidin-3-yl)-3-(pyrrolidin-1-yl)pyrazolo[1,5-a]pyrimidine, 7-(1-Benzylpiperidin-3-yl)-2-methyl-3-(pyrrolidin-1-yl)pyrazolo[1,5-a]pyrimidine, 7-(1-Benzylpiperidin-3-yl)-2-methylpyrazolo[1,5-a]pyrimidin-3-amine, 7-(1-Benzylpiperidin-3-yl)pyrazolo[1,5-a]pyrimidine-2-carbonitrile, 1-(7-(1-Benzylpiperidin-3-yl)pyrazolo[1,5-a]pyrimidin-2-yl)-N,N-dimethylmethanamine, 1-(7-(1-Benzylpiperidin-3-yl)pyrazolo[1,5-a]pyrimidin-2-yl)-N-methylmethanamine, N-Benzyl-1-(7-(1-benzylpiperidin-3-yl)pyrazolo[1,5-a]pyrimidin-2-yl)methanamine, (7-(1-Benzylpiperidin-3-yl)-2-methylpyrazolo[1,5-a]pyrimidin-3-yl)methanol, 1-(7-(1-Benzylpiperidin-3-yl)-2-methylpyrazolo[1,5-a]pyrimidin-3-yl)-N-methylmethanamine, N-((7-(1-Benzylpiperidin-3-yl)-2-methylpyrazolo[1,5-a]pyrimidin-3-yl)methyl)-2-phenylethanamine, N-Benzyl-1-(7-(1-benzylpiperidin-3-yl)-2-methylpyrazolo[1,5-a]pyrimidin-3-yl)methanamine, (7-(1-Benzylpiperidin-3-yl)-2-methylpyrazolo[1,5-a]pyrimidin-3-yl)methanamine, 7-(1-Benzylpiperidin-3-yl)-2-methyl-3-(piperazin-1-ylmethyl)pyrazolo[1,5-a]pyrimidine, 3-((Benzyloxy)methyl)-7-(1-benzylpiperidin-3-yl)-2-methylpyrazolo[1,5-a]pyrimidine, 7-(1-Benzylpiperidin-3-yl)-2-methyl-3-(phenoxymethyl)pyrazolo[1,5-a]pyrimidine, 3-(7-(1-Benzylpiperidin-3-yl)-2-methylpyrazolo[1,5-a]pyrimidin-3-yl)propan-1-amine, 7-(1-Benzylpiperidin-3-yl)pyrazolo[1,5-a]pyrimidin-2-ol, 7-(1-Benzylpiperidin-3-yl)-3-bromopyrazolo[1,5-a]pyrimidin-2-ol, (S)-2-((R)-3-(2-Methyl-3-(pyridin-4-yl)pyrazolo[1,5-a]pyrimidin-7-yl)piperidin-1-yl)-2-phenylethanol, (S)-2-((S)-3-(2-methyl-3-(pyridin-4-yl)pyrazolo[1,5-a]pyrimidin-7-yl)piperidin-1-yl)-2-phenylethanol, (R)-2-((S)-3-(2-Methyl-3-(pyridin-4-yl)pyrazolo[1,5-a]pyrimidin-7-yl)piperidin-1-yl)-2-phenylethanol, (R)-2-((R)-3-(2-Methyl-3-(pyridin-4-yl)pyrazolo[1,5-a]pyrimidin-7-yl)piperidin-1-yl)-2-phenylethanol, 2-Bromo-7-(1-(4-chlorobenzyl)piperidin-3-yl)pyrazolo[1,5-a]pyrimidine, 2-Bromo-7-(1-(3-chlorobenzyl)piperidin-3-yl)pyrazolo[1,5-a]pyrimidine, 2-Bromo-7-(1-(3,4-dichlorobenzyl)piperidin-3-yl)pyrazolo[1,5-a]pyrimidine, 2-Bromo-7-(1-(3,4-difluorobenzyl)piperidin-3-yl)pyrazolo[1,5-a]pyrimidine, 7-(1-(4-Chlorobenzyl)piperidin-3-yl)-2-(2-methoxypyridin-3-yl)pyrazolo[1,5-a]pyrimidine, 3-(7-(1-(4-Chlorobenzyl)piperidin-3-yl)pyrazolo[1,5-a]pyrimidin-2-yl)pyridin-2-ol, 7-(1-(3-Chlorobenzyl)piperidin-3-yl)-2-(2-methoxypyridin-3-yl)pyrazolo[1,5-a]pyrimidine, 3-(7-(1-(3-Chlorobenzyl)piperidin-3-yl)pyrazolo[1,5-a]pyrimidin-2-yl)pyridin-2-ol, 7-(1-(3,4-Dichlorobenzyl)piperidin-3-yl)-2-(2-methoxypyridin-3-yl)pyrazolo[1,5-a]pyrimidine, 7-(1-(3,4-Difluorobenzyl)piperidin-3-yl)-2-(2-methoxypyridin-3-yl)pyrazolo[1,5-a]pyrimidine, 1-(2-Bromo-7-(1-(4-chlorobenzyl)piperidin-3-yl)pyrazolo[1,5-a]pyrimidin-3-yl)-N-((tetrahydro-2H-pyran-4-yl)methyl)methanamine, 7-(1-(4-Chlorobenzyl)piperidin-3-yl)-2-methyl-3-(pyridin-4-yl)pyrazolo[1,5-a]pyrimidine, 7-(1-(3-Chlorobenzyl)piperidin-3-yl)-2-methyl-3-(pyridin-4-yl)pyrazolo[1,5-a]pyrimidine, 7-(1-(3,4-Dichlorobenzyl)piperidin-3-yl)-2-methyl-3-(pyridin-4-yl)pyrazolo[1,5-a]pyrimidine, 7-(1-(2,4-Dichlorobenzyl)piperidin-3-yl)-2-methyl-3-(pyridin-4-yl)pyrazolo[1,5-a]pyrimidine, 7-(1-(3,4-Difluorobenzyl)piperidin-3-yl)-2-methyl-3-(pyridin-4-yl)pyrazolo[1,5-a]pyrimidine, 2-Methyl-3-(pyridin-4-yl)-7-(1-(4-(trifluoromethyl)benzyl)piperidin-3-yl)pyrazolo[1,5-a]pyrimidine, 7-(1-Isopentylpiperidin-3-yl)-2-methyl-3-(pyridin-4-yl)pyrazolo[1,5-a]pyrimidine, 3-(7-(1-(4-Chlorobenzyl)piperidin-3-yl)-2-methylpyrazolo[1,5-a]pyrimidin-3-yl)-N,N-dimethylbenzamide, 4-(7-(1-(4-Chlorobenzyl)piperidin-3-yl)-2-methylpyrazolo[1,5-a]pyrimidin-3-yl)benzamide, 7-(1-(4-Chlorobenzyl)piperidin-3-yl)-2-methyl-3-(pyrimidin-5-yl)pyrazolo[1,5-a]pyrimidine, 5-(7-(1-(4-Chlorobenzyl)piperidin-3-yl)-2-methylpyrazolo[1,5-a]pyrimidin-3-yl)pyrimidin-2-amine, 7-(1-(4-Chlorobenzyl)piperidin-3-yl)-2-methyl-3-(1-methyl-1H-pyrazol-4-yl)pyrazolo[1,5-a]pyrimidine, 4-(7-(1-(4-Chlorobenzyl)piperidin-3-yl)-2-methylpyrazolo[1,5-a]pyrimidin-3-yl)-3,5-dimethylisoxazole, (4-(7-(1-(4-Chlorobenzyl)piperidin-3-yl)-2-methylpyrazolo[1,5-a]pyrimidin-3-yl)pyridin-2-yl)methanol, (5-(7-(1-(4-Chlorobenzyl)piperidin-3-yl)-2-methylpyrazolo[1,5-a]pyrimidin-3-ye)pyridin-2-yl)methanol, 7-(1-(4-Chlorobenzyl)piperidin-3-yl)-3-(2-ethoxypyridin-4-yl)-2-methylpyrazolo[1,5-a]pyrimidine, 7-(1-(4-Chlorobenzyl)piperidin-3-yl)-3-(2-(cyclopropylmethoxy)pyridin-4-yl)-2-methylpyrazolo[1,5-a]pyrimidine, 7-(1-(4-Chlorobenzyl)piperidin-3-yl)-2-methyl-3-(1-methyl-1H-imidazol-5-yl)pyrazolo[1,5-a]pyrimidine, 7-(1-(4-Chlorobenzyl)piperidin-3-yl)-2-methyl-3-(pyrimidin-4-yl)pyrazolo[1,5-a]pyrimidine, 4-(7-(1-(4-Chlorobenzyl)piperidin-3-yl)-2-methylpyrazolo[1,5-a]pyrimidin-3-yl)pyrimidin-2-amine, 7-(1-(4-Chlorobenzyl)piperidin-3-yl)-N,N,2-trimethylpyrazolo[1,5-a]pyrimidin-3-amine, 7-(1-Benzylpiperidin-3-yl)-N,N,2-trimethylpyrazolo[1,5-a]pyrimidin-3-amine, N-Benzyl-7-(1-benzylpiperidin-3-yl)-N,2-dimethylpyrazolo[1,5-a]pyrimidin-3-amine, N-Benzyl-1-(7-(1-(4-chlorobenzyl)piperidin-3-yl)-2-methylpyrazolo[1,5-a]pyrimidin-3-yl)methanamine, N-Benzyl-1-(7-(1-(4-chlorobenzyl)piperidin-3-yl)-2-methylpyrazolo[1,5-a]pyrimidin-3-yl)-N-methylmethanamine,
1-(7-(1-(4-Chlorobenzyl)piperidin-3-yl)-2-methylpyrazolo[1,5-a]pyrimidin-3-yl)-N-(4-fluorobenzyl)methanamine,
(4-((((7-(1-(4-Chlorobenzyl)piperidin-3-yl)-2-methylpyrazolo[1,5-a]pyrimidin-3-yl)methyl)amino)methyl)phenyl)methanol,
1-(7-(1-(4-Chlorobenzyl)piperidin-3-yl)-2-methylpyrazolo[1,5-a]pyrimidin-3-yl)-N-(pyridin-4-ylmethyl)methanamine,
1-(7-(1-(4-Chlorobenzyl)piperidin-3-yl)-2-methylpyrazolo[1,5-a]pyrimidin-3-yl)-N-(thiophen-2-ylmethyl)methanamine,
1-(7-(1-(4-Chlorobenzyl)piperidin-3-yl)-2-methylpyrazolo[1,5-a]pyrimidin-3-yl)-N-((5-methylthiophen-2-yl)methyl)methanamine,
1-(7-(1-(4-Chlorobenzyl)piperidin-3-yl)-2-methylpyrazolo[1,5-a]pyrimidin-3-yl)-N-((1-methyl-1H-pyrazol-3-yl)methyl)methanamine,
1-(7-(1-(4-Chlorobenzyl)piperidin-3-yl)-2-methylpyrazolo[1,5-a]pyrimidin-3-yl)-N-((5-methyl-1,3,4-oxadiazol-2-yl)methyl)methanamine,
N-((7-(1-(4-Chlorobenzyl)piperidin-3-yl)-2-methylpyrazolo[1,5-a]pyrimidin-3-yl)methyl)-2-phenylethan-1-amine,
N-((7-(1-(4-Chlorobenzyl)piperidin-3-yl)-2-methylpyrazolo[1,5-a]pyrimidin-3-yl)methyl)-2-(4-methoxyphenyl)ethan-1-amine,
N-((7-(1-(4-Chlorobenzyl)piperidin-3-yl)-2-methylpyrazolo[1,5-a]pyrimidin-3-yl)methyl)ethanamine,
N-((7-(1-(4-Chlorobenzyl)piperidin-3-yl)-2-methylpyrazolo[1,5-a]pyrimidin-3-yl)methyl)-2,2,2-trifluoroethan-1-amine,
1-(7-(1-(4-Chlorobenzyl)piperidin-3-yl)-2-methylpyrazolo[1,5-a]pyrimidin-3-yl)-N-(cyclopropylmethyl)methanamine,
2-(((7-(1-(4-Chlorobenzyl)piperidin-3-yl)-2-methylpyrazolo[1,5-a]pyrimidin-3-yl)methyl)amino)ethan-1-ol,
N-((7-(1-(4-Chlorobenzyl)piperidin-3-yl)-2-methylpyrazolo[1,5-a]pyrimidin-3-yl)methyl)propan-2-amine,
N-((7-(1-(4-Chlorobenzyl)piperidin-3-yl)-2-methylpyrazolo[1,5-a]pyrimidin-3-yl)methyl)-2-methylpropan-1-amine,
N-((7-(1-(4-Chlorobenzyl)piperidin-3-yl)-2-methylpyrazolo[1,5-a]pyrimidin-3-yl)methyl)-3-methylbutan-1-amine,
N-((7-(1-(4-Chlorobenzyl)piperidin-3-yl)-2-methylpyrazolo[1,5-a]pyrimidin-3-yl)methyl)-2-isopropoxyethan-1-amine,
N-((7-(1-(4-Chlorobenzyl)piperidin-3-yl)-2-methylpyrazolo[1,5-a]pyrimidin-3-yl)methyl)-4-methoxybutan-1-amine,
(2S,6R)-4-((7-(1-(4-Chlorobenzyl)piperidin-3-yl)-2-methylpyrazolo[1,5-a]pyrimidin-3-yl)methyl)-2,6-dimethylmorpholine,
4-((7-(1-(4-Chlorobenzyl)piperidin-3-yl)-2-methylpyrazolo[1,5-a]pyrimidin-3-yl)methyl)morpholine,
N-((7-(1-(4-Chlorobenzyl)piperidin-3-yl)-2-methylpyrazolo[1,5-a]pyrimidin-3-yl)methyl)-2-morpholinoethan-1-amine,
4-((7-(1-(4-Chlorobenzyl)piperidin-3-yl)-2-methylpyrazolo[1,5-a]pyrimidin-3-yl)methyl)thiomorpholine,
4-((7-(1-(4-Chlorobenzyl)piperidin-3-yl)-2-methylpyrazolo[1,5-a]pyrimidin-3-yl)methyl)thiomorpholine 1,1-dioxide,
7-(1-(4-Chlorobenzyl)piperidin-3-yl)-2-methyl-3-(piperidin-1-ylmethyl)pyrazolo[1,5-a]pyrimidine,
7-(1-(4-Chlorobenzyl)piperidin-3-yl)-3-((4-(methoxymethyl)piperidin-1-yl)methyl)-2-methylpyrazolo[1,5-a]pyrimidine,
1-((7-(1-(4-Chlorobenzyl)piperidin-3-yl)-2-methylpyrazolo[1,5-a]pyrimidin-3-yl)methyl)piperidine-4-carboxamide,
1-((7-(1-(4-Chlorobenzyl)piperidin-3-yl)-2-methylpyrazolo[1,5-a]pyrimidin-3-yl)methyl)piperidine-4-carbonitrile,
4-((7-(1-(4-Chlorobenzyl)piperidin-3-yl)-2-methylpyrazolo[1,5-a]pyrimidin-3-yl)methyl)piperazin-2-one,
1-(4-((7-(1-(4-Chlorobenzyl)piperidin-3-yl)-2-methylpyrazolo[1,5-a]pyrimidin-3-yl)methyl)piperazin-1-yl)ethan-1-one,
7-(1-(4-Chlorobenzyl)piperidin-3-yl)-2-methyl-3-((4-(methylsulfonyl)piperazin-1-yl)methyl)pyrazolo[1,5-a]pyrimidine,
1-(3-(((7-(1-(4-Chlorobenzyl)piperidin-3-yl)-2-methylpyrazolo[1,5-a]pyrimidin-3-yl)methyl)amino)propyl)pyrrolidin-2-one,
1-(7-(1-(4-Chlorobenzyl)piperidin-3-yl)-2-methylpyrazolo[1,5-a]pyrimidin-3-yl)-N-((4-fluorotetrahydro-2H-pyran-4-yl)methyl)methanamine,
N-((7-(1-(4-Chlorobenzyl)piperidin-3-yl)-2-methylpyrazolo[1,5-a]pyrimidin-3-yl)methyl)-2-(tetrahydro-2H-pyran-4-yl)ethan-1-amine,
1-(7-(1-(4-Chlorobenzyl)piperidin-3-yl)-2-methylpyrazolo[1,5-a]pyrimidin-3-yl)-N-((1-(methylsulfonyl)piperidin-4-yl)methyl)methanamine,
1-(4-((((7-(1-Benzylpiperidin-3-yl)-2-methylpyrazolo[1,5-a]pyrimidin-3-yl)methyl)amino)methyl)piperidin-1-yl)ethan-1-one,
1-(7-(1-(3-Fluorobenzyl)piperidin-3-yl)-2-methylpyrazolo[1,5-a]pyrimidin-3-yl)-N-((tetrahydro-2H-pyran-4-yl)methyl)methanamine,
1-(7-(1-(3,4-Difluorobenzyl)piperidin-3-yl)-2-methylpyrazolo[1,5-a]pyrimidin-3-yl)-N-((tetrahydro-2H-pyran-4-yl)methyl)methanamine,
4-((3-(2-Methyl-3-((((tetrahydro-2H-pyran-4-yl)methyl)amino)methyl)pyrazolo[1,5-a]pyrimidin-7-yl)piperidin-1-yl)methyl)benzonitrile,
1-(2-Methyl-7-(1-((6-(trifluoromethyl)pyridin-3-yl)methyl)piperidin-3-yl)pyrazolo[1,5-a]pyrimidin-3-yl)-N-((tetrahydro-2H-pyran-4-yl)methyl)methanamine,
1-(2-Methyl-7-(1-((tetrahydro-2H-pyran-4-yl)methyl)piperidin-3-yl)pyrazolo[1,5-a]pyrimidin-3-yl)-N-((tetrahydro-2H-pyran-4-yl)methyl)methanamine,
1-(7-(1-(2,4-Dichlorobenzyl)piperidin-3-yl)-2-methylpyrazolo[1,5-a]pyrimidin-3-yl)-N,N-dimethylmethanamine,
1-(7-(1-(4-Chlorobenzyl)piperidin-3-yl)-2-ethylpyrazolo[1,5-a]pyrimidin-3-yl)-N-((tetrahydro-2H-pyran-4-yl)methyl)methanamine,
1-(7-(1-(4-Chlorobenzyl)piperidin-3-yl)-2-cyclopropylpyrazolo[1,5-a]pyrimidin-3-yl)-N-((tetrahydro-2H-pyran-4-yl)methyl)methanamine,
1-(7-(1-(4-Chlorobenzyl)piperidin-3-yl)-2-methoxypyrazolo[1,5-a]pyrimidin-3-yl)-N-((tetrahydro-2H-pyran-4-yl)methyl)methanamine,
1-(2-Chloro-7-(1-(4-chlorobenzyl)piperidin-3-yl)pyrazolo[1,5-a]pyrimidin-3-yl)-N-((tetrahydro-2H-pyran-4-yl)methyl)methanamine,
1-(2-Chloro-7-(1-isopentylpiperidin-3-yl)pyrazolo[1,5-a]pyrimidin-3-yl)-N-((tetrahydro-2H-pyran-4-yl)methyl)methanamine, 1-(4-((((2-Chloro-7-(1-isopentylpiperidin-3-yl)pyrazolo[1,5-a]pyrimidin-3-yl)methyl)amino)methyl)piperidin-1-yl)ethan-1-one, (S)-1-(4-((((7-(1-(4-Chlorobenzyl)piperidin-3-yl)-2-methylpyrazolo[1,5-a]pyrimidin-3-yl)methyl)amino)methyl)piperidin-1-yl)ethan-1-one, (R)-1-(4-((((7-(1-(4-chlorobenzyl)piperidin-3-yl)-2-methylpyrazolo[1,5-a]pyrimidin-3-yl)methyl)amino)methyl)piperidin-1-yl)ethan-1-one, (R)—N-((7-((R)-1-(4-Chlorobenzyl)piperidin-3-yl)-2-methylpyrazolo[1,5-a]pyrimidin-3-yl)methyl)-1-phenylethan-1-amine, (R)—N-((7-((S)-1-(4-Chlorobenzyl)piperidin-3-yl)-2-methylpyrazolo[1,5-a]pyrimidin-3-yl)methyl)-1-phenylethan-1-amine, (S)—N-((7-((R)-1-(4-Chlorobenzyl)piperidin-3-yl)-2-methylpyrazolo[1,5-a]pyrimidin-3-yl)methyl)-1-phenylethan-1-amine, (S)—N-((7-((S)-1-(4-Chlorobenzyl)piperidin-3-yl)-2-methylpyrazolo[1,5-a]pyrimidin-3-yl)methyl)-1-phenylethan-1-amine, (S)-1-(7-(1-(4-Chlorobenzyl)piperidin-3-yl)-2-methylpyrazolo[1,5-a]pyrimidin-3-yl)-N-((tetrahydro-2H-pyran-4-yl)methyl)methanamine, (R)-1-(7-(1-(4-Chlorobenzyl)piperidin-3-yl)-2-methylpyrazolo[1,5-a]pyrimidin-3-yl)-N-((tetrahydro-2H-pyran-4-yl)methyl)methanamine, (+/−)-1-(7-((R/S)-1-(4-Chlorobenzyl)piperidin-3-yl)-2-methylpyrazolo[1,5-a]pyrimidin-3-yl)-N—(((S/R)-tetrahydrofuran-3-yl)methyl)methanamine, 1-(7-((R)-1-(4-Chlorobenzyl)piperidin-3-yl)-2-methylpyrazolo[1,5-a]pyrimidin-3-yl)-N—(((R)-tetrahydrofuran-3-yl)methyl)methanamine, 1-(7-((S)-1-(4-Chlorobenzyl)piperidin-3-yl)-2-methylpyrazolo[1,5-a]pyrimidin-3-yl)-N—(((S)-tetrahydrofuran-3-yl)methyl)methanamine, (S)-1-(7-(1-Benzylpiperidin-3-yl)-2-methylpyrazolo[1,5-a]pyrimidin-3-yl)-N-((tetrahydro-2H-pyran-4-yl)methyl)methanamine, (R)-1-(7-(1-Benzylpiperidin-3-yl)-2-methylpyrazolo[1,5-a]pyrimidin-3-yl)-N-((tetrahydro-2H-pyran-4-yl)methyl)methanamine, (S)-1-(7-(1-(4-Fluorobenzyl)piperidin-3-yl)-2-methylpyrazolo[1,5-a]pyrimidin-3-yl)-N-((tetrahydro-2H-pyran-4-yl)methyl)methanamine, (R)-1-(7-(1-(4-Fluorobenzyl)piperidin-3-yl)-2-methylpyrazolo[1,5-a]pyrimidin-3-yl)-N-((tetrahydro-2H-pyran-4-yl)methyl)methanamine, (S)-3-((3-(2-Methyl-3-((((tetrahydro-2H-pyran-4-yl)methyl)amino)methyl)pyrazolo[1,5-a]pyrimidin-7-yl)piperidin-1-yl)methyl)benzonitrile, (R)-3-((3-(2-Methyl-3-((((tetrahydro-2H-pyran-4-yl)methyl)amino)methyl)pyrazolo[1,5-a]pyrimidin-7-yl)piperidin-1-yl)methyl)benzonitrile, (S)-1-(7-(1-(4-Chlorobenzyl)piperidin-3-yl)-2-methylpyrazolo[1,5-a]pyrimidin-3-yl)-N,N-dimethylmethanamine, (R)-1-(7-(1-(4-Chlorobenzyl)piperidin-3-yl)-2-methylpyrazolo[1,5-a]pyrimidin-3-yl)-N,N-dimethylmethanamine, (R)-1-(7-(1-(4-Chlorobenzyl)piperidin-3-yl)-2-methylpyrazolo[1,5-a]pyrimidin-3-yl)-N-methylmethanamine, (S)-1-(7-(1-(4-Chlorobenzyl)piperidin-3-yl)-2-methylpyrazolo[1,5-a]pyrimidin-3-yl)-N-methylmethanamine, ((S)-1-(7-(1-Benzylpiperidin-3-yl)-2-chloropyrazolo[1,5-a]pyrimidin-3-yl)-N-((tetrahydro-2H-pyran-4-yl)methyl)methanamine, ((R)-1-(7-(1-Benzylpiperidin-3-yl)-2-chloropyrazolo[1,5-a]pyrimidin-3-yl)-N-((tetrahydro-2H-pyran-4-yl)methyl)methanamine, (S)-1-(4-((((7-(1-Benzylpiperidin-3-yl)-2-chloropyrazolo[1,5-a]pyrimidin-3-yl)methyl)amino)methyl)piperidin-1-yl)ethan-1-one, (R)-1-(4-((((7-(1-benzylpiperidin-3-yl)-2-chloropyrazolo[1,5-a]pyrimidin-3-yl)methyl)amino)methyl)piperidin-1-yl)ethan-1-one, 4-((((7-(1-(4-Chlorobenzyl)piperidin-3-yl)-2-methylpyrazolo[1,5-a]pyrimidin-3-yl)methyl)amino)methyl)piperidine-1-carboxamide, (7-(1-(4-Chlorobenzyl)piperidin-3-yl)-2-methylpyrazolo[1,5-a]pyrimidin-3-yl)methanamine, 1-(7-(1-Benzylpiperidin-3-yl)-2-methylpyrazolo[1,5-a]pyrimidin-3-yl)-N-(((2R,6S)-2,6-dimethyltetrahydro-2H-pyran-4-yl)methyl)methanamine, (+/−)-1-(7-((R/S)-1-(4-Chlorobenzyl)piperidin-3-yl)-2-methylpyrazolo[1,5-a]pyrimidin-3-yl)-N—(((R/S)-2,2-dimethyltetrahydro-2H-pyran-4-yl)methyl)methanamine, (1-(7-((R)-1-(4-Chlorobenzyl)piperidin-3-yl)-2-methylpyrazolo[1,5-a]pyrimidin-3-yl)-N—(((S)-2,2-dimethyltetrahydro-2H-pyran-4-yl)methyl)methanamine, (1-(7-((S)-1-(4-Chlorobenzyl)piperidin-3-yl)-2-methylpyrazolo[1,5-a]pyrimidin-3-yl)-N—(((R)-2,2-dimethyltetrahydro-2H-pyran-4-yl)methyl)methanamine, (+/−)-(R/S)—N-((7-((R/S)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine, (S)—N-((7-((R)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine, (R)—N-((7-((S)-1-(4-Chlorobenzyl)piperidin-3-yl)-2-methylpyrazolo[1,5-a]pyrimidin-3-yl)methyl)-1-(tetrahydro-2H-pyran-4-yl)ethan-1-amine, (R)-1-(7-(1-(4-Chlorobenzyl)piperidin-3-yl)-2-methylpyrazolo[1,5-a]pyrimidin-3-yl)-N-(cyclopropylmethyl)-N-methylmethanamine, (S)-1-(7-(1-(4-Chlorobenzyl)piperidin-3-yl)-2-methylpyrazolo[1,5-a]pyrimidin-3-yl)-N-(cyclopropylmethyl)-N-methylmethanamine, 1-(7-(1-(4-Chlorobenzyl)piperidin-3-yl)-2-methylpyrazolo[1,5-a]pyrimidin-3-yl)-N-(2,6-difluorobenzyl)-N-methylmethanamine, (4-((((7-(1-(4-Chlorobenzyl)piperidin-3-yl)-2-methylpyrazolo[1,5-a]pyrimidin-3-yl)methyl)(methyl)amino)methyl)phenyl)methanol, 1-(7-(1-(4-Chlorobenzyl)piperidin-3-yl)-2-methylpyrazolo[1,5-a]pyrimidin-3-yl)-N-methyl-N-((tetrahydro-2H-pyran-4-yl)methyl)methanamine, N-((7-(1-(4-Chlorobenzyl)piperidin-3-yl)-2-methylpyrazolo[1,5-a]pyrimidin-3-yl)methyl)-N-((tetrahydro-2H-pyran-4-yl)methyl)propan-2-amine, N-((7-(1-Benzylpiperidin-3-yl)-2-methylpyrazolo[1,5-a]pyrimidin-3-yl)methyl)-N-(((2R,6S)-2,6-dimethyltetrahydro-2H-pyran-4-yl)methyl)propan-2-amine, 1-(7-(1-Benzylpiperidin-3-yl)-2-methylpyrazolo[1,5-a]pyrimidin-3-yl)-N-(cyclopropylmethyl)-N-methylmethanamine, N-((7-(1-(4-Chlorobenzyl)piperidin-3-yl)-2-methylpyrazolo[1,5-a]pyrimidin-3-yl)methyl)-2,2,2-trifluoro-N-((tetrahydro-2H-pyran-4-yl)methyl)ethan-1-amine, 2-(7-(1-(4-Chlorobenzyl)piperidin-3-yl)-2-methylpyrazolo[1,5-a]pyrimidin-3-yl)-N,N-dimethylethan-1-amine, 1-(7-(1-(4-Chlorobenzyl)piperidin-3-yl)-2,6-dimethylpyrazolo[1,5-a]pyrimidin-3-yl)-N-((tetrahydro-2H-pyran-4-yl)methyl)methanamine, 1-(7-(1-(4-Chlorobenzyl)piperidin-3-yl)-2,5-dimethylpyrazolo[1,5-a]pyrimidin-3-yl)-N-((tetrahydro-2H-pyran-4-yl)methyl)methanamine, (S)-1-(7-(1-(2-Fluorobenzyl)piperidin-3-yl)-2-methylpyrazolo[1,5-a]pyrimidin-3-yl)-N-((tetrahydro-2H-pyran-4-yl)methyl)methanamine, (S)-1-(7-(1-(2,4-Difluorobenzyl)piperidin-3-yl)-2-methylpyrazolo[1,5-a]pyrimidin-3-yl)-N-((tetrahydro-2H-pyran-4-yl)methyl)methanamine, (S)-1-(7-(1-(3,5-Difluorobenzyl)piperidin-3-yl)-2-methylpyrazolo[1,5-a]pyrimidin-3-yl)-N-((tetrahydro-2H-pyran-4-yl)methyl)methanamine, 1-(7-(1-(4-Methoxybenzyl)piperidin-3-yl)-2-methylpyrazolo[1,5-a]pyrimidin-3-yl)-N-((tetrahydro-2H-pyran-4-yl)methyl)methanamine, (R)-4-((((7-((S)-1-Benzylpiperidin-3-yl)-2-methylpyrazolo[1,5-a]pyrimidin-3-yl)methyl)amino)methyl)-1-methylpiperidin-2-one, (S)-4-((((7-((S)-1-Benzylpiperidin-3-yl)-2-methylpyrazolo[1,5-a]pyrimidin-3-yl)methyl)amino)methyl)-1-methylpiperidin-2-one, (R)-5-((((7-((S)-1-Benzylpiperidin-3-yl)-2-methylpyrazolo[1,5-a]pyrimidin-3-yl)methyl)amino)methyl)piperidin-2-one, (S)-5-((((7-((S)-1-Benzylpiperidin-3-yl)-2-methylpyrazolo[1,5-a]pyrimidin-3-yl)methyl)amino)methyl)piperidin-2-one, (S)-1-(4-((((7-(1-(3,4-Difluorobenzyl)piperidin-3-yl)-2-methylpyrazolo[1,5-a]pyrimidin-3-yl)methyl)amino)methyl)piperidin-1-yl)ethan-1-one, 1-(7-(1-Benzylpiperidin-3-yl)-2-methoxypyrazolo[1,5-a]pyrimidin-3-yl)-N-((tetrahydro-2H-pyran-4-yl)methyl)methanamine, 7-((1-(4-Chlorobenzyl)piperidin-3-yl)methyl)-2-methyl-3-(pyridin-4-yl)pyrazolo[1,5-a]pyrimidine, 7-((1-(3-Chlorobenzyl)piperidin-3-yl)methyl)-2-methyl-3-(pyridin-4-yl)pyrazolo[1,5-a]pyrimidine, 1-(7-((1-(4-Chlorobenzyl)piperidin-3-yl)methyl)-2-methylpyrazolo[1,5-a]pyrimidin-3-yl)-N,N-dimethylmethanamine, 1-(7-((1-(3-Chlorobenzyl)piperidin-3-yl)methyl)-2-methylpyrazolo[1,5-a]pyrimidin-3-yl)-N,N-dimethylmethanamine and 1-(7-(1-(4-Chlorobenzyl)azepan-3-yl)-2-methylpyrazolo[1,5-a]pyrimidin-3-yl)-N-((tetrahydro-2H-pyran-4-yl)methyl)methanamine, or a pharmaceutically acceptable salt thereof.

8. A pharmaceutical composition comprising a pharmaceutically acceptable carrier, adjuvant, or vehicle and the compound according to claim 1, or a pharmaceutically acceptable salt or stereoisomer thereof.

9. A method for treating pain in a subject in need thereof, wherein the method comprises administering to the subject an effective amount of the compound according to claim 1, or a pharmaceutically acceptable salt or stereoisomer thereof.

10. The method according to claim 9, wherein the pain is selected from the group consisting of acute pain, allodynia, cancer pain, chronic pain, hyperalgesia, inflammatory pain, medium to severe pain, migraine, neuropathic pain, and visceral pain.

11. A process for the production of the compound of Formula (I) according to claim 1, wherein the process comprises any one of the following steps:

(1) treating a compound of formula VI:

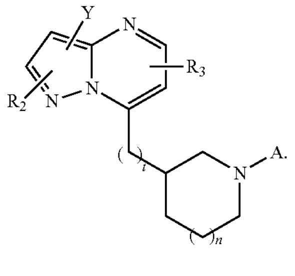

VI wherein:

A is $—C(R_5R_{5'})_m—R_4$;

Y is halogen; and $R_2$, $R_3$, $R_4$, $R_5$, $R_{5'}$, m, n, and t are defined as in claim 1;

with a compound of formula VII:

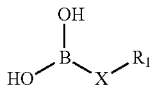

VI wherein:

X and $R_1$ are defined as in claim 1;

in the presence of a Pd catalyst, a base, and a solvent; or (2) alkylating a compound of formula Ia:

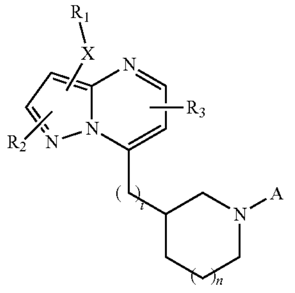

Ia wherein:

A is H; and

X, $R_1$, $R_2$, $R_3$, n, and t are defined as in claim 1;

with a compound of formula XI:

Z-T XI wherein:

T is $—C(R_5R_{5'})_m—R_4$;

Z is Cl, Br, or I; and $R_4$, $R_5$, $R_{5'}$, and m are defined as in claim 1.

12. A process for the production of the compound of Formula (I) according to claim 1, wherein $XR_1$ is $—CH_2NR_6R_{6'}$, wherein the process comprises any one of the following steps:

(1) reacting a compound of formula VI:

VI

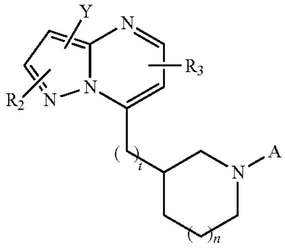

wherein:

A is —$C(R_5R_{5'})_m$—$R_4$;

Y is an acid functionality; and $R_2$, $R_3$, $R_4$, $R_5$, $R_{5'}$, m, n, and t are defined as in claim 1;

with a compound of formula IX:

IX

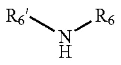

wherein:

$R_6$ and $R_{6'}$ are defined as in claim 1; or (2) reacting a compound of formula VI:

VI

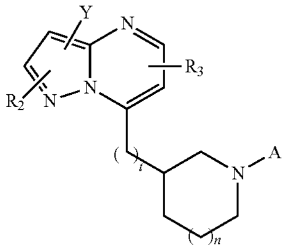

wherein:

A is —$C(R_5R_{5'})_m$—$R_4$;

Y is halogen; and $R_2$, $R_3$, $R_4$, $R_5$, $R_{5'}$, m, n, and t are defined as in claim 1;

with a compound of formula X:

X

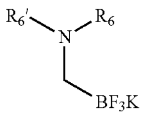

wherein:

$R_6$ and $R_{6'}$ are defined as in claim 1; or in the presence of a Pd catalyst, a base, a phosphine ligand, and a solvent; or (3) reacting a compound of formula VIII:

VIII

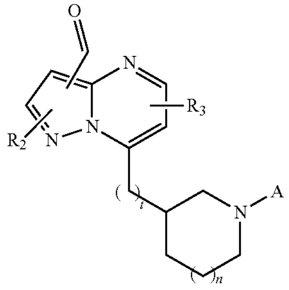

wherein:

A is —$C(R_5R_{5'})_m$—$R_4$; and $R_2$, $R_3$, $R_4$, $R_5$, $R_{5'}$, m, n, and t are defined as in claim 1;

with a compound of formula IX:

IX

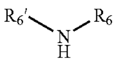

wherein:

$R_6$ and $R_{6'}$ are defined as in claim 1;

in the presence of a reducing agent, a solvent, and optionally, an acid; or (4) alkylating a compound of formula Ib:

Ib

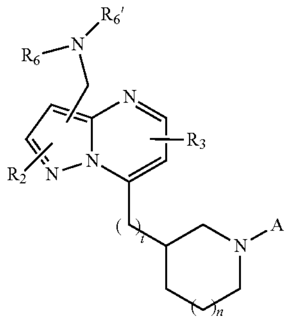

wherein:

A is H; and $R_2$, $R_3$, $R_6$, $R_6'$, n, and t are defined as in claim 1;

with a compound of formula XI:

Z-T XI wherein:

T is —$C(R_5R_{5'})_m$—$R_4$;

Z is Cl, Br, or I; and $R_4$, $R_5$, $R_{5'}$, and m are defined as in claim 1.

13. A compound selected from the group consisting of:
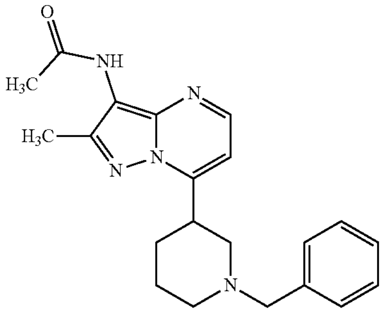
and
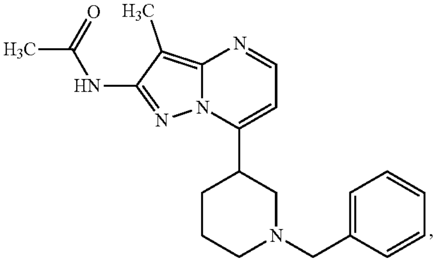
,
or a pharmaceutically acceptable salt or stereoisomer thereof.
* * * * *